United States Patent
Ho et al.

(10) Patent No.: US 9,586,959 B2
(45) Date of Patent: Mar. 7, 2017

(54) SUBSTITUTED TRICYCLIC HETEROCYCLES AS HISTAMINE 4 RECEPTOR INHIBITORS

(71) Applicants: Pil Su Ho, Gyeonggi-do (KR); Dong Oh Yoon, Gyeonggi-do (KR); Sun Young Han, Gyeonggi-do (KR); Won Il Lee, Gyeonggi-do (KR); Jung Sook Kim, Gyeonggi-do (KR); Woul Seong Park, Gyeonggi-do (KR); Sung Oh Ahn, Gyeonggi-do (KR); Hye Jung Kim, Gyeonggi-do (KR)

(72) Inventors: Pil Su Ho, Gyeonggi-do (KR); Dong Oh Yoon, Gyeonggi-do (KR); Sun Young Han, Gyeonggi-do (KR); Won Il Lee, Gyeonggi-do (KR); Jung Sook Kim, Gyeonggi-do (KR); Woul Seong Park, Gyeonggi-do (KR); Sung Oh Ahn, Gyeonggi-do (KR); Hye Jung Kim, Gyeonggi-do (KR)

(73) Assignee: C&C RESEARCH LABORATORIES, Gyeonggi-Do (KR)

( * ) Notice: Subject to any disclaimer, the term of this patent is extended or adjusted under 35 U.S.C. 154(b) by 0 days.

(21) Appl. No.: 14/347,950

(22) PCT Filed: Sep. 28, 2012

(86) PCT No.: PCT/KR2012/007965
§ 371 (c)(1),
(2) Date: Mar. 27, 2014

(87) PCT Pub. No.: WO2013/048214
PCT Pub. Date: Apr. 4, 2013

(65) Prior Publication Data
US 2014/0315888 A1 Oct. 23, 2014

(30) Foreign Application Priority Data

Sep. 30, 2011 (KR) .................. 10-2011-0100369
Mar. 30, 2012 (KR) .................. 10-2012-0033444

(51) Int. Cl.
*A61K 31/4353* (2006.01)
*A61K 31/4985* (2006.01)
*A61K 31/519* (2006.01)
*C07D 471/14* (2006.01)
*C07D 487/14* (2006.01)
*C07D 491/147* (2006.01)
*C07D 498/14* (2006.01)
*C07D 519/00* (2006.01)

(52) U.S. Cl.
CPC ......... *C07D 471/14* (2013.01); *C07D 487/14* (2013.01); *C07D 498/14* (2013.01); *C07D 519/00* (2013.01)

(58) Field of Classification Search
CPC ............ A61K 31/4353; A61K 31/4985; A61K 31/519; C07D 471/14; C07D 487/14; C07D 491/147; C07D 498/14
USPC ................ 514/250, 267, 293; 544/252, 346; 546/84, 89
See application file for complete search history.

(56) References Cited

U.S. PATENT DOCUMENTS 4,831,013 A * 5/1989 Francis ................ C07D 471/14
514/23
5,070,086 A 12/1991 Friary .......................... 514/183
(Continued)

FOREIGN PATENT DOCUMENTS

EP  1104764  6/2001  .......... C07D 471/04
JP  2000-119271  4/2000  .......... C07D 471/04
(Continued)

OTHER PUBLICATIONS

Jordan, V. C. Nature Reviews: Drug Discovery, 2, 2003, 205.*
(Continued)

*Primary Examiner* — Douglas M Willis
(74) *Attorney, Agent, or Firm* — Harness, Dickey & Pierce, P.L.C.

(57) ABSTRACT

The present invention relates to novel heterocyclic compounds of formula 1 useful in preparing drugs for treatment of diseases associated with various functions of the histamine 4 receptor. Especially, the said drugs are useful for treatment of inflammatory diseases, allergy, pain, nasal polyps, rhinitis, chronic sinusitis, nasal congestion, nasal itch, asthma, chronic obstructive pulmonary disease, rheumatoid arthritis, atopic dermatitis, psoriasis, eczema, pruritus, itchy skin, urticaria, idiopathic chronic urticaria, scleroderma, conjunctivitis, keratoconjunctivitis, ocular inflammation, dry eye, cardiac dysfunction, arrhythmia, atherosclerosis, multiple sclerosis, inflammatory bowel disease (including colitis, Crohn's disease, ulcerative colitis), inflammatory pain, neuropathic pain, osteoarthritic pain, autoimmune thyroid disease, immune-mediated (also known as type I) diabetes, lupus, post-operative adhesions, vestibular disorders and cancer.

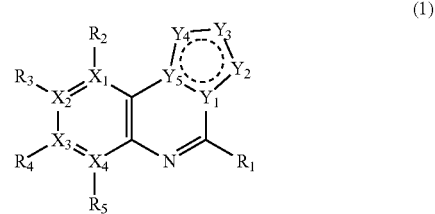

(1)

13 Claims, No Drawings

(56) References Cited

U.S. PATENT DOCUMENTS

| | | | | |
|---|---|---|---|---|
| 6,451,796 | B1* | 9/2002 | Kobayashi | A61K 31/4985 514/249 |
| 2009/0075980 | A1* | 3/2009 | Hays | C07D 471/14 514/217.07 |
| 2009/0143392 | A1 | 6/2009 | Hofgen et al. | 514/250 |
| 2010/0120741 | A1 | 5/2010 | Borchardt et al. | 514/210.21 |

FOREIGN PATENT DOCUMENTS

| | | | |
|---|---|---|---|
| JP | 2000-319277 | 11/2000 | C07D 471/14 |
| WO | WO 99/45009 | 9/1999 | C07D 471/14 |
| WO | 2004/085439 A1 | 10/2004 | C07D 487/04 |
| WO | WO 2010/030785 | 3/2010 | |
| WO | WO 2010/077530 | 7/2010 | C07D 471/04 |
| WO | WO 2010/085570 | 7/2010 | C07D 471/04 |
| WO | WO 2011/014681 | 2/2011 | C07D 471/14 |
| WO | 2011/060207 A1 | 5/2011 | C07D 491/00 |
| WO | WO 2011/054846 | 5/2011 | C07D 471/04 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Debenham, et al. Bioorganic & Medicinal Chemistry Letters, 19(9), 2009, 2591-2594.*

Bowie, R. Journal of the Chemical Society (Section) D: Chemical Communications, 9, 1970, 565.*

International Search Report issued in PCTKR2012007965, dated Mar. 26, 2013.

Arrang, et al. (1983) "Auto-inhibition of brain histamine release mediated by a novel class ($H_3$) of histamine receptor." Nature, 302:832-837.

Ash, et al. (1966) "Receptors mediating some actions of histamine." Br. J. Pharmac. Chemother., 27:427-439.

Baumer, et al. (2010) "Histamine as an immunomodulator." J. Dtsch. Dermatol. Ges.(JDDG), 8(7):495-504.

Black, et al. (1972) "Definition and antagonism of histamine $H_2$-receptors." Nature, 236:385-390.

Cowden, et al. (2010) "The histamine $H_4$ receptor mediates inflammation and pruritus in Th2-dependent dermal inflammation." J. Invest. Dermatol., 130:1023-1033.

Dijkstra, et al. (2007) "Histamine downregulates monocyte CCL2 production through the histamine $H_4$ receptor." J. Allergy Clin. Immunol., 120(2):300-307.

Dunford, et al. (2007) "Histamine $H_4$ receptor antagonists are superior to traditional antihistamines in the attenuation of experimental pruritus." J. Allergy Clin. Immunol., 119(1):176-183.

Gutzmer, et al. (2005) "Histamine H4 receptor stimulation suppresses IL-12p70 production and mediates chemotaxis in human monocyte-derived dendritic cells." J. Immunol., 174:5224-5232.

Hofstra, et al. (2003) "Histamine $H_4$ receptor mediates chemotaxis and calcium mobilization of mast cells." J. Pharmacol. Exp. Ther. (JPET), 305(3):1212-1221.

Inagaki, et al. (2002) "Involvement of unique mechanisms in the induction of scratching behavior in BALB/c mice by compound 48/80." Eur. J. Pharmacol., 448:175-183.

Khan, et al. (2010) "Gut hormones: emerging role in immune activation and inflammation." British Society for Immunology, Clinical and Experimental Immunology, 161:19-27.

Kim, et al. (2011) Glucosamine improved atopic dermatitis-like skin lesions in NC/Nga mice by inhibition of Th2 cell development. Scandinavian Journal of Immunology, 73:536-545.

Man, et al. (2008) "Characterization of a hapten-induced, murine model with multiple features of atopic dermatitis: structural, immunologic, and biochemical changes following single versus multiple oxazolone challenges." J. Invest. Dermatol., 128:79-86.

Nakamura, et al. (2000) "Molecular cloning and characterization of a new human histamine receptor, HH4R." Biochem. Biophys. Res. Commun., 279:615-620.

Ohmori, et al. (1997) 8-(1 H-Imidazol-1-yl)-7-nitro-4(5 H)-imidazol[1,2-a]quinoxalinone and related compounds: synthesis and structure-activity relationships for the AMPA-type non-NMDA receptor. J. Med. Chem., 40:2053-2063.

O'Reilly, et al. (2002) "Identification of a histamine $H_4$ Receptor on human eosinophils—role in eosinophil chemotaxis." J. Recept. Signal Transduct., 22(1-4):431-448.

Parsons, et al. (2006) "Histamine and its receptors." Br. J. Pharmacol., 147:S127-S135.

Sarges, et al. (1990) "4-amino[1,2,4]triazolo[4,3-a]quinoxalines. A novel class of potent adenosine receptor antagonists and potential rapid-onset antidepressants." J. Med. Chem., 33:2240-2254.

Shahid, et al. (2009) "Histamine, histamine receptors, and their role in immunomodulation: an updated systematic review." The Open Immunology Journal, 2:9-41.

Takubo, et al. (2006) "Characteristics of scratching behavior induced by some chemical mediators in hairless mice." J. Pharmacol. Sci., 100:285-288.

Thurmond, et al. (2004) "A potent and selective histamine $H_4$ receptor antagonist with anti-inflammatory properties." J. Pharmacol. Exp. Ther.(JPET), 309(1):404-413.

Thurmond, et al. (2008) "The role of histamine $H_1$ and $H_4$ receptors in allergic inflammation: the search for new antihistamines." Nature Reviews Drug Discovery, 7:41-53.

Verheij, et al. (2011) "Fragment library screening reveals remarkable similarities between the G protein-coupled receptor histamine $H_4$ and the ion channel serotonin 5-$HT_{3A}$." Bioorg. Med. Chem. Lett., 21:5460-5464.

Vestergaard, et al. (1999) Overproduction of Th2-specific chemokines in NC/Nga mice exhibiting atopic dermatitis-like lesions. J. Clin. Invest., 104(8) 1097-1105.

Walstab, et al. (2010) "5-$HT_3$ receptors: role in disease and target of drugs." Pharmacology & Therapeutics, 128:146-169.

Yamaura, et al. (2009) "Expression of histamine H4 receptor in human epidermal tissues and attenuation of experimental pruritus using H4 receptor antagonist." J. Toxicol. Sci., 34(4):427-431.

Y. Blache et al., (1994). "Heterocyclizations in the pyrido[2,3-b]pyrazine series." Journal of Heterocyclic Chemistry. vol. 31(1):161-166.

D.J. Brown et al., (1981). "Triazolopteridines.II* simple s-triazolo[3,4-h]pteridines and some [5,1-h] and [4,3-a] isomers." Australian Journal of Chemistry, vol. 34:2635-2639.

S. Butini et al., (2009). "Novel, potent, and selective quinoxaline-based 5-ht3 receptor ligands. 1. Further structure-activity relationships and pharmacological characterization." Journal of Medicinal Chemistry. vol. 52:6946-6950.

G. Campiani (1999). "Pyrroloquinoxaline derivatives as high-affinity and selective 5-ht3 receptor agonists: synthesis, further structure-activity relationships, and biological studies." Journal of Medicinal Chemistry. vol. 42:4362-4379.

S.A. Hitchcock et al., (2006). "Structure-brain exposure relationships." Journal of Medicinal Chemistry. vol. 49(26):7559-7583.

H. Prunier et al., (1997). "Novel and selective partial agonists of 5-$ht_3$ receptors. 2. synthesis and biological evaluation of piperazinopyridopyrrolopyrazines, piperazinopyrroloquinoxalines, and piperazinopyridopyrroloquinoxalines." J. Med. Chem. vol. 40:1808-1819.

J.T. Reeves et al., (2010). "Copper-catalyzed annulation of 2-formylazoles with o-aminoiodoarenes." Journal of Organic Chemistry. vol. 75:992-994.

A. Unciti-Broceta et al., (2010). "Synthesis of 9-alkyl-6-amino[1,2,4]triazolo[3,4-c]-5-azaquinoxalines. Mild and effective $S_NAr$ amination of highly electron-poor heterocycles." Tetrahedron Letters. vol. 51:2262-2264.

J. Weinstock et al., (1968). "Pteridines. VII. Some 2,4-diamino-6-phenylpteridines." Journal of Medicinal Chemistry. vol. 11:557-560.

European Search Opinion dated Feb. 13, 2015, in European Patent Application No. 12834688.

Suppl. EP Search Report dated Jan. 29, 2015, in European Patent Application No. 12834688.
Said, S.A., et al. (2010) "Synthesis and anti-inflammatory activities of some new pyridopyridine, pyridopyrimidine and pyridopyrimidotriazine deriviatives." *World Applied Sciences Journal*, vol. 9(6):589-599.
Temple, C., et al. (1990) "Potential antimitotic agents. Synthesis of some ethyl benzopyrazin-7-ylcarbamates, ethyl prido[3,4-*b*]pyrazine-7-ylcarbamates, and ethyl pyrido[3,4,*e*]-as-triazin-7-ylcarbamates." *J. Med. Chem.*, vol. 33:3044-3050.

\* cited by examiner

SUBSTITUTED TRICYCLIC HETEROCYCLES AS HISTAMINE 4 RECEPTOR INHIBITORS

CROSS-REFERENCE TO RELATED APPLICATIONS

This application is a national phase application of PCT Application No. PCT/KR2012/007965, filed on Sep. 28, 2012, which claims the benefit and priority to Korean Patent Application No. 10-2011-0100369, filed Sep. 30, 2011 and claims the benefit and priority to Korean Patent Application No. 10-2012-0033444, filed Mar. 30, 2012. The entire disclosures of the applications identified in this paragraph are incorporated herein by references.

TECHNICAL FIELD

The present invention relates to novel heterocyclic compounds useful in preparing drugs for treatment of diseases associated with various functions of the histamine 4 receptor. Especially, the said drugs are useful for treatment of inflammatory diseases, allergy, pain, nasal polyps, rhinitis, chronic sinusitis, nasal congestion, nasal itch, asthma, chronic obstructive pulmonary disease, rheumatoid arthritis, atopic dermatitis, psoriasis, eczema, pruritus, itchy skin, urticaria, idiopathic chronic urticaria, scleroderma, conjunctivitis, keratoconjunctivitis, ocular inflammation, dry eye, cardiac dysfunction, arrhythmia, atherosclerosis, multiple sclerosis, inflammatory bowel disease (including colitis, Crohn's disease, ulcerative colitis), inflammatory pain, neuropathic pain, osteoarthritic pain, autoimmune thyroid disease, immune-mediated (also known as type I) diabetes, lupus, post-operative adhesions, vestibular disorders and cancer.

BACKGROUND ART

Histamine, which is a biogenic amine, plays a central role in the immune and inflammatory response and is also a neurotransmitter. For example, histamine controls various functions of antigen-presenting cells (dendritic cells and macrophages), T cells, B cells, epithelial and endothelial cells, and proliferation of T cells or cytokine secretion in dendritic cells and mast cells (JDDG, 2010, 8, 495-504). There are 4 histamine receptors (histamine 1 receptor, histamine 2 receptor, histamine 3 receptor and histamine 4 receptor) (Br. J. Pharm 2006, 147, S127-S135). An acute allergic reaction is controlled by the histamine 1 receptor which is distributed ubiquitously in the body (Br. J. Pharmac. Chemother. 1966, 27, 427-439) and a gastric acid secretion is controlled by the histamine 2 receptor which also are distributed ubiquitously in the body like histamine 1 receptor (Nature 1972, 236, 385-390). It is well known that the neurotransmitter secretion in the central nervous system is controlled by the histamine 3 receptor which is expressed in neurons (Nature 1983, 302, 832-837). The histamine 4 receptor further explains physiological functions of many signaling processes which are not explained only by the histamine 1 receptor, histamine 2 receptor and histamine 3 receptor. The histamine 4 receptor was reported for the first time in 1994 and its cloning was performed only since 2000. The histamine 4 receptor, which is a G-protein coupled receptor, consists of 390 amino acids and is activated by binding with Gi/o protein to increase calcium concentration or suppress cyclic adenosine monophosphate (cAMP) (The Open Immunology Journal, 2009, 2, 9-41). The histamine 4 receptor is mainly expressed in bone marrow or eosinophils, basophils, T cells, mast cells, monocytes and dendritic cells, and is also observed in the spleen, thymus, lung, heart and intestines (Nat. Rev. Drug Discov. 2008, 7, 41-53; Biochem. Biophys. Res. Commun. 2000, 279, 615-620). The histamine 4 receptor not only plays a central role in the immune response but also has effects on the activation and migration of various immunocytes, and the production of cytokines and chemokines (J. Immunol. 2005, 174, 5224-5232; J. Pharmacol. Exp. Ther. 2003, 305, 1212-1221; J. Allergy Clin. Immunol. 2007, 120, 300-307; J. Recept. Signal Transduct. Res. 2002, 22, 431-448).

In various in vivo experiments, it is well known that the histamine 4 receptor plays an important role in inflammation and itch (J. Allergy Clin. Immunol. 2007, 119, 176-183; J. Pharmacol. Exp. Ther. 2004, 309, 404-413). Especially, as results of researches, it has been found in an allergic mouse asthma model that the histamine 4 antagonists alleviate lung inflammation by controlling Th2 (T helper type 2) reaction, and confirmed that histamine 4 antagonists effectively suppress histamine-induced itch. Such a dual effect against allergic inflammation and itch is a basis for the fact that the histamine 4 receptor may be a good target for treating allergic skin diseases such as atopic dermatitis (J. Invest. Dermatol. 2010, 130(4), 1023-1033).

In such an immunocyte, antagonism against the various functions of the histamine 4 receptor is a key focus of study of inflammatory diseases, pruritus, pain, allergic rhinitis, asthma, rheumatoid arthritis, atopic dermatitis, idiopathic chronic urticaria, inflammatory pain, neuropathic pain and osteoarthritic pain. In addition, a recent study related to effectiveness of the histamine 4 receptor against cancer has been announced, and thereby its development as an anti-cancer drug is expected.

Recently, it has been reported in WO2010/030785 that quinoxaline-based derivatives show activity on the histamine 4 receptor. However, they did not show a sufficient pharmacological in vivo activity in animal model because their solubility and metabolic stability are not high.

DISCLOSURE OF INVENTION

Technical Problem

The heterocyclic compounds of the present invention including pyridopyrazine, pyridopyrimidine and naphthyridine exhibit the same or a stronger histamine 4 receptor inhibitory activity, as compared with conventional human histamine 4 receptor (hH4R) inhibitors such as those disclosed in WO2010/030785; show a selectivity for each of the subtype receptors of histamine and receptors, transporters and ion channels on a membrane; have higher solubility, metabolic stability and accordingly effective pharmacokinetics so as to be used for treatment with lower dosage and fewer administration times; show the suppressive effect against the histamine-induced infiltration of inflammatory cells such as mast cells and eosinophils, and thus have strong anti-inflammatory and anti-itching effects in an atopic dermatitis model; and have a selectivity for the serotonin 3 receptor to prevent side effects such as diarrhea or constipation (Clinical and Experimental Immunology, 2010, 161, 19-27; Pharmacology & Therapeutics, 2010, 128, 146-169) because of the high structural similarity between the histamine 4 receptor (hH4R) ligands and the serotonin 3 receptor ligands (BMCL, 2011, 21, 5460-5464). Thus, the purpose of the present invention is to provide such novel heterocyclic compounds and pharmaceutical compositions comprising the same.

As novel heterocyclic compounds according to the present invention and pharmaceutical compositions comprising the same show strong human histamine 4 receptor (hH4R) inhibitory activity, they are useful in treating or preventing inflammatory diseases, allergy, pain, nasal polyps, rhinitis, chronic sinusitis, nasal congestion, nasal itch, asthma, chronic obstructive pulmonary disease, rheumatoid arthritis, atopic dermatitis, psoriasis, eczema, pruritus, itchy skin, urticaria, idiopathic chronic urticaria, scleroderma, conjunctivitis, keratoconjunctivitis, ocular inflammation, dry eye, cardiac dysfunction, arrhythmia, atherosclerosis, multiple sclerosis, inflammatory bowel disease (including colitis, Crohn's disease, ulcerative colitis), inflammatory pain, neuropathic pain, osteoarthritic pain, autoimmune thyroid disease, immune-mediated (also known as type I) diabetes, lupus, post-operative adhesions, vestibular disorders and cancer.

Solution to Problem

The present invention provides a heterocyclic compound of formula 1

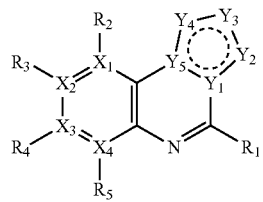

[Formula 1]

or a racemate, isomer or pharmaceutically acceptable salt thereof:
wherein
each of $X_1$, $X_2$, $X_3$ and $X_4$ is independently C or N, provided that at least one of $X_1$, $X_2$, $X_3$ and $X_4$ is N, $R_1$ is a saturated or unsaturated 3-12 membered mono- or poly-heterocyclyl containing 1-3 heteroatoms (preferably heteroatoms selected from N, O and S), where $R_1$ is unsubstituted or substituted with 1-3 substituents selected from —$NR_6R_7$, —$C_1$-$C_6$ alkyl-$NR_6R_7$, and $R_8$; or $R_1$ is selected from —H, —$NR_6R_7$ and $R_8$, $R_2$, $R_3$, $R_4$ and $R_5$ may be the same or different; and each of them is independently selected from —H; —$C_1$-$C_6$alkyl; —$C_1$-$C_6$haloalkyl; —$C_1$-$C_6$ perhaloalkyl; -amino-$C_1$-$C_6$alkyl; —$C_3$-$C_8$cycloalkyl; -halogen (—F, —Cl, —Br, —I); —CN; —$C_1$-$C_6$alkoxy; —$C_1$-$C_6$haloalkoxy; —$C_1$-$C_6$ perhaloalkoxy; —$C_2$-$C_7$alkenyl; —$C_2$-$C_8$alkynyl; -amino; -amido; —$C_1$-$C_6$alkylcarboxyl; -carboxyl (—COOH); —$C_1$-$C_6$acyl; —OH; -nitro (—$NO_2$); —$C_6$-$C_{10}$aryl; -heterocyclyl; and —O—$C_1$-$C_6$alkyl-heterocyclyl, where the heterocyclyl is a saturated or unsaturated 3-6 membered heterocyclyl containing 1-3 heteroatoms (preferably heteroatoms selected from N, O and S), provided that when $X_1$ is N, $R_2$ does not exist; when $X_2$ is N, $R_3$ does not exist; when $X_3$ is N, $R_4$ does not exist; and when $X_4$ is N, $R_5$ does not exist, each of $Y_1$, $Y_2$, $Y_3$, $Y_4$ and $Y_5$ is independently C or a heteroatom (preferably a heteroatom independently selected from N, O and S), provided that at least one of $Y_1$, $Y_2$, $Y_3$, $Y_4$ and $Y_5$ is a heteroatom independently selected from N, O and S, each of $Y_2$ and $Y_3$ may be independently substituted with $R_9$, $Y_4$ may be substituted with —H or —$C_1$-$C_6$alkyl, each of $R_6$ and $R_7$ is independently selected from —H; —$C_1$-$C_6$alkyl; —$C_3$-$C_8$cycloalkyl; -heterocyclyl; -amino-$C_1$-$C_6$mono- or di-alkyl; —$C_1$-$C_6$alkyl-amino-$C_1$-$C_6$mono- or di-alkyl; —$C_1$-$C_6$alkyl-heterocyclyl; —$C_1$-$C_6$alkylcarboxyl; -carboxyl (—COOH); and phenyl, where the heterocyclyl is a saturated or unsaturated 3-6 membered heterocyclyl containing 1-3 heteroatoms (preferably heteroatoms selected from N, O and S), $R_8$ is —$C_1$-$C_6$alkyl; —$C_1$-$C_6$alkoxy; —OH; -amino; —$C_1$-$C_6$alkyl-amino; —$C_3$-$C_8$cycloalkyl; —S—$C_1$-$C_6$alkyl-amino-$C_1$-$C_6$mono- or di-alkyl; —S—$C_1$-$C_6$alkyl-heterocyclyl; —O-heterocyclyl; or —O—$C_1$-$C_6$alkyl-heterocyclyl, where the heterocyclyl is a saturated or unsaturated 3-6 membered heterocyclyl containing 1-3 heteroatoms (preferably heteroatoms selected from N, O and S), and $R_9$ is selected from —H; —OH; —$C_1$-$C_6$alkyl; —$C_1$-$C_6$haloalkyl; —$C_1$-$C_6$ perhaloalkyl; -amino-$C_1$-$C_6$mono- or di-alkyl; —$C_3$-$C_7$cycloalkyl; -heterocyclyl; —$C_6$-$C_{10}$aryl; 5-12 membered heteroaryl; —$C_1$-$C_6$alkoxy; —$C_1$-$C_6$haloalkoxy; -halogen (—F, —Cl, —Br, —I); -amino; -amido; —$C_1$-$C_6$acyl; —CN; -carboxyl (—COOH); —$C_1$-$C_6$alkylcarboxyl; and -nitro (—$NO_2$), with proviso that when $Y_4$ is N and $Y_1$, $Y_2$, $Y_3$ and $Y_5$ is C, $Y_3$ is not substituted with a substituent having —C(=O)— moiety, wherein each of the alkyl, cycloalkyl, heterocyclyl, alkoxy, alkenyl, alkynyl, acyl and aryl groups may be independently unsubstituted or substituted with one or more substituents (for example, 1-3 substituents) selected from the group consisting of —$C_1$-$C_4$ alkyl, -halogen (—F, —Cl, —Br, —I), —CN, —$C_1$-$C_4$alkoxy, -amino, -amido, -carboxyl (—COOH), —$C_1$-$C_6$acyl, —OH, -nitro (—$NO_2$), heterocyclyl and phenyl, where the heterocyclyl is a saturated or unsaturated 3-6 membered heterocyclyl containing 1-3 heteroatoms (preferably, heteroatoms selected from N, O and S).

According to a preferred embodiment of the present invention, in the above formula 1, each of $X_1$, $X_2$ and $X_3$ is independently C or N, and $X_4$ is N.

According to another preferred embodiment of the present invention, in the above formula 1, each of $Y_1$, $Y_2$, $Y_3$, $Y_4$ and $Y_5$ is independently C or a heteroatom (preferably a heteroatom independently selected from N, O and S), provided that at least three of $Y_1$, $Y_2$, $Y_3$, $Y_4$ and $Y_5$ are N.

According to another preferred embodiment of the present invention, in the above formula 1, $R_1$ is a saturated or unsaturated 3-8 membered mono- or poly-heterocyclyl containing 1-3 heteroatoms (preferably heteroatoms selected from N, O and S), where $R_1$ is unsubstituted or substituted with 1-3 substituents selected from $NR_6R_7$, $C_1$-$C_6$ alkyl-$NR_6R_7$ and $R_8$.

According to another preferred embodiment of the present invention, in the above formula 1, $R_3$ is selected from —H; —$C_1$-$C_6$alkyl; —$C_1$-$C_6$haloalkyl; —$C_1$-$C_6$ perhaloalkyl; -halogen (—F, Cl, —Br, —I); —CN; —$C_1$-$C_6$alkoxy; —$C_1$-$C_6$haloalkoxy; —$C_1$-$C_6$ perhaloalkoxy; —$C_2$-$C_7$alkenyl; —$C_2$-$C_8$alkynyl and —OH.

According to another preferred embodiment of the present invention, in the above formula 1,
each of $X_1$, $X_2$, $X_3$ and $X_4$ is independently C or N, provided that at least one of $X_1$, $X_2$, $X_3$ and $X_4$ is N, $R_1$ is a saturated or unsaturated 3-12 membered mono- or poly-heterocyclyl containing 1-3 heteroatoms (preferably heteroatoms selected from N, O and S), where $R_1$ is unsubstituted or substituted with 1-3 substituents selected from —$NR_6R_7$, —$C_1$-$C_6$ alkyl-$NR_6R_7$ and $R_8$; or $R_1$ is selected from —$NR_6R_7$ and $R_8$, $R_2$, $R_3$, $R_4$ and $R_5$ may be the same or different; and each of them is independently selected from —H; —$C_1$-$C_6$alkyl; —$C_1$-$C_6$haloalkyl; —$C_1$-$C_6$ perhaloalkyl; -halogen (—F, —Cl, —Br, —I); —CN; —$C_1$-$C_6$alkoxy; —$C_1$-$C_6$haloalkoxy; —$C_1$-$C_6$ perhaloalkoxy; —$C_2$-$C_7$alkenyl; —$C_2$-$C_8$alkynyl; and —OH, provided that when $X_1$ is N, $R_2$ does not exist; when $X_2$ is N, $R_3$ does not exist; when $X_3$ is N, $R_4$ does not exist; and when $X_4$ is N, $R_5$ does not exist, each of $Y_1$, $Y_2$, $Y_3$, $Y_4$ and $Y_5$ is independently C or a heteroatom (preferably a heteroatom independently selected from N, O and S), provided that at least two of $Y_1$, $Y_2$, $Y_3$, $Y_4$ and $Y_5$ are heteroatoms independently selected from N, O and S, each of $Y_2$ and $Y_3$ may be independently substituted with $R_9$, $Y_4$ may be substituted with —H or —$C_1$-$C_6$alkyl, each of $R_6$ and $R_7$ is independently selected from —H; —$C_1$-$C_6$alkyl; and -carboxyl (—COOH), $R_8$ is selected from —$C_1$-$C_6$alkyl; and —$C_3$-$C_8$cycloalkyl, and $R_9$ is selected from —H; —$C_1$-$C_6$alkyl; and —$C_3$-$C_7$cycloalkyl, wherein each of the alkyl, cycloalkyl, heterocyclyl, alkoxy, alkenyl and alkynyl groups may be independently unsubstituted or substituted with one or more substituents selected from the group consisting of —$C_1$-$C_4$alkyl, —OH and —$C_1$-$C_4$alkoxy, where the heterocyclyl is a saturated or unsaturated 3-6 membered heterocyclyl containing 1-3 heteroatoms (preferably heteroatoms selected from N, O and S).

According to another preferred embodiment of the present invention, in the above formula 1, each of $X_1$, $X_2$, $X_3$ and $X_4$ is independently C or N, provided that at least one of $X_1$, $X_2$, $X_3$ and $X_4$ is N, $R_1$ is a saturated or unsaturated 3-12 membered mono- or poly-heterocyclyl containing 1-3 heteroatoms (preferably heteroatoms selected from N, O and S), where $R_1$ is unsubstituted or substituted with 1-3 substituents selected from —$NR_6R_7$, and $R_8$, $R_2$, $R_3$, $R_4$ and $R_5$ may be the same or different; and each of them is independently selected from —H; —$C_1$-$C_6$alkyl; —$C_1$-$C_6$haloalkyl; -halogen (—F, —Cl, —Br, —I); —CN; —$C_1$-$C_6$ alkoxy; —$C_1$-$C_6$haloalkoxy; —$C_2$-$C_7$alkenyl; and —$C_2$-$C_8$alkynyl, provided that when $X_1$ is N, $R_2$ does not exist; when $X_2$ is N, $R_3$ does not exist; when $X_3$ is N, $R_4$ does not exist; and when $X_4$ is N, $R_5$ does not exist, each of $Y_1$, $Y_2$, $Y_3$, $Y_4$ and $Y_5$ is independently selected from C, N and O, provided that at least two of $Y_1$, $Y_2$, $Y_3$, $Y_4$ and $Y_5$ are N or O, each of $Y_2$ and $Y_3$ may be independently substituted with $R_9$, each of $R_6$ and $R_7$ is independently selected from —H and —$C_1$-$C_6$alkyl, $R_8$ is selected from —$C_1$-$C_6$alkyl, and $R_9$ is selected from —H, —$C_1$-$C_6$alkyl and —$C_3$-$C_7$cycloalkyl, wherein each of the alkyl, cycloalkyl, heterocyclyl, alkoxy, alkenyl and alkynyl groups may be independently unsubstituted or substituted with one or more substituents selected from the group consisting of —$C_1$-$C_4$alkyl, —OH and —$C_1$-$C_4$alkoxy, where the heterocyclyl is a saturated or unsaturated 3-6 membered heterocyclyl containing 1-3 heteroatoms (preferably heteroatoms selected from N, O and S).

According to another preferred embodiment of the present invention, in the above formula 1, each of $X_1$, $X_2$, $X_3$ and $X_4$ is independently C or N, provided that at least one of $X_1$, $X_2$, $X_3$ and $X_4$ is N, $R_1$ is a saturated or unsaturated 3-6 membered heterocyclyl containing 1-3 heteroatoms (preferably heteroatoms selected from N, O and S), where $R_1$ is unsubstituted or substituted with —$NR_6R_7$, $R_2$, $R_3$, $R_4$ and $R_5$ may be the same or different; and each of them is independently selected from —H; —$C_1$-$C_6$alkyl; —$C_1$-$C_6$haloalkyl; -halogen (—F, Cl, —Br, —I); —CN; —$C_1$-$C_6$ alkoxy; —$C_1$-$C_6$haloalkoxy; —$C_2$-$C_7$alkenyl; and —$C_2$-$C_8$alkynyl, provided that when $X_1$ is N, $R_2$ does not exist; when $X_2$ is N, $R_3$ does not exist; when $X_3$ is N, $R_4$ does not exist; and when $X_4$ is N, $R_5$ does not exist, each of $Y_1$, $Y_2$, $Y_3$, $Y_4$ and $Y_5$ is independently selected from C, N and O, provided that at least two of $Y_1$, $Y_2$, $Y_3$, $Y_4$ and $Y_5$ are N, each of $Y_2$ and $Y_3$ may be independently substituted with $R_9$, each of $R_6$ and $R_7$ is independently selected from —H and —$C_1$-$C_6$alkyl, and $R_9$ is selected from —H, —$C_1$-$C_6$alkyl and —$C_3$-$C_7$cycloalkyl, wherein each of the alkyl, cycloalkyl, heterocyclyl, alkoxy, alkenyl and alkynyl groups may be independently unsubstituted or substituted with one or more substituents selected from the group consisting of —$C_1$-$C_4$alkyl, —OH and —$C_1$-$C_4$alkoxy, where the heterocyclyl is a saturated or unsaturated 3-6 membered heterocyclyl containing 1-3 heteroatoms (preferably heteroatoms selected from N, O and S).

According to another preferred embodiment of the present invention, in the above formula 1, each of $X_1$, $X_2$, $X_3$ and $X_4$ is independently C or N, provided that at least one of $X_1$, $X_2$, $X_3$ and $X_4$ is N, $R_1$ is a saturated or unsaturated 3-6 membered heterocyclyl containing 1-3 heteroatoms (preferably heteroatoms selected from N, O and S), where $R_1$ is unsubstituted or substituted with —$NR_6R_7$, $R_2$, $R_3$, $R_4$ and $R_5$ may be the same or different; and each of them is independently selected from —H; —$C_1$-$C_6$alkyl; —$C_1$-$C_6$haloalkyl; and -halogen (—F, —Cl, —Br, —I), provided that when $X_1$ is N, $R_2$ does not exist; when $X_2$ is N, $R_3$ does not exist; when $X_3$ is N, $R_4$ does not exist; and when $X_4$ is N, $R_5$ does not exist, each of $Y_1$, $Y_2$, $Y_3$, $Y_4$ and $Y_5$ is independently selected from C, N and O, provided that at least two of $Y_1$, $Y_2$, $Y_3$, $Y_4$ and $Y_5$ are N, each of $Y_2$ and $Y_3$ may be independently substituted with $R_9$, each of $R_6$ and $R_7$ is independently selected from —H and —$C_1$-$C_6$alkyl, and $R_9$ is selected from —H and —$C_1$-$C_6$alkyl, wherein each of the alkyl and heterocyclyl groups may be independently unsubstituted or substituted with one or more substituents selected from the group consisting of —$C_1$-$C_4$alkyl, —OH and —$C_1$-$C_4$alkoxy, where the heterocyclyl is a saturated or unsaturated 3-6 membered heterocyclyl containing 1-3 heteroatoms (preferably heteroatoms selected from N, O and S.

The compound of the present invention is a human histamine 4 receptor (hH4R) inhibitor and is useful for treating or preventing inflammatory diseases, allergy, pain, nasal polyps, rhinitis, chronic sinusitis, nasal congestion, nasal itch, asthma, chronic obstructive pulmonary disease, rheumatoid arthritis, atopic dermatitis, psoriasis, eczema, pruritus, itchy skin, urticaria, idiopathic chronic urticaria, scleroderma, conjunctivitis, keratoconjunctivitis, ocular inflammation, dry eye, cardiac dysfuction, arrhythmia, atherosclerosis, multiple sclerosis, inflammatory bowel disease (including colitis, Crohn's disease, ulcerative colitis), inflammatory pain, neuropathic pain, osteoarthritic pain, autoimmune thyroid disease, immune-mediated (also known as type I) diabetes, lupus, post-operative adhesions, vestibular disorders and cancer, and especially useful as an agent for treating atopic dermatitis.

Unless mentioned otherwise, alkyl substituent as described herein and alkyl residue in other substituents (for example, alkoxy) as described herein may be linear or branched. Also, halogen includes fluorine (F), chlorine (Cl), bromine (Br) and iodine (I).

As representative examples of the compound of formula 1 according to the present invention, the following compounds may be mentioned:

3-Methyl-6-(4-methylpiperazin-1-yl)pyrido[3,2-e][1,2,4]triazolo[4,3-a]pyrazine (compound 1);
8-Methyl-4-(4-methylpiperazin-1-yl)pyrido[2,3-e][1,2,4]triazolo[4,3-a]pyrazine (compound 2);
4-(4-Methylpiperazin-1-yl)pyrido[2,3-e][1,2,4]triazolo[4,3-a]pyrazine (compound 3);
8-Chloro-4-(4-methylpiperazin-1-yl)pyrido[2,3-e][1,2,4]triazolo[4,3-a]pyrazine (compound 4);
3-Chloro-6-(4-methylpiperazin-1-yl)pyrido[3,2-e][1,2,4]triazolo[4,3-a]pyrazine (compound 5);
6-(4-Methylpiperazin-1-yl)pyrido[3,2-e][1,2,4]triazolo[4,3-a]pyrazine (compound 6);
8-Chloro-4-(piperazin-1-yl)pyrido[2,3-e][1,2,4]triazolo[4,3-a]pyrazine (compound 7);
1-(8-Chloropyrido[2,3-e][1,2,4]triazolo[4,3-a]pyrazin-4-yl)azetidin-3-amine (compound 8);
(R)-1-(8-chloropyrido[2,3-e][1,2,4]triazolo[4,3-a]pyrazin-4-yl)-N,N-dimethylpyrrolidin-3-amine (compound 9);
(R)-1-(8-chloropyrido[2,3-e][1,2,4]triazolo[4,3-a]pyrazin-4-yl)-N-methylpyrrolidin-3-amine (compound 10);
(R)-1-(3-chloropyrido[3,2-e][1,2,4]triazolo[4,3-a]pyrazin-6-yl)-N-methylpyrrolidin-3-amine (compound 11);
8-Bromo-4-(4-methylpiperazin-1-yl)pyrido[2,3-e][1,2,4]triazolo[4,3-a]pyrazine (compound 12);
4-(4-Methylpiperazin-1-yl)pyrido[2,3-e][1,2,4]triazolo[4,3-a]pyrazin-8-carbonitrile (compound 13);
8-Chloro-1-methyl-4-(4-methylpiperazin-1-yl)pyrido[2,3-e][1,2,4]triazolo[4,3-a]pyrazine (compound 14);
8-Chloro-1-methyl-4-(piperazin-1-yl)pyrido[2,3-e][1,2,4]triazolo[4,3-a]pyrazine (compound 15);
8-Bromo-4-(piperazin-1-yl)pyrido[2,3-e][1,2,4]triazolo[4,3-a]pyrazine (compound 16);
7,8-Dichloro-4-(4-methylpiperazin-1-yl)pyrido[2,3-e][1,2,4]triazolo[4,3-a]pyrazine (compound 17);
1-(8-Chloropyrido[2,3-e][1,2,4]triazolo[4,3-a]pyrazin-4-yl)-N-methylazetidin-3-amine (compound 18);
(S)-8-chloro-4-(3-methylpiperazin-1-yl)pyrido[2,3-e][1,2,4]triazolo[4,3-a]pyrazine (compound 19);
(S)-8-chloro-4-(3,4-dimethylpiperazin-1-yl)pyrido[2,3-e][1,2,4]triazolo[4,3-a]pyrazine (compound 20);
8-Chloro-4-(4-methylpiperazin-1-yl)pyrido[2,3-e][1,2,4]triazolo[4,3-a]pyrazin-7-carbonitrile (compound 21);
8-Chloro-4-(3,4,5-trimethylpiperazin-1-yl)pyrido[2,3-e][1,2,4]triazolo[4,3-a]pyrazine (compound 22);
8-Chloro-7-ethoxy-4-(4-methylpiperazin-1-yl)pyrido[2,3-e][1,2,4]triazolo[4,3-a]pyrazine (compound 23);
1-(8-Bromopyrido[2,3-e][1,2,4]triazolo[4,3-a]pyrazin-4-yl)-N-methylazetidin-3-amine (compound 24);
4-(3-(Methylamino)azetidin-1-yl)pyrido[2,3-e][1,2,4]triazolo[4,3-a]pyrazin-8-carbonitrile (compound 25);
4-(piperazin-1-yl)pyrido[2,3-e][1,2,4]triazolo[4,3-a]pyrazin-8-carbonitrile (compound 26);
1-(7,8-Dichloropyrido[2,3-e][1,2,4]triazolo[4,3-a]pyrazin-4-yl)-N-methylazetidin-3-amine (compound 27);
8-Chloro-4-(3-(methylamino)azetidin-1-yl)pyrido[2,3-e][1,2,4]triazolo[4,3-a]pyrazin-7-carbonitrile (compound 28);
8-Chloro-4-(hexahydropyrrolo[1,2-a]pyrazin-2(1H)-yl)pyrido[2,3-e][1,2,4]triazolo[4,3-a]pyrazine (compound 29);
(R)-1-(8-chloropyrido[2,3-e][1,2,4]triazolo[4,3-a]pyrazin-4-yl)pyrrolidin-3-amine (compound 30);
9-Chloro-2-methyl-5-(4-methylpiperazin-1-yl)pyrido[3,2-e][1,2,4]triazolo[1,5-c]pyrimidine (compound 31);
9-Chloro-2-methyl-5-(piperazin-1-yl)pyrido[3,2-e][1,2,4]triazolo[1,5-c]pyrimidine (compound 32);
1-(9-Chloro-2-methylpyrido[3,2-e][1,2,4]triazolo[1,5-c]pyrimidin-5-yl)-N-methylazetidin-3-amine (compound 33);
9-Chloro-2-cyclopropyl-N,N-diethylpyrido[3,2-e][1,2,4]triazolo[1,5-c]pyrimidin-5-amine (compound 34);
9-Chloro-5-(4-methylpiperazin-1-yl)pyrido[3,2-e][1,2,4]triazolo[1,5-c]pyrimidine (compound 35);
1-(9-Chloropyrido[3,2-e][1,2,4]triazolo[1,5-c]pyrimidin-5-yl)-N-methylazetidin-3-amine (compound 36);
9-Chloro-5-(piperazin-1-yl)pyrido[3,2-e][1,2,4]triazolo[1,5-c]pyrimidine (compound 37);
9-Chloro-2-cyclopropyl-5-(4-methylpiperazin-1-yl)pyrido[3,2-e][1,2,4]triazolo[1,5-c]pyrimidine (compound 38);
9-Chloro-2-cyclopropyl-5-(piperazin-1-yl)pyrido[3,2-e][1,2,4]triazolo[1,5-c]pyrimidine (compound 39);
9-Chloro-2-(methoxymethyl)-5-(4-methylpiperazin-1-yl)pyrido[3,2-e][1,2,4]triazolo[1,5-c]pyrimidine (compound 40);
9-Chloro-2-ethyl-5-(4-methylpiperazin-1-yl)pyrido[3,2-e][1,2,4]triazolo[1,5-c]pyrimidine (compound 41);
9-Chloro-5-(4-methylpiperazin-1-yl)pyrido[3,2-e][1,2,4]triazolo[4,3-c]pyrimidine (compound 42);
8-Chloro-2-methyl-4-(4-methylpiperazin-1-yl)-2H-pyrazolo[3,4-c][1,8]naphthylidine (compound 43);
1-(8-Chloro-2-methyl-2H-pyrazolo[3,4-c][1,8]naphthylidin-4-yl)-N-methylazetidin-3-amine (compound 44);
8-Chloro-2-methyl-4-(piperazin-1-yl)-2H-pyrazolo[3,4-c][1,8]naphthylidine (compound 45);
8-Chloro-4-(4-methylpiperazin-1-yl)imidazo[1,2-a]pyrido[2,3-e]pyrazine (compound 46);
8-Chloro-4-(piperazin-1-yl)imidazo[1,2-a]pyrido[2,3-e]pyrazine (compound 47).
1-(8-Iodopyrido[2,3-e][1,2,4]triazolo[4,3-a]pyrazin-4-yl)-N-methylazetidin-3-amine (compound 48);
8-Iodo-4-(4-methylpiperazin-1-yl)pyrido[2,3-e][1,2,4]triazolo[4,3-a]pyrazine (compound 49);
N-Methyl-1-(8-methylpyrido[2,3-e][1,2,4]triazolo[4,3-a]pyrazin-4-yl)azetidin-3-amine (compound 50);
1-(8-(Difluoromethyl)pyrido[2,3-e][1,2,4]triazolo[4,3-a]pyrazin-4-yl)-N-methylazetidin-3-amine (compound 51);
N-Methyl-1-(8-(trifluoromethyl)pyrido[2,3-e][1,2,4]triazolo[4,3-a]pyrazin-4-yl)azetidin-3-amine (compound 52);
4-(4-Methylpiperazin-1-yl)-8-(trifluoromethyl)pyrido[2,3-e][1,2,4]triazolo[4,3-a]pyrazine (compound 53);

1-(8-Ethynylpyrido[2,3-e][1,2,4]triazolo[4,3-a]pyrazin-4-yl)-N-methylazetidin-3-amine (compound 54);
N-Methyl-1-(8-vinylpyrido[2,3-e][1,2,4]triazolo[4,3-a]pyrazin-4-yl)azetidin-3-amine (compound 55);
1-(8-Ethylpyrido[2,3-e][1,2,4]triazolo[4,3-a]pyrazin-4-yl)-N-methylazetidin-3-amine (compound 56);
4-(3-(Methylamino)azetidin-1-yl)pyrido[2,3-e][1,2,4]triazolo[4,3-a]pyrazin-8-ol (compound 57);
1-(8-Methoxypyrido[2,3-e][1,2,4]triazolo[4,3-a]pyrazin-4-yl)-N-methylazetidin-3-amine (compound 58);
1-(8-(Difluoromethoxy)pyrido[2,3-e][1,2,4]triazolo[4,3-a]pyrazin-4-yl)-N-methylazetidin-3-amine (compound 59);
8-Chloro-7-methoxy-4-(4-methylpiperazin-1-yl)pyrido[2,3-e][1,2,4]triazolo[4,3-a]pyrazine (compound 60);
8-Chloro-7-methoxy-4-(piperazin-1-yl)pyrido[2,3-e][1,2,4]triazolo[4,3-a]pyrazine (compound 61);
7,8-Dichloro-4-(piperazin-1-yl)pyrido[2,3-e][1,2,4]triazolo[4,3-a]pyrazine (compound 62);
8-Chloro-7-ethoxy-4-(piperazin-1-yl)pyrido[2,3-e][1,2,4]triazolo[4,3-a]pyrazine (compound 63);
8-Chloro-4-(4-methylpiperazin-1-yl)-7-(2,2,2-trifluoroethoxy)pyrido[2,3-e][1,2,4]triazolo[4,3-a]pyrazine (compound 64);
1-(8-Bromo-9-methylpyrido[2,3-e][1,2,4]triazolo[4,3-a]pyrazin-4-yl)-N-methylazetidin-3-amine (compound 65);
8-Bromo-9-methyl-4-(4-methylpiperazin-1-yl)pyrido[2,3-e][1,2,4]triazolo[4,3-a]pyrazine (compound 66);
1-(8,9-Dichloropyrido[2,3-e][1,2,4]triazolo[4,3-a]pyrazin-4-yl)-N-methylazetidin-3-amine (compound 67);
1-(8-Bromopyrido[2,3-e][1,2,4]triazolo[4,3-a]pyrazin-4-yl)-N-methylazetidin-3-amine hydrochloride (compound 68);
1-(8-Bromopyrido[2,3-e]tetrazolo[1,5-a]pyrazin-4-yl)-N-methylazetidin-3-amine hydrochloride (compound 69);
8-Chloro-4-(5-methylhexahydropyrrolo[3,4-c]pyrrole-2(1H)-yl)pyrido[2,3-e][1,2,4]triazolo[4,3-a]pyrazine (compound 70);
8-Bromo-4-(5-methylhexahydropyrrolo[3,4-c]pyrrole-2(1H)-yl)pyrido[2,3-e][1,2,4]triazolo[4,3-a]pyrazine (compound 71);
1-(8-Bromopyrido[2,3-e][1,2,4]triazolo[4,3-a]pyrazin-4-yl)-3-methylazetidin-3-amine (compound 72);
1-(8-Bromopyrido[2,3-e][1,2,4]triazolo[4,3-a]pyrazin-4-yl)-N,3-dimethylazetidin-3-amine (compound 73);
8-Bromo-4-(hexahydropyrrolo[1,2-a]pyrazin-2(1H)-yl)pyrido[2,3-e][1,2,4]triazolo[4,3-a]pyrazine (compound 74);
4-(Hexahydropyrrolo[1,2-a]pyrazin-2(1H)-yl)-8-iodopyrido[2,3-e][1,2,4]triazolo[4,3-a]pyrazine (compound 75);
8-Chloro-4-(4-cyclopropylpiperazin-1-yl)pyrido[2,3-e][1,2,4]triazolo[4,3-a]pyrazine (compound 76);
4-((1S,4S)-2,5-diazabicyclo[2.2.1]heptan-2-yl)-8-chloropyrido[2,3-e][1,2,4]triazolo[4,3-a]pyrazine (compound 77);
8-Chloro-4-((1S,4S)-5-methyl-2,5-diazabicyclo[2.2.1]heptan-2-yl)pyrido[2,3-e][1,2,4]triazolo[4,3-a]pyrazine (compound 78);
8-Chloro-4-(1,4-diazepan-1-yl)pyrido[2,3-e][1,2,4]triazolo[4,3-a]pyrazine (compound 79);
8-Chloro-4-(4-methyl-1,4-diazepan-1-yl)pyrido[2,3-e][1,2,4]triazolo[4,3-a]pyrazine (compound 80);
(R)-1-(8-bromopyrido[2,3-e][1,2,4]triazolo[4,3-a]pyrazin-4-yl)-N-methylpyrrolidin-3-amine (compound 81);
8-Chloro-4-(hexahydro-1H-pyrrolo[3,4-b]pyridin-6(2H)-yl)pyrido[2,3-e][1,2,4]triazolo[4,3-a]pyrazine (compound 82);
8-Chloro-4-(1-methylhexahydro-1H-pyrrolo[3,4-b]pyridin-6(2H)-yl)pyrido[2,3-e][1,2,4]triazolo[4,3-a]pyrazine (compound 83);
1-(8-Chloropyrido[2,3-e][1,2,4]triazolo[4,3-a]pyrazin-4-yl)-N,N-dimethylazetidin-3-amine (compound 84);
1-(8-Bromopyrido[2,3-e][1,2,4]triazolo[4,3-a]pyrazin-4-yl)-N,N-dimethylazetidin-3-amine (compound 85);
(1-(8-Bromopyrido[2,3-e][1,2,4]triazolo[4,3-a]pyrazin-4-yl)azetidin-3-yl)(methyl)carbamic acid (compound 86);
2-((8-Chloropyrido[2,3-e][1,2,4]triazolo[4,3-a]pyrazin-4-yl)amino)ethanol (compound 87);
1-(8-Chloroimidazo[1,2-a]pyrido[2,3-e]pyrazin-4-yl)-N-methylazetidin-3-amine (compound 88);
1-(8-Bromoimidazo[1,2-a]pyrido[2,3-e]pyrazin-4-yl)-N-methylazetidin-3-amine (compound 89);
tert-Butyl (1-(8-chloro-2-methyloxazolo[4,5-c][1,8]naphthylidine-4-yl)azetidin-3-yl)(methyl)carbamate (compound 90);
1-(8-Chloro-2-methyloxazolo[4,5-c][1,8]naphthylidine-4-yl)-N-methylazetidin-3-amine (compound 91);
8-Chloro-2-methyl-4-(4-methylpiperazin-1-yl)oxazolo[4,5-c][1,8]naphthylidine (compound 92);
1-(8-Chloropyrido[2,3-e]tetrazolo[1,5-a]pyrazin-4-yl)-N-methylazetidin-3-amine (compound 93);
8-Chloro-4-(4-methylpiperazin-1-yl)pyrido[2,3-e]tetrazolo[1,5-a]pyrazine (compound 94);
1-(8-Bromopyrido[2,3-e]tetrazolo[1,5-a]pyrazin-4-yl)-N-methylazetidin-3-amine (compound 95);
8-Bromo-4-(4-methylpiperazin-1-yl)pyrido[2,3-e]tetrazolo[1,5-a]pyrazine (compound 96);
1-(8-Chloro-2-methylpyrido[2,3-e][1,2,4]triazolo[1,5-a]pyrazin-4-yl)-N-methylazetidin-3-amine (compound 97);
8-Chloro-2-methyl-4-(4-methylpiperazin-1-yl)pyrido[2,3-e][1,2,4]triazolo[1,5-a]pyrazine (compound 98);
1-(8-bromo-7-methylpyrido[2,3-e][1,2,4]triazolo[4,3-a]pyrazin-4-yl)-N-methylazetidin-3-amine (compound 99);
8-bromo-7-methyl-4-(4-methylpiperazin-1-yl)pyrido[2,3-e][1,2,4]triazolo[4,3-a]pyrazine (compound 100);
8-chloro-4-(3-(methylamino)azetidin-1-yl)pyrido[2,3-e][1,2,4]triazolo[4,3-a]pyrazin-7-ol HCl salt (compound 101);
N-(1-(8-bromopyrido[2,3-e][1,2,4]triazolo[4,3-a]pyrazin-4-yl)azetidin-3-yl)-N-methylhydroxylamine (compound 102);
1-(2-bromopyrido[3,2-e]pyrrolo[1,2-c]pyrimidin-6-yl)-N-methylazetidin-3-amine (compound 103);
1-(8-bromopyrido[2,3-e][1,2,4]triazolo[4,3-a]pyrazin-4-yl)-N-methylazetidin-3-amine 2,2,2-trifluoroacetate (compound 104);
(S)-1-(8-bromo-2-methyl-1,2-dihydroimidazo[1,2-a]pyrido[2,3-e]pyrazin-4-yl)-N-methylazetidin-3-amine (compound 105);
(R)-1-(8-bromo-2-methyl-1,2-dihydroimidazo[1,2-a]pyrido[2,3-e]pyrazin-4-yl)-N-methylazetidin-3-amine (compound 106);
1-(8-bromo-1,2-dihydroimidazo[1,2-a]pyrido[2,3-e]pyrazin-4-yl)-N-methylazetidin-3-amine (compound 107);
1-(8-bromo-2-methylimidazo[1,2-a]pyrido[2,3-e]pyrazin-4-yl)-N-methylazetidin-3-amine (compound 108);
1-(9-bromo-2-methylpyrazolo[1,5-c]pyrido[3,2-e]pyrimidin-5-yl)-N-methylazetidin-3-amine (compound 109);
1-(9-bromopyrazolo[1,5-c]pyrido[3,2-e]pyrimidin-5-yl)-N-methylazetidin-3-amine (compound 110);
N-methyl-1-(8-nitropyrido[2,3-e][1,2,4]triazolo[4,3-a]pyrazin-4-yl)azetidin-3-amine (compound 111);
4-(3-(methylamino)azetidin-1-yl)pyrido[2,3-e][1,2,4]triazolo[4,3-a]pyrazin-8-amine (compound 112);
N-methyl-1-(8-phenylpyrido[2,3-e][1,2,4]triazolo[4,3-a]pyrazin-4-yl)azetidin-3-amine (compound 113);
1-(8-(furan-2-yl)pyrido[2,3-e][1,2,4]triazolo[4,3-a]pyrazin-4-yl)-N-methylazetidin-3-amine (compound 114);
1-(2-bromopyrido[2,3-e]pyrrolo[1,2-a]pyrazin-6-yl)-N-methylazetidin-3-amine (compound 115);

1-(2-chloropyrido[3,2-e][1,2,4]triazolo[4,3-a]pyrazin-6-yl)-N-methylazetidin-3-amine (compound 116);
1-(8-chloropyrido[3,4-e][1,2,4]triazolo[4,3-a]pyrazin-4-yl)-N-methylazetidin-3-amine (compound 117);
1-(8-bromopyrido[2,3-e][1,2,4]triazolo[4,3-a]pyrazin-4-yl)-N-methylazetidin-3-amine methanesulfonic acid salt (compound 118);
1-(8-bromopyrido[2,3-e][1,2,4]triazolo[4,3-a]pyrazin-4-yl)-N-methylazetidin-3-amine maleic acid salt (compound 119);
1-(8-bromopyrido[2,3-e][1,2,4]triazolo[4,3-a]pyrazin-4-yl)-N-methylazetidin-3-amine 2-hydroxypropane-1,2,3-tricarboxylic acid salt (compound 120);
1-(8-bromopyrido[2,3-e][1,2,4]triazolo[4,3-a]pyrazin-4-yl)-N-methylazetidin-3-amine nitric acid salt (compound 121);
1-(8-bromopyrido[2,3-e][1,2,4]triazolo[4,3-a]pyrazin-4-yl)-N-methylazetidin-3-amine hydroiodic acid salt (compound 122);
1-(8-bromopyrido[2,3-e][1,2,4]triazolo[4,3-a]pyrazin-4-yl)-N-methylazetidin-3-amine phosphoric acid salt (compound 123);
1-(8-bromopyrido[2,3-e][1,2,4]triazolo[4,3-a]pyrazin-4-yl)-N-methylazetidin-3-amine 4,4'-methylenebis(3-hydroxy-2-naphthoic acid) salt (compound 124);
1-(8-bromopyrido[2,3-e][1,2,4]triazolo[4,3-a]pyrazin-4-yl)-N-methylazetidin-3-amine hydrobromic acid salt (compound 125);
1-(8-bromopyrido[2,3-e][1,2,4]triazolo[4,3-a]pyrazin-4-yl)-N-methylazetidin-3-amine sulfuric acid salt (compound 126);
1-(8-bromopyrido[2,3-e][1,2,4]triazolo[4,3-a]pyrazin-4-yl)-N-methylazetidin-3-amine (2R,3R)-2,3-dihydroxysuccinic acid salt (compound 127);
1-(8-bromopyrido[2,3-e][1,2,4]triazolo[4,3-a]pyrazin-4-yl)-N-methylazetidin-3-amine (1S)-(+)-10-Camphorsulfonic acid salt (compound 128);
8-bromo-N-(1-methylpyrrolidin-3-yl)pyrido[2,3-e][1,2,4]triazolo[4,3-a]pyrazin-4-amine (compound 129);
1-(8-bromopyrido[2,3-e][1,2,4]triazolo[4,3-a]pyrazin-4-yl)-N-methylazetidin-3-amine(S)-2-hydroxypropanoic acid salt (compound 130);
N-(azetidin-3-ylmethyl)-8-bromopyrido[2,3-e][1,2,4]triazolo[4,3-a]pyrazin-4-amine trifluoroacetic acid salt (compound 131); and
4-(azetidin-3-ylmethoxy)-8-bromopyrido[2,3-e][1,2,4]triazolo[4,3-a]pyrazine hydrochloric acid salt (compound 132).

The above-listed names of the compounds are described in accordance with the nomenclature method provided by ChemBioDraw Ultra software (Version 12.02.1076) of CambridgeSoft.

In case of the compound of formula 1 according to the present invention being a racemate, the racemate may be separated into its respective isomers by using a conventional separation method, for example, such as a general column chromatography packed with normal-phase silica gel (Isu Chemical Co., particle diameter: 0.040~0.063 mm and 0.063~0.200 mm), a general column chromatography packed with amine silica gel (Isu Chemical Co., particle diameter: 0.040~0.075 mm), or a pressurized fractionating column chromatography packed in reverse phase (Yamazen, W-Prep 2XY), and employing the corresponding solvent, preferably a solvent mixture of hexane, ethyl acetate, dichloromethane and methanol in normal-phase and a solvent mixture of water and acetonitrile in reverse-phase.

The compound of formula 1 according to the present invention may also form a pharmaceutically acceptable salt. Representative acids useful in preparing such a pharmaceutically acceptable salt (for example, acid addition salts) include, but not limited to, hydrochloric acid, sulfuric acid, nitric acid, phosphoric acid, hydrobromic acid, hydroiodic acid, formic acid, citric acid, acetic acid, trichloroacetic acid or trifluoroacetic acid, benzoic acid, fumaric acid, maleic acid, methane sulfonic acid, benzene sulfonic acid, p-toluene sulfonic acid, 2,2-dichloroacetic acid, acylated amino acids, adipic acid, alginic acid, ascorbic acid, L-aspartic acid, 4-acetamidobenzoic acid, (+)-camphoric acid, camphorsulfonic acid, (+)-(1S)-camphorsulfonic acid, capric acid, caproic acid, caprylic acid, cinnamic acid, cyclamic acid, dodecyl sulfuric acid, ethane-1,2-disulfonic acid, ethanesulfonic acid, 2-hydroxyethanesulfonic acid, galactaric acid, gentisic acid, glucoheptanoic acid, D-gluconic acid, D-glucuronic acid, L-glutamic acid, α-oxo-glutaric acid, glycolic acid, hippuric acid, (+)-L-lactic acid, (±)-DL-lactic acid, lactobionic acid, (−)-L-malic acid, malonic acid, (±)-DL-mandelic acid, methane sulfonic acid, naphthalene-2-sulfonic acid, naphthalene-1,5-disulfonic acid, 1-hydroxy-2-naphthoic acid, nicotinic acid, oleic acid, orotic acid, oxalic acid, palmitic acid, pamoic acid, L-pyroglutamic acid, salicylic acid, 4-amino-salicylic acid, sebacic acid, stearic acid, succinic acid, tannic acid, (+)-L-tartaric acid, thiocyanic acid, undecylenic acid and the like. In addition, other acid salts that are known and used in the art of amine derivatives may be included. They may be prepared by conventionally known processes.

The compound of formula 1 as defined above according to the present invention may be prepared by, but not limited to, the methods described in the following embodiments.

The heterocyclic compound having a structure of formula 1, or a racemate, isomer or pharmaceutically acceptable salt thereof may be prepared by a method comprising the steps of:

(a) preparing a compound of formula 3 via arylation of a compound of formula 4 with a compound of formula $R_1$—H (except that $R_1$ is —H);

(b) preparing a compound of formula 2 via arylation of the prepared compound of formula 3; and (c) cyclizing the prepared compound of formula 2 (or, a step of deprotecting $R_1$ may be comprised):

[Formula 2]

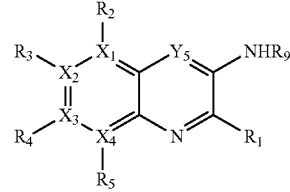

[Formula 3]

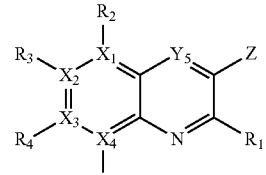

[Formula 4]

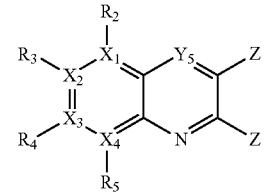

wherein, in formulas 2 to 4, $X_1$, $X_2$, $X_3$, $X_4$, $R_1$, $R_2$, $R_3$, $R_4$, $R_5$, $R_9$ and $Y_5$ are the same as defined in formula 1; and Z represents a reactive leaving group such as halogen (—F, —Cl, —Br).

The heterocyclic compound having a structure of formula 5 which is formula 1 as defined above wherein $Y_1$, $Y_2$ and $Y_4$ are N, or a racemate, isomer or pharmaceutically acceptable salt thereof may be prepared by a method comprising the steps of:

(a) preparing a compound of formula 9 via halogenation of a compound of formula 10;

(b) preparing a compound of formula 8 via cyanation of the prepared compound of formula 9;

(c) preparing a compound of formula 7 via acylation of the prepared compound of formula 8;

(d) preparing a compound of formula 6 via cyclization of the prepared compound of formula 7 followed by halogenation; and (e) conducting arylation of the prepared compound of formula 6 with a compound of formula $R_1$—H (except that $R_1$ is —H) (or, a step of deprotecting $R_1$ may be comprised):

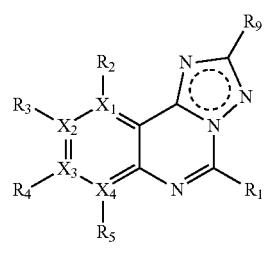

[Formula 5]

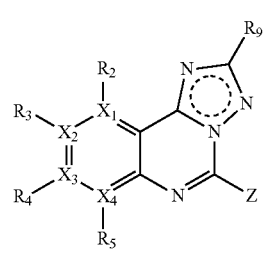

[Formula 6]

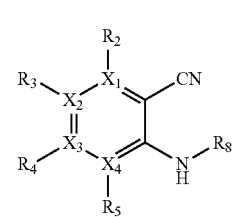

[Formula 7]

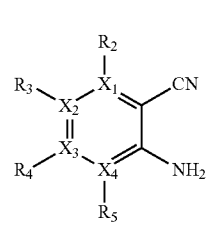

[Formula 8]

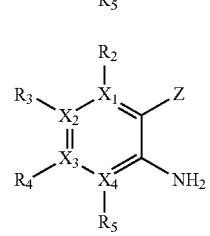

[Formula 9]

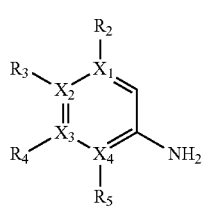

[Formula 10]

wherein, in formulas 5 to 10, $X_1$, $X_2$, $X_3$, $X_4$, $R_1$, $R_2$, $R_3$, $R_4$, $R_5$, $R_8$ and $R_9$ are the same as defined in formula 1; and Z represents a reactive leaving group such as halogen (—F, —Cl, —Br), methanesulfonate, triflate, and tosylate.

The heterocyclic compound having a structure of formula 11 which is formula 1 as defined above wherein $Y_2$, $Y_4$ and $Y_5$ are N, or a racemate, isomer or pharmaceutically acceptable salt thereof may be prepared by a method comprising the steps of:

(a) preparing a compound of formula 16 via arylation of a compound of formula 17;

(b) preparing a compound of formula 15 via imidation of the prepared compound of formula 16;

(c) preparing a compound of formula 14 via acylation of the prepared compound of formula 15;

(d) preparing a compound of formula 13 via cyclization of the prepared compound of formula 14;

(e) preparing a compound of formula 12 via reduction of the prepared compound of formula 13 followed by halogenation; and (f) conducting arylation of the prepared compound of formula 12 with a compound of formula $R_1$—H (except that $R_1$ is —H) (or, a step of deprotecting $R_1$ may be comprised):

[Formula 11]

[Formula 12]

[Formula 13]

[Formula 14]

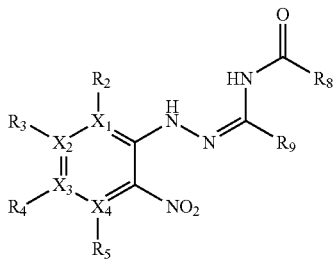

[Formula 15]

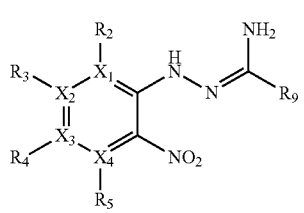

[Formula 16]

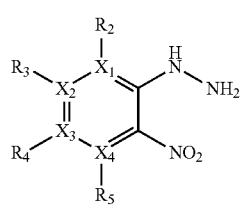

[Formula 17]

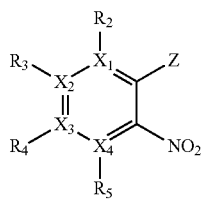

wherein, in formulas 11 to 17, $X_1$, $X_2$, $X_3$, $X_4$, $R_1$, $R_2$, $R_3$, $R_4$, $R_5$, $R_8$ and $R_9$ are the same as defined in formula 1; and Z represents a reactive leaving group such as halogen (—F, —Cl, —Br).

The heterocyclic compound having a structure of formula 18 which is formula 1 as defined above wherein $Y_2$ and $Y_3$ are N, or a racemate, isomer or pharmaceutically acceptable salt thereof may be prepared by a method comprising the steps of:

(a) preparing a compound of formula 21 via Friedel-Craft reaction of a compound of formula 23 with a compound of formula 22;

(b) preparing a compound of formula 20 via cyclization of the prepared compound of formula 21;

(c) preparing a compound of formula 19 via halogenation of the prepared compound of formula 20; and (d) conducting arylation of the prepared compound of formula 19 with a compound of formula $R_1$—H (except that $R_1$ is —H) (or, a step of deprotecting $R_1$ may be comprised):

[Formula 18]

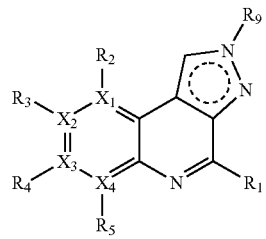

[Formula 19]

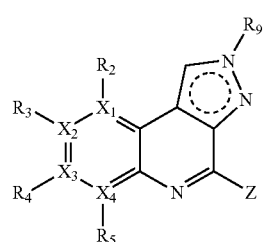

[Formula 20]

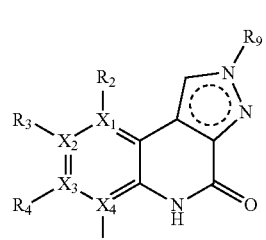

[Formula 21]

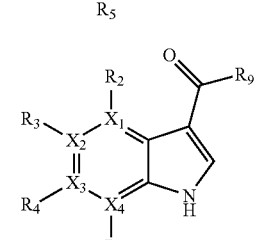

[Formula 22]

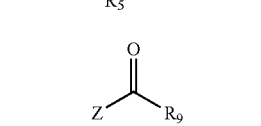

[Formula 23]

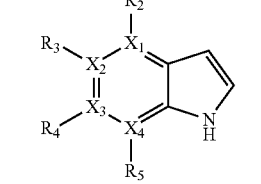

wherein, in formulas 18 to 23, $X_1$, $X_2$, $X_3$, $X_4$, $R_1$, $R_2$, $R_3$, $R_4$, $R_5$ and $R_9$ are the same as defined in formula 1; and Z represents a reactive leaving group such as halogen (—F, —Cl, —Br).

The heterocyclic compound having a structure of formula 24 which is formula 1 as defined above wherein $Y_1$, $Y_3$ and $Y_4$ are N, or a racemate, isomer or pharmaceutically acceptable salt thereof may be prepared by a method comprising the steps of:

(a) preparing a compound of formula 28 via cyclization of a compound of formula 29;

(b) preparing a compound of formula 27 via halogenation of the prepared compound of formula 28 followed by hydroxylation;

(c) preparing a compound of formula 26 via arylation of the prepared compound of formula 27 with a compound of formula R₁—H (except that R₁ is —H) followed by halogenation;

(d) preparing a compound of formula 25 via arylation of the prepared compound of formula 26; and (e) cyclizing the prepared compound of formula 25 (or, a step of deprotecting R₁ may be comprised):

[Formula 24]
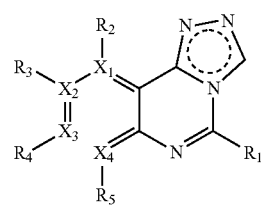

[Formula 25]
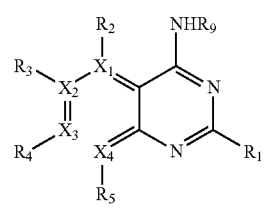

[Formula 26]
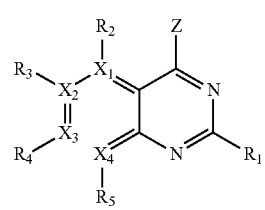

[Formula 27]
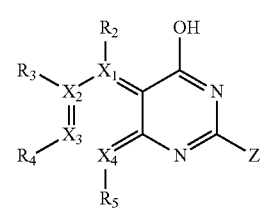

[Formula 28]
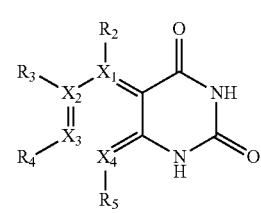

[Formula 29]
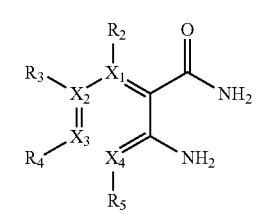

wherein, in formulas 24 to 29, $X_1$, $X_2$, $X_3$, $X_4$, $R_1$, $R_2$, $R_3$, $R_4$, $R_5$ and $R_9$ are the same as defined in formula 1; and Z represents a reactive leaving group such as halogen (—F, —Cl, —Br).

The heterocyclic compound having a structure of formula 30 which is formula 1 as defined above wherein $Y_2$ is N and $Y_4$ is O, or a racemate, isomer or pharmaceutically acceptable salt thereof may be prepared by a method comprising the steps of:

(a) preparing a compound of formula 36 via esterification of a compound of formula 37;

(b) preparing a compound of formula 35 via arylation of the prepared compound of formula 36;

(c) preparing a compound of formula 34 via cyclization of the prepared compound of formula 35;

(d) preparing a compound of formula 33 via enolate addition reaction of the prepared compound of formula 34;

(e) preparing a compound of formula 32 via cyclization of the prepared compound of formula 33;

(f) preparing a compound of formula 31 via halogenation of the prepared compound of formula 32; and (g) conducting arylation of the prepared compound of formula 31 with a compound of formula R₁—H (except that R₁ is —H) (or, a step of deprotecting R₁ may be comprised):

[Formula 30]
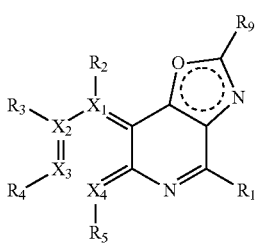

[Formula 31]
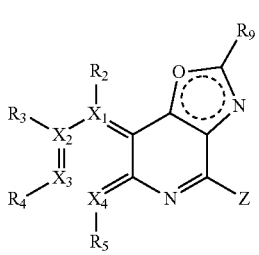

[Formula 32]
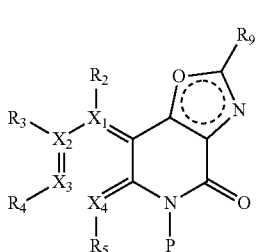

[Formula 33]
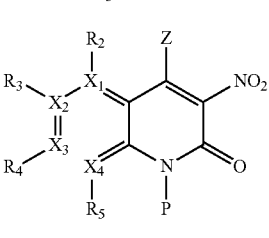

[Formula 34]
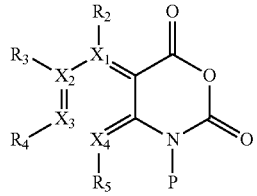

[Formula 35]

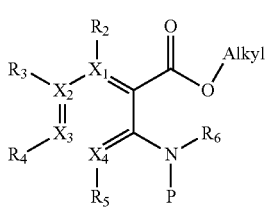

[Formula 36]

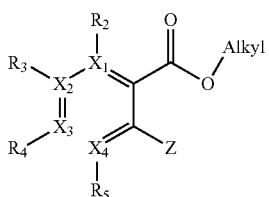

[Formula 37]

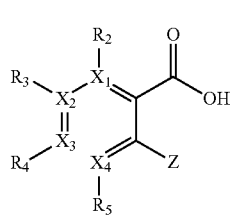

wherein, in formulas 30 to 37, $X_1$, $X_2$, $X_3$, $X_4$, $R_1$, $R_2$, $R_3$, $R_4$, $R_5$, $R_6$ and $R_9$ are the same as defined in formula 1; P represents a protecting group such as paramethoxybenzyl, 3',5'-dimethoxybenzyl, tri-methoxybenzyl; and Z represents a reactive leaving group such as halogen (—F, —Cl, —Br).

The heterocyclic compound having a structure of formula 38 which is formula 1 as defined above wherein $Y_1$ is N and each of $Y_2$ and $Y_3$ is independently C or N, or a racemate, isomer or pharmaceutically acceptable salt thereof may be prepared by a method comprising the steps of:

(a) preparing a compound of formula 40 via the Suzuki coupling reaction of a compound of formula 42 with a compound of formula 41;

(b) preparing a compound of formula 39 via halogenation of the prepared compound of formula 40; and (c) conducting arylation of the prepared compound of formula 39 with a compound of formula $R_1$—H (except that $R_1$ is —H) (or, a step of deprotecting $R_1$ may be comprised):

[Formula 38]

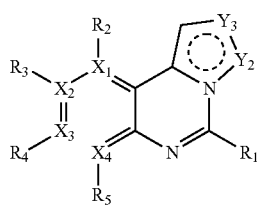

[Formula 39]

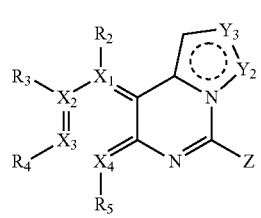

[Formula 40]

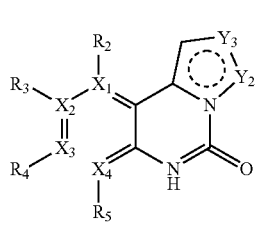

[Formula 41]

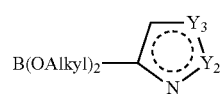

[Formula 42]

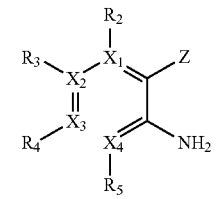

wherein, in formulas 38 to 42, $X_1$, $X_2$, $X_3$, $X_4$, $R_1$, $R_2$, $R_3$, $R_4$ and $R_5$ are the same as defined in formula 1; and Z represents a reactive leaving group such as halogen (—F, —Cl, —Br).

The heterocyclic compound having a structure of formula 43 which is formula 1 as defined above wherein $Y_5$ is N, or a racemate, isomer or pharmaceutically acceptable salt thereof may be prepared by a method comprising the steps of:

(a) preparing a compound of formula 46 via pyrrolation of a compound of formula 47;

(b) preparing a compound of formula 45 via cyclization of the prepared compound of formula 46;

(c) preparing a compound of formula 44 via halogenation of the prepared compound of formula 45; and (d) conducting arylation of the prepared compound of formula 44 with a compound of formula $R_1$—H (except that $R_1$ is —H) (or, a step of deprotecting $R_1$ may be comprised):

[Formula 43]

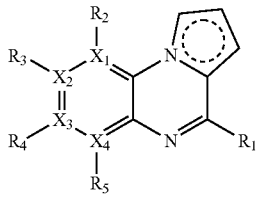

[Formula 44]

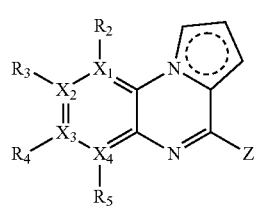

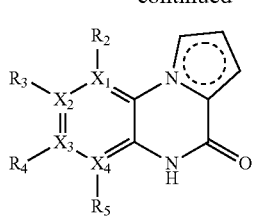
[Formula 45]

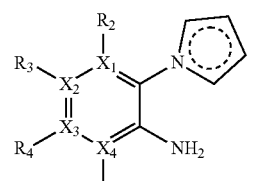
[Formula 46]

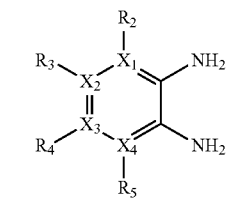
[Formula 47]

wherein, in formulas 43 to 47, $X_1$, $X_2$, $X_3$, $X_4$, $R_1$, $R_2$, $R_3$, $R_4$ and $R_5$ are the same as defined in formula 1; and Z represents a reactive leaving group such as halogen (—F, —Cl, —Br).

The compound of formula 1 according to the present invention has an excellent human histamine 4 receptor (hH4R) inhibitory activity. Therefore, the present invention also provides a pharmaceutical composition comprising an effective amount of a compound of formula 1, or a racemate, isomer or pharmaceutically acceptable salt thereof; and a pharmaceutically acceptable carrier.

A pharmaceutical composition according to the present invention can be prepared by mixing an effective amount of a compound of formula 1, or a racemate, isomer or pharmaceutically acceptable salt thereof, with a pharmaceutically acceptable carrier, binder, stabilizer and/or diluent. In addition, when the pharmaceutical composition according to the present invention is prepared in an injection liquid form, a pharmaceutically acceptable buffer, dissolution adjuvant and/or isotonic agent may be mixed with the compound of formula 1, or a racemate, isomer or pharmaceutically acceptable salt thereof.

Since the pharmaceutical composition according to the present invention shows a strong human histamine 4 receptor (hH4R) inhibitory activity, it is useful for treating or preventing inflammatory diseases, allergy, pain, nasal polyps, rhinitis, chronic sinusitis, nasal congestion, nasal itch, asthma, chronic obstructive pulmonary disease, rheumatoid arthritis, atopic dermatitis, psoriasis, eczema, pruritus, itchy skin, urticaria, idiopathic chronic urticaria, scleroderma, conjunctivitis, keratoconjunctivitis, ocular inflammation, dry eye, cardiac dysfunction, arrhythmia, atherosclerosis, multiple sclerosis, inflammatory bowel disease (including colitis, Crohn's disease, ulcerative colitis), inflammatory pain, neuropathic pain, osteoarthritic pain, autoimmune thyroid disease, immune-mediated (also known as type I) diabetes, lupus, post-operative adhesions, vestibular disorders and cancer.

The pharmaceutical composition according to the prevent invention may be prepared in a delivery form of a pharmaceutical composition comprising one or more dosage units of pharmaceutical agent by using a preparation technique known or available to a skilled artisan, and a suitable pharmaceutical excipient. In a method of the present invention, the composition may be administered via suitable delivery route, for example, such as oral or parenteral, percutaneous, rectal, topical or ocular administration, or by inhalation. The pharmaceutical formulation may be in a form of tablet, capsule, sachet, sugar-coated pill, powder, granule, lozenge, powder for reconstitution, liquid preparation or suppository. For example, the composition may be formulated in a form for intravenous injection, spray, topical or oral administration.

In case of preparing a formulation in oral dosage form, any conventional pharmaceutical carriers may be used. For example, water, glycols, oils, alcohols and the like may be used as a carrier in case of oral liquid formulations such as suspensions, syrups, elixirs and solutions; and starches, sugars, kaolin, lubricants, binders, disintegrating agents and the like may be used as a carrier in case of solid formulations such as powders, pills, capsules and tablets. Because of the easiness of administration, tablets and capsules are the most convenient dose forms, and tablets and pills are preferably prepared as enteric coating formulations.

In case of parenteral formulations, sterilized water is used usually and other ingredient(s) such as a dissolution adjuvant may also be comprised. Injection formulations, for example, sterilized aqueous- or oil-based suspension for injection may be prepared according to known techniques by using appropriate dispersing agent, wetting agent or suspending agent. The solvents useful for this purpose include water, ringer solution and isotonic NaCl solution, and sterilized, immobilized oils are also used as a solvent or a suspending medium conventionally. Any non-irritant immobilized oils including mono- and di-glycerides may be used for this purpose, and fatty acids such as an oleic acid may be used for an injection formulation.

In case of percutaneous formulations, a penetration-enhancing agent and/or a suitable wetting agent may be used as a carrier, optionally in combination with suitable non-irritant additive(s) to the skin. As such additives, those helpful in enhancing the administration through the skin and/or preparing the desired composition may be selected. The percutaneous formulation may be administered in various ways, for example, such as a transdermal patch, a spot-on treatment or an ointment.

The administration time and dosage of the pharmaceutical composition according to the present invention may be suitably determined according to the patient's disease, condition, age, body weight and administration form. In case of adults, the pharmaceutical composition may be administered in an amount of 0.1~2,000 mg, preferably 1~200 mg per day, in a single dose or multiple doses, but not limited thereto.

Since the pharmaceutical composition according to the present invention shows a strong human histamine 4 receptor (hH4R) inhibitory activity, it is useful for treating or preventing inflammatory diseases, allergy, pain, nasal polyps, rhinitis, chronic sinusitis, nasal congestion, nasal itch, asthma, chronic obstructive pulmonary disease, rheumatoid arthritis, atopic dermatitis, psoriasis, eczema, pruritus, itchy skin, urticaria, idiopathic chronic urticaria, scleroderma, conjunctivitis, keratoconjunctivitis, ocular inflammation, dry eye, cardiac dysfunction, arrhythmia, atherosclerosis, multiple sclerosis, inflammatory bowel disease (including colitis, Crohn's disease, ulcerative colitis), inflammatory pain, neuropathic pain, osteoarthritic pain, autoimmune thyroid disease, immune-mediated (also known as type I) diabetes, lupus, post-operative adhesions, vestibular disorders and cancer.

Unless stated otherwise, alkyl moiety and alkyl moiety of other groups (for example, alkoxy group) described in the present invention may be of the linear or branched species. In addition, halogen includes fluorine, chlorine, bromine and iodine.

The compound of formula 1 according to the present invention may be a racemate. The racemate may be separated to its respective isomer by using a conventional separation method—for example, normal column chromatography packed with normal-phase silica gel (Merck, 0.040~0.063 mm and 0.063~0.200 mm), normal column chromatography packed with amine silica gel (chromatorex, 100~200 mesh), or preparative pressure reverse-phase column chromatography (Yonglin, SDV 30 plus), employing the corresponding solvent, preferably a solvent mixture of hexane, ethyl acetate, dichloromethane and methanol in normal phase and a solvent mixture of water and acetonitrile in reverse phase.

The compound of formula 1 according to the present invention may also form a pharmaceutically acceptable salt. Such a pharmaceutically acceptable salt includes acid addition salts derived from acids which form non-toxic addition salts containing pharmaceutically acceptable anions—for example, inorganic acids such as hydrochloric acid, sulfuric acid, nitric acid, phosphoric acid, hydrobromic acid, hydroiodic acid, organic acids such as tartaric acid, formic acid, citric acid, acetic acid, trichloroacetic acid or trifluoroacetic acid, gluconic acid, benzoic acid, lactic acid, fumaric acid, maleic acid, sulfonic acids such as methane sulfonic acid, benzene sulfonic acid, p-toluene sulfonic acid, naphthalene sulfonic acid; and salts of alkali metal such as sodium, potassium, etc. In addition, acid or alkali salts known and used in the art of aromatic amidine derivatives and lactam derivatives may be included. Conventional processes may be used to make the salts.

The compound of formula 1 according to the present invention may be prepared by the following process. Accordingly, the present invention also provides a method for preparing the compound of formula 1.

More specifically, the compound of formula 1 may be prepared by, but not limited to, each of Methods 1 to 8 described in the following.

Method 1

A compound having a structure of the following formula 2, which is formula 1 as defined above wherein $Y_2$ and $Y_5$ are N, may be prepared by a method comprising the steps of: preparing a compound of formula 3 via arylation of a compound of formula 4 with a compound of formula $R_1$—H (except that $R_1$ is —H); preparing a compound of formula 2 via arylation of the prepared compound of formula 3; and cyclizing the prepared compound of formula 2:

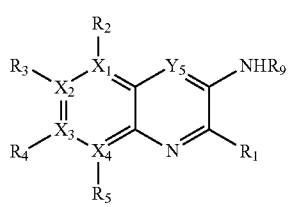

[Formula 2]

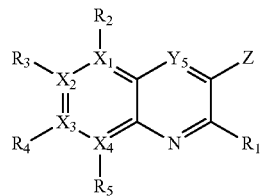

[Formula 3]

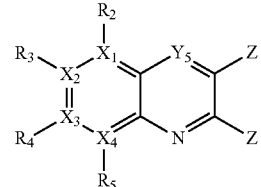

[Formula 4]

wherein, in formulas 2 to 4, $X_1$, $X_2$, $X_3$, $X_4$, $R_1$, $R_2$, $R_3$, $R_4$, $R_5$, $R_6$, $R_7$, $R_8$ and $R_9$ are the same as defined in formula 1; and Z represents a reactive leaving group, preferably a halogen atom (—F, —Cl, —Br).

Method 1 is more specifically described in the following.

Compounds of formulas 2, 3 and 4 used as starting material may be prepared according to the known methods in the art (for example, J. Med. Chem. 1990, 33, 2240-2254, J. Med. Chem. 1997, 40, 2053-2063).

Preparing a compound of formula 3 via arylation of a compound of formula 4 with a compound of formula $R_1$—H (except that $R_1$ is —H) is carried out according to a conventional method in the presence of suitable solvent and base.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is dichloromethane.

The next step for preparing a compound of formula 2 via arylation of the prepared compound of formula 3 is carried out according to a conventional method in the presence of a suitable solvent.

Generally, conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is ethanol.

The next step for preparing a compound of formula 1 via cyclization of the prepared compound of formula 2 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is ethanol.

The cyclization reaction is carried out at 50~200° C. for 0.1 to 24 hours, preferably under the conditions of 80° C. and 1 hour with trimethyl orthoformate or triethyl orthoformate.

The above method for making a compound of formula 2 is more specifically described in the following example.

Method 2

A compound having a structure of the following formula 5, which is formula 1 as defined above wherein $Y_1$, $Y_2$ and $Y_4$ are N, may be prepared by a method comprising the steps of: preparing a compound of formula 9 via halogenation of a compound of the following formula 10; preparing a compound of formula 8 via cyanation of the prepared compound of formula 9; preparing a compound of formula 7 via acylation of the prepared compound of formula 8; preparing a compound of formula 6 via cyclization of the prepared compound of formula 7 followed by halogenation; and conducting arylation of the prepared compound of formula 6 with a compound of formula $R_1$—H (except that $R_1$ is —H):

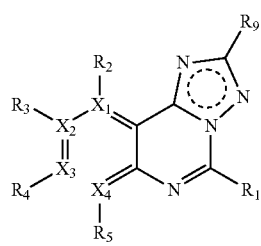

[Formula 5]

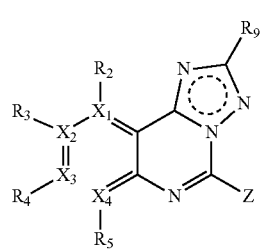

[Formula 6]

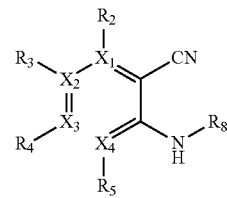

[Formula 7]

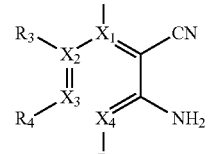

[Formula 8]

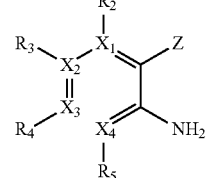

[Formula 9]

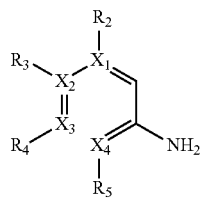

[Formula 10]

wherein, in formulas 5 to 10, $X_1$, $X_2$, $X_3$, $X_4$, $R_1$, $R_2$, $R_3$, $R_4$, $R_5$, $R_6$, $R_7$, $R_8$, and $R_9$ are the same as defined in formula 1; and Z represents a reactive leaving group, preferably a halogen atom (—F, —Cl, —Br), methanesulfonate, triflate and tosylate.

Method 2 is more specifically described in the following.

Compounds of formulas 5, 6, 7, 8, 9 and 10 used as starting material may be prepared according to known methods in the art.

Preparing a compound of formula 9 via halogenation of a compound of formula 10 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is chloroform.

Exemplary halogenating agents for the reaction include bromine, phosphorous trichloride, phosphoryl chloride, phosphorous oxybromide, phenylphosphonyl chloride and phosphorous pentachloride. Preferred is bromine. The reaction may be conducted at, but not limited to, 50 to 200° C. for about 0.1 to 24 hours.

The next step for preparing a compound of formula 8 via cyanation of the prepared compound of formula 9 is carried out according to a conventional method in the presence of suitable solvent and cyanating agent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is N-methylpyrrolidone.

Exemplary cyanating agents for the reaction include KCN, NaCN, $Zn(CN)_2$, CuCN, $(CH_3)_2C(OH)CN$ and TMSCN. Preferred is $Zn(CN)_2$. The reaction may be conducted at, but not limited to, 50 to 200° C. for about 0.1 to 24 hours.

The next step for preparing a compound of formula 7 via acylation of the prepared compound of formula 8 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is 2-butanone.

The next step for preparing a compound of formula 6 via cyclization of the prepared compound of formula 7 followed by halogenation is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is diphenyl ether.

Exemplary halogenating agents for the reaction include phosphorous trichloride, phosphoryl chloride, phosphorous oxybromide, phenylphosphonyl chloride and phosphorous pentachloride. Preferred is phosphoryl chloride. The reaction may be conducted at, but not limited to, 50 to 200° C. for about 0.1 to 24 hours.

The next step for preparing a compound of formula 5 via arylation of the prepared compound of formula 6 with a compound of formula $R_1$—H (except that $R_1$ is —H) is carried out according to a conventional method in the presence of suitable solvent and base.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is N,N-dimethyl formamide.

The above method for making a compound of formula 5 is more specifically described in the following example.

Method 3

A compound having a structure of the following formula 11, which is formula 1 as defined above wherein $Y_2$, $Y_4$ and $Y_5$ are N, may be prepared by a method comprising the steps of: preparing a compound of formula 16 via arylation of a compound of formula 17; preparing a compound of formula 15 via imidation of the prepared compound of formula 16; preparing a compound of formula 14 via acylation of the prepared compound of formula 15; preparing a compound of formula 13 via cyclization of the prepared compound of formula 14; preparing a compound of formula 12 via reduction of the prepared compound of formula 13 followed by halogenation; and conducting arylation of the prepared compound of formula 12 with a compound of formula $R_1$—H (except that $R_1$ is —H):

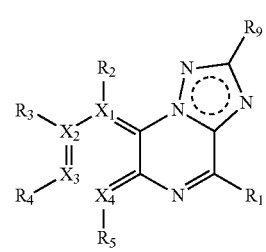

[Formula 11]

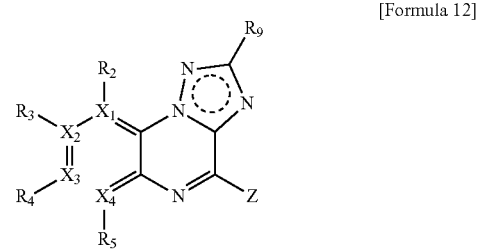

[Formula 12]

-continued

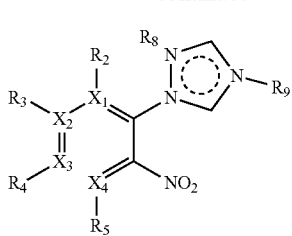

[Formula 13]

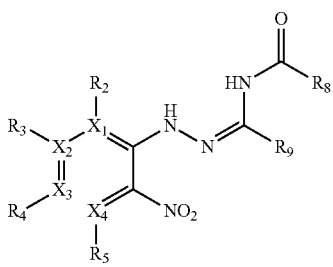

[Formula 14]

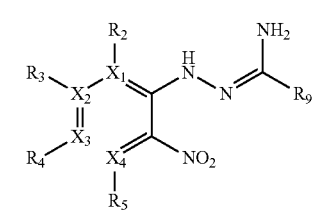

[Formula 15]

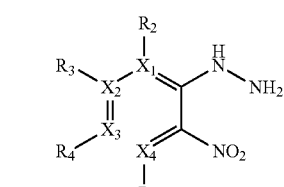

[Formula 16]

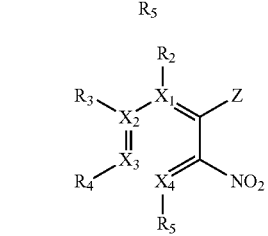

[Formula 17]

wherein, in formulas 11 to 17, $X_1$, $X_2$, $X_3$, $X_4$, $R_1$, $R_2$, $R_3$, $R_4$, $R_5$, $R_6$, $R_7$, $R_8$, and $R_9$ are the same as defined in formula 1; and Z represents a reactive leaving group, preferably a halogen atom (—F, —Cl, —Br).

Method 3 is more specifically described in the following.

Compounds of formulas 11, 12, 13, 14, 15, 16 and 17 used as starting material may be prepared according to the known methods in the art.

Preparing a compound of formula 16 via arylation of a compound of formula 17 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is ethanol.

The next step for preparing a compound of formula 15 via imidation of the prepared compound of formula 16 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is pyridine.

The next step for preparing a compound of formula 14 via acylation of the prepared compound of formula 15 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is diethyl ether.

The next step for preparing a compound of formula 13 via cyclization of the prepared compound of formula 14 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is toluene.

The reaction may be conducted at, but not limited to, 50 to 200° C. for about 0.1 to 24 hours.

The next step for preparing a compound of formula 12 via reduction of the prepared compound of formula 13 followed by halogenation is carried out according to a conventional method in the presence of a suitable solvent, reducing agent and halogenating agent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is acetic acid.

Exemplary reducing agents for the reaction include palladium on carbon catalyst (5% w/w), palladium on carbon catalyst (10% w/w), raney nickel, zinc and iron. Particularly preferred is iron. The reaction may be conducted at, but not limited to, 50 to 200° C. for about 0.1 to 24 hours.

In addition, exemplary halogenating agents for the reaction include phosphorous trichloride, phosphoryl chloride, phosphorous oxybromide, phenylphosphonyl chloride and phosphorous pentachloride. Preferred is phosphoryl chloride. The reaction may be conducted at, but not limited to, 50 to 200° C. for about 0.1 to 24 hours.

The next step for preparing a compound of formula 11 via arylation of the prepared compound of formula 12 with a compound of formula $R_1$—H (except that $R_1$ is —H) is carried out according to a conventional method in the presence of a suitable solvent and base.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is N,N-dimethyl formamide.

The above method for making a compound of formula 11 is more specifically described in the following example.

Method 4

A compound having a structure of the following formula 18, which is formula 1 as defined above wherein $Y_2$ and $Y_3$ are N, may be prepared by a method comprising the steps of: preparing a compound of the following formula 21 via Friedel-Craft reaction of a compound of the following formula 23 with a compound of the following formula 22; preparing a compound of formula 20 via cyclization of the prepared compound of formula 21; preparing a compound of formula 19 via halogenation of the prepared compound of formula 20; and conducting arylation of the prepared compound of formula 19 with a compound of formula $R_1$—H (except that $R_1$ is —H):

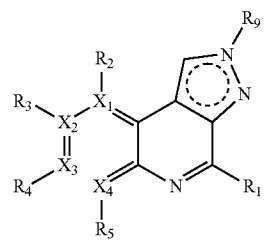

[Formula 18]

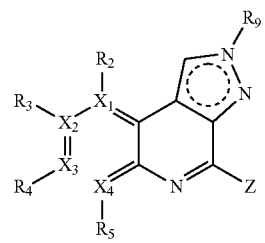

[Formula 19]

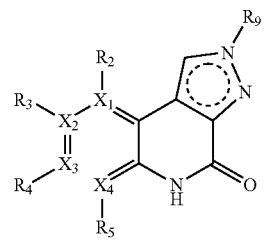

[Formula 20]

[Formula 21]

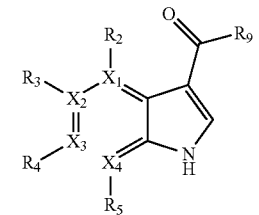

[Formula 22]

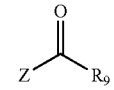

[Formula 23]

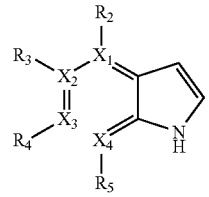

wherein, in formulas 18 to 23, $X_1$, $X_2$, $X_3$, $X_4$, $R_1$, $R_2$, $R_3$, $R_4$, $R_5$, $R_6$, $R_7$, $R_8$, and $R_9$ are the same as defined in formula 1; and Z represents a reactive leaving group, preferably a halogen atom (—F, —Cl, —Br).

Method 4 is more specifically described in the following.

Compounds of formulas 18, 19, 20, 21, 22 and 23 used as starting material may be prepared according to known methods in the art.

Preparing a compound of formula 21 via Friedel-Craft reaction of a compound of formula 23 with a compound of formula 22 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is dichloromethane.

The next step for preparing a compound of formula 20 via cyclization of the prepared compound of formula 21 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is ethanol.

The reaction may be conducted at, but not limited to, 50 to 200° C. for about 0.1 to 24 hours.

The next step for preparing a compound of formula 19 via halogenation of the prepared compound of formula 20 is carried out according to a conventional method in the presence of a suitable solvent and halogenating agent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is toluene. A solvent may not be used in the present reaction.

Exemplary halogenating agents for the reaction include phosphorous trichloride, phosphoryl chloride, phosphorous oxybromide, phenylphosphonyl chloride and phosphorous pentachloride. Preferred is phosphoryl chloride. The reaction may be conducted at, but not limited to, 50 to 200° C. for about 0.1 to 24 hours.

The next step for preparing a compound of formula 18 via arylation of the prepared compound of formula 19 with a compound of formula $R_1$—H (except that $R_1$ is —H) is carried out according to a conventional method in the presence of a suitable solvent and base.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is N,N-dimethyl formamide.

The above method for making a compound of formula 18 is more specifically described in the following example.

Method 5

A compound having a structure of the following formula 24, which is formula 1 as defined above wherein $Y_1$, $Y_3$ and $Y_4$ are N, may be prepared by a method comprising the steps of: preparing a compound of the following formula 28 via cyclization of a compound of the following formula 29; preparing a compound of formula 27 via halogenation of the prepared compound of formula 28 followed by hydroxylation; preparing a compound of formula 26 via arylation of the prepared compound of formula 27 with a compound of formula $R_1$—H (except that $R_1$ is —H) followed by halogenation; preparing a compound of formula 25 via arylation of the prepared compound of formula 26; and cyclizing the prepared compound of formula 25:

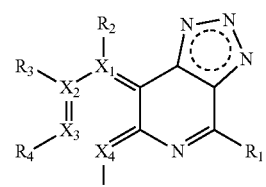

[Formula 24]

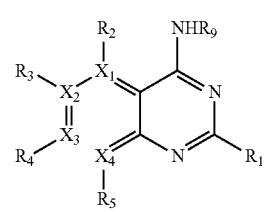

[Formula 25]

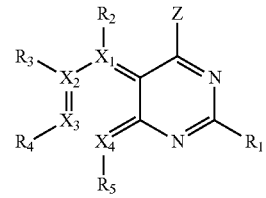

[Formula 26]

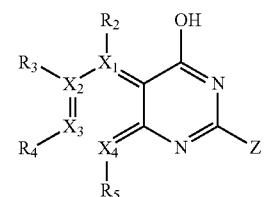

[Formula 27]

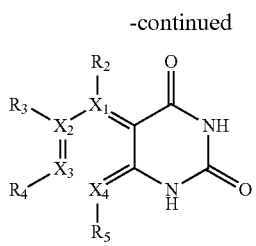

[Formula 28]

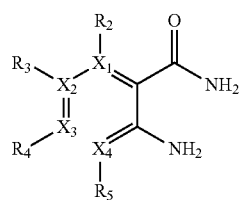

[Formula 29]

wherein, in formulas 24 to 29, $X_1$, $X_2$, $X_3$, $X_4$, $R_1$, $R_2$, $R_3$, $R_4$, $R_5$, $R_6$, $R_7$, $R_8$ and $R_9$ are the same as defined in formula 1; and Z represents a reactive leaving group, preferably a halogen atom (—F, —Cl, —Br).

Method 5 is more specifically described in the following.

Compounds of formulas 24, 25, 26, 27, 28 and 29 used as starting material may be prepared according to known methods in the art.

Preparing a compound of formula 28 via cyclization of a compound of formula 29 is carried out according to a conventional method in the presence of suitable solvent and cyclizing agent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is dioxane.

Exemplary cyclizing agents for the reaction include diphosgene and triphosgene. Preferred is diphosgene. The reaction may be conducted at, but not limited to, 50 to 200° C. for about 0.1 to 24 hours.

The next step for preparing a compound of formula 27 via halogenation of the prepared compound of formula 28 followed by hydroxylation is carried out according to a conventional method in the presence of a suitable solvent, halogenating agent and hydroxylating agent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is n-butanol.

Exemplary halogenating agents for the reaction include phosphorous trichloride, phosphoryl chloride, phosphorous oxybromide, phenylphosphonyl chloride and phosphorous pentachloride. Preferred is phosphoryl chloride. The reaction may be conducted at, but not limited to, 50 to 200° C. for about 0.1 to 24 hours.

Exemplary hydroxylating agents for the reaction include lithium hydroxide, sodium hydroxide, potassium hydroxide, calcium hydroxide and magnesium hydroxide. Preferred is sodium hydroxide. The reaction may be conducted at, but not limited to, room temperature for about 0.1 to 24 hours.

The next step for preparing a compound of formula 26 via arylation of the prepared compound of formula 27 with a compound of formula $R_1$—H (except that $R_1$ is —H) followed by halogenation is carried out according to a conventional method in the presence of a suitable solvent and halogenating agent.

Conventional solvents which have no adverse effects on the reaction may be used in the arylation reaction. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is ethanol.

Exemplary halogenating agents for the reaction include phosphorous trichloride, phosphoryl chloride, phosphorous oxybromide, phenylphosphonyl chloride and phosphorous pentachloride. Preferred is phosphoryl chloride. The reaction may be conducted at, but not limited to, 50 to 200° C. for about 0.1 to 24 hours.

The next step for preparing a compound of formula 25 via arylation of the prepared compound of formula 26 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is ethanol.

The next step for preparing a compound of formula 24 via cyclization of the prepared compound of formula 25 is carried out according to a conventional method in the presence of a suitable solvent and cyclizing agent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is ethanol.

Exemplary preferred cyclizing agents for the reaction include trimethyl orthoformate and triethyl orthoformate. The reaction may be conducted at, but not limited to, 50 to 200° C. for about 0.1 to 24 hours.

The above method for making a compound of formula 24 is more specifically described in the following example.

Method 6

A compound having a structure of the following formula 30, which is formula 1 as defined above wherein $Y_2$ is N and $Y_4$ is O, may be prepared by a method comprising the steps of: preparing a compound of the following formula 36 via esterification of a compound of the following formula 37; preparing a compound of formula 35 via arylation of the prepared compound of formula 36; preparing a compound of formula 34 via cyclization of the prepared compound of formula 35; preparing a compound of formula 33 via enolate addition reaction of the prepared compound of formula 34; preparing a compound of formula 32 via cyclization of the prepared compound of formula 33; preparing a compound of formula 31 via halogenation of the prepared compound of formula 32; and conducting arylation of the prepared compound of formula 31 with a compound of formula $R_1$—H (except that $R_1$ is —H):

[Formula 30]

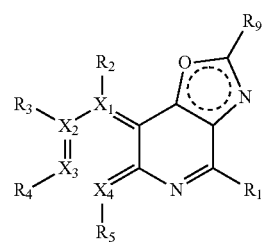

[Formula 31]

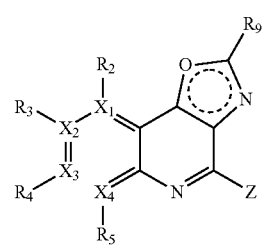

[Formula 32]

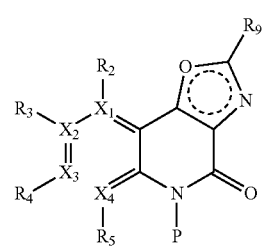

[Formula 33]

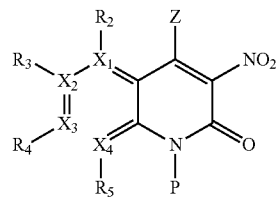

[Formula 34]

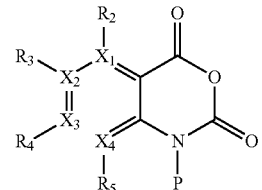

[Formula 35]

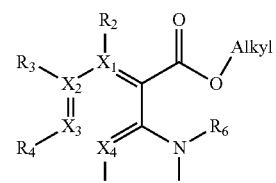

[Formula 36]

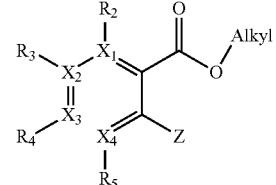

[Formula 37]

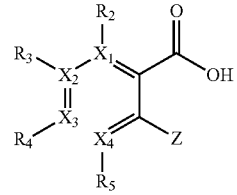

wherein, in formulas 30 to 37, $X_1$, $X_2$, $X_3$, $X_4$, $R_1$, $R_2$, $R_3$, $R_4$, $R_5$, $R_6$, $R_7$, $R_8$ and $R_9$ are the same as defined in formula 1; Z represents a reactive leaving group, preferably a halogen atom (—F, —Cl, —Br); and P represents a protecting group, preferably paramethoxybenzyl, 3',5'-dimethoxybenzyl and tri-methoxybenzyl.

Method 6 is more specifically described in the following.

Compounds of formulas 30, 31, 32, 33, 34, 35, 36 and 37 used as starting material may be prepared according to known methods in the art.

Preparing a compound of the following formula 36 via esterification of a compound of the following formula 37 is carried out according to a conventional method in the presence of a suitable solvent and esterification agent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvents for the reaction are dichloromethane and methanol.

The next step for preparing a compound of formula 35 via arylation of the prepared compound of formula 36 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is ethanol.

The next step for preparing a compound of formula 34 via cyclization of the prepared compound of formula 35 is carried out according to a conventional method in the presence of a suitable solvent and cyclizing agent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is dioxane.

Exemplary cyclizing agents for the reaction include diphosgene and triphosgene. Preferred is diphosgene. The reaction may be conducted at, but not limited to, 50 to 200° C. for about 0.1 to 24 hours.

The next step for preparing a compound of formula 33 via enolate addition reaction of the prepared compound of formula 34 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is tetrahydrofuran.

The reaction may be conducted at, but not limited to, 50 to 200° C. for about 0.1 to 24 hours.

The next step for preparing a compound of formula 32 via cyclization of the prepared compound of formula 33 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is acetic acid.

The reaction may be conducted at, but not limited to, 50 to 200° C. for about 0.1 to 24 hours.

The next step for preparing a compound of formula 31 via halogenation of the prepared compound of formula 32 is carried out according to a conventional method in the presence of a suitable halogenating agent.

Exemplary halogenating agents for the reaction include phosphorous trichloride, phosphoryl chloride, phosphorous oxybromide, phenylphosphonyl chloride and phosphorous pentachloride. Preferred is phosphoryl chloride. The reaction may be conducted at, but not limited to, 50 to 200° C. for about 0.1 to 24 hours.

The next step for preparing a compound of formula 30 via arylation of the prepared compound of formula 31 with a compound of formula $R_1$—H (except that $R_1$ is —H) is carried out according to a conventional method in the presence of a suitable solvent and base.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is N,N-dimethyl formamide.

The above method for making a compound of formula 30 is more specifically described in the following example.

Method 7

A compound having a structure of the following formula 38, which is formula 1 as defined above wherein $Y_1$ is N, each of $Y_2$ and $Y_3$ is independently C or N and at least one of $Y_1$, $Y_2$ and $Y_3$ is N, may be prepared by a method comprising the steps of: preparing a compound of the following formula 40 via the Suzuki coupling reaction of a compound of the following formula 42 with a compound of the following formula 41; preparing a compound of formula 39 via halogenation of the prepared compound of formula 40; and conducting arylation of the prepared compound of formula 39 with a compound of formula $R_1$—H (except that $R_1$ is —H):

[Formula 38]

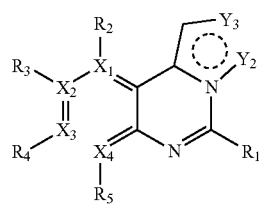

[Formula 39]

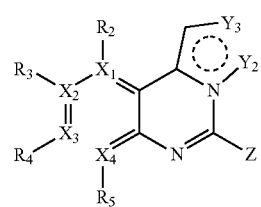

[Formula 40]

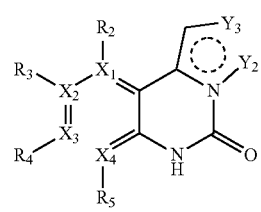

[Formula 41]

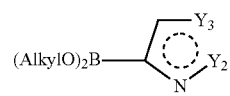

[Formula 42]

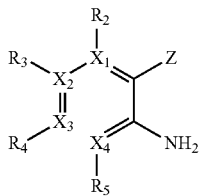

wherein, in formulas 38 to 42, $X_1$, $X_2$, $X_3$, $X_4$, $R_1$, $R_2$, $R_3$, $R_4$, $R_5$, $R_6$, $R_7$, $R_8$ and $R_9$ are the same as defined in formula 1; and Z represents a reactive leaving group, preferably a halogen atom (—F, —Cl, —Br).

Method 7 is more specifically described in the following.

Compounds of formulas 38, 39, 40, 41 and 42 used as starting material may be prepared according to known methods in the art.

Preparing a compound of formula 40 via the Suzuki coupling reaction of a compound of formula 42 with a compound of formula 41 is carried out according to a conventional method in the presence of a suitable solvent and catalyst.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvents for the reaction are N,N-dimethyl formamide and water.

Exemplary catalysts for the reaction include tetrakis(triphenylphosphine)palladium ($Pd(PPh_3)_4$), palladium(II)acetate ($Pd(OAc)_2$), bis(triphenylphosphine)palladium(II)dichloride ($Pd/Cl_2(PPh_3)_2$), [1,1-bis(diphenylphosphino)ferrocene]dichloro-palladium(II) ($Pd/Cl_2(dppf)$), (dibenzylideneacetone)dipalladium(0) ($Pd(dba)_2$) and palladium(II)chloride ($Pd/Cl_2$). Preferred is tetrakis(triphenylphosphine)palladium ($Pd(PPh_3)_4$). The reaction may be conducted at, but not limited to, 50 to 200° C. for about 0.1 to 24 hours.

The next step for preparing a compound of formula 39 via halogenation of the prepared compound of formula 40 is carried out according to a conventional method in the presence of a suitable halogenating agent.

Exemplary halogenating agents for the reaction include phosphorous trichloride, phosphoryl chloride, phosphorous oxybromide, phenylphosphonyl chloride and phosphorous pentachloride. Preferred is phosphoryl chloride. The reaction may be conducted at, but not limited to, 50 to 200° C. for about 0.1 to 24 hours.

The next step for preparing a compound of formula 38 via arylation of the prepared compound of formula 39 with a compound of formula $R_1$—H (except that $R_1$ is —H) is carried out according to a conventional method in the presence of suitable solvent and base.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is dichloromethane.

The above method for making a compound of formula 5 is more specifically described in the following example.

Method 8

A compound having a structure of the following formula 43, which is formula 1 as defined above wherein $Y_5$ is N, may be prepared by a method comprising the steps of: preparing a compound of the following formula 46 via pyrrolation of a compound of the following formula 47; preparing a compound of formula 45 via cyclization of the prepared compound of formula 46; preparing a compound of formula 44 via halogenation of the prepared compound of formula 45; and conducting arylation of the prepared compound of formula 44 with a compound of formula $R_1$—H (except that $R_1$ is —H):

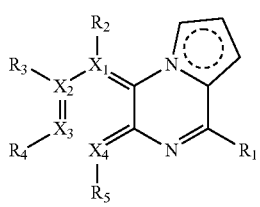

[Formula 43]

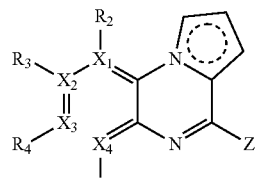

[Formula 44]

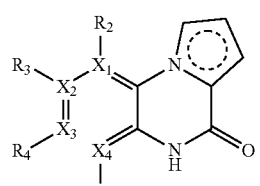

[Formula 45]

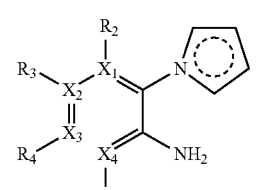

[Formula 46]

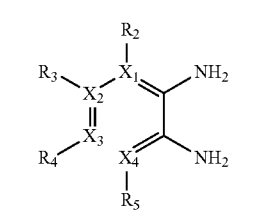

[Formula 47]

wherein, in formulas 43 to 47, $X_1$, $X_2$, $X_3$, $X_4$, $R_1$, $R_2$, $R_3$, $R_4$, $R_5$, $R_6$, $R_7$, $R_8$ and $R_9$ are the same as defined in formula 1; and Z represents a reactive leaving group, preferably a halogen atom (—F, —Cl, —Br).

Method 8 is more specifically described in the following.

Compounds of formulas 43, 44, 45, 46 and 47 used as starting material may be prepared according to known methods in the art.

Preparing a compound of formula 46 via pyrrolation of a compound of formula 47 is carried out according to a conventional method in the presence of a suitable solvent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is acetic acid. The reaction may be conducted at, but not limited to, 50 to 200° C. for about 0.1 to 24 hours.

The next step for preparing a compound of formula 45 via cyclization of the prepared compound of formula 46 is carried out according to a conventional method in the presence of suitable solvent and cyclizing agent.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is toluene.

Exemplary cyclizing agents for the reaction include diphosgene and triphosgene. Preferred is triphosgene. The reaction may be conducted at, but not limited to, 50 to 200° C. for about 0.1 to 24 hours.

The next step for preparing a compound of formula 44 via halogenation of the prepared compound of formula 45 is carried out according to a conventional method in the presence of a suitable halogenating agent.

Exemplary halogenating agents for the reaction include phosphorous trichloride, phosphoryl chloride, phosphorous oxybromide, phenylphosphonyl chloride and phosphorous pentachloride. Preferred is phosphoryl chloride. The reaction may be conducted at, but not limited to, 50 to 200° C. for about 0.1 to 24 hours.

The next step for preparing a compound of formula 43 via arylation of the prepared compound of formula 44 with a compound of formula $R_1$—H (except that $R_1$ is —H) is carried out according to a conventional method in the presence of suitable solvent and base.

Conventional solvents which have no adverse effects on the reaction may be used in this step. Preferable examples of the solvent include ether-based solvents such as diethyl ether, tetrahydrofuran, dioxane, 1,2-dimethoxyethane, 2-butanone, diglyme, etc.; hydrocarbon-based solvents such as benzene, pyridine, toluene, hexane, xylene, etc.; halogenated hydrocarbon-based solvents such as dichloromethane, chloroform, carbon tetrachloride, 1,2-dichloroethane, etc.; alcohol-based solvents such as methanol, ethanol, isopropyl alcohol, tert-butyl alcohol, etc.; ester-based solvents such as ethyl acetate, methyl acetate, butyl acetate, etc.; polar solvents such as acetone, N,N-dimethyl formamide, N,N-dimethyl acetamide, N-methylpyrrolidone, dimethyl sulfoxide, acetonitrile, etc.; and a mixed solvent thereof. The particularly preferable solvent for the reaction is N,N-dimethyl acetamide.

Advantageous Effects of Invention

The novel heterocyclic compounds according to the present invention exhibit the same or a stronger histamine 4 receptor inhibitory activity, as compared with conventional human histamine 4 receptor (hH4R) inhibitors; show a selectivity for each of the subtype receptors of histamine and receptors, transporters and ion channels on a membrane; and have higher solubility, metabolic stability, and accordingly as a result of pharmacokinetic analysis and comparison with a compound disclosed in WO2010/030785 by using an animal model such as the SD rat, the compounds of the invention showed superior effects in pharmacokinetics profile such as $AUC_{inf}$ and maximum blood concentration, 7-8 times as much as the comparative compound. Regarding symptoms, it is found that itch induced by histamine, Substance P and Compound 48/80, etc. is effectively suppressed, and that the heterocyclic compound according to the present invention has a superior effect, 3 times as much as a compound disclosed in WO2010/030785 for the suppression of the histamine-induced infiltration of inflammatory cells such as mast cells and eosinophils. In the oxazolone-induced atopic dermatitis model, the heterocyclic compound according to the present invention shows a very stronger anti-inflammatory effect than a compound disclosed in WO2010/030785. Especially, in the dermatophagoides farina-induced NC/Nga mouse atopic dermatitis model, it is found that the heterocyclic compound according to the present invention shows an anti-inflammatory effect, as much as a Tacrolimus which is an immunosuppressive drug, and a compound having selectivity for serotonin 3 receptor is found.

Therefore, the novel heterocyclic compounds according to the present invention and pharmaceutical compositions comprising the same may be highly effective in treating or preventing inflammatory diseases, allergy, pain, nasal polyps, rhinitis, chronic sinusitis, nasal congestion, nasal itch, asthma, chronic obstructive pulmonary disease, rheumatoid arthritis, atopic dermatitis, psoriasis, eczema, pruritus, itchy skin, urticaria, idiopathic chronic urticaria, scleroderma, conjunctivitis, keratoconjunctivitis, ocular inflammation, dry eye, cardiac dysfunction, arrhythmia, atherosclerosis, multiple sclerosis, inflammatory bowel disease (including colitis, Crohn's disease, ulcerative colitis), inflammatory pain, neuropathic pain, osteoarthritic pain, autoimmune thyroid disease, immune-mediated (also known as type I) diabetes, lupus, post-operative adhesions, vestibular disorders and cancer.

MODE FOR THE INVENTION

The present invention will be explained in further detail with reference to the following examples and experiments. However, these examples and experiments are intended only to illustrate the present invention, and the present invention is not limited to them in any way.

The abbreviations used in the following examples are defined as follows.

| Abbreviation | |
|---|---|
| Abb. | Full |
| ACN | Acetonitrile |
| AcOH | Acetic acid |
| $AlCl_3$ | Aluminium chloride |
| Boc | tert-Butyloxycarbonyl |
| $(Boc)_2O$ | Di-tert-butyl dicarbonate |
| BPOD | Phenylphosphonic dichloride |
| $Br_2$ | Bromine |
| Brine | Brine is water, saturated or nearly saturated with salt (usually sodium chloride). |
| n-BuLi | n-Butyllithium |
| BuOH | Butanol |
| $CaCl_2$ | Calcium chloride |
| Celite | Celite |
| $CHCl_3$ | Chloroform |
| $CH_3CN$ | Acetonitrile |
| $CF_3CH_2OH$ | 2,2,2-Trifluoroethanol |
| CuI | Copper iodide |
| $CDCl_3$ | Deuterated chloroform |
| $Cs_2CO_3$ | Cesium carbonate |
| CsF | Cesium fluoride |
| DCM | Dichloromethane |
| DDQ | 2,3-Dichloro-5,6-dicyano-1,4-benzoquinone |
| Deoxo-Fluor | Bis(2-methoxyethyl)aminosulfur trifluoride |
| DIPEA | N,N-Diisopropylethylamine |
| DMA | Dimethylacetamide |
| DMB | 3',5'-Dimethoxybenzyl |
| DME | Dimethoxyethane |
| DMF | N,N-Dimethylformamide |
| DMSO | Dimethylsulfoxide |
| $DMSO-d_6$ | Fully deuterated dimethylsulfoxide |
| EDTA | Ethylenediaminetetraacetic acid |
| EtOH | Ethyl alcohol |
| $Et_2O$ | Diethyl ether |
| EtOAc | Ethyl acetate |
| Fe | Iron |
| HCl | Hydrochloric acid |
| tris-HCl | tris-Hydrochloride |
| n-Hex | n-Hexane |
| HI | Hydrogen iodide |
| $HNO_3$ | Nitric acid |
| $H_2SO_4$ | Sulfuric acid |
| IPA | iso-Propyl alcohol |
| $K_2CO_3$ | Potassium carbonate |
| KI | Potassium iodide |
| KOH | Potassium hydroxide |
| MEK | Methyl ethyl ketone |
| MeI | Methyl iodide |
| MeOH | Methyl alcohol |
| $MgCl_2$ | Magnesium chloride |
| $MgSO_4$ | Magnesium sulfate |
| $MeOH-d_4$ | Fully deuterated methyl alcohol |
| MsCl | Methanesulfonyl chloride |
| NADPH | Nicotinamide adenine dinucleotide phosphate |
| $Na_2SO_4$ | Sodium sulfate |
| $Na_2S_2O_8$ | Sodium persulfate |
| $NaHCO_3$ | Sodium bicarbonate |
| $NaH_2PO_4$ | Monosodium phosphate |
| NaOH | Sodium hydroxide |
| $NaBH_4$ | Sodium borohydride |
| NaH | Sodium hydride |
| $NaN_3$ | Sodium azide |
| NaOEt | Sodium ethoxide |
| $NEt_3$ | Triethylamine |
| NMP | N-Methylpyrrolidone |
| $NH_4Cl$ | Ammonium chloride |
| $PdCl_2(PPh_3)_2$ | Bis(triphenylphosphine)palladium(II) dichloride |
| $Pd(OAc)_2$ | Palladium(II) acetate |
| $P(o-Tol)_3$ | Tri(o-tolyl)phosphine |
| $Pd(PPh_3)_4$ | Tetrakis(triphenylphosphine)Palladium |
| PMB | Para-methoxybenzyl |
| $POCl_3$ | Phosphoryl chloride |
| OMs | Methanesulfonate |
| OTf | Triflate |
| OTs | Tosylate |
| $SnCl_2·2H_2O$ | Stannous chloride dihydrate |
| $SnCl_2$ | Tin(II) chloride |
| TBAF | Tetra-n-butylammonium fluoride |
| TMB | Tri-methoxybenzyl |
| TEA | Triethylamine |
| TFA | Trifluoroacetic acid |
| THF | Tetrahydrofuran |
| TsOH | p-Toluenesulfonic acid |
| Xylene | Xylene |
| $Zn(CN)_2$ | Zinc cyanide |

Example 1

Synthesis of 3-methyl-6-(4-methylpiperazin-1-yl) pyrido[3,2-e][1,2,4]triazolo[4,3-a]pyrazine (a) Synthesis of 2-chloro-3-hydrazinyl-7-methyl-pyrido[2,3-b]pyrazine 2,3-Dichloro-7-methylpyrido[2,3-b]pyrazine (500.0 mg, 2.33 mmol) and hydrazine monohydrate (234.0 mg, 4.66 mmol) were dissolved in EtOH (10.0 mL), stirred for 12 hours at room temperature and then distilled under reduced pressure. $Et_2O$ was added thereto to form a solid. The formed solid was then filtered and dried under reduced pressure to obtain yellow solid compound of 2-chloro-3-hydrazinyl-7-methylpyrido[2,3-b]pyrazine.

LC/MS ESI (+): 210 (M+1), 212 (M+3)

(b) Synthesis of 6-chloro-3-methylpyrido[3,2-e][1,2,4]triazolo[4,3-a]pyrazine

The mixture of unpurified 2-chloro-3-hydrazinyl-7-methylpyrido[2,3-b]pyrazine and trimethyl orthoformate (5.0 mL) was stirred at 100° C. for one hour and then cooled to room temperature. $Et_2O$ was added thereto to form a solid. The formed solid was then filtered and dried under reduced pressure to obtain ivory solid compound of 6-chloro-3-methylpyrido[3,2-e][1,2,4]triazolo[4,3-a]pyrazine (340.0 mg, 66% in 2 steps).

LC/MS ESI (+): 220 (M+1), 222 (M+3)

(c) Synthesis of 3-methyl-6-(4-methylpiperazin-1-yl)pyrido[3,2-e][1,2,4]triazolo[4,3-a]pyrazine 6-Chloro-3-methylpyrido[3,2-e][1,2,4]triazolo[4,3-a] pyrazine (50.0 mg, 0.23 mmol) was dissolved in DMF (2.0 mL), and N-methyl piperazine (48.0 mg, 0.48 mmol) was slowly added thereto at 0° C. The reaction mixture was stirred at room temperature for one hour and distilled under reduced pressure. The residue was purified by column chromatography (DCM:MeOH=100:0 to DCM:MeOH=98:2) on amine silica. The fractions containing the product were collected and evaporated to obtain white solid compound of 3-methyl-6-(4-methyl-1-yl)pyrido[3,2-e][1,2,4]triazolo[4,3-a]pyrazine (25.0 mg, 38%).

LC/MS ESI (+): 284 (M+1), 286 (M+3)
$^1$H-NMR (300 MHz, DMSO-$d_6$); δ: 9.83 (s, 1H), 8.20 (m, 1H), 7.82 (m, 1H), 4.34 (bs, 4H), 2.50 (m, 4H), 2.42 (s, 3H), 2.24 (s, 3H)

Example 2

Synthesis of 8-methyl-4-(4-methylpiperazin-1-yl) pyrido[2,3-e][1,2,4]triazolo[4,3-a]pyrazine (a) Synthesis of 2-chloro-7-methyl-3-(4-methylpiperazin-1-yl)pyrido[2,3-b]pyrazine 2,3-Dichloro-7-methylpyrido[2,3-b]pyrazine (500.0 mg, 2.30 mmol) was dissolved in DCM (8.0 mL), and N-methyl piperazine (468.0 mg, 2.60 mmol) was slowly added thereto at 0° C. The reaction mixture was stirred at room temperature for 12 hours, and it was poured into water and extracted with DCM (30.0 mL). The organic layer was washed with brine, dried over anhydrous $Na_2SO_4$, filtered and then distilled under reduced pressure. The residue was purified by column chromatography (DCM:MeOH=100:0 to 99:1) on amine silica. The fractions containing the product were collected and evaporated to obtain yellow solid compound of 2-chloro-7-methyl-3-(4-methylpiperazine-1-yl)pyrido[2,3-b]pyrazine.

LC/MS ESI (+): 278 (M+1), 280 (M+3)

(b) Synthesis of 8-methyl-4-(4-methylpiperazin-1-yl)pyrido[2,3-e][1,2,4]triazolo[4,3-a]pyrazine Unpurified 2-chloro-7-methyl-3-(4-methylpiperazin-1-yl)pyrido[2,3-b]pyrazine (300.0 mg, 1.08 mmol) and hydrazine monohydrate (108.0 mg, 2.16 mmol) were dissolved in EtOH (10.0 mL), stirred for 12 hours at 50° C. and then distilled under reduced pressure. The reaction mixture was poured into water and extracted with DCM. The organic layer was washed with brine, dried over anhydrous $Na_2SO_4$, filtered and then evaporated under reduced pressure to obtain yellow solid compound of 2-hydrazinyl-7-methyl-3-(4-methylpiperazin-1-yl)pyrido[2,3-b]pyrazine. The mixture of unpurified 2-hydrazinyl-7-methyl-3-(4-methylpiperazin-1-yl)pyrido[2,3-b]pyrazine and trimethyl orthoformate (2.0 mL) was stirred at 100° C. for one hour and then cooled to room temperature. $Et_2O$ was added thereto to form a solid and the formed solid was filtered. The residue was purified by column chromatography (DCM:MeOH=99:1) on amine silica. The fractions containing the product were collected and evaporated to obtain ivory solid compound of 8-methyl-4-(4-methylpiperazin-1-yl)pyrido[2,3-e][1,2,4]triazolo[4,3-a]pyrazine (94.0 mg, 31%)

LC/MS ESI (+): 284 (M+1)
$^1$H-NMR (300 MHz, DMSO-$d_6$); δ: 9.99 (s, 1H), 8.45 (m, 2H), 4.37 (bs, 4H), 2.50 (m, 4H), 2.43 (s, 3H), 2.24 (s, 3H)

Example 3

Synthesis of 4-(4-methylpiperazin-1-yl)pyrido[2,3-e][1,2,4]triazolo[4,3-a]pyrazine (a) Synthesis of 2-chloro-3-(4-methylpiperazine-1-yl)pyrido[2,3-b]pyrazine 2,3-Dichloropyrido[2,3-b]pyrazine (300.0 mg, 1.50 mmol) was dissolved in DMF (5.0 mL), and N-methyl piperazine (0.3 mL, 2.97 mmol) was slowly added thereto at 0° C. The reaction mixture was stirred at room temperature for 2 hours, and it was then poured into saturated $NH_4Cl$ aqueous solution and extracted with DCM (30.0 mL). The organic layer was washed with brine, dried over anhydrous $Na_2SO_4$, filtered and then distilled under reduced pressure. The residue was purified by column chromatography (DCM:MeOH=100:0) on amine silica. The fractions containing products were collected and evaporated to obtain pale yellow solid compound of 2-chloro-3-(4-methylpiperazin-1-yl)pyrido[2,3-b]pyrazine (265.0 mg, 67%).

LC/MS ESI (+): 264 (M+1), 266 (M+3)

(b) Synthesis of 4-(4-methylpiperazin-1-yl)pyrido[2,3-e][1,2,4]triazolo[4,3-a]pyrazine 2-Chloro-3-(4-methylpiperazin-1-yl)pyrido[2,3-b]pyrazine (260.0 mg, 0.99 mmol) and hydrazine monohydrate (63.0 mg, 1.97 mmol) were dissolved in EtOH (10.0 mL), stirred at room temperature for 2 hours and then distilled under reduced pressure. The reaction mixture was poured into saturated $NH_4Cl$ aqueous solution and extracted with DCM (30.0 mL). The organic layer was washed with brine, dried over anhydrous $Na_2SO_4$, filtered and then evaporated under reduced pressure to obtain yellow solid compound of 2-hydrazinyl-3-(4-methylpiperazin-1-yl)pyrido[2,3-b]pyrazine. The mixture of unpurified 2-hydrazinyl-3-(4-methylpiperazin-1-yl)pyrido[2,3-b]pyrazine and trimethyl orthoformate (2.0 mL) was stirred at 80° C. for one hour and then cooled to room temperature. Et$_2$O was added thereto to form a solid, and the formed solid was filtered and then dried under reduced pressure. The residue was purified by column chromatography (DCM:MeOH=100:0) on amine silica. The fractions containing the product were collected to obtain pale yellow solid compound of 4-(4-methylpiperazin-1-yl)pyrido[2,3-e][1,2,4]triazolo[4,3-a]pyrazine (186.0 mg, 70%).

LC/MS ESI (+): 270 (M+1)

$^1$H-NMR (300 MHz, DMSO-d$_6$); δ: 10.04 (s, 1H), 8.61-8.54 (m, 2H), 7.39-7.32 (m, 1H), 4.60-4.21 (m, 4H), 2.55-2.44 (m, 4H), 2.25 (s, 3H)

Example 4

Synthesis of 8-chloro-4-(4-methylpiperazin-1-yl)pyrido[2,3-e][1,2,4]triazolo[4,3-a]pyrazine (a) Synthesis of 2,3,7-trichloropyrido[2,3-b]pyrazine 5-Chloropyridin-2,3-diamine (10000.0 mg, 69.65 mmol) was added to diethyl oxalate (30.0 mL) and the reaction mixture was stirred at 100° C. for 12 hours and then cooled to room temperature. Et$_2$O was added thereto to form a solid. The formed solid was then filtered and dried under reduced pressure to obtain bright brown solid compound of 7-chloropyrido[2,3-b]pyrazin-2,3-diol. The mixture of unpurified 7-chloropyrido[2,3-b]pyrazin-2,3-diol and POCl$_3$ (30.0 mL) was stirred at 130° C. for 12 hours and then cooled to room temperature. The reaction mixture was poured into ice water. The formed solid was filtered and dried under reduced pressure to obtain brown solid compound of 2,3,7-trichloropyrido[2,3-b]pyrazine (13700.0 mg, 84% in 2 steps).

LC/MS ESI (+): 234 (M+1), 236 (M+3)

$^1$H-NMR (300 MHz, DMSO-d$_6$); δ: 9.23 (d, 1H, J=2.6 Hz), 8.86 (d, 1H, J=2.6 Hz)

(b) Synthesis of 2,7-dichloro-3-(4-methylpiperazin-1-yl)pyrido[2,3-b]pyrazine 2,3,7-Trichloropyrido[2,3-b]pyrazine (428.0 mg, 1.83 mmol) and TEA (2.5 mL, 18.30 mmol) were dissolved in DCM (10.0 mL) and N-methyl piperazine (0.2 mL, 2.01 mmol) diluted in DCM (5.0 mL) was added slowly at 0° C. The reaction mixture was stirred at room temperature for 2 hours and then poured into saturated NH$_4$Cl aqueous solution and extracted with DCM (30.0 mL). The organic layer was washed with brine, dried over anhydrous Na$_2$SO$_4$, filtered and then distilled under reduced pressure. The residue was purified by column chromatography (DCM:MeOH=100:0) on amine silica. The fractions containing the product were collected to obtain yellow solid compound of 2,7-dichloro-3-(4-methylpiperazin-1-yl)pyrido[2,3-b]pyrazine (290.0 mg, 53%).

LC/MS ESI (+): 298 (M+1), 300 (M+3)

(c) Synthesis of 8-chloro-4-(4-methylpiperazin-1-yl)pyrido[2,3-e][1,2,4]triazolo[4,3-a]pyrazine 2,7-Dichloro-3-(4-methylpiperazin-1-yl)pyrido[2,3-b]pyrazine (290.0 mg, 0.97 mmol) and hydrazine monohydrate (98.0 mg, 1.96 mmol) were dissolved in EtOH (10.0 mL), stirred for 2 hours at room temperature and then distilled under reduced pressure. The reaction mixture was poured into saturated NH$_4$Cl aqueous solution and extracted with DCM (30.0 mL). The organic layer was washed with brine, dried over anhydrous Na$_2$SO$_4$, filtered and then evaporated under reduced pressure to obtain yellow solid compound of 7-chloro-2-hydrazinyl-3-(4-methylpiperazin-1-yl)pyrido[2,3-b]pyrazine. The mixture of unpurified 7-chloro-2-hydrazinyl-3-(4-methylpiperazin-1-yl)pyrido[2,3-b]pyrazine and trimethyl orthoformate (5.0 mL) was stirred at 80° C. for one hour and then cooled to room temperature. Et$_2$O was added thereto to form a solid, and the formed solid was filtered and then dried under reduced pressure. The residue was purified by column chromatography (DCM:MeOH=100:0) on amine silica. The fractions containing the product were collected and evaporated to obtain ivory solid compound of 8-chloro-4-(4-methylpiperazin-1-yl)pyrido[2,3-e][1,2,4]triazolo[4,3-a]pyrazine (215.0 mg, 73% in 2 steps).

LC/MS ESI (+): 304 (M+1), 306 (M+3)

$^1$H-NMR (300 MHz, DMSO-d$_6$); δ: 10.01 (s, 1H), 8.85 (d, 1H, J=2.4 Hz), 8.58 (d, 1H, J=2.4 Hz), 4.40 (bs, 4H), 2.53 (m, 4H), 2.24 (s, 3H)

Example 5

Synthesis of 3-chloro-6-(4-methylpiperazin-1-yl)pyrido[3,2-e][1,2,4]triazolo[4,3-a]pyrazine (a) Synthesis of 2,7-dichloro-3-hydrazinylpyrido[2,3-b]pyrazine 2,3,7-Trichloropyrido[2,3-b]pyrazine (150.0 mg, 0.64 mmol), TEA (129.0 mg, 1.28 mmol), hydrazine monohydrate (35.0 mg, 0.74 mmol) were dissolved in EtOH (5.0 mL), stirred at room temperature for 12 hours and then distilled under reduced pressure. Et$_2$O was added thereto to form a solid. The formed solid was filtered and then dried under reduced pressure to obtain yellow solid compound of 2,7-dichloro-3-hydrazinylpyrido[2,3-b]pyrazine.

LC/MS ESI (+): 230 (M+1), 232 (M+3)

(b) Synthesis of 3-chloro-6-(4-methylpiperazin-1-yl)pyrido[3,2-e][1,2,4]triazolo[4,3-a]pyrazine The mixture of unpurified 2,7-dichloro-3-hydrazinylpyrido[2,3-b]pyrazine and trimethyl orthoformate (2.0 mL) was stirred at 100° C. for 2 hours and then cooled to room temperature. Et$_2$O was added thereto to form a solid. The formed solid was filtered to obtain yellow solid compound of 3,6-dichloropyrido[3,2-e][1,2,4]triazolo[4,3-a]pyrazine. Unpurified 3,6-dichloropyrido[3,2-e][1,2,4]triazolo[4,3-a]pyrazine was dissolved in DMF (2.0 mL), and then N-methyl piperazin (0.1 mL, 0.90 mmol) diluted in DMF (1.0 mL) was slowly added thereto at 0° C. The reaction mixture was stirred at room temperature for 2 hours, and it was poured into water and extracted with EtOAc (30.0 mL). The organic layer was washed with brine, dried over anhydrous Na$_2$SO$_4$, filtered and then distilled under reduced pressure. The residue was purified by column chromatography (DCM:MeOH=99:1) on amine silica. The fractions containing product were collected and evaporated to obtain ivory solid compound of 3-chloro-6-(4-methylpiperazin-1-yl)pyrido[3,2-e][1,2,4]triazolo[4,3-a]pyrazine (24.0 mg, 12% in 3 steps).

LC/MS ESI (+): 304 (M+1), 306 (M+3)

$^1$H-NMR (300 MHz, CDCl$_3$); δ: 9.46 (s, 1H), 8.22 (d, 1H, J=2.4 Hz), 7.93 (d, 1H, J=2.4 Hz), 4.54 (bs, 4H), 2.61 (m, 4H), 2.37 (s, 3H)

Example 6

Synthesis of 6-(4-methylpiperazin-1-yl)pyrido[3,2-e][1,2,4]triazolo[4,3-a]pyrazine 2,3-Dichloropyrido[2,3-b]pyrazine (300.0 mg, 1.50 mmol) and hydrazine monohydrate (48.1 mg, 1.50 mmol) were dissolved in EtOH (7.0 mL), stirred at room temperature for 2 hours and then distilled under reduced pressure. The reaction mixture was poured into saturated NH$_4$Cl aqueous solution and extracted with DCM (30.0 mL). The organic layer was washed with brine, dried over anhydrous Na$_2$SO$_4$, filtered and then evaporated under reduced pressure to obtain 2-chloro-3-hydrazinylpyrido[2,3-b]pyrazine. The mixture of unpurified 2-chloro-3-hydrazinylpyrido[2,3-b]pyrazine and trimethyl orthoformate (2.0 mL) was stirred at 80° C. for one hour and then cooled to room temperature. Et$_2$O was added thereto to form a solid. The formed solid was filtered and then dried under reduced pressure to obtain 6-chloropyrido[3,2-e][1,2,4]triazolo[4,3-a]pyrazine. Unpurified 6-chloropyrido[3,2-e][1,2,4]triazolo[4,3-a]pyrazine was dissolved in DMF (5.0 mL), and then N-methyl piperazin (0.3 mL, 2.97 mmol) was slowly added thereto at 0° C. The reaction mixture was stirred at room temperature for 2 hours, then poured into saturated NH$_4$Cl aqueous solution and extracted with DCM. The organic layer was washed with brine, dried over anhydrous Na$_2$SO$_4$, filtered and then distilled under reduced pressure. The residue was purified by column chromatography (DCM:MeOH=100:0) on amine silica. The fractions containing the product were collected and evaporated to obtain pale yellow solid compound of 6-(4-methylpiperazin-1-yl)pyrido[3,2-e][1,2,4]triazolo[4,3-a]pyrazine (70.0 mg, 17% in 3 steps).

LC/MS ESI (+): 270 (M+1)

$^1$H-NMR (300 MHz, CDCl$_3$); δ: 9.51 (s, 1H), 8.30 (dd, 1H, J=1.5 Hz, J=4.6 Hz), 7.94 (dd, 1H, J=1.5 Hz, J=8.0 Hz), 7.44 (dd, 1H, J=4.6 Hz, J=8.0 Hz), 4.70-4.34 (m, 4H), 2.58-2.56 (m, 4H), 2.38 (s, 3H)

Example 7

Synthesis of 8-chloro-4-(piperazin-1-yl)pyrido[2,3-e][1,2,4]triazolo[4,3-a]pyrazine

(a) Synthesis of tert-butyl 4-(2,7-dichloropyrido[2,3-b]pyrazin-3-yl)piperazin-1-carboxylate 2,3,7-Trichloropyrido[2,3-b]pyrazine (800.0 mg, 3.41 mmol) and TEA (2.4 mL, 17.05 mmol) were dissolved in DCM (20.0 mL) and then tert-butyl piperazin-1-carboxylate (667.0 mg, 3.58 mmol) diluted in DCM (10.0 mL) was slowly added thereto at 0° C. The reaction mixture was stirred at room temperature for 12 hours and then poured into saturated NH$_4$Cl aqueous solution and extracted with DCM (50.0 mL). The organic layer was washed with brine, dried over anhydrous Na$_2$SO$_4$, filtered and then distilled under reduced pressure. The residue was purified by column chromatography (n-Hex:EtOAc=90:10 to 80:20) on amine silica. The fractions containing the product were collected and evaporated to obtain yellow solid compound of tert-butyl 4-(2,7-dichloropyrido[2,3-b]pyrazin-3-yl)piperazin-1-carboxylate (892.0 mg, 68%).

LC/MS ESI (+): 384 (M+1), 389 (M+3)

(b) Synthesis of tert-butyl 4-(7-chloro-2-hydrazinylpyrido[2,3-b]pyrazin-3-yl)piperazin-1-carboxylate tert-Butyl 4-(2,7-dichloropyrido[2,3-b]pyrazin-3-yl)piperazin-1-carboxylate (892.0 mg, 2.32 mmol) and hydrazine monohydrate (244.0 mg, 4.87 mmol) were dissolved in EtOH (50.0 mL), stirred at room temperature for 2 hours and then distilled under reduced pressure. The reaction mixture was poured into saturated NH$_4$Cl aqueous solution and extracted with DCM (50.0 mL). The organic layer was washed with brine, dried over anhydrous Na$_2$SO$_4$, filtered and then dried under reduced pressure to obtain yellow solid compound of tert-butyl 4-(7-chloro-2-hydrazinylpyrido[2,3-b]pyrazin-3-yl)piperazin-1-carboxylate.

LC/MS ESI (+): 380 (M+1), 382 (M+3)

(c) Synthesis of tert-butyl 4-(8-chloropyrido[2,3-e][1,2,4]triazolo[4,3-a]pyrazin-4-yl)piperazin-1-carboxylate The mixture of unpurified tert-butyl 4-(7-chloro-2-hydrazinylpyrido[2,3-b]pyrazin-3-yl)piperazin-1-carboxylate and trimethyl orthoformate (20.0 mL) was stirred at 70° C. for one hour and then cooled to room temperature. Et$_2$O was added thereto to form a solid. The formed solid was filtered and then dried under reduced pressure. The residue was purified by column chromatography (DCM:MeOH=100:0) on amine silica. The fractions containing product were collected and evaporated to obtain ivory solid compound of tert-butyl 4-(8-chloropyrido[2,3-e][1,2,4]triazolo[4,3-a]pyrazin-4-yl)piperazin-1-carboxylate (814.0 mg, 90%).

LC/MS ESI (+): 390 (M+1), 392 (M+3)

(d) Synthesis of 8-chloro-4-(piperazin-1-yl)pyrido[2,3-e][1,2,4]triazolo[4,3-a]pyrazine tert-Butyl 4-(8-chloropyrido[2,3-e][1,2,4]triazolo[4,3-a]pyrazin-4-yl)piperazin-1-carboxylate (814.0 mg, 2.09 mmol) was dissolved in DCM (20.0 mL), and TFA (5.0 mL) was slowly added thereto at 0° C. The reaction mixture was stirred at room temperature for 2 hours and then distilled under reduced pressure. The residue was neutralized with NaHCO$_3$ aqueous solution (pH=7), and it was then extracted with DCM (50.0 mL). The organic layer was washed with brine, dried over anhydrous Na$_2$SO$_4$, filtered and then distilled under reduced pressure. The residue was purified by column chromatography (DCM:MeOH=90:10 to 80:20) on amine silica. The fractions containing the product were collected and evaporated to obtain ivory solid compound of 8-chloro-4-(piperazin-1-yl)pyrido[2,3-e][1,2,4]triazolo[4,3-a]pyrazine (503.0 mg, 83%).

LC/MS ESI (+): 290 (M+1), 292 (M+3)

$^1$H-NMR (300 MHz, DMSO-d$_6$); δ: 10.00 (s, 1H), 8.84 (d, 1H, J=2.4 Hz), 8.56 (d, 1H, J=2.4 Hz), 4.40 (bs, 4H), 2.88 (m, 4H)

Example 8

Synthesis of 1-(8-chloropyrido[2,3-e][1,2,4]triazolo[4,3-a]pyrazin-4-yl)azetidin-3-amine

(a) Synthesis of tert-butyl (1-(2,7-dichloropyrido[2,3-b]pyrazin-3-yl)azetidin-3-yl)carbamate 2,3,7-Trichloropyrido[2,3-b]pyrazine (200.0 mg, 0.85 mmol) and TEA (1.2 mL, 8.50 mmol) were dissolved in DCM (10.0 mL), and tert-butyl azetidin-3-ylcarbamate (162.0 mg, 0.94 mmol) diluted in DCM (5.0 mL) was slowly added thereto at 0° C. The reaction mixture was stirred at room temperature for 12 hours, and it was poured into saturated NH$_4$Cl aqueous solution and extracted with DCM (30.0 mL). The organic layer was washed with brine, dried over anhydrous $Na_2SO_4$, filtered and then distilled under reduced pressure. The residue was purified by column chromatography (DCM:MeOH=100:0 to 99:1) on silica. The fractions containing the product were collected and evaporated to obtain brown solid compound of tert-butyl (1-(2,7-dichloropyrido[2,3-b]pyrazin-3-yl)azetidin-3-yl) carbamate (224.0 mg, 71%).

LC/MS ESI (+): 370 (M+1), 372 (M+3)

(b) Synthesis of tert-butyl (1-(7-chloro-2-hydrazinylpyrido[2,3-b]pyrazin-3-yl)azetidin-3-yl)carbamate tert-Butyl (1-(2,7-dichloropyrido[2,3-b]pyrazin-3-yl)azetidin-3-yl)carbamate (224.0 mg, 0.61 mmol) and hydrazine monohydrate (76.0 mg, 1.53 mmol) were dissolved in EtOH (10.0 mL), stirred at room temperature for 2 hours and then distilled under reduced pressure. $Et_2O$ was added thereto to form a solid, and the formed solid was filtered and then dried under reduced pressure to obtain yellow solid compound of tert-butyl (1-(7-chloro-2-hydrazinylpyrido[2,3-b]pyrazin-3-yl)azetidin-3-yl)carbamate (100.0 mg, 41%).

LC/MS ESI (+): 366 (M+1), 368 (M+3)

c) Synthesis of tert-butyl (1-(8-chloropyrido[2,3-e][1,2,4]triazolo[4,3-a]pyrazin-4-yl)azetidin-3-yl)carbamate The mixture of tert-butyl (1-(7-chloro-2-hydrazinylpyrido[2,3-b]pyrazin-3-yl)azetidin-3-yl)carbamate (100.0 mg, 0.27 mmol) and trimethyl orthoformate (5.0 mL) was stirred at 70° C. for one hour and then cooled to room temperature. $Et_2O$ was added thereto to form a solid, and the formed solid was filtered and then dried under reduced pressure to obtain ivory solid compound of tert-butyl (1-(8-chloropyrido[2,3-e][1,2,4]triazolo[4,3-a]pyrazin-4-yl)azetidin-3-yl)carbamate (70.0 mg, 68%).

LC/MS ESI (+): 376 (M+1), 378 (M+3)

(d) Synthesis of 1-(8-chloropyrido[2,3-e][1,2,4]triazolo[4,3-a]pyrazin-4-yl)azetidin-3-amine tert-Butyl (1-(8-chloropyrido[2,3-e][1,2,4]triazolo[4,3-a]pyrazin-4-yl)azetidin-3-yl)carbamate (70.0 mg, 0.19 mmol) was dissolved in DCM (5.0 mL), and TFA (2.0 mL) was slowly added thereto at 0° C. The reaction mixture was stirred at room temperature for 2 hours and then distilled under reduced pressure. The residue was neutralized with $NaHCO_3$ aqueous solution (pH=7), and it was then extracted with DCM (30.0 mL). The organic layer was washed with brine, dried over anhydrous $Na_2SO_4$, filtered and then distilled under reduced pressure. The residue was purified by column chromatography (DCM:MeOH=90:10 to 50:50) on amine silica. The fractions containing the product were collected and evaporated to obtain ivory solid compound of 1-(8-chloropyrido[2,3-e][1,2,4]triazolo[4,3-a]pyrazin-4-yl)azetidin-3-amine (6.3 mg, 12%).

LC/MS ESI (+): 276 (M+1), 278 (M+3)
$^1$H-NMR (300 MHz, DMSO-$d_6$); δ: 9.95 (s, 1H), 8.80 (d, 1H, J=2.3 Hz), 8.53 (d, 1H, J=2.4 Hz), 4.93 (m, 1H), 4.47 (m, 1H), 4.35 (m, 1H), 3.93 (m, 2H)

Example 9

Synthesis of (R)-1-(8-chloropyrido[2,3-e][1,2,4]triazolo[4,3-a]pyrazin-4-yl)-N,N-dimethylpyrrolidin-3-amine (R)-1-(8-chloropyrido[2,3-e][1,2,4]triazolo[4,3-a]pyrazin-4-yl)pyrrolidin-3-amine (20.0 mg, 0.07 mmol) and sodium formate (20.0 mg, 0.29 mmol) were dissolved in formic acid/formamide (1.0 mL/1.0 mL), stirred at 100° C. for one hour and then distilled under reduced pressure. The reaction mixture was neutralized with $NaHCO_3$ aqueous solution (pH=7), and it was then extracted with DCM (30.0 mL). The organic layer was washed with brine, dried over anhydrous $Na_2SO_4$, filtered and then distilled under reduced pressure. The residue was purified by column chromatography (DCM:MeOH=90:10 to 80:20) on silica. The fractions containing the product were collected and evaporated to obtain ivory solid compound of (R)-1-(8-chloropyrido[2,3-e][1,2,4]triazolo[4,3-a]pyrazin-4-yl)-N,N-dimethylpyrrolidin-3-amine (13.0 mg, 59%).

LC/MS ESI (+): 318 (M+1), 320 (M+3)
$^1$H-NMR (300 MHz, $CDCl_3$); δ: 9.15 (s, 1H), 8.59 (d, 1H, J=2.2 Hz), 8.01 (d, 1H, J=2.3 Hz), 4.90 (m, 1H), 4.40-3.60 (m, 3H), 2.90 (m, 1H), 2.39 (s, 3H), 2.37 (s, 3H), 2.30 (m, 1H), 2.00 (m, 1H)

Example 10

Synthesis of (R)-1-(8-chloropyrido[2,3-e][1,2,4]triazolo[4,3-a]pyrazin-4-yl)-N-methylpyrrolidin-3-amine (a) Synthesis of (R)-tert-butyl (1-(2,7-dichloropyrido[2,3-b]pyrazin-3-yl)pyrrolidin-3-yl)(methyl)carbamate 2,3,7-Trichloropyrido[2,3-b]pyrazine (100.0 mg, 0.43 mmol) and TEA (0.6 mL, 4.30 mmol) were dissolved in DCM (10.0 mL), (R)-tert-butyl pyrrolidin-3-ylcarbamate (94.0 mg, 0.47 mmol) diluted in DCM (5.0 mL) was slowly added thereto at 0° C. The reaction mixture was stirred at room temperature for 12 hours, and it was then poured into saturated $NH_4Cl$ aqueous solution and extracted with DCM (30.0 mL). The organic layer was washed with brine, dried over anhydrous $Na_2SO_4$, filtered and then distilled under reduced pressure. The residue was purified by column chromatography (DCM:MeOH=100:0) on amine silica. The fractions containing the product were collected and evaporated to obtain ivory solid compound of (R)-tert-butyl (1-(2,7-dichloropyrido[2,3-b]pyrazin-3-yl)pyrrolidin-3-yl)(methyl)carbamate (169.0 mg, 99%).

LC/MS ESI (+): 398 (M+1), 400 (M+3)

(b) Synthesis of (R)-tert-butyl (1-(7-chloro-2-hydrazinylpyrido[2,3-b]pyrazin-3-yl)pyrrolidin-3-yl)(methyl)carbamate (R)-tert-butyl (1-(2,7-dichloropyrido[2,3-b]pyrazin-3-yl)pyrrolidin-3-yl)(methyl)carbamate (169.0 mg, 0.42 mmol) and hydrazine monohydrate (53.0 mg, 1.05 mmol) were dissolved in EtOH (5.0 mL), stirred at room temperature for 2 hours and then distilled under reduced pressure to obtain yellow solid compound of (R)-tert-butyl (1-(7-chloro-2-hydrazinylpyrido[2,3-b]pyrazin-3-yl)pyrrolidin-3-yl)(methyl)carbamate.

LC/MS ESI (+): 394 (M+1), 396 (M+3)

(c) Synthesis of (R)-tert-butyl (1-(8-chloropyrido[2,3-e][1,2,4]triazolo[4,3-a]pyrazin-4-yl)pyrrolidin-3-yl)(methyl)carbamate The mixture of unpurified (R)-tert-butyl (1-(7-chloro-2-hydrazinylpyrido[2,3-b]pyrazin-3-yl)pyrrolidin-3-yl)(methyl)carbamate and trimethyl orthoformate (5.0 mL) was stirred at 80° C. for one hour and then cooled to room temperature. Et$_2$O was added thereto to form a solid, and the formed solid was filtered and then dried under reduced pressure to obtain ivory solid compound of (R)-tert-butyl (1-(8-chloropyrido[2,3-e][1,2,4]triazolo[4,3-a]pyrazin-4-yl)pyrrolidin-3-yl)(methyl)carbamate.

LC/MS ESI (+): 404 (M+1), 406 (M+3)

(d) Synthesis of (R)-1-(8-chloropyrido[2,3-e][1,2,4]triazolo[4,3-a]pyrazin-4-yl)-N-methylpyrrolidin-3-amine Unpurified (R)-tert-butyl (1-(8-chloropyrido[2,3-e][1,2,4]triazolo[4,3-a]pyrazin-4-yl)pyrrolidin-3-yl)(methyl)carbamate was dissolved in DCM (3.0 mL), and TFA (1.0 mL) was slowly added thereto at 0° C. The reaction mixture was stirred at room temperature for 2 hours and then distilled under reduced pressure. The residue was neutralized with NaHCO$_3$ aqueous solution (pH=7), and it was then extracted with DCM (30.0 mL). The organic layer was washed with brine, dried over anhydrous Na$_2$SO$_4$, filtered and then distilled under reduced pressure. The residue was purified by column chromatography (DCM:MeOH=90:10 to 50:50) on silica. The fractions containing the product were collected and evaporated to obtain ivory solid compound of (R)-1-(8-chloropyrido[2,3-e][1,2,4]triazolo[4,3-a]pyrazin-4-yl)-N-methylpyrrolidin-3-amine (58.6 mg, 45% in 3 steps).

LC/MS ESI (+): 304 (M+1), 306 (M+3)

$^1$H-NMR (300 MHz, DMSO-d$_6$); δ: 9.97 (s, 1H), 8.80 (d, 1H, J=2.4 Hz), 8.53 (d, 1H, J=2.4 Hz), 4.50-4.20 (m, 2H), 3.90-3.40 (m, 2H), 3.30 (m, 1H), 2.32 (s, 3H), 2.20-1.80 (m, 2H)

Example 11

Synthesis of (R)-1-(3-chloropyrido[3,2-e][1,2,4]triazolo[4,3-a]pyrazin-6-yl)-N-methylpyrrolidin-3-amine Ivory solid compound of (R)-1-(3-chloropyrido[3,2-e][1,2,4]triazolo[4,3-a]pyrazin-6-yl)-N-methylpyrrolidin-3-amine (18.0 mg, 14%) was prepared as described in Example 10.

LC/MS ESI (+): 304 (M+1), 306 (M+3)

$^1$H-NMR (300 MHz, DMSO-d$_6$); δ: 9.84 (s, 1H), 8.31 (d, 1H, J=2.2 Hz), 8.04 (d, 1H, J=2.2 Hz), 4.50-4.20 (m, 2H), 3.90-3.50 (m, 2H), 3.30 (m, 1H), 2.33 (s, 3H), 2.20-1.80 (m, 2H)

Example 12

Synthesis of 8-bromo-4-(4-methylpiperazin-1-yl)pyrido[2,3-e][1,2,4]triazolo[4,3-a]pyrazine (a) Synthesis of 7-bromo-2,3-dichloropyrido[2,3-b]pyrazine 5-Bromopyridin-2,3-diamine (5000.0 mg, 2.66 mmol) was added to diethyl oxalate (20.0 mL), and the mixture was stirred at 120° C. for 12 hours and then cooled to room temperature. Et$_2$O was added thereto to form a solid. The formed solid was then filtered and dried under reduced pressure to obtain light brown solid compound of 7-bromopyrido[2,3-b]pyrazin-2,3-diol. The mixture of unpurified 7-bromopyrido[2,3-b]pyrazin-2,3-diol and POCl$_3$ (20.0 mL) was stirred at 130° C. for 12 hours and then cooled to room temperature. The reaction mixture was poured into ice water to form a solid. The formed solid was filtered and then dried under reduced pressure to obtain brown solid compound of 7-bromo-2,3-dichloropyrido[2,3-b]pyrazine (6500.0 mg, 72% in 2 steps).

LC/MS ESI (+): 278 (M+1), 280 (M+3)

$^1$H-NMR (300 MHz, DMSO-d$_6$); δ: 9.28 (d, 1H, J=2.4 Hz), 8.99 (d, 1H, J=2.4 Hz)

(b) Synthesis of 7-bromo-2-chloro-3-(4-methylpiperazin-1-yl)pyrido[2,3-b]pyrazine 7-Bromo-2,3-dichloropyrido[2,3-b]pyrazine (1000.0 mg, 3.59 mmol) and TEA (5.0 mL, 35.90 mmol) were dissolved in DCM (20.0 mL), and N-methyl piperazine (0.2 mL, 2.01 mmol) diluted in DCM (1.0 mL) was slowly added thereto at −10° C. The reaction mixture was stirred for 12 hours and then poured into saturated NH$_4$Cl aqueous solution and extracted with DCM (30.0 mL). The organic layer was washed with brine, dried over anhydrous Na$_2$SO$_4$, filtered and then distilled under reduced pressure. The residue was purified by column chromatography (DCM:MeOH=100:0) on amine silica. The fractions containing the product were collected and evaporated to obtain yellow solid compound of 7-bromo-2-chloro-3-(4-methylpiperazin-1-yl)pyrido[2,3-b]pyrazine (1000.0 mg, 81%).

LC/MS ESI (+): 342 (M+1), 344 (M+3)

(c) Synthesis of 8-bromo-4-(4-methylpiperazin-1-yl)pyrido[2,3-e][1,2,4]triazolo[4,3-a]pyrazine 7-Bromo-2-chloro-3-(4-methylpiperazin-1-yl)pyrido[2,3-b]pyrazine (413.0 mg, 0.12 mmol) and hydrazine monohydrate (150.0 mg, 0.30 mmol) were dissolved in EtOH (10.0 mL), stirred at room temperature for 4 hours and then distilled under reduced pressure. Et$_2$O was added thereto to form a solid. The formed solid was then filtered and dried under reduced pressure to obtain yellow solid compound of 7-bromo-2-hydrazinyl-3-(4-methylpiperazin-1-yl)pyrido[2,3-b]pyrazine. The mixture of unpurified 7-bromo-2-hydrazinyl-3-(4-methylpiperazin-1-yl)pyrido[2,3-b]pyrazine and trimethyl orthoformate (10.0 mL) was stirred at 80° C. for 2 hours and then cooled to room temperature. Et$_2$O was added thereto to form a solid. The formed solid was then filtered and dried under reduced pressure. The residue was purified by column chromatography (DCM:MeOH=100:0 to 95:5) on amine silica. The fractions containing the product were collected and evaporated to obtain ivory solid compound of 8-bromo-4-(4-methylpiperazin-1-yl)pyrido[2,3-e][1,2,4]triazolo[4,3-a]pyrazine (368.0 mg, 29% in 3 steps).

LC/MS ESI (+): 348 (M+1), 350 (M+3)

$^1$H-NMR (300 MHz, DMSO-d$_6$); δ: 10.01 (s, 1H), 8.95 (d, 1H, J=2.3 Hz), 8.63 (d, 1H, J=2.2 Hz), 4.40 (bs, 4H), 2.53 (m, 4H), 2.24 (s, 3H)

Example 13

Synthesis of 4-(4-methylpiperazin-1-yl)pyrido[2,3-e][1,2,4]triazolo[4,3-a]pyrazin-8-carbonitrile 8-Bromo-4-(4-methylpiperazin-1-yl)pyrido[2,3-e][1,2,4]triazolo[4,3-a]pyrazine (50.0 mg, 0.14 mmol), Zn(CN)$_2$ (17.0 mg, 0.14 mmol) and Pd(PPh$_3$)$_4$ (33.0 mg, 0.01 mmol) were dissolved in DMF (1.0 mL), and it was allowed to react in microwave under conditions of 60 W, 90° C. for 2 hours and then cooled to room temperature. The reaction mixture was then poured into water and extracted with DCM (30.0 mL). The organic layer was washed with brine, dried over anhydrous Na₂SO₄, filtered and then distilled under reduced pressure. The residue was purified by column chromatography (DCM:MeOH=100:0 to 95:5) on amine silica. The fractions containing the product were collected and evaporated to obtain ivory solid compound of 4-(4-methylpiperazin-1-yl)pyrido[2,3-e][1,2,4]triazolo[4,3-a]pyrazin-8-carbonitrile (6.0 mg, 13%).

LC/MS ESI (+): 295 (M+1)

$^1$H-NMR (300 MHz, DMSO-d₆); δ: 10.01 (s, 1H), 9.13 (d, 1H, J=2.0 Hz), 8.93 (d, 1H, J=2.0 Hz), 4.88 (bs, 2H), 4.14 (bs, 2H), 2.51 (m, 4H), 2.26 (s, 3H)

Example 14

Synthesis of 8-chloro-1-methyl-4-(4-methylpiperazin-1-yl)pyrido[2,3-e][1,2,4]triazolo[4,3-a]pyrazine (a) Synthesis of 2,7-dichloro-3-(4-methylpiperazin-1-yl)pyrido[2,3-b]pyrazine 2,3,7-Trichloropyrido[2,3-b]pyrazine (200.0 mg, 0.85 mmol) and TEA (1180.0 μL, 8.53 mmol) were dissolved in DCM (8.5 mL), and N-methyl piperazine (220.0 μL, 0.94 mmol) diluted in DCM (0.5 mL) was slowly added thereto at −20° C. The reaction mixture was stirred at −20° C. for 12 hours, and it was then poured into saturated NH₄Cl aqueous solution and extracted with DCM (30.0 mL). The organic layer was washed with brine, dried over anhydrous Na₂SO₄, filtered and then distilled under reduced pressure. The residue was purified by column chromatography (DCM:MeOH=99:1) on amine silica. The fractions containing the product were collected and evaporated to obtain yellow solid compound of 2,7-dichloro-3-(4-methylpiperazin-1-yl)pyrido[2,3-b]pyrazine (110.0 mg, 43%).

LC/MS ESI(+): 298 (M+1), 300 (M+3)

$^1$H-NMR (300 MHz, DMSO-d₆); δ: 8.94 (d, 1H, J=2.7 Hz), 8.51 (d, 1H, J=2.7 Hz), 3.61 (m, 4H), 2.52 (m, 4H), 2.25 (s, 3H).

(b) Synthesis of 7-chloro-2-hydrazinyl-3-(4-methylpiperazin-1-yl)pyrido[2,3-b]pyrazine 2,7-Dichloro-3-(4-methylpiperazin-1-yl)pyrido[2,3-b]pyrazine (100.0 mg, 0.36 mmol) and hydrazine monohydrate (46.0 μL, 0.84 mmol) were dissolved in EtOH (3.0 mL), stirred at room temperature for 12 hours and then evaporated under reduced pressure to obtain yellow solid compound of 7-chloro-2-hydrazinyl-3-(4-methylpiperazin-1-yl)pyrido[2,3-b]pyrazine (50.0 mg, 57%).

LC/MS ESI(+): 294 (M+1), 296 (M+3)

(c) Synthesis of 8-chloro-1-methyl-4-(4-methylpiperazin-1-yl)pyrido[2,3-e][1,2,4]triazolo[4,3-a]pyrazine The mixture of unpurified 7-chloro-2-hydrazinyl-3-(4-methylpiperazin-1-yl)pyrido[2,3-b]pyrazine (50.0 mg, 0.17 mmol) and trimethyl orthoacetate (1.0 mL) was stirred at 80° C. for 2 hours and then cooled to room temperature. Et₂O was added thereto to form a solid, and the formed solid was filtered and then dried under reduced pressure. The residue was purified by column chromatography (DCM:MeOH=95:5) on amine silica. The fractions containing the product were collected and evaporated ivory solid compound of 8-chloro-1-methyl-4-(4-methylpiperazin-1-yl)pyrido[2,3-e][1,2,4]triazolo[4,3-a]pyrazine (30.0 mg, 56%).

LC/MS ESI(+): 318 (M+1), 320 (M+3)

$^1$H-NMR (300 MHz, DMSO-d₆); δ: 8.56 (d, 1H, J=2.4 Hz), 8.42 (d, 1H, J=2.4 Hz), 4.36 (m, 4H), 3.02 (s, 3H), 2.49 (m, 4H), 2.25 (s, 3H)

Example 15

Synthesis of 8-chloro-1-methyl-4-(piperazin-1-yl)pyrido[2,3-e][1,2,4]triazolo[4,3-a]pyrazine (a) Synthesis of tert-butyl 4-(2,7-dichloropyrido[2,3-b]pyrazin-3-yl)piperazin-1-carboxylate 2,3,7-Trichloropyrido[2,3-b]pyrazine (200.0 mg, 0.85 mmol) and TEA (1.2 mL, 8.53 mmol) were dissolved in DCM (8.5 mL), and tert-butyl piperazin-1-carboxylate (174.7 mg, 0.94 mmol) diluted in DCM (0.5 mL) was slowly added thereto at −20° C. The reaction mixture was stirred at −20° C. for 12 hours, and it was then poured into saturated NH₄Cl aqueous solution and extracted with DCM (30.0 mL). The organic layer was washed with brine, dried over anhydrous Na₂SO₄, filtered and then distilled under reduced pressure. The residue was purified by column chromatography (DCM:MeOH=100:0) on amine silica. The fractions containing the product were collected and evaporated to obtain yellow solid compound of tert-butyl 4-(2,7-dichloropyrido[2,3-b]pyrazin-3-yl)piperazin-1-carboxylate (110.0 mg, 64%).

LC/MS ESI(+): 384 (M+1), 386 (M+3)

$^1$H-NMR (300 MHz, DMSO-d₆); δ: 8.96 (d, 1H, J=2.4 Hz), 8.54 (d, 1H, J=2.4 Hz), 3.61 (m, 4H), 3.54 (m, 4H), 1.43 (s, 9H)

(b) Synthesis of tert-butyl 4-(7-chloro-2-hydrazinylpyrido[2,3-b]pyrazin-3-yl)piperazin-1-carboxylate tert-Butyl 4-(2,7-dichloropyrido[2,3-b]pyrazin-3-yl)piperazin-1-carboxylate (110.0 mg, 0.29 mmol) and hydrazine monohydrate (35.0 μL, 0.72 mmol) were dissolved in EtOH (2.0 mL), stirred at room temperature for 12 hours and then evaporated under reduced pressure to obtain yellow solid compound of tert-butyl 4-(7-chloro-2-hydrazinylpyrido[2,3-b]pyrazin-3-yl)piperazin-1-carboxylate (55.0 mg, 51%).

LC/MS ESI(+): 380 (M+1), 382 (M+3)

(c) Synthesis of tert-butyl 4-(8-chloro-1-methylpyrido[2,3-e][1,2,4]triazolo[4,3-a]pyrazin-4-yl)piperazin-1-carboxylate The mixture of unpurified tert-butyl 4-(7-chloro-2-hydrazinylpyrido[2,3-b]pyrazin-3-yl)piperazin-1-carboxylate (55.0 mg, 0.15 mmol) and trimethyl orthoacetate (0.7 mL) was stirred at 80° C. for 2 hours and then cooled to room temperature. Et₂O and n-Hex (30.0 mL) were added thereto to form a solid, and the formed solid was filtered and then dried under reduced pressure to obtain tert-butyl 4-(8-chloro-1-methylpyrido[2,3-e][1,2,4]triazolo[4,3-a]pyrazin-4-yl)piperazin-1-carboxylate (35.0 mg, 60%).

(d) Synthesis of 8-chloro-1-methyl-4-(piperazin-1-yl)pyrido[2,3-e][1,2,4]triazolo[4,3-a]pyrazine Unpurified tert-butyl 4-(8-chloro-1-methylpyrido[2,3-e][1,2,4]triazolo[4,3-a]pyrazin-4-yl)piperazin-1-carboxylate (35.0 mg, 0.09 mmol) was dissolved in DCM (2.0 mL), and TFA (0.5 mL) was slowly added thereto at room temperature, and it was then stirred at room temperature for 2 hours.

The reaction mixture was distilled under reduced pressure. The residue was purified by column chromatography (DCM:MeOH=80:20) on silica. The fractions containing the product were collected and evaporated to obtain yellow solid compound of 8-chloro-1-methyl-4-(piperazin-1-yl)pyrido[2,3-e][1,2,4]triazolo[4,3-a]pyrazine (9.0 mg, 35%).

LC/MS ESI(+): 304 (M+1), 306 (M+3)

$^1$H-NMR (300 MHz, DMSO-$d_6$); δ: 8.55 (m, 1H), 8.42 (m, 1H), 4.34 (m, 4H), 3.04 (s, 3H), 2.87 (m, 4H)

Example 16

Synthesis of 8-bromo-4-(piperazin-1-yl)pyrido[2,3-e][1,2,4]triazolo[4,3-a]pyrazine (a) Synthesis of tert-butyl 4-(7-bromo-2-chloropyrido[2,3-b]pyrazin-3-yl)piperazin-1-carboxylate 7-Bromo-2,3-dichloropyrido[2,3-b]pyrazine (1000.0 mg, 2.33 mmol) and TEA (3.3 mL, 23.30 mmol) were dissolved in DCM (20.0 mL), and tert-butyl piperazin-1-carboxylate (478.0 mg, 2.56 mmol) diluted in DCM (10.0 mL) was slowly added thereto at 0° C. The reaction mixture was stirred at room temperature for 12 hours, and it was then poured into saturated NH$_4$Cl aqueous solution and extracted with DCM (30.0 mL). The organic layer was washed with brine, dried over anhydrous Na$_2$SO$_4$, filtered and then distilled under reduced pressure. The residue was purified by column chromatography (DCM:MeOH=100:0) on amine silica. The fractions containing the product were collected and evaporated to obtain yellow solid compound of tert-butyl 4-(7-bromo-2-chloropyrido[2,3-b]pyrazin-3-yl)piperazin-1-carboxylate

LC/MS ESI (+): 428 (M+1), 430 (M+3)

(b) Synthesis of tert-butyl 4-(7-bromo-2-hydrazinylpyrido[2,3-b]pyrazin-3-yl)piperazin-1-carboxylate Unpurified tert-butyl 4-(7-bromo-2-chloropyrido[2,3-b]pyrazin-3-yl)piperazin-1-carboxylate and hydrazine monohydrate (292.0 mg, 5.83 mmol) were dissolved in EtOH (50.0 mL), stirred at room temperature for 12 hours and then distilled under reduced pressure. Et$_2$O was added thereto to form a solid, and the formed solid was filtered and then dried under reduced pressure to obtain yellow solid compound of tert-butyl 4-(7-bromo-2-hydrazinylpyrido[2,3-b]pyrazin-3-yl)piperazin-1-carboxylate.

LC/MS ESI (+): 424 (M+1), 426 (M+3)

(c) Synthesis of tert-butyl 4-(8-bromopyrido[2,3-e][1,2,4]triazolo[4,3-a]pyrazin-4-yl)piperazin-1-carboxylate The mixture of unpurified tert-butyl 4-(7-bromo-2-hydrazinylpyrido[2,3-b]pyrazin-3-yl)piperazin-1-carboxylate and trimethyl orthoformate (10.0 mL) was stirred at 80° C. for one hour and then cooled to room temperature. Et$_2$O was added thereto to form a solid, and the formed solid was filtered and then dried under reduced pressure to obtain yellow solid compound of tert-butyl 4-(8-bromopyrido[2,3-e][1,2,4]triazolo[4,3-a]pyrazin-4-yl)piperazin-1-carboxylate.

LC/MS ESI (+): 434 (M+1), 436 (M+3)

(d) Synthesis of 8-bromo-4-(piperazin-1-yl)pyrido[2,3-e][1,2,4]triazolo[4,3-a]pyrazine Unpurified tert-butyl 4-(8-bromopyrido[2,3-e][1,2,4]triazolo[4,3-a]pyrazin-4-yl)piperazin-1-carboxylate was dissolved in DCM (8.0 mL), and TFA (2.0 mL) was slowly added thereto at 0° C. The reaction mixture was stirred at room temperature for 2 hours and then distilled under reduced pressure. The residue was neutralized with NaHCO$_3$ aqueous solution (pH=7) and extracted with DCM (30.0 mL). The organic layer was washed with brine, dried over anhydrous Na$_2$SO$_4$, filtered and then distilled under reduced pressure. The residue was purified by column chromatography (DCM:MeOH=99:1) on amine silica. The fractions containing the product were collected and evaporated to obtain ivory solid compound of 8-bromo-4-(piperazin-1-yl)pyrido[2,3-e][1,2,4]triazolo[4,3-a]pyrazine (270.0 mg, 35% in 3 steps).

LC/MS ESI (+): 334 (M+1), 336 (M+3)

$^1$H-NMR (300 MHz, DMSO-$d_6$); δ: 10.01 (s, 1H), 8.94 (d, 1H, J=2.3 Hz), 8.63 (d, 1H, J=2.2 Hz), 4.36 (bs, 4H), 2.89 (m, 4H)

Example 17

Synthesis of 7,8-dichloro-4-(4-methylpiperazin-1-yl)pyrido[2,3-e][1,2,4]triazolo[4,3-a]pyrazine (a) Synthesis of 5,6-dichloropyridin-2,3-diamine 5-Chloro-3-nitropyridin-2-amine (2000.0 mg, 11.52 mmol) and SnCl$_2$ (8740.0 mg, 46.09 mmol) were added in conc. HCl (20.0 mL) and then stirred at 80-100° C. for 0.5 hour. The reaction mixture was neutralized with saturated 1N NaOH aqueous solution (pH=7), and it was then extracted with EtOAc (200.0 mL). The organic layer was washed with brine, dried over anhydrous Na$_2$SO$_4$, filtered and then distilled under reduced pressure. The residue was purified by column chromatography (n-Hex:EtOAc=90:10) on silica. The fractions containing the product were collected and evaporated to obtain ivory solid compound of 5,6-dichloropyridin-2,3-diamine (1000.0 mg, 49%).

$^1$H-NMR (300 MHz, DMSO-$d_6$); δ: 6.80 (s, 1H), 6.04 (s, 2H), 5.11 (s, 2H)

(b) Synthesis of 2,3,6,7-tetrachloropyrido[2,3-b]pyrazine 5,6-Dichloropyridin-2,3-diamine (1000.0 mg, 5.62 mmol) was added to diethyl oxalate (20.0 mL), and the mixture was stirred at 120° C. for 12 hours and then cooled to room temperature. Et$_2$O was added thereto to form a solid, and the formed solid was filtered and dried under reduced pressure to obtain brown solid compound of 6,7-dichloropyrido[2,3-b]pyrazin-2,3(1H,4H)-dione. The mixture of unpurified 6,7-dichloropyrido[2,3-b]pyrazin-2,3(1H,4H)-dione and POCl$_3$ (20.0 mL) was stirred at 130° C. for 48 hours and then cooled to room temperature. The reaction mixture was poured into ice water to form a solid, and the formed solid was filtered and then dried under reduced pressure to obtain brown solid compound of 2,3,6,7-tetrachloropyrido[2,3-b]pyrazine (1200.0 mg, 72% in 2 steps).

$^1$H-NMR (300 MHz, DMSO-$d_6$); δ: 9.09 (s, 1H)

(c) Synthesis of 2,6,7-trichloro-3-(4-methylpiperazin-1-yl)pyrido[2,3-b]pyrazine 2,3,6,7-Tetrachloropyrido[2,3-b]pyrazine (190.0 mg, 0.71 mmol) and TEA (1.0 mL, 7.10 mmol) were dissolved in DCM (8.0 mL), N-methyl piperazine (85.0 mg, 0.85 mmol) diluted in DCM (2.0 mL) was slowly added thereto at −20° C. and stirred for 12 hours. The reaction mixture was poured into saturated NH₄Cl aqueous solution and extracted with DCM (30.0 mL). The organic layer was washed with brine, dried over anhydrous Na₂SO₄, filtered and then distilled under reduced pressure to obtain yellow solid compound of 2,6,7-trichloro-3-(4-methylpiperazin-1-yl)pyrido[2,3-b]pyrazine.

LC/MS ESI (+): 332 (M+1), 334 (M+3)

(d) Synthesis of 7,8-dichloro-4-(4-methylpiperazin-1-yl)pyrido[2,3-e][1,2,4]triazolo[4,3-a]pyrazine Unpurified 2,6,7-trichloro-3-(4-methylpiperazin-1-yl)pyrido[2,3-b]pyrazine and hydrazine monohydrate (89.0 mg, 1.78 mmol) were dissolved in EtOH (10.0 mL), stirred at room temperature for 12 hours and then distilled under reduced pressure to obtain yellow solid compound of 6,7-dichloro-2-hydrazinyl-3-(4-methylpiperazin-1-yl)pyrido[2,3-b]pyrazine. The mixture of unpurified 6,7-dichloro-2-hydrazinyl-3-(4-methylpiperazin-1-yl)pyrido[2,3-b]pyrazine and trimethyl orthoformate (5.0 mL) was stirred at 80° C. for one hour and then cooled to room temperature. Et₂O was added thereto to form a solid, and the formed solid was filtered and then dried under reduced pressure. The residue was column chromatography (DCM:MeOH=100:0) on amine silica. The fractions containing the product were collected and evaporated to obtain ivory solid compound of 7,8-dichloro-4-(4-methylpiperazin-1-yl)pyrido[2,3-e][1,2,4]triazolo[4,3-a]pyrazine (107.0 mg, 45% in 3 steps).

LC/MS ESI (+): 338 (M+1), 340 (M+3)
¹H-NMR (300 MHz, DMSO-d₆); δ: 9.99 (s, 1H), 9.01 (s, 1H), 4.80-3.80 (m, 4H), 2.51 (m, 4H), 2.24 (s, 3H)

Example 18

Synthesis of 1-(8-chloropyrido[2,3-e][1,2,4]triazolo[4,3-a]pyrazin-4-yl)-N-methylazetidin-3-amine (a) Synthesis of tert-butyl (1-(2,7-dichloropyrido[2,3-b]pyrazin-3-yl)azetidin-3-yl)(methyl)carbamate 2,3,7-Trichloropyrido[2,3-b]pyrazine (100.0 mg, 0.43 mmol) was dissolved in DCM (4.2 mL), tert-butyl azetidin-3-yl(methyl)carbamate (88.0 mg, 0.47 mmol) and TEA (0.2 mL, 1.28 mmol) were added thereto at 0° C., and it was then stirred for one hour. Solvent was removed from the reaction mixture under reduced pressure. The residue was purified by column chromatography (EtOAc:n-Hex=1:5) on silica. The fractions containing the product were collected and evaporated to obtain yellow solid compound of tert-butyl (1-(2,7-dichloropyrido[2,3-b]pyrazin-3-yl)azetidin-3-yl)(methyl)carbamate (118.0 mg, 72%).

LC/MS ESI(+): 384 (M+1), 386 (M+3)
¹H-NMR (300 MHz, DMSO-d₆); δ: 8.83 (d, 1H, J=2.4 Hz), 8.40 (d, 1H, J=2.4 Hz), 4.86 (m, 1H), 4.62 (m, 2H), 4.48 (m, 2H), 2.90 (s, 3H), 1.41 (s, 9H)

(b) Synthesis of tert-butyl (1-(7-chloro-2-hydrazinylpyrido[2,3-b]pyrazin-3-yl)azetidin-3-yl)(methyl)carbamate tert-Butyl (1-(2,7-dichloropyrido[2,3-b]pyrazin-3-yl)azetidin-3-yl)(methyl)carbamate (116.0 mg, 0.30 mmol) was dissolved in EtOH (4.2 mL), and hydrazine monohydrate (24.0 μL, 0.76 mmol) was then added thereto. The reaction mixture was stirred at room temperature for one hour. Et₂O was added thereto to form a solid, and the formed solid was filtered and then dried under reduced pressure to obtain yellow solid compound of tert-butyl (1-(7-chloro-2-hydrazinylpyrido[2,3-b]pyrazin-3-yl)azetidin-3-yl)(methyl)carbamate (114.0 mg, 100%).

LC/MS ESI(+): 380 (M+1), 382 (M+3)
¹H-NMR (300 MHz, DMSO-d₆); δ: 7.77 (bs, 1H), 7.25 (bs, 1H), 7.05 (m, 3H), 4.65 (m, 2H), 4.46 (m, 1H), 4.24 (m, 2H), 2.86 (s, 3H), 1.40 (s, 9H)

(c) Synthesis of tert-butyl (1-(8-chloropyrido[2,3-e][1,2,4]triazolo[4,3-a]pyrazin-4-yl)azetidin-3-yl)(methyl)carbamate tert-Butyl (1-(7-chloro-2-hydrazinylpyrido[2,3-b]pyrazin-3-yl)azetidin-3-yl)(methyl)carbamate (119.0 mg, 0.31 mmol) was dissolved in trimethyl orthoformate (1.5 mL) and then stirred at 75° C. for one hour. The reaction mixture was cooled to room temperature and then dried under reduced pressure to obtain yellow solid compound of tert-butyl (1-(8-chloropyrido[2,3-e][1,2,4]triazolo[4,3-a]pyrazin-4-yl)azetidin-3-yl)(methyl)carba mate (120.0 mg, 98%).

LC/MS ESI(+): 390 (M+1), 392 (M+3)

(d) Synthesis of 1-(8-chloropyrido[2,3-e][1,2,4]triazolo[4,3-a]pyrazin-4-yl)-N-methylazetidin-3-amine tert-Butyl (1-(8-chloropyrido[2,3-e][1,2,4]triazolo[4,3-a]pyrazin-4-yl)azetidin-3-yl)(methyl)carba mate (120.0 mg, 0.31 mmol) was dissolved in DCM (0.6 mL), and then TFA (0.4 mL) was added thereto. The reaction mixture was stirred at room temperature for one hour. Solvent was then removed from the reaction mixture under reduced pressure. The residue was purified by column chromatography (MeOH:DCM=1:60) on amine silica. The fractions containing the product were collected and evaporated to obtain yellow solid compound of 1-(8-chloropyrido[2,3-e][1,2,4]triazolo[4,3-a]pyrazin-4-yl)-N-methylazetidin-3-amine (50.0 mg, 57%).

LC/MS ESI(+): 290 (M+1), 292 (M+3)
¹H-NMR (300 MHz, DMSO-d₆); δ: 9.95 (s, 1H), 8.81 (d, 1H, J=2.4 Hz), 8.54 (d, 1H, J=2.4 Hz), 4.89 (m, 1H), 4.43 (m, 2H), 3.99 (m, 1H), 3.71 (m, 1H), 2.29 (s, 3H)

Example 19

Synthesis of (S)-8-chloro-4-(3-methylpiperazin-1-yl)pyrido[2,3-e][1,2,4]triazolo[4,3-a]pyrazine (a) Synthesis of (S)-tert-butyl 4-(2,7-dichloropyrido[2,3-b]pyrazin-3-yl)-2-methylpiperazin-1-carboxylate 2,3,7-Trichloropyrido[2,3-b]pyrazine (200.0 mg, 0.85 mmol) and TEA (1180.0 μL, 8.53 mmol) were dissolved in DCM (8.5 mL), and (S)-tert-butyl 2-methylpiperazin-1-carboxylate (187.8 mg, 0.94 mmol) diluted in DCM (0.5 mL) was slowly added thereto at −20° C. The reaction mixture was stirred at −20° C. for 12 hours, and it was poured into saturated NH₄Cl aqueous solution and extracted with DCM (30.0 mL). The organic layer was washed with brine, dried over anhydrous Na₂SO₄, filtered and then distilled under reduced pressure. The residue was purified by column chromatography (EtOAc:n-Hex=30:70) on silica. The fractions containing the product were collected and evaporated to obtain yellow solid compound of (S)-tertbutyl 4-(2,7-dichloropyrido[2,3-b]pyrazin-3-yl)-2-methylpiperazin-1-carboxylate (233.0 mg, 67%).

LC/MS ESI(+): 398 (M+1), 400 (M+3)

$^1$H-NMR (300 MHz, DMSO-d$_6$); δ: 8.96 (d, 1H, J=2.7 Hz), 8.54 (d, 1H, J=2.7 Hz), 4.30 (m, 1H), 4.09 (m, 2H), 3.88 (m, 1H), 3.20 (m, 2H), 3.04 (m, 1H), 1.43 (s, 9H), 1.24 (d, 3H, J=6.6 Hz)

(b) Synthesis of (S)-tert-butyl 4-(7-chloro-2-hydrazinylpyrido[2,3-b]pyrazin-3-yl)-2-methylpiperazin-1-carboxylate (S)-tert-butyl 4-(2,7-dichloropyrido[2,3-b]pyrazin-3-yl)-2-methylpiperazin-1-carboxylate (230.0 mg, 0.58 mmol) and hydrazine monohydrate (70.0 μL, 1.44 mmol) were dissolved in EtOH (2.0 mL). The mixture was then stirred at room temperature for 12 hours under reduced pressure to obtain yellow solid compound of (S)-tert-butyl 4-(7-chloro-2-hydrazinylpyrido[2,3-b]pyrazin-3-yl)-2-methylpiperazin-1-carboxylate (220.0 mg, 97%).

LC/MS ESI(+): 394 (M+1), 396 (M+3)

(c) Synthesis of (S)-tert-butyl 4-(8-chloropyrido[2,3-e][1,2,4]triazolo[4,3-a]pyrazin-4-yl)-2-methylpiperazin-1-carboxylate The mixture of unpurified (S)-tert-butyl 4-(7-chloro-2-hydrazinylpyrido[2,3-b]pyrazin-3-yl)-2-methylpiperazin-1-carboxylate (150.0 mg, 0.38 mmol) and trimethyl orthoformate (2.0 mL) was stirred at 80° C. for 2 hours and then cooled to room temperature. Et$_2$O was added thereto to form a solid, and the formed solid was filtered and then dried under reduced pressure to obtain (S)-tert-butyl 4-(8-chloropyrido[2,3-e][1,2,4]triazolo[4,3-a]pyrazin-4-yl)-2-methylpiperazin-1-carboxylate (150.0 mg, 81%).

(d) Synthesis of (S)-8-chloro-4-(3-methylpiperazin-1-yl)pyrido[2,3-e][1,2,4]triazolo[4,3-a]pyrazine Unpurified (S)-tert-butyl 4-(8-chloropyrido[2,3-e][1,2,4]triazolo[4,3-a]pyrazin-4-yl)-2-methylpiperazin-1-carboxylate (150.0 mg, 0.37 mmol) was dissolved in DCM (1.0 mL). TFA (0.2 mL) was slowly added thereto at room temperature, and it was then stirred at room temperature for 2 hours. The reaction mixture was distilled under reduced pressure. The residue was purified by column chromatography (DCM:MeOH=95:5) on amine silica. The fractions containing the product were collected and evaporated to obtain yellow solid compound of (S)-8-chloro-4-(3-methylpiperazin-1-yl)pyrido[2,3-e][1,2,4]triazolo[4,3-a]pyrazine (70.0 mg, 63%).

LC/MS ESI(+): 304 (M+1), 306 (M+3)

$^1$H-NMR (300 MHz, CDCl$_3$); δ: 9.15 (s, 1H), 8.61 (d, 1H, J=2.4 Hz), 8.04 (d, 1H, J=2.4 Hz), 6.24 (m, 1H), 5.21 (m, 1H), 3.02 (m, 5H), 1.21 (d, 3H, J=6 Hz)

Example 20

Synthesis of (S)-8-chloro-4-(3,4-dimethylpiperazin-1-yl)pyrido[2,3-e][1,2,4]triazolo[4,3-a]pyrazine (S)-8-Chloro-4-(3-methylpiperazin-1-yl)pyrido[2,3-e][1,2,4]triazolo[4,3-a]pyrazine (50.0 mg, 0.16 mmol) obtained from (d) of Example 19 and 37% formaldehyde (73.5 μL, 0.99 mmol) were dissolved in MeOH (0.5 mL). NaBH$_4$ (37.0 mg, 0.99 mmol) was slowly added thereto, and it was then stirred at room temperature for 12 hours. Brine was poured into the reaction mixture, and it was extracted with DCM (30.0 mL). The organic layer was dried over anhydrous Na$_2$SO$_4$, filtered and then distilled under reduced pressure. The residue was purified column chromatography (DCM:MeOH=95:5) on silica to obtain yellow solid compound of (S)-8-chloro-4-(3,4-dimethylpiperazin-1-yl)pyrido[2,3-e][1,2,4]triazolo[4,3-a]pyrazine (70.0 mg, 48%).

LC/MS ESI(+): 318 (M+1), 320 (M+3)

$^1$H-NMR (300 MHz, CDCl$_3$); δ: 9.15 (s, 1H), 8.62 (d, 1H, J=2.4 Hz), 8.03 (d, 1H, J=2.1 Hz), 6.06 (m, 1H), 5.12 (m, 1H), 3.56 (m, 2H), 2.99 (m, 1H), 2.37 (m, 5H), 1.22 (d, 3H, J=6.3 Hz)

Example 21

Synthesis of 8-chloro-4-(4-methylpiperazin-1-yl)pyrido[2,3-e][1,2,4]triazolo[4,3-a]pyrazin-7-carbonitrile 7,8-Dichloro-4-(4-methylpiperazin-1-yl)pyrido[2,3-e][1,2,4]triazolo[4,3-a]pyrazine (10.0 mg, 0.03 mmol), Zn(CN)$_2$ (4.0 mg, 0.03 mmol) and Pd(PPh$_3$)$_4$ (3.0 mg, 0.003 mmol) were dissolved in DMF (1.0 mL). The mixture was allowed to react in microwaver under conditions of 60 W, 100° C. for one hour and then cooled to room temperature. The reaction mixture was poured into water and extracted with DCM (30.0 mL). The organic layer was washed with brine, dried over anhydrous Na$_2$SO$_4$, filtered and then distilled under reduced pressure. The residue was purified by column chromatography (DCM:MeOH=100:0) on amine silica. The fractions containing the product were collected and evaporated to obtain ivory solid compound of 8-chloro-4-(4-methylpiperazin-1-yl)pyrido[2,3-e][1,2,4]triazolo[4,3-a]pyrazin-7-carbonitrile (2.0 mg, 20%).

LC/MS ESI (+): 329 (M+1), 331 (M+3)

$^1$H-NMR (300 MHz, DMSO-d$_6$); δ: 10.04 (s, 1H), 9.07 (s, 1H), 4.80 (m, 2H), 4.09 (m, 2H), 2.54 (m, 4H), 2.25 (s, 3H)

Example 22

Synthesis of 8-chloro-4-(3,4,5-trimethylpiperazin-1-yl)pyrido[2,3-e][1,2,4]triazolo[4,3-a]pyrazine (a) Synthesis of tert-butyl 3,5-dimethylpiperazin-1-carboxylate 2,6-Dimethylpiperazine (200.0 mg, 1.75 mmol) and TEA (0.6 mL, 4.37 mmol) were dissolved in DCM (6.0 mL), and (Boc)$_2$O (458.7 mg, 2.10 mmol) was slowly added thereto at 0° C. The reaction mixture was stirred at room temperature for 12 hours and then distilled under reduced pressure. The residue was purified by column chromatography (DCM:MeOH=95:5) on silica. The fractions containing the product were collected and evaporated to obtain yellow liquid compound of tert-butyl 3,5-dimethylpiperazin-1-carboxylate (210.0 mg, 56%).

$^1$H-NMR (300 MHz, CDCl$_3$); δ: 3.95 (m, 2H), 2.79 (m, 2H), 2.33 (m, 2H), 1.46 (s, 9H), 1.07 (d, 6H, J=6.3 Hz)

(b) Synthesis of tert-butyl 3,4,5-trimethylpiperazin-1-carboxylate tert-Butyl 3,5-dimethylpiperazin-1-carboxylate (200.0 mg, 0.93 mmol) and 37% formaldehyde (440.0 μL, 5.56 mmol) were dissolved in MeOH (5.0 mL), and NaBH$_4$ (172.6 mg, 5.56 mmol) was slowly added thereto and stirred at room temperature for 12 hours. Brine was poured into the reaction mixture, and it was extracted with DCM (30.0 mL).

The organic layer was dried over anhydrous Na₂SO₄, filtered and then distilled under reduced pressure. The residue was purified column chromatography (DCM:MeOH=95:5) on silica to obtain yellow liquid compound of tert-butyl 3,4,5-trimethylpiperazin-1-carboxylate (57.0 mg, 27%).

(c) Synthesis of 1,2,6-trimethylpiperazine tert-Butyl 3,4,5-trimethylpiperazin-1-carboxylate (57.0 mg, 0.25 mmol) was dissolved in DCM (1.0 mL), and TFA (0.2 mL) was slowly added thereto at room temperature. The reaction mixture was stirred at room temperature for 2 hours, then distilled under reduced pressure and purified by column chromatography (DCM:MeOH=95:5) on amine silica. The fractions containing the product were collected and evaporated to obtain yellow liquid compound of 1,2,6-trimethylpiperazine (32.0 mg, 100%).

$^1$H-NMR (300 MHz, CDCl₃); δ: 2.88 (m, 2H), 2.58 (m, 2H), 2.28 (s, 3H), 2.14 (m, 2H), 1.07 (d, 6H, J=6 Hz)

(d) Synthesis of 2,7-dichloro-3-(3,4,5-trimethylpiperazin-1-yl)pyrido[2,3-b]pyrazine 2,3,7-Trichloropyrido[2,3-b]pyrazine (58.4 mg, 0.25 mmol) and TEA (347.0 μL, 2.49 mmol) were dissolved in DCM (1.0 mL), and 1,2,6-trimethylpiperazine (32.0 mg, 0.25 mmol) in DCM (0.5 mL) was slowly added thereto at −20° C. The reaction mixture was stirred at −20° C. for 12 hours, and it was then poured into saturated NH₄Cl aqueous solution and extracted with DCM (30.0 mL). The organic layer was washed with brine, dried over anhydrous Na₂SO₄, filtered and then evaporated under reduced pressure to obtain yellow solid compound of 2,7-dichloro-3-(3,4,5-trimethylpiperazin-1-yl)pyrido[2,3-b]pyrazine (23.0 mg, 28%).

LC/MS ESI(+): 326 (M+1), 328 (M+3)

(e) Synthesis of 7-chloro-2-hydrazinyl-3-(3,4,5-trimethylpiperazin-1-yl)pyrido[2,3-b]pyrazine 2,7-Dichloro-3-(3,4,5-trimethylpiperazin-1-yl)pyrido[2,3-b]pyrazine (23.0 mg, 0.07 mmol) and hydrazine monohydrate (8.0 μL, 0.18 mmol) were dissolved in EtOH (0.3 mL), and it was stirred at room temperature for 12 hours and then evaporated under reduced pressure to obtain yellow solid compound of 7-chloro-2-hydrazinyl-3-(3,4,5-trimethylpiperazin-1-yl)pyrido[2,3-b]pyrazine (23.0 mg, 100%).

LC/MS ESI(+): 322 (M+1), 324 (M+3)

(f) Synthesis of Synthesis of 8-chloro-4-(3,4,5-trimethylpiperazin-1-yl)pyrido[2,3-e][1,2,4]triazolo[4,3-a]pyrazine The mixture of unpurified 7-chloro-2-hydrazinyl-3-(3,4,5-trimethylpiperazin-1-yl)pyrido[2,3-b]pyrazine (23.0 mg, 0.07 mmol) and trimethyl orthoformate (2.0 mL) was stirred at 80° C. for 2 hours and then cooled to room temperature. Et₂O was added thereto to form a solid, and the formed solid was filtered and then dried under reduced pressure to obtain 8-chloro-4-(3,4,5-trimethylpiperazin-1-yl)pyrido[2,3-e][1,2,4]triazolo[4,3-a]pyrazine (5.0 mg, 21%).

LC/MS ESI(+): 332 (M+1), 334 (M+3)

$^1$H-NMR (300 MHz, CDCl₃); δ: 9.15 (s, 1H), 8.62 (d, 1H, J=2.4 Hz), 8.04 (d, 1H, J=2.4 Hz), 6.17 (m, 1H), 5.18 (m, 1H), 3.28 (m, 1H), 2.93 (m, 1H), 2.39 (m, 2H), 2.34 (s, 3H) 1.26 (s, 6H)

Example 23

Synthesis of 8-chloro-7-ethoxy-4-(4-methylpiperazin-1-yl)pyrido[2,3-e][1,2,4]triazolo[4,3-a]pyrazine 7,8-Dichloro-4-(4-methylpiperazin-1-yl)pyrido[2,3-e][1,2,4]triazolo[4,3-a]pyrazine (20.0 mg, 0.06 mmol) and NaOEt (5.0 mg, 0.07 mmol) were dissolved in EtOH (1.0 mL), and it was allowed to react in microwaver under conditions of 60 W, 90° C. for 2 hours and then cooled to room temperature. The reaction mixture was purified by column chromatography (DCM:MeOH=98:2) on amine silica. The fractions containing the product were collected and evaporated to obtain ivory solid compound of 8-chloro-7-ethoxy-4-(4-methylpiperazin-1-yl)pyrido[2,3-e][1,2,4]triazolo[4,3-a]pyrazine (3.0 mg, 14%).

LC/MS ESI (+): 348 (M+1), 350 (M+3)

$^1$H-NMR (300 MHz, DMSO-d₆); δ: 9.91 (s, 1H), 8.84 (s, 1H), 4.44 (q, 2H, J=7.0 Hz), 4.40 (m, 4H), 2.50 (m, 4H), 2.24 (s, 3H), 2.24 (t, 3H, J=7.0 Hz)

Example 24

Synthesis of 1-(8-bromopyrido[2,3-e][1,2,4]triazolo[4,3-a]pyrazin-4-yl)-N-methylazetidin-3-amine (a) Synthesis of tert-butyl (1-(7-bromo-2-chloropyrido[2,3-b]pyrazin-3-yl)azetidin-3-yl)(methyl)carbamate 7-Bromo-2,3-dichloropyrido[2,3-b]pyrazine (200.0 mg, 0.72 mmol) and TEA (1.0 mL, 7.20 mmol) were dissolved in DCM (8.0 mL), and tert-butyl azetidin-3-yl(methyl)carbamate (147.0 mg, 0.79 mmol) diluted in DCM (2.0 mL) was slowly added thereto at 0° C. The reaction mixture was stirred at room temperature for 12 hours, and it was then poured into saturated NH₄Cl aqueous solution and extracted with DCM (30.0 mL). The organic layer was washed with brine, dried over anhydrous Na₂SO₄, filtered and then distilled under reduced pressure. The residue was purified by column chromatography (DCM:MeOH=100:0) on amine silica. The fractions containing the product were collected and evaporated to obtain brown solid compound of tert-butyl (1-(7-bromo-2-chloropyrido[2,3-b]pyrazin-3-yl)azetidin-3-yl)(methyl)carbamate.

LC/MS ESI (+): 428 (M+1), 430 (M+3)

(b) Synthesis of tert-butyl (1-(7-bromo-2-hydrazinylpyrido[2,3-b]pyrazin-3-yl)azetidin-3-yl)(methyl)carbamate Unpurified tert-butyl (1-(7-bromo-2-chloropyrido[2,3-b]pyrazin-3-yl)azetidin-3-yl)(methyl)carbamate (224.0 mg, 0.61 mmol) and hydrazine monohydrate (72.0 mg, 3.78 mmol) were dissolved in EtOH (10.0 mL), stirred at room temperature for 12 hours and then distilled under reduced pressure. Et₂O was added thereto to form a solid, and the formed solid was filtered and then dried under reduced pressure to obtain yellow solid compound of tert-butyl (1-(7-bromo-2-hydrazinylpyrido[2,3-b]pyrazin-3-yl)azetidin-3-yl)(methyl)carbamate.

LC/MS ESI (+): 424 (M+1), 426 (M+3)

(c) Synthesis of tert-butyl (1-(8-bromopyrido[2,3-e][1,2,4]triazolo[4,3-a]pyrazin-4-yl)azetidin-3-yl)(methyl)carbamate The mixture of unpurified tert-butyl (1-(7-bromo-2-hydrazinylpyrido[2,3-b]pyrazin-3-yl)azetidin-3-yl)(methyl)

carbamate and trimethyl orthoformate (10.0 mL) was stirred at 80° C. for one hour and then cooled to room temperature. Et$_2$O was added thereto to form a solid, and the formed solid was filtered and then dried under reduced pressure to obtain ivory solid compound of tert-butyl (1-(8-bromopyrido[2,3-e][1,2,4]triazolo[4,3-a]pyrazin-4-yl)azetidin-3-yl)(methyl) carbamate (137.0 mg, 45% in 3 steps).

LC/MS ESI (+): 434 (M+1), 436 (M+3)

(d) Synthesis of 1-(8-bromopyrido[2,3-e][1,2,4] triazolo[4,3-a]pyrazin-4-yl)-N-methylazetidin-3-amine tert-Butyl (1-(8-bromopyrido[2,3-e][1,2,4]triazolo[4,3-a]pyrazin-4-yl)azetidin-3-yl)(methyl)carbamate (87.0 mg, 0.20 mmol) was dissolved in DCM (4.0 mL), and TFA (1.0 mL) was slowly added thereto at 0° C. The reaction mixture was stirred at room temperature for 12 hours and distilled under reduced pressure. The residue was neutralized with NaHCO$_3$ aqueous solution (pH=7), and it was then extracted with DCM (30.0 mL). The organic layer was washed with brine, dried over anhydrous Na$_2$SO$_4$, filtered and then distilled under reduced pressure. The residue was purified by column chromatography (DCM:MeOH=98:2) on amine silica. The fractions containing the product were collected and evaporated to obtain ivory solid compound of 1-(8-bromopyrido[2,3-e][1,2,4]triazolo[4,3-a]pyrazin-4-yl)-N-methylazetidin-3-amine (16.0 mg, 23%).

LC/MS ESI (+): 334 (M+1), 336 (M+3)

$^1$H-NMR (300 MHz, DMSO-d$_6$); δ: 9.95 (s, 1H), 8.90 (d, 1H, J=2.1 Hz), 8.59 (d, 1H, J=2.1 Hz), 4.89 (m, 1H), 4.42 (m, 2H), 4.00 (m, 1H), 3.73 (m, 1H), 2.29 (s, 3H)

Example 25

Synthesis of 4-(3-(methylamino)azetidin-1-yl)pyrido[2,3-e][1,2,4]triazolo[4,3-a]pyrazin-8-carbonitrile tert-Butyl (1-(8-bromopyrido[2,3-e][1,2,4]triazolo[4,3-a]pyrazin-4-yl)azetidin-3-yl)(methyl)carbamate (50.0 mg, 0.12 mmol), Zn(CN)$_2$ (14.0 mg, 0.12 mmol) and Pd(PPh$_3$)$_4$ (13.0 mg, 0.01 mmol) were dissolved in DMF (1.0 mL), and it was allowed to react in microwaver under conditions of 60 W, 90° C. for 2 hours and then cooled to room temperature. The reaction mixture was then purified by column chromatography (DCM:MeOH=98:2) on amine silica. The fractions containing the product were collected and evaporated to obtain ivory solid compound of tert-butyl (1-(8-cyanopyrido[2,3-e][1,2,4]triazolo[4,3-a]pyrazin-4-yl)azetidin-3-yl)(methyl)carbamate. tert-Butyl (1-(8-cyanopyrido[2,3-e][1,2,4]triazolo[4,3-a]pyrazin-4-yl)azetidin-3-yl)(methyl)carbamate was dissolved in DCM (4.0 mL), and TFA (1.0 mL) was slowly added thereto at 0° C. The reaction mixture was stirred at room temperature for 12 hours and then distilled under reduced pressure. The residue was neutralized with NaHCO$_3$ aqueous solution (pH=7), and it was then extracted with DCM (30.0 mL). The organic layer was washed with brine, dried over anhydrous Na$_2$SO$_4$, filtered and then distilled under reduced pressure. The residue was purified by column chromatography (DCM:MeOH=98:2) on amine silica. The fractions containing the product were collected and evaporated to obtain ivory solid compound of 4-(3-(methylamino)azetidin-1-yl)pyrido[2,3-e][1,2,4]triazolo[4,3-a]pyrazin-8-carbonitrile (10.0 mg, 22%).

LC/MS ESI (+): 281 (M+1)

$^1$H-NMR (300 MHz, DMSO-d$_6$); δ: 9.93 (s, 1H), 9.06 (d, 1H, J=1.9 Hz), 8.88 (d, 1H, J=1.9 Hz), 4.95 (m, 1H), 4.49 (m, 2H), 4.04 (m, 1H), 3.73 (m, 1H), 2.30 (s, 3H)

Example 26

Synthesis of 4-(piperazin-1-yl)pyrido[2,3-e][1,2,4] triazolo[4,3-a]pyrazin-8-carbonitrile 8-Bromo-4-(piperazin-1-yl)pyrido[2,3-e][1,2,4]triazolo[4,3-a]pyrazine (50.0 mg, 0.15 mmol), Zn(CN)$_2$ (18.0 mg, 0.15 mmol) and Pd(PPh$_3$)$_4$ (3.0 mg, 0.02 mmol) were dissolved in DMF (1.0 mL), and it was allowed to react in microwaver under conditions of 60 W, 90° C. for one hour and then cooled to room temperature. The reaction mixture was purified by column chromatography (DCM:MeOH=98:2) on amine silica. The fractions containing the product were collected and evaporated to obtain ivory solid compound of 4-(piperazin-1-yl)pyrido[2,3-e][1,2,4]triazolo[4,3-a]pyrazin-8-carbonitrile (4.4 mg, 10%).

LC/MS ESI (+): 281 (M+1)

$^1$H-NMR (300 MHz, DMSO-d$_6$); δ: 9.98 (s, 1H), 9.09 (d, 1H, J=2.0 Hz), 8.90 (d, 1H, J=2.1 Hz), 4.80 (m, 2H), 4.05 (m, 2H), 2.90 (m, 4H)

Example 27

Synthesis of 1-(7,8-dichloropyrido[2,3-e][1,2,4] triazolo[4,3-a]pyrazin-4-yl)-N-methylazetidin-3-amine (a) Synthesis of tert-butyl methyl(1-(2,6,7-trichloropyrido[2,3-b]pyrazin-3-yl)azetidin-3-yl)carbamate 2,3,6,7-Tetrachloropyrido[2,3-b]pyrazine (200.0 mg, 0.74 mmol) and TEA (1.0 mL, 7.40 mmol) were dissolved in DCM (8.0 mL), and tert-butyl azetidin-3-yl(methyl)carbamate (162.0 mg, 0.94 mmol) diluted in DCM (2.0 mL) was slowly added thereto at 0° C. The reaction mixture was stirred at room temperature for 12 hours, poured into saturated NH$_4$Cl aqueous solution and extracted with DCM (30.0 mL). The organic layer was washed with brine, dried over anhydrous Na$_2$SO$_4$, filtered and then distilled under reduced pressure. The residue was purified by column chromatography (DCM:MeOH=100:0) on amine silica. The fractions containing the product were collected and evaporated to obtain brown solid compound of tert-butyl methyl (1-(2,6,7-trichloropyrido[2,3-b]pyrazin-3-yl)azetidin-3-yl) carbamate.

LC/MS ESI (+): 418 (M+1), 420 (M+3)

(b) Synthesis of tert-butyl (1-(6,7-dichloro-2-hydrazinylpyrido[2,3-b]pyrazin-3-yl)azetidin-3-yl) (methyl)carbamate Unpurified tert-butyl methyl(1-(2,6,7-trichloropyrido[2,3-b]pyrazin-3-yl)azetidin-3-yl)carbamate and hydrazine monohydrate (37.0 mg, 1.85 mmol) were dissolved in EtOH (10.0 mL), and it was then stirred at room temperature for 12 hours and then distilled under reduced pressure. Et$_2$O was added thereto to form a solid, and the formed solid was filtered and then dried under reduced pressure to obtain yellow solid compound of tert-butyl (1-(6,7-dichloro-2-hydrazinylpyrido[2,3-b]pyrazin-3-yl)azetidin-3-yl)(methyl) carbamate.

LC/MS ESI (+): 414 (M+1), 416 (M+3)

(c) Synthesis of tert-butyl (1-(7,8-dichloropyrido[2,3-e][1,2,4]triazolo[4,3-a]pyrazin-4-yl)azetidin-3-yl)(methyl)carbamate The mixture of unpurified tert-butyl (1-(6,7-dichloro-2-hydrazinylpyrido[2,3-b]pyrazin-3-yl)azetidin-3-yl)(methyl)carbamate and trimethyl orthoformate (20.0 mL) was stirred at 70° C. for one hour and then cooled to room temperature. Et$_2$O was slowly added thereto, and the formed solid was filtered and then dried under reduced pressure to obtain ivory solid compound of tert-butyl (1-(7,8-dichloropyrido[2,3-e][1,2,4]triazolo[4,3-a]pyrazin-4-yl)azetidin-3-yl)(methyl)carbamate (173.0 mg, 55% in 3 steps).

LC/MS ESI (+): 424 (M$^+$+1), 426 (M+3)

(d) Synthesis of 1-(7,8-dichloropyrido[2,3-e][1,2,4]triazolo[4,3-a]pyrazin-4-yl)-N-methylazetidin-3-amine tert-Butyl (1-(7,8-dichloropyrido[2,3-e][1,2,4]triazolo[4,3-a]pyrazin-4-yl)azetidin-3-yl)(methyl)carbamate (123.0 mg, 0.29 mmol) was dissolved in DCM (4.0 mL), and TFA (1.0 mL) was slowly added thereto at 0° C. The reaction mixture was stirred at room temperature for 2 hours and distilled under reduced pressure. The residue was neutralized with NaHCO$_3$ aqueous solution (pH=7) and extracted with DCM (30.0 mL). The organic layer was washed with brine, dried over anhydrous Na$_2$SO$_4$, filtered and then distilled under reduced pressure. The residue was purified by column chromatography (DCM:MeOH=98:2) on amine silica. The fractions containing the product were collected and evaporated to obtain ivory solid compound of 1-(7,8-dichloropyrido[2,3-e][1,2,4]triazolo[4,3-a]pyrazin-4-yl)-N-methylazetidin-3-amine (19.0 mg, 20%).

LC/MS ESI (+): 324 (M+1), 326 (M+3)

$^1$H-NMR (300 MHz, DMSO-d$_6$); δ: 9.95 (s, 1H), 8.98 (s, 1H), 4.94 (m, 1H), 4.46 (m, 2H), 4.00 (m, 1H), 3.73 (m, 1H), 2.30 (s, 3H)

Example 28

Synthesis of 8-chloro-4-(3-(methylamino)azetidin-1-yl)pyrido[2,3-e][1,2,4]triazolo[4,3-a]pyrazin-7-carbonitrile tert-Butyl (1-(7,8-dichloropyrido[2,3-e][1,2,4]triazolo[4,3-a]pyrazin-4-yl)azetidin-3-yl)(methyl)carbamate (50.0 mg, 0.15 mmol), Zn(CN)$_2$ (18.0 mg, 0.15 mmol) and Pd(PPh$_3$)$_4$ (18.0 mg, 0.02 mmol) were dissolved in DMF (1.0 mL), and it was allowed to react in microwaver under conditions of 60 W, 90° C. for one hour and then cooled to room temperature. The reaction mixture was purified by column chromatography (DCM:MeOH=98:2) on amine silica. The fractions containing the product were collected and evaporated to obtain ivory solid compound of tert-butyl (1-(8-chloro-7-cyanopyrido[2,3-e][1,2,4]triazolo[4,3-a]pyrazin-4-yl)azetidin-3-yl)(methyl)carbamate. Unpurified tert-butyl (1-(8-chloro-7-cyanopyrido[2,3-e][1,2,4]triazolo[4,3-a]pyrazin-4-yl)azetidin-3-yl)(methyl)carbamate was dissolved in DCM (2.0 mL), and TFA (0.5 mL) was slowly added thereto at 0° C. The reaction mixture was stirred at room temperature for 12 hours and then distilled under reduced pressure. The residue was neutralized with NaHCO$_3$ aqueous solution (pH=7) and extracted with DCM (30.0 mL). The organic layer was washed with brine, dried over anhydrous Na$_2$SO$_4$, filtered and then distilled under reduced pressure. The residue was purified by column chromatography (DCM:MeOH=98:2) on amine silica. The fractions containing the product were collected and evaporated to obtain ivory solid compound of 8-chloro-4-(3-(methylamino)azetidin-1-yl)pyrido[2,3-e][1,2,4]triazolo[4,3-a]pyrazin-7-carbonitrile (20.0 mg, 41%).

LC/MS ESI (+): 315 (M+1), 317 (M+3)

$^1$H-NMR (300 MHz, DMSO-d$_6$); δ: 9.98 (s, 1H), 9.03 (s, 1H), 4.93 (m, 1H), 4.48 (m, 2H), 4.00 (m, 1H), 3.73 (m, 1H), 2.30 (s, 3H)

Example 29

Synthesis of 8-chloro-4-(hexahydropyrrolo[1,2-a]pyrazin-2(1H)-yl)pyrido[2,3-e][1,2,4]triazolo[4,3-a]pyrazine (a) Synthesis of 2,7-dichloro-3-(hexahydropyrrolo[1,2-a]pyrazin-2(1H)-yl)pyrido[2,3-b]pyrazine 2,3,7-Trichloropyrido[2,3-b]pyrazine (100.0 mg, 0.43 mmol) and octahydropyrrolo[1,2-a]pyrazine (60.0 mg, 0.47 mmol) were reacted to obtain yellow solid compound of 2,7-dichloro-3-(hexahydropyrrolo[1,2-a]pyrazin-2(1H)-yl)pyrido[2,3-b]pyrazine (83.0 mg, 60%) in the same way as Example 18 (a).

LC/MS ESI(+): 324 (M+1), 326 (M+3)

$^1$H-NMR (300 MHz, CDCl$_3$); δ: 8.86 (d, 1H, J=2.7 Hz), 8.17 (d, 1H, J=2.4 Hz), 4.45 (m, 2H), 3.32 (m, 1H), 3.19 (m, 2H), 2.97 (m, 1H), 2.49 (m, 1H), 2.26 (m, 2H), 1.91 (m, 2H), 1.81 (m, 1H), 1.51 (m, 1H)

(b) Synthesis of 7-chloro-3-(hexahydropyrrolo[1,2-a]pyrazin-2(1H)-yl)-2-hydrazinylpyrido[2,3-b]pyrazine 2,7-Dichloro-3-(hexahydropyrrolo[1,2-a]pyrazin-2(1H)-yl)pyrido[2,3-b]pyrazine (80.0 mg, 0.25 mmol) and hydrazine monohydrate (19.0 μL, 0.62 mmol) were reacted in the same way as Example 18 (b) to obtain orange solid compound of 7-chloro-3-(hexahydropyrrolo[1,2-a]pyrazin-2(1H)-yl)-2-hydrazinylpyrido[2,3-b]pyrazine (50.0 mg, 63%).

LC/MS ESI(+): 320 (M+1), 322 (M+3)

$^1$H-NMR (300 MHz, CDCl$_3$); δ: 8.60 (d, 1H, J=3.0 Hz), 8.01 (d, 1H, J=3.0 Hz), 6.49 (bs, 1H), 4.20 (d, 2H, J=3.0 Hz), 3.94 (m, 2H), 3.17 (m, 3H), 2.87 (m, 1H), 2.46 (m, 1H), 2.22 (m, 2H), 1.89 (m, 2H), 1.78 (m, 1H), 1.50 (m, 1H)

(c) Synthesis of 8-chloro-4-(hexahydropyrrolo[1,2-a]pyrazin-2(1H)-yl)pyrido[2,3-e][1,2,4]triazolo[4,3-a]pyrazine 7-Chloro-3-(hexahydropyrrolo[1,2-a]pyrazin-2(1H)-yl)-2-hydrazinylpyrido[2,3-b]pyrazine (45.0 mg, 0.14 mmol) and trimethyl orthoformate (1.0 mL) were reacted in the same way as Example 18 (c) at 90° C. for 5 hours to obtain orange solid compound of 8-chloro-4-(hexahydropyrrolo[1,2-a]pyrazin-2(1H)-yl)pyrido[2,3-e][1,2,4]triazolo[4,3-a]pyrazine (37.0 mg, 79%).

LC/MS ESI(+): 330 (M+1), 332 (M+3)

$^1$H-NMR (300 MHz, CDCl$_3$); δ: 9.16 (s, 1H), 8.61 (d, 1H, J=2.1 Hz), 8.04 (d, 1H, J=2.4 Hz), 6.39 (m, 1H), 5.50 (m,

1H), 3.55 (m, 0.5H), 3.20 (m, 3H), 2.90 (m, 0.5H), 2.42 (m, 1H), 2.20 (m, 2H), 1.88 (m, 3H), 1.52 (m, 1H)

Example 30

Synthesis of (R)-1-(8-chloropyrido[2,3-e][1,2,4]triazolo[4,3-a]pyrazin-4-yl)pyrrolidin-3-amine (a) Synthesis of (R)-tert-butyl (1-(2,7-dichloropyrido[2,3-b]pyrazin-3-yl)pyrrolidin-3-yl)carbamate 2,3,7-Trichloropyrido[2,3-b]pyrazine (200.0 mg, 0.85 mmol) and TEA (1.2 mL, 8.50 mmol) were dissolved in DCM (10.0 mL), and (R)-tert-butyl pyrrolidin-3-ylcarbamate (175.0 mg, 0.94 mmol) diluted in DCM (5.0 mL) was slowly added thereto at 0° C. The reaction mixture was stirred at room temperature for 12 hours, poured into saturated NH$_4$Cl aqueous solution, and it was then extracted with DCM (30.0 mL). The organic layer was washed with brine, dried over anhydrous Na$_2$SO$_4$, filtered and then distilled under reduced pressure. The residue was purified by column chromatography (DCM:MeOH=100:0 to 98:2) on silica. The fractions containing the product were collected and evaporated to obtain yellow solid compound of (R)-tert-butyl (1-(2,7-dichloropyrido[2,3-b]pyrazin-3-yl)pyrrolidin-3-yl)carbamate (284.0 mg, 86%).

LC/MS ESI (+): 384 (M+1), 386 (M+3)

(b) Synthesis of (R)-tert-butyl (1-(7-chloro-2-hydrazinylpyrido[2,3-b]pyrazin-3-yl)pyrrolidin-3-yl)carbamate (R)-tert-butyl (1-(2,7-dichloropyrido[2,3-b]pyrazin-3-yl)pyrrolidin-3-yl)carbamate (284.0 mg, 0.74 mmol) and hydrazine monohydrate (92.0 mg, 1.85 mmol) were dissolved in EtOH (10.0 mL), stirred at room temperature for 2 hours and then distilled reduced pressure to obtain yellow solid compound of (R)-tert-butyl (1-(7-chloro-2-hydrazinylpyrido[2,3-b]pyrazin-3-yl)pyrrolidin-3-yl)carbamate.

LC/MS ESI (+): 380 (M+1), 382 (M+3)

(c) Synthesis of (R)-tert-butyl (1-(8-chloropyrido[2,3-e][1,2,4]triazolo[4,3-a]pyrazin-4-yl)pyrrolidin-3-yl)carbamate The mixture of unpurified (R)-tert-butyl (1-(7-chloro-2-hydrazinylpyrido[2,3-b]pyrazin-3-yl)pyrrolidin-3-yl)carbamate and trimethyl orthoformate (5.0 mL) was stirred at 70° C. for one hour and then cooled to room temperature. Et$_2$O was added thereto to form a solid, and the formed solid was filtered and dried under reduced pressure to obtain ivory solid compound of (R)-tert-butyl (1-(8-chloropyrido[2,3-e][1,2,4]triazolo[4,3-a]pyrazin-4-yl)pyrrolidin-3-yl)carbamate (272.0 mg, 94% in 2 steps).

LC/MS ESI (+): 390 (M+1), 392 (M+3)

(d) Synthesis of (R)-1-(8-chloropyrido[2,3-e][1,2,4]triazolo[4,3-a]pyrazin-4-yl)pyrrolidin-3-amine (R)-tert-butyl (1-(8-chloropyrido[2,3-e][1,2,4]triazolo[4,3-a]pyrazin-4-yl)pyrrolidin-3-yl)carbamate (272.0 mg, 0.70 mmol) was dissolved in DCM (20.0 mL), and TFA (4.0 mL) was then slowly added thereto at 0° C. The reaction mixture was stirred at room temperature for 2 hours and distilled under reduced pressure. The residue was neutralized with NaHCO$_3$ aqueous solution (pH=7), and it was extracted with DCM (30.0 mL). The organic layer was washed with brine, dried over anhydrous Na$_2$SO$_4$, filtered and then distilled under reduced pressure. The residue was purified by column chromatography (DCM:MeOH=90:10 to 50:50) on silica. The fractions containing the product were collected and evaporated to obtain ivory solid compound of (R)-1-(8-chloropyrido[2,3-e][1,2,4]triazolo[4,3-a]pyrazin-4-yl)pyrrolidin-3-amine (79.0 mg, 39%).

LC/MS ESI (+): 290 (M+1), 292 (M+3)

$^1$H-NMR (300 MHz, DMSO-d$_6$); δ: 9.99 (s, 1H), 8.81 (d, 1H, J=2.4 Hz), 8.53 (d, 1H, J=2.4 Hz), 4.6-3.4 (m, 5H), 2.4-1.6 (m, 2H)

Example 31

Synthesis of 9-chloro-2-methyl-5-(4-methylpiperazin-1-yl)pyrido[3,2-e][1,2,4]triazolo[1,5-c]pyrimidine (a) Synthesis of 3-bromo-5-chloropyridin-2-amine 5-Chloropyridin-2-amine (5000.0 mg, 38.90 mmol) was dissolved in CHCl$_3$ (78.0 mL), and then Br$_2$ (2.0 mL, 38.90 mmol) was added thereto. The reaction mixture was stirred at room temperature for one hour and solvent was removed therefrom under reduced pressure. The residue was dissolved in EtOAc, and it was then washed with saturated NaHCO$_3$ aqueous solution and brine, dried over anhydrous Na$_2$SO$_4$, filtered and then distilled under reduced pressure. The residue was purified by column chromatography (EtOAc:n-Hex=1:9) on silica. The fractions containing the product were collected and evaporated to obtain yellow solid compound of 3-bromo-5-chloropyridin-2-amine (7500.0 mg, 93%).

LC/MS ESI(+): 207 (M+1), 209 (M+3)

$^1$H-NMR (300 MHz, CDCl$_3$); δ: 7.98 (d, 1H, J=2.1 Hz), 7.66 (d, 1H, J=2.1 Hz), 4.93 (bs, 2H)

(b) Synthesis of 2-amino-5-chloronicotinonitrile

3-Bromo-5-chloropyridin-2-amine (2700.0 mg, 13.00 mmol) was dissolved in NMP (60.0 mL), and then Zn(CN)$_2$ (2300.0 mg, 19.50 mmol) and Pd(PPh$_3$)$_4$ (1500.0 mg, 1.30 mmol) were added thereto. The reaction mixture was stirred at 110° C. for 5 hours and then cooled to room temperature. Water and EtOAc were added to the reaction mixture, and it was stirred for 10 minutes and then filtered through celite. The filtrate was extracted with EtOAc. The organic layer was washed with brine, dried over anhydrous Na$_2$SO$_4$, filtered and then distilled under reduced pressure. The residue was purified by column chromatography (EtOAc:n-Hex=1:9) on silica. The fractions containing the product were collected and evaporated to obtain white solid compound of 2-amino-5-chloronicotinonitrile (1900.0 mg, 100%).

LC/MS ESI(+): 154 (M+1), 156 (M+3)

$^1$H-NMR (300 MHz, DMSO-d$_6$); δ: 8.22 (d, 1H, J=2.7 Hz), 8.07 (d, 1H, J=2.7 Hz), 7.14 (s, 2H)

(c) Synthesis of 9-chloro-2-methylpyrido[3,2-e][1,2,4]triazolo[1,5-c]pyrimidin-5-ol 2-Amino-5-chloronicotinonitrile (300.0 mg, 1.95 mmol) was dissolved in MEK (2.0 mL), and NaHCO$_3$ (492.0 mg, 5.86 mmol) and chloroethyl formate (3.0 mL) were added thereto. The reaction mixture was refluxed and then cooled to room temperature, and it was filtered and then dried under reduced pressure to obtain atypical yellow compound of ethyl (5-chloro-3-cyanopyridin-2-yl)carbamate. Unpurified ethyl (5-chloro-3-cyanopyridin-2-yl)carbamate was dissolved in diphenylether (2.0 mL) and acetohydrazide (144.0 mg, 1.95 mmol) was added thereto. The reaction mixture was stirred at 180° C. for 30 minutes and then cooled to room temperature, and then distilled under reduced pressure. The residue was purified by column chromatography (EtOAc: n-Hex=1:4) on silica. The fractions containing the product were collected and evaporated to obtain yellow solid compound of 9-chloro-2-methylpyrido[3,2-e][1,2,4]triazolo[1,5-c]pyrimidin-5-ol (91.0 mg, 20% in 2 steps).

LC/MS ESI(+): 236 (M+1), 238 (M+3)

$^1$H-NMR (300 MHz, DMSO-d$_6$); δ: 12.9 (s, 1H), 8.73 (d, 1H, J=2.4 Hz), 8.58 (d, 1H, J=2.4 Hz)

(d) Synthesis of 5,9-dichloro-2-methylpyrido[3,2-e][1,2,4]triazolo[1,5-c]pyrimidine 9-Chloro-2-methylpyrido[3,2-e][1,2,4]triazolo[1,5-c]pyrimidin-5-ol (80.0 mg, 0.34 mmol) was dissolved POCl$_3$ (1.5 mL), and DIPEA (120.0 µL, 0.68 mmol) was added thereto. The reaction mixture was refluxed for 12 hours and then cooled to room temperature. The reaction mixture was poured into ice water, neutralized with saturated NaHCO$_3$ aqueous solution, and it was then extracted EtOAc. The organic layer was washed with brine, dried over anhydrous Na$_2$SO$_4$, filtered and then distilled under reduced pressure. The residue was purified by column chromatography (EtOAc:n-Hex=1:5) on silica. The fractions containing the product were collected and evaporated to obtain white solid compound of 5,9-dichloro-2-methylpyrido[3,2-e][1,2,4]triazolo[1,5-c]pyrimidine (30.0 mg, 35%).

LC/MS ESI(+): 254 (M+1), 256 (M+3)

(e) Synthesis of 9-chloro-2-methyl-5-(4-methylpiperazin-1-yl)pyrido[3,2-e][1,2,4]triazolo[1,5-c]pyrimidine 5,9-Dichloro-2-methylpyrido[3,2-e][1,2,4]triazolo[1,5-c]pyrimidine (28.0 mg, 0.11 mmol) was dissolved in DMF (1.1 mL), and N-methylpiperazin (24.0 µL, 0.22 mmol) was added thereto. The reaction mixture was stirred at room temperature for one hour and the residue was purified by column chromatography (MeOH:DCM=1:40) on amine silica. The fractions containing the product were collected and evaporated to obtain ivory solid compound of 9-chloro-2-methyl-5-(4-methylpiperazin-1-yl)pyrido[3,2-e][1,2,4]triazolo[1,5-c]pyrimi dine (18.0 mg, 51%).

LC/MS ESI(+): 318 (M+1), 320 (M+3)

$^1$H-NMR (300 MHz, DMSO-d$_6$); δ: 8.84 (d, 1H, J=2.4 Hz), 8.63 (d, 1H, J=2.4 Hz), 4.12 (m, 4H), 2.56 (s, 3H), 2.54 (m, 4H), 2.24 (s, 3H)

Example 32

Synthesis of 9-chloro-2-methyl-5-(piperazin-1-yl)pyrido[3,2-e][1,2,4]triazolo[1,5-c]pyrimidine (a) Synthesis of tert-butyl 4-(9-chloro-2-methylpyrido[3,2-e][1,2,4]triazolo[1,5-c]pyrimidin-5-yl)piperazin-1-carboxylate 5,9-Dichloro-2-methylpyrido[3,2-e][1,2,4]triazolo[1,5-c]pyrimidin (20.0 mg, 0.08 mmol) obtained from Example 31 (d) was dissolved in DMF (1.0 mL), and tert-butyl piperazin-1-carboxylate (29.0 mg, 0.16 mmol) was added thereto. The reaction mixture was stirred at room temperature for one hour and purified by column chromatography (EtOAc: n-Hex=1:5) on silica. The fractions containing the product were collected and evaporated to obtain ivory solid compound of tert-butyl 4-(9-chloro-2-methylpyrido[3,2-e][1,2,4]triazolo[1,5-c]pyrimidin-5-yl)piperazin-1-carboxylate (32.0 mg, 100%).

LC/MS ESI(+): 404 (M+1), 406 (M+3)

(b) Synthesis of 9-chloro-2-methyl-5-(piperazin-1-yl)pyrido[3,2-e][1,2,4]triazolo[1,5-c]pyrimidine tert-Butyl-4-(9-chloro-2-methylpyrido[3,2-e][1,2,4]triazolo[1,5-c]pyrimidin-5-yl)piperazin-1-carboxylate (30.0 mg, 0.07 mmol) was dissolved in DCM (0.6 mL), and TFA (0.4 mL) was added thereto. The reaction mixture was stirred at room temperature for one hour and purified by column chromatography (MeOH:DCM=1:40) on amine silica. The fractions containing the product were collected and evaporated to obtain ivory solid compound of 9-chloro-2-methyl-5-(piperazin-1-yl)pyrido[3,2-e][1,2,4]triazolo[1,5-c]pyrimidine (22.5 mg, 100%).

LC/MS ESI(+): 304 (M+1), 306 (M+3)

$^1$H-NMR (300 MHz, CDCl$_3$); δ: 8.79 (d, 1H, J=2.7 Hz), 8.58 (d, 1H, J=2.7 Hz), 4.26 (m, 4H), 3.11 (m, 4H), 2.64 (s, 3H)

Example 33

Synthesis of 1-(9-chloro-2-methylpyrido[3,2-e][1,2,4]triazolo[1,5-c]pyrimidin-5-yl)-N-methylazetidin-3-amine (a) Synthesis of tert-butyl (1-(9-chloro-2-methylpyrido[3,2-e][1,2,4]triazolo[1,5-c]pyrimidin-5-yl)azetidin-3-yl)(methyl)carbamate 5,9-Dichloro-2-methylpyrido[3,2-e][1,2,4]triazolo[1,5-c]pyrimidine (12.0 mg, 0.05 mmol) obtained from Example 31 (d) was dissolved in DMF (1.0 mL) and tert-butyl azetidin-3-yl(methyl)carbamate (17.6 mg, 0.09 mmol) was added thereto. The reaction mixture was stirred at room temperature for one hour and solvent was removed therefrom under reduced pressure. The residue was purified by column chromatography (MeOH:DCM=1:40) on silica. The fractions containing the product were collected and evaporated to obtain ivory solid compound of tert-butyl (1-(9-chloro-2-methylpyrido[3,2-e][1,2,4]triazolo[1,5-c]pyrimidin-5-yl)azetidin-3-yl)(methyl)carbamate (19.0 mg, 100%).

LC/MS ESI(+): 404 (M+1), 406 (M+3)

(b) Synthesis of 1-(9-chloro-2-methylpyrido[3,2-e][1,2,4]triazolo[1,5-c]pyrimidin-5-yl)-N-methylazetidin-3-amine tert-Butyl (1-(9-chloro-2-methylpyrido[3,2-e][1,2,4]triazolo[1,5-c]pyrimidin-5-yl)azetidin-3-yl)(methyl)carbamate (18.0 mg, 0.04 mmol) was dissolved in DCM (0.6 mL), and TFA (0.4 mL) was added thereto. The reaction mixture was stirred at room temperature for one hour and was purified by column chromatography (MeOH:DCM=1:40) on amine silica. The fractions containing the product were collected and evaporated to obtain ivory solid compound of 1-(9-chloro-2-methylpyrido[3,2-e][1,2,4]triazolo[1,5-c]pyrimidin-5-yl)-N-methylazetidin-3-amine (7.0 mg, 55%).

LC/MS ESI(+): 304 (M+1), 306 (M+3)

¹H-NMR (300 MHz, CDCl₃); δ: 8.73 (d, 1H, J=2.7 Hz), 8.51 (d, 1H, J=2.7 Hz), 4.84 (m, 2H), 4.38 (m, 2H), 3.80 (m, 1H), 2.60 (s, 3H), 2.49 (s, 3H)

Example 34

Synthesis of 9-chloro-2-cyclopropyl-N,N-diethyl-pyrido[3,2-e][1,2,4]triazolo[1,5-c]pyrimidin-5-amine (a) Synthesis of 9-chloro-2-cyclopropylpyrido[3,2-e][1,2,4]triazolo[1,5-c]pyrimidin-5-ol Ethyl (5-chloro-3-cyanopyridin-2-yl)carbamate was synthesized from 2-amino-5-chloronicotinonitrile (500.0 mg, 3.26 mmol) in the same way as Example 31 (c), and allowed to react with cyclopropanecarbohydrazide (326.0 mg, 3.26 mmol) to obtain brown solid compound of 9-chloro-2-cyclopropylpyrido[3,2-e][1,2,4]triazolo[1,5-c]pyrimidin-5-ol (37.0 mg, 4% in 2 steps).
LC/MS ESI(+): 262 (M+1), 264 (M+3)
¹H-NMR (300 MHz, DMSO-d₆); δ: 12.86 (bs, 1H), 8.71 (d, 1H, J=2.7 Hz), 8.53 (d, 1H, J=2.7 Hz), 2.23 (m, 1H), 1.09 (m, 2H), 0.99 (m, 2H)

(b) Synthesis of 9-chloro-2-cyclopropyl-N,N-diethylpyrido[3,2-e][1,2,4]triazolo[1,5-c]pyrimidin-5-amine 9-Chloro-2-cyclopropylpyrido[3,2-e][1,2,4]triazolo[1,5-c]pyrimidin-5-ol (35.0 mg, 0.13 mmol) was dissolved in POCl₃ (1.5 mL), and TEA (37.0 μL, 0.27 mmol) was added thereto. The reaction mixture was refluxed for 12 hours and then cooled to room temperature. The reaction mixture was poured into ice water and neutralized with saturated NaHCO₃ aqueous solution, and it was extracted with EtOAc. The organic layer was washed with brine, dried over anhydrous Na₂SO₄, filtered and then distilled under reduced pressure. The residue was purified by column chromatography (EtOAc:n-Hex=1:4) on silica. The fractions containing the product were collected and evaporated to obtain yellow solid compound of 9-chloro-2-cyclopropyl-N,N-diethylpyrido[3,2-e][1,2,4]triazolo[1,5-c]pyrimidin-5-amine (32.0 mg, 74%).
LC/MS ESI(+): 317 (M+1), 319 (M+3)
¹H-NMR (300 MHz, CDCl₃); δ: 8.71 (d, 1H, J=2.7 Hz), 8.51 (d, 1H, J=2.7 Hz), 4.04 (q, 4H, J=6.9 Hz), 2.23 (m, 1H), 1.39 (t, 6H, J=6.9 Hz), 1.13 (m, 4H)

Example 35

Synthesis of 9-chloro-5-(4-methylpiperazin-1-yl)pyrido[3,2-e][1,2,4]triazolo[1,5-c]pyrimidine (a) Synthesis of 9-chloropyrido[3,2-e][1,2,4]triazolo[1,5-c]pyrimidin-5(6H)-one 2-Amino-5-chloronicotinonitrile (500.0 mg, 3.26 mmol) was dissolved in MEK (3.5 mL), and NaHCO₃ (820.4 mg, 9.77 mmol) and chloroethyl formate (5.0 mL) were added thereto. The reaction mixture was refluxed for 24 hours and then cooled to room temperature and filtered and then dried under reduced pressure to obtain atypical yellow compound of ethyl (5-chloro-3-cyanopyridin-2-yl)carbamate. Unpurified ethyl (5-chloro-3-cyanopyridin-2-yl)carbamate was dissolved in diphenylether (3.5 mL) and formhydrazide (195.5 mg, 3.26 mmol) was then added thereto. The reaction mixture was stirred at 180° C. for one hour and then cooled to room temperature, and purified by column chromatography (EtOAc:n-Hex=1:1) on silica. The fractions containing the product were collected and evaporated to obtain yellow solid compound of 9-chloropyrido[3,2-e][1,2,4]triazolo[1,5-c]pyrimidin-5(6H)-one (63.0 mg, 9%).
LC/MS ESI(+): 221 (M+1), 223 (M+3)
¹H-NMR (300 MHz, DMSO-d₆); δ: 12.95 (s, 1H), 8.74 (d, 1H, J=2.1 Hz), 8.63 (d, 1H, J=2.4 Hz), 8.59 (s, 1H).

(b) Synthesis of 5,9-dichloropyrido[3,2-e][1,2,4]triazolo[1,5-c]pyrimidine

9-Chloropyrido[3,2-e][1,2,4]triazolo[1,5-c]pyrimidin-5(6H)-one (63.0 mg, 0.29 mmol) was dissolved in POCl₃ (2.0 mL), and DIPEA (150.0 μL, 0.86 mmol) was added. The reaction mixture was refluxed for 12 hours and then cooled to room temperature. The reaction mixture was poured into ice water and neutralized with saturated NaHCO₃ aqueous solution and extracted with EtOAc. The organic layer was washed with brine, dried over anhydrous Na₂SO₄, filtered and then distilled under reduced pressure. The residue was purified by column chromatography (EtOAc:n-Hex=1:1) on silica. The fractions containing the product were collected and evaporated to obtain white solid compound of 5,9-dichloropyrido[3,2-e][1,2,4]triazolo[1,5-c]pyrimidine (50.4 mg, 72%).
LC/MS ESI(+): 240 (M+1), 241 (M+3)

(c) Synthesis of 9-chloro-5-(4-methylpiperazin-1-yl)pyrido[3,2-e][1,2,4]triazolo[1,5-c]pyrimidine 5,9-Dichloropyrido[3,2-e][1,2,4]triazolo[1,5-c]pyrimidine (15.0 mg, 0.06 mmol) was dissolved in DMF (0.5 mL), N-methylpiperazine (10.3 μL, 0.09 mmol) and TEA (25.0 μL, 0.19 mmol) were added thereto. The reaction mixture was stirred at room temperature for one hour and then purified by column chromatography (MeOH:DCM=1:19) on silica. The fractions containing the product were collected and evaporated to obtain ivory solid compound of 9-chloro-5-(4-methylpiperazin-1-yl)pyrido[3,2-e][1,2,4]triazolo[1,5-c]pyrimidine (6.0 mg, 33%).
LC/MS ESI(+): 304 (M+1), 306 (M+3)
¹H-NMR (300 MHz, CDCl₃); δ: 8.82 (d, 1H, J=3.0 Hz), 8.63 (d, 1H, J=2.7 Hz), 8.37 (s, 1H), 4.33 (m, 4H), 2.65 (m, 4H), 2.38 (s, 3H).

Example 36

Synthesis of 1-(9-chloropyrido[3,2-e][1,2,4]triazolo[1,5-c]pyrimidin-5-yl)-N-methylazetidin-3-amine 5,9-Dichloropyrido[3,2-e][1,2,4]triazolo[1,5-c]pyrimidine (15.0 mg, 0.06 mmol) obtained from Example 35 (b) was dissolved in DMF (0.5 mL), and tert-butylazetidin-3-yl(methyl)carbamate (17.3 mg, 0.09 mmol) and TEA (25.0 μL, 0.19 mmol) were added thereto. The reaction mixture was stirred at room temperature for one hour and distilled under reduced pressure and then dissolved in DCM (1.0 mL) without purification, and TFA (0.2 mL) was then added thereto. The reaction mixture stirred at room temperature for one hour and purified by column chromatography (MeOH:DCM=1:19) on amine silica. The fractions containing the product were collected and evaporated to obtain ivory solid compound of 1-(9-chloropyrido[3,2-e][1,2,4]triazolo[1,5-c]pyrimidin-5-yl)-N-methylazetidin-3-amine (2.6 mg, 15%).
LC/MS ESI(+): 290 (M+1), 292 (M+3)

¹H-NMR (300 MHz, CDCl₃+MeOH-d₄); δ: 8.70 (d, 1H, J=2.7 Hz), 8.53 (d, 1H, J=2.7 Hz), 8.28 (d, 1H, J=2.7 Hz), 4.84 (m, 2H), 4.45 (m, 2H), 3.82 (m, 1H), 2.46 (s, 3H).

Example 37

Synthesis of 9-chloro-5-(piperazin-1-yl)pyrido[3,2-e][1,2,4]triazolo[1,5-c]pyrimidine 5,9-Dichloropyrido[3,2-e][1,2,4]triazolo[1,5-c]pyrimidine (15.0 mg, 0.06 mmol) obtained from Example 35 (b) was dissolved in DMF (0.5 mL), and tert-butyl piperazin-1-carboxylate (16.7 mg, 0.09 mmol) and TEA (25.0 μL, 0.19 mmol) were then added thereto. The reaction mixture was stirred at room temperature for one hour and concentrated under reduced pressure, and it was then dissolved in DCM (1.0 mL) without purification and TFA (0.2 mL) was added thereto. The reaction mixture was stirred at room temperature for one hour, and purified by column chromatography (MeOH:DCM=1:19) on amine silica. The fractions containing the product were collected and evaporated to obtain white solid compound of 9-chloro-5-(piperazin-1-yl)pyrido[3,2-e][1,2,4]triazolo[1,5-c]pyrimidine (1.7 mg, 10%).

LC/MS ESI(+): 290 (M+1), 292 (M+3)
¹H-NMR (300 MHz, CDCl₃+MeOH-d₄); δ: 8.82 (d, 1H, J=2.4 Hz), 8.68 (d, 1H, J=2.7 Hz), 8.38 (s, 1H), 4.51 (m, 4H), 3.39 (m, 4H).

Example 38

Synthesis of 9-chloro-2-cyclopropyl-5-(4-methylpiperazin-1-yl)pyrido[3,2-e][1,2,4]triazolo[1,5-c]pyrimidine (a) Synthesis of 5,9-dichloro-2-cyclopropylpyrido[3,2-e][1,2,4]triazolo[1,5-c]pyrimidine 9-Chloro-2-cyclopropylpyrido[3,2-e][1,2,4]triazolo[1,5-c]pyrimidin-5-ol (125.0 mg, 0.48 mmol) was allowed to react with POCl₃ (2.5 mL) and DIPEA (0.2 mL, 0.96 mmol) in the same way as Example 31 (d) to obtain ivory solid compound of 5,9-dichloro-2-cyclopropylpyrido[3,2-e][1,2,4]triazolo[1,5-c]pyrimidine (90.0 mg, 67%).

LC/MS ESI(+): 280 (M+1), 282 (M+3)
¹H-NMR (300 MHz, CDCl₃); δ: 9.01 (d, 1H, J=2.7 Hz), 8.76 (d, 1H, J=2.7 Hz), 2.34 (m, 1H), 1.22 (m, 4H)

(b) Synthesis of 9-chloro-2-cyclopropyl-5-(4-methylpiperazin-1-yl)pyrido[3,2-e][1,2,4]triazolo[1,5-c]pyrimidine 5,9-Dichloro-2-cyclopropylpyrido[3,2-e][1,2,4]triazolo[1,5-c]pyrimidine (25.0 mg, 0.09 mmol) and N-methylpiperazine (20.0 μL, 0.18 mmol) were allowed to react in the same way as Example 31 (e) to obtain ivory solid compound of 9-chloro-2-cyclopropyl-5-(4-methylpiperazin-1-yl)pyrido[3,2-e][1,2,4]triazolo[1,5-c]pyrimidine (22.0 mg, 72%).

LC/MS ESI(+): 344 (M+1), 346 (M+3)
¹H-NMR (300 MHz, CDCl₃); δ: 8.77 (d, 1H, J=2.7 Hz), 8.56 (d, 1H, J=2.7 Hz), 4.31 (t, 4H, J=5.1 Hz), 2.64 (t, 4H, J=5.1 Hz), 2.38 (s, 3H), 2.25 (m, 1H), 1.15 (m, 4H)

Example 39

Synthesis of 9-chloro-2-cyclopropyl-5-(piperazin-1-yl)pyrido[3,2-e][1,2,4]triazolo[1,5-c]pyrimidine 5,9-Dichloro-2-cyclopropylpyrido[3,2-e][1,2,4]triazolo[1,5-c]pyrimidine (30.0 mg, 0.11 mmol) obtained from the way as Example 38 (a) was dissolved in DCM (1.0 mL) and tert-butyl piperazin-1-carboxylate (40.0 mg, 0.21 mmol) was added thereto. The reaction mixture was stirred for one hour and TFA (0.8 mL) was then added, and it reacted for another one hour. The reaction mixture was purified by column chromatography (MeOH:DCM=1:40) on amine silica. The fractions containing the product were collected and evaporated. Et₂O and n-Hex were added thereto and the resulting solid was filtered to obtain ivory solid compound of 9-chloro-2-cyclopropyl-5-(piperazin-1-yl)pyrido[3,2-e][1,2,4]triazolo[1,5-c]pyrimidine (31.0 mg, 89%).

LC/MS ESI(+): 330 (M+1), 332 (M+3)
¹H-NMR (300 MHz, CDCl₃); δ: 8.77 (d, 1H, J=2.7 Hz), 8.56 (d, 1H, J=2.7 Hz), 4.25 (t, 4H, J=5.1 Hz), 3.10 (t, 4H, J=5.1 Hz), 2.25 (m, 1H), 1.15 (m, 4H)

Example 40

Synthesis of 9-chloro-2-(methoxymethyl)-5-(4-methylpiperazin-1-yl)pyrido[3,2-e][1,2,4]triazolo[1,5-c]pyrimidine (a) Synthesis of 9-chloro-2-(methoxymethyl)pyrido[3,2-e][1,2,4]triazolo[1,5-c]pyrimidin-5-ol 2-Amino-5-chloronicotinonitrile (500.0 mg, 3.26 mmol) was dissolved in MEK (4.0 mL) and K₂CO₃ (1350.0 mg, 9.78 mmol), MgSO₄ (250.0 mg, 1.25 mmol) and chloroethylformate (6.0 mL) were added thereto. The reaction mixture was refluxed for 24 hours, then cooled to room temperature, filtered and then dried under reduced pressure to obtain atypical yellow compound of ethyl (5-chloro-3-cyanopyridin-2-yl)carbamate. Unpurified ethyl (5-chloro-3-cyanopyridin-2-yl)carbamate was dissolved in diphenylether (2.0 mL) and 2-methoxyacetohydrazide (271.0 mg, 2.61 mmol) was added. The reaction mixture was stirred at 150° C. for 3 hours and then cooled to room temperature, and then purified by column chromatography (EtOAc:n-Hex=1:4) on silica. The fractions containing the product were collected and evaporated to obtain yellow solid compound of 9-chloro-2-(methoxymethyl)pyrido[3,2-e][1,2,4]triazolo[1,5-c]pyrimidin-5-ol (150.0 mg, 17% in 2 steps).

LC/MS ESI(+): 266 (M+1), 268 (M+3)
¹H-NMR (300 MHz, DMSO-d₆); δ: 12.99 (s, 1H), 8.74 (d, 1H, J=2.4 Hz), 8.64 (d, 1H, J=2.7 Hz), 4.63 (s, 2H), 3.38 (s, 3H)

(b) Synthesis of 5,9-dichloro-2-(methoxymethyl)pyrido[3,2-e][1,2,4]triazolo[1,5-c]pyrimidine 9-Chloro-2-(methoxymethyl)pyrido[3,2-e][1,2,4]triazolo[1,5-c]pyrimidin-5-ol (146.0 mg, 0.51 mmol) was allowed to react with POCl₃ (1.5 mL) and DIPEA (0.2 mL, 1.03 mmol) in the same way as Example 31 (d) to obtain ivory solid compound of 5,9-dichloro-2-(methoxymethyl)pyrido[3,2-e][1,2,4]triazolo[1,5-c]pyrimidine (89.0 mg, 61%).

LC/MS ESI(+): 284 (M+1), 286 (M+3)
¹H-NMR (300 MHz, CDCl₃); δ: 9.06 (d, 1H, J=2.4 Hz), 8.87 (d, 1H, J=2.7 Hz), 4.85 (s, 2H), 3.59 (s, 3H)

(c) Synthesis of 9-chloro-2-(methoxymethyl)-5-(4-methylpiperazin-1-yl)pyrido[3,2-e][1,2,4]triazolo[1,5-c]pyrimidine 5,9-Dichloro-2-(methoxymethyl)pyrido[3,2-e][1,2,4]triazolo[1,5-c]pyrimidine (25.0 mg, 0.09 mmol) and N-methylpiperazine (20.0 μL, 0.18 mmol) were allowed to react in DCM (1.0 mL) in the same way as Example 31 (e) to obtain ivory solid compound of 9-chloro-2-(methoxymethyl)-5-(4-methylpiperazin-1-yl)pyrido[3,2-e][1,2,4]triazolo[1,5-c]pyrimidine (18.0 mg, 58%).

LC/MS ESI(+): 348 (M+1), 350 (M+3)

$^1$H-NMR (300 MHz, CDCl$_3$); δ: 8.81 (d, 1H, J=2.7 Hz), 8.67 (d, 1H, J=2.7 Hz), 4.76 (s, 2H), 4.33 (t, 4H, J=4.8 Hz), 3.57 (s, 3H), 2.64 (t, 4H, J=4.8 Hz), 2.38 (s, 3H)

Example 41

Synthesis of 9-chloro-2-ethyl-5-(4-methylpiperazin-1-yl)pyrido[3,2-e][1,2,4]triazolo[1,5-c]pyrimidine (a) Synthesis of 9-chloro-2-ethylpyrido[3,2-e][1,2,4]triazolo[1,5-c]pyrimidin-5-ol Ethyl (5-chloro-3-cyanopyridin-2-yl)carbamate was synthesized from 2-Amino-5-chloronicotinonitrile (500.0 mg, 3.26 mmol) in the same way as Example 31 (c), and allowed to react with ethylcarbohydrazide (150.0 mg, 1.79 mmol) to obtain yellow solid compound of 9-chloro-2-ethylpyrido[3,2-e][1,2,4]triazolo[1,5-c]pyrimidin-5-ol (95.0 mg, 12% in 2 steps)

LC/MS ESI(+): 250 (M+1), 252 (M+3)

$^1$H-NMR (300 MHz, DMSO-d$_6$); δ: 12.90 (s, 1H), 8.72 (d, 1H, J=2.7 Hz), 8.59 (d, 1H, J=2.7 Hz), 2.86 (q, 2H, J=7.5 Hz), 1.35 (t, 3H, J=7.5 Hz)

(b) Synthesis of 5,9-dichloro-2-ethylpyrido[3,2-e][1,2,4]triazolo[1,5-c]pyrimidine 9-Chloro-2-ethylpyrido[3,2-e][1,2,4]triazolo[1,5-c]pyrimidin-5-ol (92.0 mg, 0.37 mmol) was dissolved in POCl$_3$ (1.5 mL) and DIPEA (130.0 μL, 0.74 mmol) was added thereto. The reaction mixture was refluxed for 12 hours and then cooled to room temperature. Triethylbenzyl ammonium chloride (92.0 mg, 0.42 mmol) was added to the reaction mixture, stirred at 130° C. for 2 hours and then cooled to room temperature. The reaction mixture was poured into ice water, neutralized with saturated NaHCO$_3$ aqueous solution and then extracted with EtOAc. The organic layer was washed with brine, dried over anhydrous Na$_2$SO$_4$, filtered and then distilled with reduced pressure. The residue was purified by column chromatography (DCM) on silica. The fractons containing the product were collected and evaporated to obtain pale yellow solid compound of 5,9-dichloro-2-ethylpyrido[3,2-e][1,2,4]triazolo[1,5-c]pyrimidine (21.0 mg, 21%).

LC/MS ESI(+): 268 (M+1), 270 (M+3)

$^1$H-NMR (300 MHz, CDCl$_3$); δ: 9.12 (d, 1H, J=2.7 Hz), 8.96 (d, 1H, J=2.7 Hz), 2.99 (q, 2H, J=7.5 Hz), 1.35 (t, 3H, J=7.5 Hz)

(c) Synthesis of 9-chloro-2-ethyl-5-(4-methylpiperazin-1-yl)pyrido[3,2-e][1,2,4]triazolo[1,5-c]pyrimidine 5,9-Dichloro-2-ethylpyrido[3,2-e][1,2,4]triazolo[1,5-c]pyrimidine (10.0 mg, 0.04 mmol) and N-methylpiperazine (8.3 μL, 0.08 mmol) in DCM were reacted in the same way as Example 31 (e) to obtain white solid compound of 9-chloro-2-ethyl-5-(4-methylpiperazin-1-yl)pyrido[3,2-e][1,2,4]triazolo[1,5-c]pyrimidine (5.2 mg, 42%).

LC/MS ESI(+): 332 (M+1), 334 (M+3)

$^1$H-NMR (300 MHz, CDCl$_3$); δ: 8.84 (d, 1H, J=2.7 Hz), 8.64 (d, 1H, J=2.7 Hz), 4.13 (m, 4H), 2.91 (q, 2H, J=7.5 Hz), 2.53 (m, 4H), 2.24 (s, 3H), 1.36 (t, 3H, J=7.5 Hz)

Example 42

Synthesis of 9-chloro-5-(4-methylpiperazin-1-yl)pyrido[3,2-e][1,2,4]triazolo[4,3-c]pyrimidine (a) Synthesis of 6-chloropyrido[2,3-d]pyrimidin-2,4(1H,3H)-dione The mixture of 2-amino-5-chloronicotineamide (169.0 mg, 0.98 mmol) and diphosgene (646.0 mg, 3.14 mmol) dissolved in 1,4-dioxane (10.0 mL) was stirred at 120° C. for 12 hours and then cooled to room temperature. Et$_2$O was added thereto to form a solid, and the formed solid was filtered and then dried under reduced pressure to obtain ivory solid compound of 6-chloropyrido[2,3-d]pyrimidin-2,4(1H,3H)-dione (163.0 mg, 84%).

$^1$H-NMR (300 MHz, DMSO-d$_6$); δ: 11.59 (s, 2H), 8.60 (d, 1H, J=2.8 Hz), 8.19 (d, 1H, J=2.6 Hz)

(b) Synthesis of 2,4,6-trichloropyrido[2,3-d]pyrimidine

The mixture of 6-chloropyrido[2,3-d]pyrimidin-2,4(1H,3H)-dione (163.0 mg, 0.82 mmol) and BPOD (2.0 mL) was stirred at 180° C. for 6 hours and then cooled to room temperature. The reaction mixture was poured into water, and it was neutralized with saturated NaHCO$_3$ aqueous solution (pH=7) and then extracted with EtOAc (30.0 mL). The organic layer was washed with brine, dried over anhydrous Na$_2$SO$_4$, filtered and then distilled under reduced pressure to obtain white solid compound of 2,4,6-trichloropyrido[2,3-d]pyrimidine (169.0 mg, 88%).

$^1$H-NMR (300 MHz, DMSO-d$_6$); δ: 8.97 (d, 1H, J=2.8 Hz), 8.49 (d, 1H, J=2.8 Hz)

(c) Synthesis of 2,6-dichloropyrido[2,3-d]pyrimidin-4-ol 2,4,6-Trichloropyrido[2,3-d]pyrimidine (90.0 mg, 0.38 mmol) was dissolved in 1N NaOH/BuOH (0.8 mL/0.8 mL), stirred at room temperature for 2 hours, then distilled under reduced pressure, neutralized with 1N HCl aqueous solution (pH=7) and extracted with DCM (30.0 mL). The organic layer was washed with brine, dried over anhydrous Na$_2$SO$_4$, filtered and then reduced pressure to obtain ivory solid compound of 2,6-dichloropyrido[2,3-d]pyrimidin-4-ol (63.0 mg, 76%).

LC/MS ESI (+): 216 (M+1), 218 (M+3)

(d) Synthesis of Synthesis of 6-chloro-2-(4-methylpiperazin-1-yl)pyrido[2,3-d]pyrimidin-4(3H)-one The mixture of 2,6-dichloropyrido[2,3-d]pyrimidin-4-ol (63.0 mg, 0.29 mmol) and N-methyl piperazine (0.5 mL) dissolved in EtOH (5.0 mL) was stirred at 80° C. for one hour, then cooled to room temperature and distilled in reduced pressure. The reaction mixture was poured into water, and it was extracted with DCM (30.0 mL). The organic layer was washed with brine, dried over anhydrous Na$_2$SO$_4$, filtered and then distilled reduced pressure to obtain ivory solid compound of 6-chloro-2-(4-methylpiperazin-1-yl)pyrido[2,3-d]pyrimidin-4(3H)-one (63.0 mg, 77%).

LC/MS ESI (+): 280 (M+1), 282 (M+3)

(e) Synthesis of 4,6-dichloro-2-(4-methylpiperazin-1-yl)pyrido[2,3-d]pyrimidine The mixture of 6-chloro-2-(4-methylpiperazin-1-yl)pyrido[2,3-d]pyrimidin-4(3H)-one (63.0 mg, 0.23 mmol) and $POCl_3$ (1.0 mL) was stirred at 90° C. for 12 hours, and then distilled under reduced pressure to obtain brown solid compound of 4,6-dichloro-2-(4-methylpiperazin-1-yl)pyrido[2,3-d]pyrimidine.

LC/MS ESI (+): 298 (M+1), 300 (M+3)

(f) Synthesis of 6-chloro-4-hydrazinyl-2-(4-methylpiperazin-1-yl)pyrido[2,3-d]pyrimidine Unpurified 4,6-dichloro-2-(4-methylpiperazin-1-yl)pyrido[2,3-d]pyrimidine, TEA (233.0 mg, 2.30 mmol) and hydrazine monohydrate (115.0 mg, 2.30 mmol) were dissolved in EtOH (10.0 mL). The mixture was stirred at −20° C. for one hour and then distilled under reduced pressure to obtain yellow solid compound of 6-chloro-4-hydrazinyl-2-(4-methylpiperazin-1-yl)pyrido[2,3-d]pyrimidine.

LC/MS ESI (+): 294 (M+1), 296 (M+3)

(g) Synthesis of 9-chloro-5-(4-methylpiperazin-1-yl)pyrido[3,2-e][1,2,4]triazolo[4,3-c]pyrimidine The mixture of unpurified 6-chloro-4-hydrazinyl-2-(4-methylpiperazin-1-yl)pyrido[2,3-d]pyrimidine and trimethyl orthoformate (2.0 mL) was stirred at 100° C. for 2 hours and then cooled to room temperature. $Et_2O$ was added thereto to form a solid, and the formed solid was filtered to obtain purple solid compound of 9-chloro-5-(4-methylpiperazin-1-yl)pyrido[3,2-e][1,2,4]triazolo[4,3-c]pyrimidine (0.1 mg, 0.1%).

LC/MS ESI (+): 304 (M+1), 306 (M+3)
$^1$H-NMR (300 MHz, DMSO-$d_6$); δ: 9.54 (s, 1H), 8.82 (s, 1H), 8.76 (s, 1H), 3.66 (bs, 4H), 2.55 (m, 4H), 2.26 (s, 3H)

Example 43

Synthesis of 8-chloro-2-methyl-4-(4-methylpiperazin-1-yl)-2H-pyrazolo[3,4-c][1,8]naphthylidine

(a) Synthesis of ethyl 2-(5-chloro-1H-pyrrolo[2,3-b]pyridin-3-yl)-2-oxoacetate 5-Chloro-1H-pyrrolo[2,3-b]pyridine (500.0 mg, 3.28 mmol) and $AlCl_3$ (2180.0 mg, 16.38 mmol) were dissolved in DCM (10.0 mL), and ethyl 2-chloro-2-oxoacetate (44.0 μL, 3.93 mmol) was slowly added thereto at 0° C. The reaction mixture was stirred at room temperature for 12 hours. EtOH and ice were added to the reaction mixture at 0° C. and then extracted with DCM. The organic layer was washed with brine, dried over anhydrous $Na_2SO_4$, filtered and then distilled under reduced pressure to obtain yellow solid of compound of ethyl 2-(5-chloro-1H-pyrrolo[2,3-b]pyridin-3-yl)-2-oxoacetate (200.0 mg, 23%).

LC/MS ESI(+): 253 (M+1), 255 (M+3)
$^1$H-NMR (300 MHz, $CDCl_3$); δ: 10.39 (s, 1H), 8.72 (d, 1H, J=2.4 Hz), 8.68 (d, 1H, J=3 Hz), 8.39 (d, 1H, J=2.4 Hz), 4.44 (q, 2H, J=7.2 Hz), 1.45 (t, 3H, J=6.9 Hz)

(b) Synthesis of 8-chloro-2-methyl-2H-pyrazolo[3,4-c][1,8]naphthylidine-4(5H)-one Ethyl 2-(5-chloro-1H-pyrrolo[2,3-b]pyridin-3-yl)-2-oxoacetate (200.0 mg, 0.79 mmol), methylhydrazine sulfate (228.0 mg, 1.58 mmol) and acetic acid (68.0 μL, 11.87 mmol) were dissolved in EtOH (2.0 mL), and it was allowed to react in microwave under conditions of 100 W, 120° C. for 30 minutes, and then cooled to room temperature. $NH_4Cl$ aqueous solution was then added thereto and extracted with DCM. The organic layer was washed with brine, dried over anhydrous $Na_2SO_4$, filtered, then distilled under reduced pressure and purified by column chromatography (MeOH:DCM=5:95) on silica. The fractions containing the product were collected and evaporated to obtain ivory solid compound of 8-chloro-2-methyl-2H-pyrazolo[3,4-c][1,8]naphthylidine-4(5H)-one (30.0 mg, 16%).

LC/MS ESI(+): 235 (M+1), 237 (M+3)
$^1$H-NMR (300 MHz, $CDCl_3$); δ: 11.88 (s, 1H), 8.71 (s, 1H), 8.52 (d, 1H, J=2.7 Hz), 8.38 (d, 1H, J=2.4 Hz), 4.14 (s, 3H)

(c) Synthesis of 4,8-dichloro-2-methyl-2H-pyrazolo[3,4-c][1,8]naphthylidine 8-Chloro-2-methyl-2H-pyrazolo[3,4-c][1,8]naphthylidine-4(5H)-one (30.0 mg, 0.13 mmol) was dissolved in $POCl_3$ (1.5 mL) and DIPEA (66.0 μL, 0.38 mmol) was then added thereto. The reaction mixture was refluxed for 12 hours and then cooled to room temperature. The reaction mixture was poured into ice water, neutralized with saturated $NaHCO_3$ aqueous solution (pH=7) and then extracted with EtOAc. The organic layer was washed with brine, dried over anhydrous $Na_2SO_4$, filtered and then concentrated under reduced pressure to obtain solid compound of 4,8-dichloro-2-methyl-2H-pyrazolo[3,4-c][1,8]naphthylidine (30.0 mg, 90%).

LC/MS ESI(+): 253 (M+1), 255 (M+3)

(d) Synthesis of 8-chloro-2-methyl-4-(4-methylpiperazin-1-yl)-2H-pyrazolo[3,4-c][1,8]naphthylidine 4,8-Dichloro-2-methyl-2H-pyrazolo[3,4-c][1,8]naphthylidine (10.0 mg, 0.04 mmol) was dissolved in DMF (0.3 mL), and N-methylpiperazine (23.3 μL, 0.21 mmol) and TEA (58.0 μL, 0.42 mmol) were added thereto. The reaction mixture was stirred at room temperature for one hour and purified by column chromatography (MeOH:DCM=1:9) on silica. The fractions containing the product were collected and evaporated to obtain ivory solid compound of 8-chloro-2-methyl-4-(4-methylpiperazin-1-yl)-2H-pyrazolo[3,4-c][1,8]naphthylidine (3.7 mg, 30%).

LC/MS ESI(+): 317 (M+1), 319 (M+3)
$^1$H-NMR (300 MHz, $CDCl_3$); δ: 8.55 (s, 1H), 8.11 (s, 1H), 7.99 (d, 1H, J=2.4 Hz), 4.46 (m, 4H), 4.22 (s, 3H), 2.60 (m, 4H), 2.36 (s, 3H)

Example 44

Synthesis of 1-(8-chloro-2-methyl-2H-pyrazolo[3,4-c][1,8]naphthylidine-4-yl)-N-methylazetidin-3-amine 4,8-Dichloro-2-methyl-2H-pyrazolo[3,4-c][1,8]naphthylidine (10.0 mg, 0.04 mmol) was dissolved in DMF (0.3 mL), and tert-butyl azetidin-3-yl(methyl)carbamate (39.1 mg, 0.21 mmol) and TEA (58.0 μL, 0.42 mmol) were added thereto. The reaction mixture was stirred at room temperature for one hour, concentrated under reduced pressure, dissolved in DCM (1.0 mL) without purification and then TFA (0.2 mL) was added thereto. The reaction mixture was stirred at room temperature for one hour and purified by column chromatography (MeOH:DCM=5:95) on amine silica. The fractions containing the product were collected and evaporated to obtain ivory solid compound of 1-(8-chloro-2-methyl-2H-pyrazolo[3,4-c][1,8]naphthylidine-4-yl)-N-methylazetidin-3-amine (3.2 mg, 25%).

LC/MS ESI(+): 303 (M+1), 305 (M+3)

$^1$H-NMR (300 MHz, CDCl$_3$+MeOH-d$_4$); δ: 8.47 (s, 1H), 8.27 (s, 1H), 8.13 (d, 1H, J=2.4 Hz), 4.89 (m, 2H), 4.71 (m, 2H), 4.23 (s, 3H), 3.99 (m, 1H), 2.76 (s, 3H).

Example 45

Synthesis of 8-chloro-2-methyl-4-(piperazin-1-yl)-2H-pyrazolo[3,4-c][1,8]naphthylidine 4,8-Dichloro-2-methyl-2H-pyrazolo[3,4-c][1,8]naphthylidine (10.0 mg, 0.04 mmol) was dissolved in DMF (0.3 mL), and tert-butyl piperazin-1-carboxylate (39.1 mg, 0.21 mmol) and TEA (58.0 μL, 0.42 mmol) were added thereto. The reaction mixture was stirred at room temperature for one hour, concentrated under reduced pressure, dissolved in DCM (1.0 mL) without purification and then TFA (0.2 mL) was added thereto. The reaction mixture was stirred at room temperature for one hour and purified by column chromatography (MeOH:DCM=5:95) on amine silica. The fractions containing the product were collected and evaporated to obtain ivory solid compound of 8-chloro-2-methyl-4-(piperazin-1-yl)-2H-pyrazolo[3,4-c][1,8]naphthylidine (2.0 mg, 16%).

LC/MS ESI(+): 303 (M+1), 305 (M+3)

$^1$H-NMR (300 MHz, CDCl$_3$); δ: 8.50 (d, 1H, J=2.7 Hz), 8.16 (s, 1H), 8.04 (d, 1H, J=2.7 Hz), 4.52 (m, 4H), 4.20 (s, 3H), 3.17 (m, 4H).

Example 46

Synthesis of 8-chloro-4-(4-methylpiperazin-1-yl)imidazo[1,2-a]pyrido[2,3-e]pyrazine (a) Synthesis of 2,7-dichloro-3-(4-methylpiperazin-1-yl)pyrido[2,3-b]pyrazine 2,3,7-Trichloropyrido[2,3-b]pyrazine (500.0 mg, 2.13 mmol) and TEA (3.1 mL, 21.30 mmol) were dissolved in DCM (15.0 mL), and N-methyl piperazine (0.3 mL, 2.34 mmol) diluted in DCM (5.0 mL) was slowly added thereto at 0° C. The reaction mixture was stirred at room temperature for 12 hours, poured into saturated NH$_4$Cl aqueous solution and then extracted with DCM (30.0 mL). The organic layer was washed with brine, dried over anhydrous Na$_2$SO$_4$, filtered and then distilled under reduced pressure. The residue was purified by column chromatography (DCM:MeOH=20:1) on amine silica. The fractions containing the product were collected and evaporated to obtain yellow solid compound of 2,7-dichloro-3-(4-methylpiperazin-1-yl)pyrido[2,3-b]pyrazine (331.0 mg, 52%).

LC/MS ESI (+): 298 (M+1), 300 (M+3)

(b) Synthesis of 7-chloro-N-(2,2-diethoxyethyl)-3-(4-methylpiperazin-1-yl)pyrido[2,3-b]pyrazin-2-amine The mixture of 2,7-dichloro-3-(4-methylpiperazin-1-yl)pyrido[2,3-b]pyrazine (100.0 mg, 0.34 mmol) and 2,2-diethoxyethylamine (2.0 mL) was stirred at room temperature for 2 hours. The reaction mixture was poured into water and extracted with DCM (30.0 mL). The organic layer was washed with brine, dried over anhydrous Na$_2$SO$_4$, filtered and then distilled under reduced pressure to obtain yellow solid compound of 7-chloro-N-(2,2-diethoxyethyl)-3-(4-methylpiperazin-1-yl)pyrido[2,3-b]pyrazin-2-amine.

LC/MS ESI (+): 395 (M+1), 397 (M+3)

(c) Synthesis of 8-chloro-4-(4-methylpiperazin-1-yl)imidazo[1,2-a]pyrido[2,3-e]pyrazine The mixture of unpurified 7-chloro-N-(2,2-diethoxyethyl)-3-(4-methylpiperazin-1-yl)pyrido[2,3-b]pyrazin-2-amine and TsOH (128.0 mg, 0.68 mmol) dissolved in IPA (5.0 mL) was stirred at 100° C. for 2 hours, then cooled to room temperature and distilled under reduced pressure. The reaction mixture was poured into and extracted with DCM (30.0 mL). The organic layer was washed with brine, dried under anhydrous Na$_2$SO$_4$, filtered and then distilled under reduced pressure. The residue was purified by column chromatography (DCM:MeOH=20:1 to 90:10) on silica. The fractions containing the product were collected and evaporated to obtain yellow solid compound of 8-chloro-4-(4-methylpiperazin-1-yl)imidazo[1,2-a]pyrido[2,3-e]pyrazine (56.0 mg, 55% in 2 steps).

LC/MS ESI (+): 303 (M+1), 305 (M+3)

$^1$H-NMR (300 MHz, DMSO-d$_6$); δ: 8.81 (d, 1H, J=2.4 Hz), 8.74 (d, 1H, J=1.2 Hz), 8.53 (d, 1H, J=2.4 Hz), 7.72 (d, 1H, J=1.4 Hz), 4.42 (bs, 4H), 2.49 (m, 4H), 2.23 (s, 3H)

Example 47

Synthesis of 8-chloro-4-(piperazin-1-yl)imidazo[1,2-a]pyrido[2,3-e]pyrazine (a) Synthesis of tert-butyl 4-(2,7-dichloropyrido[2,3-b]pyrazin-3-yl)piperazin-1-carboxylate 2,3,7-Trichloropyrido[2,3-b]pyrazine (400.0 mg, 1.71 mmol) and TEA (2.4 mL, 17.10 mmol) were dissolved in DCM (8.0 mL) and tert-butyl piperazin-1-carboxylate (350.0 mg, 1.88 mmol) diluted in DCM (2.0 mL) was slowly added thereto at 0° C. The reaction mixture was stirred at room temperature for 2 hours, poured into saturated NH$_4$Cl aqueous solution and then extracted with DCM (30.0 mL). The organic layer was washed with brine, dried over anhydrous Na$_2$SO$_4$, filtered and then distilled under reduced pressure. The residue was purified by column chromatography (DCM:MeOH=19:1) on silica. The fractions containing the product were collected and evaporated to obtain yellow solid compound of tert-butyl 4-(2,7-dichloropyrido[2,3-b]pyrazin-3-yl)piperazin-1-carboxylate.

LC/MS ESI (+): 384 (M+1), 386 (M+3)

(b) Synthesis of tert-butyl 4-(7-chloro-2-((2,2-diethoxyethyl)amino)pyrido[2,3-b]pyrazin-3-yl)piperazin-1-carboxylate The mixture of unpurified tert-butyl 4-(2,7-dichloropyrido[2,3-b]pyrazin-3-yl)piperazin-1-carboxylate and 2,2-diethoxyethylamine (2.0 mL) was stirred at room temperature for 12 hours, poured into water and then extracted with EtOAc (30.0 mL). The organic layer was washed with brine, dried over anhydrous Na$_2$SO$_4$, filtered and then distilled under reduced pressure to obtain yellow solid compound of tert-butyl 4-(7-chloro-2-((2,2-diethoxyethyl)amino)pyrido[2,3-b]pyrazin-3-yl)piperazin-1-carboxylate.

LC/MS ESI (+): 481 (M+1), 483 (M+3)

(c) Synthesis of 8-chloro-4-(piperazin-1-yl)imidazo[1,2-a]pyrido[2,3-e]pyrazine The mixture of unpurified tert-butyl 4-(7-chloro-2-((2,2-diethoxyethyl)amino)pyrido[2,3-b]pyrazin-3-yl)piperazin-1-carboxylate and TsOH (662.0 mg, 3.48 mmol) dissolved in IPA (10.0 mL) was stirred at 100° C. for one hour, then cooled to room temperature and distilled under reduced pressure. The reaction mixture was poured into water, neutralized with NaHCO$_3$ aqueous solution (pH=7) and then extracted with DCM (50.0 mL). The organic layer was washed with brine, dried over anhydrous Na$_2$SO$_4$, filtered and then distilled under reduced pressure. The residue was purified by column chromatography (DCM:MeOH=20:1 to 90:10) on silica. The fractions containing the product were collected and evaporated to obtain yellow solid compound of 8-chloro-4-(piperazin-1-yl)imidazo[1,2-a]pyrido[2,3-e]pyrazine (155.0 mg, 31% in 2 steps).

LC/MS ESI (+): 289 (M+1), 291 (M+3)

$^1$H-NMR (300 MHz, DMSO-d$_6$); δ: 8.79 (d, 1H, J=2.5 Hz), 8.74 (m, 1H), 8.52 (d, 1H, J=2.4 Hz), 7.72 (m, 1H), 4.35 (bs, 4H), 2.84 (m, 4H)

Example 48

Synthesis of 1-(8-iodopyrido[2,3-e][1,2,4]triazolo[4,3-a]pyrazin-4-yl)-N-methylazetidin-3-amine

(a) Synthesis of tert-butyl (1-(8-iodopyrido[2,3-e][1,2,4]triazolo[4,3-a]pyrazin-4-yl)azetidin-3-yl)(methyl)carbamate tert-Butyl (1-(8-bromopyrido[2,3-e][1,2,4]triazolo[4,3-a]pyrazin-4-yl)azetidin-3-yl)(methyl)carbamate (50.0 mg, 0.11 mmol), N,N'-dimethylethane-1,2-diamine (1.0 mg, 0.01 mmol), CuI (1.1 mg, 5.50 μmmol) and KI (38.0 mg, 0.22 mmol) were added to 1-butanol (1.0 mL), stirred at 100° C. for 18 hours, distilled under reduced pressure and then purified by column chromatography (DCM:MeOH=98:2 to 95:5) on silica. The fractions containing the product were collected and evaporated to obtain white solid compound of tert-butyl (1-(8-iodopyrido[2,3-e][1,2,4]triazolo[4,3-a]pyrazin-4-yl)azetidin-3-yl)(methyl)carbamate (25.0 mg, 45%).

LC/MS ESI (+): 482 (M+1)

(b) Synthesis of 1-(8-iodopyrido[2,3-e][1,2,4]triazolo[4,3-a]pyrazin-4-yl)-N-methylazetidin-3-amine tert-Butyl (1-(8-iodopyrido[2,3-e][1,2,4]triazolo[4,3-a]pyrazin-4-yl)azetidin-3-yl)(methyl)carbamate (25.0 mg, 0.05 mmol) was dissolved in DCM (3.0 mL), and TFA (0.5 mL) was slowly added thereto at 0° C. The reaction mixture was stirred at room temperature for one hour and distilled under reduced pressure. The residue was neutralized with NaHCO$_3$ aqueous solution (pH=7) and extracted with DCM-MeOH (9/1, 30.0 mL). The organic layer was washed with brine, dried over anhydrous Na$_2$SO$_4$, filtered, distilled under reduced pressure and then purified by column chromatography (DCM:MeOH=96:4) on amine silica. The fractions containing the product were collected and evaporated to obtain ivory solid compound of 1-(8-iodopyrido[2,3-e][1,2,4]triazolo[4,3-a]pyrazin-4-yl)-N-methylazetidin-3-amine (15.0 mg, 75%).

LC/MS ESI (+): 382 (M+1)

$^1$H-NMR (300 MHz, DMSO-d$_6$); δ: 9.96 (s, 1H), 8.97 (d, 1H, J=2.1 Hz), 8.68 (d, 1H, J=2.1 Hz), 4.89 (m, 1H), 4.42 (m, 2H), 4.00 (m, 1H), 3.70 (m, 1H), 2.29 (s, 3H)

Example 49

Synthesis of 8-iodo-4-(4-methylpiperazin-1-yl)pyrido[2,3-e][1,2,4]triazolo[4,3-a]pyrazine

(a) Synthesis of 5-iodopyridin-2,3-diamine

5-Iodo-3-nitropyridin-2-amine (2000.0 mg, 7.55 mmol), Fe (4800.0 mg, 85.90 mmol) and conc. HCl (0.1 mL) were added to a mixture of EtOH (7.0 mL) and water (2.0 mL), and the suspension was stirred at 100° C. for 30. The reaction mixture was cooled to room temperature, filtered through celite and then distilled under reduced pressure. The residue was purified by column chromatography (MeOH:DCM=1:40) on silica. The fractions containing the product were collected and evaporated to obtain brown solid compound of 5-iodopyridin-2,3-diamine (1710.0 mg, 97%).

LC/MS ESI(+): 236 (M+1)

$^1$H-NMR (300 MHz, DMSO-d$_6$); δ: 7.37 (d, 1H, J=2.1 Hz), 6.91 (d, 1H, J=2.1 Hz), 5.59 (s, 2H), 4.91 (s, 2H)

(b) Synthesis of 2,3-dichloro-7-iodopyrido[2,3-b]pyrazine

The mixture of 5-iodopyridin-2,3-diamine (1400.0 mg, 5.96 mmol) and diethyl oxalate (10.0 mL) was stirred at 100° C. for 12 hours and then cooled to room temperature. Et$_2$O was added to the reaction mixture to form a solid, and the formed solid was then filtered and dried under reduced pressure to obtain brown solid compound of 7-iodopyrido[2,3-b]pyrazin-2,3-diol. The mixture of unpurified 7-iodopyrido[2,3-b]pyrazin-2,3-diol and POCl$_3$ (15.0 mL) was stirred at 150° C. for 12 hours and then cooled to room temperature. The reaction mixture was poured into ice water, and the formed solid was filtered and then dried under reduced pressure to obtain brown solid compound of 2,3-dichloro-7-iodopyrido[2,3-b]pyrazine (1080.0 mg, 56%).

LC/MS ESI(+): 326 (M+1), 328 (M+3)

(c) Synthesis of 2-chloro-7-iodo-3-(4-methylpiperazin-1-yl)pyrido[2,3-b]pyrazine 2,3-Dichloro-7-iodopyrido[2,3-b]pyrazine (50.0 mg, 0.15 mmol) and TEA (213.0 μL, 1.53 mmol) were dissolved in DCM (2.0 mL) and N-methylpiperazine (16.0 μL, 0.15 mmol) was slowly added thereto at 0° C. The reaction mixture was stirred at 0° C. for one hour, concentrated, and then purified by column chromatography (MeOH:DCM=5:95) on silica. The fractions containing the product were collected and evaporated to obtain yellow solid compound of 2-chloro-7-iodo-3-(4-methylpiperazin-1-yl)pyrido[2,3-b]pyrazine (40.0 mg, 67%).

LC/MS ESI (+): 390 (M+1), 392 (M+3)

(d) Synthesis of 2-hydrazinyl-7-iodo-3-(4-methylpiperazin-1-yl)pyrido[2,3-b]pyrazine 2-Chloro-7-iodo-3-(4-methylpiperazin-1-yl)pyrido[2,3-b]pyrazine (40.0 mg, 0.10 mmol) and hydrazine monohydrate (7.5 μL, 0.15 mmol) were dissolved in EtOH (1.0 mL), stirred at room temperature for 3 hours to form a solid. The formed solid was filtered to obtain yellow solid compound of 2-hydrazinyl-7-iodo-3-(4-methylpiperazin-1-yl)pyrido[2,3-b]pyrazine (39.4 mg, 100%).

LC/MS ESI(+): 386 (M+1)

(e) Synthesis of 8-iodo-4-(4-methylpiperazin-1-yl)pyrido[2,3-e][1,2,4]triazolo[4,3-a]pyrazine The mixture of 2-hydrazinyl-7-iodo-3-(4-methylpiperazin-1-yl)pyrido[2,3-b]pyrazine (39.4 mg, 0.10 mmol) and trimethyl orthoformate (2.0 mL) was stirred at 80° C. for 3 hours and then cooled to room temperature. Et$_2$O was added thereto to form a solid, and the formed solid was filtered and dried under reduced pressure. The residue was purified by column chromatography (MeOH:DCM=5:95) on silica. The fractions containing the product were collected and evaporated to obtain yellow solid compound of 8-iodo-4-(4-methylpiperazin-1-yl)pyrido[2,3-e][1,2,4]triazolo[4,3-a]pyrazine (13.5 mg, 34%).

LC/MS ESI(+): 396 (M+1)

$^1$H-NMR (300 MHz, DMSO-d$_6$); δ: 10.00 (s, 1H), 9.00 (d, 1H, J=2.1 Hz), 8.71 (d, 1H, J=2.1 Hz), 4.57-4.17 (m, 4H), 2.52 (m, 4H), 2.24 (s, 3H)

Example 50

Synthesis of N-methyl-1-(8-methylpyrido[2,3-e][1,2,4]triazolo[4,3-a]pyrazin-4-yl)azetidin-3-amine (a) Synthesis of 5-methylpyridin-2,3-diamine 5-Methyl-3-nitropyridin-2-amine (50000.0 mg, 0.33 mol) was dissolved in MeOH/EtOAc (1000.0 mL), and 10% of Pd/C (5000.0 mg) was added thereto. The flask was substituted with hydrogen. The reaction mixture was reacted at room temperature for 8 hours, then filtered through celite and evaporated under reduced pressure to obtain brown solid compound of 5-methylpyridin-2,3-diamine (98000.0 mg, 82%).

$^1$H-NMR (300 MHz, CDCl$_3$); δ: 7.48 (s, 1H), 6.74 (s, 1H), 4.06 (bs, 2H), 3.27 (bs, 2H), 2.16 (s, 3H)

(b) Synthesis of 7-methylpyrido[2,3-b]pyrazin-2,3-diol

5-Methylpyridin-2,3-diamine (98000.0 mg, 0.80 mol) and oxalic acid (76900.0 mg, 0.85 mol) were added to 3N HCl (784.0 mL). The mixture was stirred at 120° C. for 24 hours and then cooled to room temperature. The formed solid was filtered and dried under reduced pressure to obtain brown solid compound of 7-methylpyrido[2,3-b]pyrazin-2,3-diol (140000.0 mg, 100%).

$^1$H-NMR (300 MHz, DMSO-d$_6$); δ: 12.26 (bs, 1H), 11.97 (bs, 1H), 7.90 (s, 1H), 7.25 (s, 1H), 2.25 (s, 3H)

(c) Synthesis of 2,3-dichloro-7-methylpyrido[2,3-b]pyrazine

The mixture of 7-methylpyrido[2,3-b]pyrazin-2,3-diol (140000.0 mg, 0.79 mol) and POCl$_3$ (900.0 mL) was stirred at 130° C. for 24 hours and then cooled to room temperature. The reaction mixture was poured into ice water to form a solid. The formed solid was filtered, dried under reduced pressure and then purified by column chromatography (DCM) on silica. The fractions containing the product were collected and evaporated to obtain brown solid compound of 2,3-dichloro-7-methylpyrido[2,3-b]pyrazine (55000.0 mg, 33%).

(d) Synthesis of tert-butyl (1-(2-chloro-7-methylpyrido[2,3-b]pyrazin-3-yl)azetidin-3-yl)(methyl)carbamate 2,3-Dichloro-7-methylpyrido[2,3-b]pyrazine (750.0 mg, 3.47 mmol) and tert-butyl azetidin-3-yl(methyl)carbamate hydrochloride (850.0 mg, 3.82 mmol) were allowed to react in the same way as Example 2 (c) to obtain pale yellow solid compound of tert-butyl (1-(2-chloro-7-methylpyrido[2,3-b]pyrazin-3-yl)azetidin-3-yl)(methyl)carbamate (720.0 mg, 57%).

LC/MS ESI(+): 364 (M+1)

$^1$H-NMR (300 MHz, CDCl$_3$); δ: 8.74 (d, 1H, J=2.1 Hz), 7.91 (d, 1H, J=2.1 Hz), 5.05 (m, 1H), 4.71 (m, 2H), 4.53 (m, 2H), 2.99 (s, 3H), 2.51 (s, 3H), 1.50 (s, 9H)

(e) Synthesis of tert-butyl methyl(1-(8-methylpyrido[2,3-e][1,2,4]triazolo[4,3-a]pyrazin-4-yl)azetidin-3-yl)carbamate tert-Butyl (1-(2-chloro-7-methylpyrido[2,3-b]pyrazin-3-yl)azetidin-3-yl)(methyl)carbamate (320.0 mg, 0.88 mmol) and hydrazine monohydrate (0.1 mL, 3.50 mmol) were dissolved in EtOH (8.0 mL) and stirred at 40° C. for 12 hours. Et$_2$O was added thereto to form a solid, and the formed solid was filtered and dried under reduced pressure to obtain dark brown compound of tert-butyl (1-(2-hydrazinyl-7-methylpyrido[2,3-b]pyrazin-3-yl)azetidin-3-yl)(methyl)carbamate. Unpurified compound of tert-butyl (1-(2-hydrazinyl-7-methylpyrido[2,3-b]pyrazin-3-yl)azetidin-3-yl)(methyl)carbamate and trimethyl orthoformate (4.0 mL) were reacted to obtain brown solid compound of tert-butyl methyl(1-(8-methylpyrido[2,3-e][1,2,4]triazolo[4,3-a]pyrazin-4-yl)azetidin-3-yl)carbamate (92.0 mg, 29% in 2 steps).

LC/MS ESI(+): 370 (M+1)

$^1$H-NMR (300 MHz, CDCl$_3$); δ: 9.14 (s, 1H), 8.52 (d, 1H, J=2.1 Hz), 7.84 (d, 1H, J=2.1 Hz), 4.60 (m, 5H), 2.99 (s, 3H), 2.46 (s, 3H), 1.47 (s, 9H)

(f) Synthesis of N-methyl-1-(8-methylpyrido[2,3-e][1,2,4]triazolo[4,3-a]pyrazin-4-yl)azetidin-3-amine tert-Butyl methyl(1-(8-methylpyrido[2,3-e][1,2,4]triazolo[4,3-a]pyrazin-4-yl)azetidin-3-yl)carbamate (90.0 mg, 0.24 mmol) was dissolved in a mixture of DCM (2.0 mL) and TFA (3.0 mL). The reaction mixture was stirred at 0° C. for one hour and then purified by column chromatography (DCM:MeOH=50:1) on amine silica. The fractions containing the product were collected and evaporated to obtain yellow solid compound of N-methyl-1-(8-methylpyrido[2,3-e][1,2,4]triazolo[4,3-a]pyrazin-4-yl)azetidin-3-amine (39.0 mg, 59%).

LC/MS ESI(+): 270 (M+1)

$^1$H-NMR (300 MHz, CDCl$_3$); δ: 9.13 (s, 1H), 8.51 (d, 1H, J=2.1 Hz), 7.83 (d, 1H, J=2.1 Hz), 5.09 (m, 1H), 4.75-4.55 (m, 2H), 4.20 (m, 1H), 3.89 (m, 1H), 2.50 (s, 6H)

Example 51

Synthesis of 1-(8-(difluoromethyl)pyrido[2,3-e][1,2,4]triazolo[4,3-a]pyrazin-4-yl)-N-methylazetidin-3-amine (a) Synthesis of tert-butyl (1-(8-formylpyrido[2,3-e][1,2,4]triazolo[4,3-a]pyrazin-4-yl)azetidin-3-yl)(methyl)carbamate 2.5M of n-BuLi in hexane solution was slowly added to a suspension of tert-butyl (1-(8-iodopyrido[2,3-e][1,2,4]triazolo[4,3-a]pyrazin-4-yl)azetidin-3-yl)(methyl)carbamate (270.0 mg, 0.56 mmol) and THF (5.6 mL) at −78° C. The reaction mixture was stirred at −78° C. for 10 minutes, and DMF (0.5 mL) and THF (2.0 mL) was then added thereto. The reaction mixture was stirred for one hour and $NH_4Cl$ aqueous solution was added thereto, and it was extracted with EtOAc. The organic layer was washed with brine, dried over anhydrous $Na_2SO_4$, filtered and then distilled under reduced pressure. The residue was purified by column chromatography (MeOH:DCM=1:60) on silica. The fractions containing the product were collected and evaporated to obtain pale white solid compound of tert-butyl (1-(8-formylpyrido[2,3-e][1,2,4]triazolo[4,3-a]pyrazin-4-yl)azetidin-3-yl)(methyl)carbamate (18.0 mg, 8%).

LC/MS ESI(+): 384 (M+1)

$^1$H-NMR (300 MHz, DMSO-$d_6$); δ: 10.14 (s, 1H), 10.10 (s, 1H), 9.04 (d, 1H, J=2.1 Hz), 8.97 (d, 1H, J=2.1 Hz), 5.09-5.00 (m, 2H), 4.89 (m, 1H), 4.60 (m, 1H), 4.46 (m, 1H), 2.94 (s, 3H), 1.42 (s, 9H)

(b) Synthesis of tert-butyl (1-(8-(difluoromethyl) pyrido[2,3-e][1,2,4]triazolo[4,3-a]pyrazin-4-yl)azetidin-3-yl)(methyl)carbamate Suspension of tert-butyl (1-(8-formylpyrido[2,3-e][1,2,4]triazolo[4,3-a]pyrazin-4-yl)azetidin-3-yl)(methyl)carbamate (11.0 mg, 0.03 mmol) and Deoxo-Fluor (0.8 mL) was allowed to react in microwaver under conditions of 50 W, 70° C. for 1.5 hours and then cooled to room temperature. The reaction mixture was poured into ice water and $NH_4Cl$ aqueous solution was added thereto, and it was extracted with MeOH:DCM=1:20 solution. The organic layer was dried over anhydrous $Na_2SO_4$, filtered and then distilled under reduced pressure. The residue was purified by column chromatography (MeOH:DCM=1:60) on silica. The fractions containing the product were collected and evaporated to obtain ivory solid compound of tert-butyl (1-(8-(difluoromethyl)pyrido[2,3-e][1,2,4]triazolo[4,3-a]pyrazin-4-yl) azetidin-3-yl)(methyl)carbamate (5.0 mg, 45%).

$^1$H-NMR (300 MHz, CDCl$_3$); δ: 9.23 (s, 1H), 8.76 (s, 1H), 8.19 (s, 1H), 7.04-6.66 (m, 1H), 5.18 (m, 1H), 4.99 (m, 1H), 4.74 (m, 1H), 4.56 (m, 1H), 4.35-4.25 (m, 1H), 3.01 (s, 3H), 1.49 (s, 9H)

(c) Synthesis of 1-(8-(difluoromethyl)pyrido[2,3-e] [1,2,4]triazolo[4,3-a]pyrazin-4-yl)-N-methylazetidin-3-amine TFA (0.4 mL) was added to the mixture of tert-butyl (1-(8-(difluoromethyl)pyrido[2,3-e][1,2,4]triazolo[4,3-a] pyrazin-4-yl)azetidin-3-yl)(methyl)carbamate (5.0 mg, 0.01 mmol) and DCM (0.6 mL), and it was then stirred at room temperature for one hour. The reaction mixture was purified by column chromatography (MeOH:DCM=1:40) on amine silica. The fractions containing the product were collected and evaporated. Et$_2$O was added to the residue to form a solid. The formed solid was filtered and dried under reduced pressure to obtain ivory solid compound of 1-(8-(difluoromethyl)pyrido[2,3-e][1,2,4]triazolo[4,3-a]pyrazin-4-yl)-N-methylazetidin-3-amine (1.5 mg, 41%).

LC/MS ESI(+): 306 (M+1)

$^1$H-NMR (300 MHz, DMSO-$d_6$); δ: 10.07 (s, 1H), 8.83 (s, 1H), 8.69 (s, 1H), 7.42-7.05 (m, 1H), 4.93 (m, 1H), 4.52-4.40 (m, 2H), 4.01 (m, 1H), 3.72 (m, 1H), 2.30 (s, 3H)

Example 52

Synthesis of N-methyl-1-(8-(trifluoromethyl)pyrido [2,3-e][1,2,4]triazolo[4,3-a]pyrazin-4-yl)azetidin-3-amine (a) Synthesis of 3-nitro-5-(trifluoromethyl)pyridin-2-amine 5-(trifluoromethyl)pyridin-2-amine (1700.0 mg, 10.49 mmol) was dissolved in conc. $H_2SO_4$ (10.0 mL), and then conc. $HNO_3$ (1.7 mL, 26.22 mmol) was slowly added thereto. The reaction mixture was stirred at 80° C. for 48 hours, then added to ice water, alkalized with 1N NaOH aqueous solution (pH=9) and then extracted with EtOAc (200.0 mL). The organic layer was washed with brine, dried over anhydrous $Na_2SO_4$, filtered and then distilled under reduced pressure. The residue was purified by column chromatography (n-Hex:EtOAc=50:50) on silica. The fractions containing the product were collected and evaporated to obtain yellow solid compound of 3-nitro-5-(trifluoromethyl)pyridin-2-amine (538.0 mg, 25%).

LC/MS ESI (+): 208 (M+1)

$^1$H-NMR (300 MHz, CDCl$_3$); δ: 8.67 (d, 1H, J=1.7 Hz), 8.59 (d, 1H, J=1.7 Hz), 7.92 (bs, 1H), 6.10 (bs, 1H)

(b) Synthesis of 5-(trifluoromethyl)pyridin-2,3-diamine

3-Nitro-5-(trifluoromethyl)pyridin-2-amine (538.0 mg, 2.60 mmol) and $SnCl_2 \cdot 2H_2O$ (2340.0 mg, 10.39 mmol) were added to DMF (5.0 mL), and it was stirred at 60° C. for 12 hours. The reaction mixture was poured into saturated $NaHCO_3$ aqueous solution and neutralized (pH=7), and it was then extracted with EtOAc (200.0 mL). The organic layer was washed with brine, dried over anhydrous $Na_2SO_4$, filtered and then evaporated under reduced pressure to obtain brown solid compound of 5-(trifluoromethyl)pyridin-2,3-diamine.

LC/MS ESI (+): 178 (M+1)

(c) Synthesis of 2,3-dichloro-7-(trifluoromethyl) pyrido[2,3-b]pyrazine

Unpurified 5-(trifluoromethyl)pyridin-2,3-diamine was added to diethyl oxalate (10.0 mL). The mixture was stirred at 120° C. for 12 hours and then cooled to room temperature. Et$_2$O was added thereto to form a solid, and the formed solid was filtered under reduced pressure to obtain brown solid compound of 7-(trifluoromethyl)pyrido[2,3-b]pyrazin-2,3-diol. The mixture of unpurified 7-(trifluoromethyl)pyrido[2,3-b]pyrazin-2,3-diol and POCl$_3$ (10.0 mL) was stirred at 130° C. for 12 hours and then cooled to room temperature. The reaction mixture was poured into ice water to form a solid. The formed solid was filtered and then dried under reduced pressure to obtain brown solid compound of 2,3-dichloro-7-(trifluoromethyl)pyrido[2,3-b]pyrazine (370.0 mg, 53% in 3 steps).

LC/MS ESI (+): 268 (M+1), 270 (M+3), 272 (M+5)

(d) Synthesis of tert-butyl (1-(2-chloro-7-(trifluoromethyl)pyrido[2,3-b]pyrazin-3-yl)azetidin-3-yl) (methyl)carbamate 2,3-Dichloro-7-(trifluoromethyl)pyrido[2,3-b]pyrazine (100.0 mg, 0.37 mmol) and TEA (0.26 mL, 1.85 mmol) were dissolved in DCM (10.0 mL), and tert-butyl azetidin-3-yl (methyl)carbamate hydrochloride (83.0 mg, 0.37 mmol) diluted in DCM (5.0 mL) and TEA (0.26 mL, 1.85 mmol) were slowly added thereto at 0° C. The reaction mixture was stirred at room temperature for one hour. The reaction mixture was poured into saturated NH$_4$Cl aqueous solution and extracted with DCM (30.0 mL). The organic layer was washed with brine, dried over anhydrous Na$_2$SO$_4$, filtered and then distilled under reduced pressure. The residue was purified by column chromatography (DCM:MeOH=100:0) on amine silica. The fractions containing the product were collected and evaporated to obtain brown solid compound of tert-butyl (1-(2-chloro-7-(trifluoromethyl)pyrido[2,3-b]pyrazin-3-yl)azetidin-3-yl)(methyl)carbamate.

LC/MS ESI (+): 418 (M+1)

(e) Synthesis of tert-butyl (1-(2-hydrazinyl-7-(trifluoromethyl)pyrido[2,3-b]pyrazin-3-yl)azetidin-3-yl)(methyl)carbamate Unpurified tert-butyl (1-(2-chloro-7-(trifluoromethyl)pyrido[2,3-b]pyrazin-3-yl)azetidin-3-yl)(methyl)carbamate and hydrazine monohydrate (47.0 mg, 0.93 mmol) were dissolved in EtOH (5.0 mL), stirred at room temperature for 12 hours and then distilled under reduced pressure. Et$_2$O was added thereto to form a solid, and the formed solid was filtered and then dried under reduced pressure to obtain yellow solid compound of tert-butyl (1-(2-hydrazinyl-7-(trifluoromethyl)pyrido[2,3-b]pyrazin-3-yl)azetidin-3-yl)(methyl)carbamate.

LC/MS ESI (+): 414 (M+1)

(f) Synthesis of tert-butyl methyl(1-(8-(trifluoromethyl)pyrido[2,3-e][1,2,4]triazolo[4,3-a]pyrazin-4-yl)azetidin-3-yl)carbamate The mixture of unpurified tert-butyl (1-(2-hydrazinyl-7-(trifluoromethyl)pyrido[2,3-b]pyrazin-3-yl)azetidin-3-yl)(methyl)carbamate and trimethyl orthoformate (10.0 mL) was stirred at 80° C. for one hour and then cooled to room temperature. Et$_2$O was added thereto to form a solid, and the formed solid was filtered and then dried under reduced pressure to obtain ivory solid compound of tert-butyl methyl(1-(8-(trifluoromethyl)pyrido[2,3-e][1,2,4]triazolo[4,3-a]pyrazin-4-yl)azetidin-3-yl)carbamate.

LC/MS ESI (+): 424 (M+1)

(g) Synthesis of N-methyl-1-(8-(trifluoromethyl)pyrido[2,3-e][1,2,4]triazolo[4,3-a]pyrazin-4-yl)azetidin-3-amine Unpurified tert-butyl methyl(1-(8-(trifluoromethyl)pyrido[2,3-e][1,2,4]triazolo[4,3-a]pyrazin-4-yl)azetidin-3-yl)carbamate was dissolved in DCM (4.0 mL) and then TFA (0.5 mL) was slowly added thereto at 0° C. The reaction mixture was stirred at room temperature for one hour. The reaction mixture was distilled under reduced pressure. The residue was neutralized with NaHCO$_3$ aqueous solution (pH=7) and then extracted with DCM (30.0 mL). The organic layer was washed with brine, dried over anhydrous Na$_2$SO$_4$, filtered and then distilled under reduced pressure. The residue was purified by column chromatography (DCM:MeOH=98:2) on amine silica. The fractions containing the product were collected and evaporated to obtain ivory solid compound of N-methyl-1-(8-(trifluoromethyl)pyrido[2,3-e][1,2,4]triazolo[4,3-a]pyrazin-4-yl)azetidin-3-amine (26.7 mg, 20% in 4 steps).

LC/MS ESI (+): 324 (M+1)

$^1$H-NMR (300 MHz, DMSO-d$_6$); δ: 10.1 (s, 1H), 9.01 (bs, 1H), 8.83 (bs, 1H), 4.95 (m, 1H), 4.48 (m, 2H), 4.03 (m, 1H), 3.74 (m, 1H), 2.30 (s, 3H)

Example 53

Synthesis of 4-(4-methylpiperazin-1-yl)-8-(trifluoromethyl)pyrido[2,3-e][1,2,4]triazolo[4,3-a]pyrazine (a) Synthesis of 2-chloro-3-(4-methylpiperazin-1-yl)-7-(trifluoromethyl)pyrido[2,3-b]pyrazine 2,3-Dichloro-7-(trifluoromethyl)pyrido[2,3-b]pyrazine (50.0 mg, 0.19 mmol) and TEA (0.3 mL, 1.90 mmol) were dissolved in DCM (5.0 mL), and N-methylpiperazine (21.0 µL, 0.19 mmol) diluted in DCM (5.0 mL) was slowly added thereto at 0° C. The reaction mixture was stirred at room temperature for 2 hours, and it was poured into saturated NH$_4$Cl aqueous solution and then extracted with DCM (30.0 mL). The organic layer was washed with brine, dried over anhydrous Na$_2$SO$_4$, filtered and then distilled under reduced pressure. The residue was purified by column chromatography (DCM:MeOH=100:0) on amine silica. The fractions containing the product were collected and evaporated to obtain yellow solid compound of 2-chloro-3-(4-methylpiperazin-1-yl)-7-(trifluoromethyl)pyrido[2,3-b]pyrazine (53.0 mg, 85%).

LC/MS ESI (+): 332 (M+1), 334 (M+3)

(b) Synthesis of 4-(4-methylpiperazin-1-yl)-8-(trifluoromethyl)pyrido[2,3-e][1,2,4]triazolo[4,3-a]pyrazine 2-Chloro-3-(4-methylpiperazin-1-yl)-7-(trifluoromethyl)pyrido[2,3-b]pyrazine (53.0 mg, 0.16 mmol) and hydrazine monohydrate (0.1 mL, 2.04 mmol) were dissolved in EtOH (2.0 mL), stirred at room temperature for one hour and then distilled under reduced pressure. The reaction mixture was poured into saturated NH$_4$Cl aqueous solution and then extracted with DCM (30.0 mL). The organic layer was washed with brine, dried over anhydrous Na$_2$SO$_4$, filtered and then dried under reduced pressure to obtain yellow solid compound of 2-hydrazinyl-3-(4-methylpiperazin-1-yl)-7-(trifluoromethyl)pyrido[2,3-b]pyrazine. The mixture of unpurified 2-hydrazinyl-3-(4-methylpiperazin-1-yl)-7-(trifluoromethyl)pyrido[2,3-b]pyrazine and trimethyl orthoformate (2.0 mL) was stirred at 80° C. for one hour and then cooled to room temperature. Et$_2$O was added thereto to form a solid, and the formed solid was filtered and then dried under reduced pressure. The residue was purified by column chromatography (DCM:MeOH=100:0) on amine silica. The fractions containing the product were collected and evaporated to obtain ivory solid compound of 4-(4-methylpiperazin-1-yl)-8-(trifluoromethyl)pyrido[2,3-e][1,2,4]triazolo[4,3-a]pyrazine (14.3 mg, 23% in 3 steps).

LC/MS ESI (+): 338 (M+1)

$^1$H-NMR (300 MHz, DMSO-d$_6$); δ: 10.13 (s, 1H), 9.05 (d, 1H, J=2.1 Hz), 8.87 (d, 1H, J=2.1 Hz), 5.00-4.00 (m, 4H), 2.53 (m, 4H), 2.26 (s, 3H)

Example 54

Synthesis of 1-(8-ethynylpyrido[2,3-e][1,2,4]triazolo[4,3-a]pyrazin-4-yl)-N-methylazetidin-3-amine (a) Synthesis of tert-butyl methyl(1-(8-((trimethylsilyl)ethynyl)pyrido[2,3-e][1,2,4]triazolo[4,3-a]pyrazin-4-yl)azetidin-3-yl)carbamate tert-Butyl (1-(8-bromopyrido[2,3-e][1,2,4]triazolo[4,3-a]pyrazin-4-yl)azetidin-3-yl)(methyl)carbamate (50.0 mg, 0.12 mmol), TMS-acetylene (81.0 μL, 0.58 mmol), Pd/Cl$_2$(PPh$_3$)$_2$ (8.1 mg, 0.01 mmol), CuI (4.4 mg, 0.02 mmol) and TEA (0.5 mL) were added to DMF (0.5 mL), and the mixture was allowed to react in microwave under conditions of 50 W, 70° C. for 1.5 hours, then cooled to room temperature. DCM and water were added to the reaction mixture to form a solid, and the formed solid was filtered to obtain gray solid. The gray solid obtained was stirred in solution of MeOH:DCM=1:9 and then filtered. The filtrate was distilled under reduced pressure to obtain gray solid compound of tert-butyl methyl(1-(8-((trimethylsilyl)ethynyl)pyrido[2,3-e][1,2,4]triazolo[4,3-a]pyrazin-4-yl)azetidin-3-yl)carbamate (50.0 mg, 96%).

LC/MS ESI(+): 452 (M+1)

$^1$H-NMR (300 MHz, DMSO-d$_6$); δ: 10.00 (s, 1H), 8.75 (d, 1H, J=2.1 Hz), 8.57 (d, 1H, J=2.1 Hz), 5.25-4.85 (m, 2H), 4.82 (m, 1H), 4.51 (m, 1H), 4.41 (m, 1H), 2.93 (s, 3H), 1.42 (s, 9H), 0.27 (s, 9H)

(b) Synthesis of 1-(8-ethynylpyrido[2,3-e][1,2,4]triazolo[4,3-a]pyrazin-4-yl)-N-methylazetidin-3-amine tert-Butyl methyl(1-(8-((trimethylsilyl)ethynyl)pyrido[2,3-e][1,2,4]triazolo[4,3-a]pyrazin-4-yl)azetidin-3-yl)carbamate (50.0 mg, 0.11 mmol) was dissolved in 4N HCl dioxane solution (1.0 mL). The reaction mixture was stirred at room temperature for one hour to form a solid, and the formed solid was filtered. The resulting solid was dissolved in THF (1.0 mL), and TBAF (0.2 mL, 0.22 mmol) was added thereto. The reaction mixture was stirred at room temperature for one hour and MeOH was added thereto to form a solid. The formed solid was filtered and then dried under reduced pressure to obtain ivory solid compound of 1-(8-ethynylpyrido[2,3-e][1,2,4]triazolo[4,3-a]pyrazin-4-yl)-N-methylazetidin-3-amine (6.0 mg, 19%).

LC/MS ESI(+): 280 (M+1)

$^1$H-NMR (300 MHz, DMSO-d$_6$); δ: 9.99 (s, 1H), 8.76 (d, 1H, J=1.8 Hz), 8.60 (d, 1H, J=1.8 Hz), 4.94 (m, 1H), 4.60-4.40 (m, 3H), 4.10 (m, 1H), 3.81 (m, 1H), 3.16 (m, 1H), 2.36 (s, 3H)

Example 55

Synthesis of N-methyl-1-(8-vinylpyrido[2,3-e][1,2,4]triazolo[4,3-a]pyrazin-4-yl)azetidin-3-amine (a) Synthesis of tert-butyl methyl(1-(8-vinylpyrido[2,3-e][1,2,4]triazolo[4,3-a]pyrazin-4-yl)azetidin-3-yl)carbamate tert-Butyl (1-(8-bromopyrido[2,3-e][1,2,4]triazolo[4,3-a]pyrazin-4-yl)azetidin-3-yl)(methyl)carbamate (150.0 mg, 0.35 mmol), tributylvinyltin (1.0 mL, 3.45 mmol), Pd(OAc)$_2$ (15.0 mg, 0.07 mmol), CuI (39.4 mg, 0.21 mmol), P(o-Tol)$_3$ (42.0 mg, 0.14 mmol) and TEA (240.0 μL, 1.73 mmol) were added to CH$_3$CN (2.5 mL). The mixture was allowed to react in microwave under conditions of 100 W, 100° C. for 3 hours and then cooled to room temperature. The reaction mixture was purified by column chromatography (MeOH:DCM=1:60) on silica. The fractions containing the product were collected and evaporated to obtain ivory solid compound of tert-butyl methyl(1-(8-vinylpyrido[2,3-e][1,2,4]triazolo[4,3-a]pyrazin-4-yl)azetidin-3-yl)carbamate (15.0 mg, 11%).

LC/MS ESI(+): 382 (M+1)

$^1$H-NMR (300 MHz, DMSO-d$_6$); δ: 10.00 (s, 1H), 8.78 (s, 1H), 8.62 (bs, 1H), 6.86 (m, 1H), 6.06 (m, 1H), 5.45 (m, 1H), 5.20-4.65 (m, 3H), 4.65-4.20 (m, 2H), 2.93 (s, 3H), 1.42 (s, 9H)

(b) Synthesis of N-methyl-1-(8-vinylpyrido[2,3-e][1,2,4]triazolo[4,3-a]pyrazin-4-yl)azetidin-3-amine tert-Butyl methyl(1-(8-vinylpyrido[2,3-e][1,2,4]triazolo[4,3-a]pyrazin-4-yl)azetidin-3-yl)carbamate (15.0 mg, 0.02 mmol) was dissolved in DCM (0.6 mL), and TFA (0.4 mL) was then added thereto. The reaction mixture was stirred at room temperature for one hour and then purified by column chromatography (MeOH:DCM=1:40) on amine silica. The fractions containing the product were collected and evaporated to obtain ivory solid compound of N-methyl-1-(8-vinylpyrido[2,3-e][1,2,4]triazolo[4,3-a]pyrazin-4-yl)azetidin-3-amine (1.5 mg, 29%).

LC/MS ESI(+): 282 (M+1)

$^1$H-NMR (300 MHz, DMSO-d$_6$); δ: 9.99 (s, 1H), 8.76 (s, 1H), 8.60 (s, 1H), 6.86 (m, 1H), 6.06 (m, 1H), 5.45 (m, 1H), 4.90 (m, 1H), 4.55-4.25 (m, 2H), 3.99 (m, 1H), 3.71 (m, 1H), 2.29 (s, 3H)

Example 56

Synthesis of 1-(8-ethylpyrido[2,3-e][1,2,4]triazolo[4,3-a]pyrazin-4-yl)-N-methylazetidin-3-amine tert-Butyl methyl(1-(8-vinylpyrido[2,3-e][1,2,4]triazolo[4,3-a]pyrazin-4-yl)azetidin-3-yl)carbamate (12.0 mg, 0.03 mmol) was dissolved in MeOH (1.0 mL), and 10% of Pd/C (4.8 mg) was added thereto. The flask was substituted with hydrogen and then allowed to react for 12 hours. The reaction mixture was filtered through celite and then distilled under reduced pressure. The residue was dissolved in DCM (0.6 mL), and TFA (0.4 mL) was added thereto. The reaction mixture was stirred for one hour and then purified by column chromatography (MeOH:DCM=1:40) on amine silica. The fractions containing the product were collected and evaporated to obtain ivory solid compound of 1-(8-ethylpyrido[2,3-e][1,2,4]triazolo[4,3-a]pyrazin-4-yl)-N-methylazetidin-3-amine (3.5 mg, 39%).

LC/MS ESI(+): 284 (M+1)

$^1$H-NMR (300 MHz, CDCl$_3$); δ: 9.15 (s, 1H), 8.52 (d, 1H, J=2.1 Hz), 7.82 (d, 1H, J=2.1 Hz), 5.09 (m, 1H), 4.78-4.50 (m, 2H), 4.22 (m, 1H), 3.85 (m, 1H), 2.80 (q, 2H, J=7.5 Hz), 2.49 (s, 3H), 1.35 (t, 3H, J=7.5 Hz)

Example 57

Synthesis of 4-(3-(methylamino)azetidin-1-yl)pyrido[2,3-e][1,2,4]triazolo[4,3-a]pyrazin-8-ol 1-(8-Methoxypyrido[2,3-e][1,2,4]triazolo[4,3-a]pyrazin-4-yl)-N-methylazetidin-3-amine (38.0 mg, 0.13 mmol) was dissolved in DCM (3.0 mL) and then cooled to −78° C. 1M of tribromoborane (3.0 mL) dissolved in DCM at concentration of 1M was added thereto. The temperature was gradually raised to 40° C. The reaction mixture was stirred for 12 hours, and then cooled to −78° C., and MeOH (3.0 mL) was added thereto. The reaction mixture temperature was allowed to increase to room temperature. Then, the reaction mixture was concentrated and purified by column chromatography (DCM:MeOH=95:5 to 90:10) on amine silica. The fractions containing the product were collected and evaporated to obtain white solid compound of 4-(3-

(methylamino)azetidin-1-yl)pyrido[2,3-e][1,2,4]triazolo[4,3-a]pyrazin-8-ol (18.0 mg, 50%).

LC/MS ESI (+): 272 (M+1)

$^1$H-NMR (300 MHz, MeOH-d$_4$); δ: 9.73 (s, 1H), 8.20 (m, 1H), 7.90 (m, 1H), 4.81 (m, 2H), 4.45 (m, 2H), 4.01 (m, 1H), 2.59 (s, 3H)

Example 58

Synthesis of 1-(8-methoxypyrido[2,3-e][1,2,4]triazolo[4,3-a]pyrazin-4-yl)-N-methylazetidin-3-amine

(a) Synthesis of tert-butyl (1-(8-methoxypyrido[2,3-e][1,2,4]triazolo[4,3-a]pyrazin-4-yl)azetidin-3-yl)(methyl)carbamate The mixture containing MeOH (4.5 mL) and NaH (450.0 mg) was stirred at room temperature for 30 minutes and then added to a solution of tert-butyl (1-(8-bromopyrido[2,3-e][1,2,4]triazolo[4,3-a]pyrazin-4-yl)azetidin-3-yl)(methyl)carbamate (300.0 mg, 0.69 mmol) and CuI (262.8 mg, 1.38 mmol) dissolved in DMF (4.5 mL). The reaction mixture was allowed to react in microwave under conditions of 60 W, 90° C. for 30 minutes, cooled to room temperature, then concentrated and purified by column chromatography (MeOH:DCM=5:95) on silica. The fractions containing the product were collected and evaporated to obtain white solid compound of tert-butyl (1-(8-methoxypyrido[2,3-e][1,2,4]triazolo[4,3-a]pyrazin-4-yl)azetidin-3-yl)(methyl)carbamate (49.0 mg, 55%).

LC/MS ESI(+): 386 (M+1)

(b) Synthesis of 1-(8-methoxypyrido[2,3-e][1,2,4]triazolo[4,3-a]pyrazin-4-yl)-N-methylazetidin-3-amine tert-Butyl (1-(8-methoxypyrido[2,3-e][1,2,4]triazolo[4,3-a]pyrazin-4-yl)azetidin-3-yl)(methyl)carbamate (49.0 mg, 0.13 mmol) was dissolved in DCM (0.6 mL), and TFA (0.4 mL) was slowly added thereto at 0° C. The reaction mixture was stirred at room temperature for one hour, then concentrated and purified by column chromatography (MeOH:DCM=5:95) on amine silica. The fractions containing the product were collected and evaporated to obtain white solid compound of 1-(8-methoxypyrido[2,3-e][1,2,4]triazolo[4,3-a]pyrazin-4-yl)-N-methylazetidin-3-amine (25.0 mg, 33%).

LC/MS ESI (+): 286 (M+1)

$^1$H-NMR (300 MHz, MeOH-d$_4$); δ: 9.82 (s, 1H), 8.30 (d, 1H, J=2.7 Hz), 8.15 (d, 1H, J=2.7 Hz), 4.76-4.19 (m, 4H), 4.00 (s, 3H), 3.83 (m, 1H), 2.43 (s, 3H)

Example 59

Synthesis of 1-(8-(difluoromethoxy)pyrido[2,3-e][1,2,4]triazolo[4,3-a]pyrazin-4-yl)-N-methylazetidin-3-amine

(a) Synthesis of tert-butyl (1-(8-(benzyloxy)pyrido[2,3-e][1,2,4]triazolo[4,3-a]pyrazin-4-yl)azetidin-3-yl)(methyl)carbamate tert-Butyl (1-(8-(benzyloxy)pyrido[2,3-e][1,2,4]triazolo[4,3-a]pyrazin-4-yl)azetidin-3-yl)(methyl)carbamate (200.0 mg, 0.60 mmol), 1,10-phenanthroline (21.6 mg, 0.12 mmol), cesium carbonate (391.0 mg, 1.20 mmol) and CuI (114.3 mg, 0.60 mmol) were dissolved in benzyl alcohol (4.0 mL). The mixture was allowed to react in microwave under conditions of 100 W, 100° C. for 2 hours and then cooled to room temperature, and 36.0 mL of water was added thereto. The reaction mixture was concentrated under reduced pressure and purified by column chromatography (MeOH:DCM=5:95) on silica. The fractions containing the product were collected and evaporated to obtain white solid compound of tert-butyl (1-(8-(benzyloxy)pyrido[2,3-e][1,2,4]triazolo[4,3-a]pyrazin-4-yl)azetidin-3-yl)(methyl)carbamate (120.0 mg, 43%).

LC/MS ESI (+): 462 (M+1)

(b) Synthesis of tert-butyl (1-(8-hydroxypyrido[2,3-e][1,2,4]triazolo[4,3-a]pyrazin-4-yl)azetidin-3-yl)(methyl)carbamate tert-Butyl (1-(8-(benzyloxy)pyrido[2,3-e][1,2,4]triazolo[4,3-a]pyrazin-4-yl)azetidin-3-yl)(methyl)carbamate (120.0 mg, 0.32 mmol) and 10% of Pd/C (30.0 mg) were dissolved in MeOH (10.0 mL). The flask was substituted with hydrogen and then stirred at room temperature for 3 days. The reaction mixture was filtered through celite, distilled under reduced pressure and then purified by column chromatography (MeOH:DCM=5:95). The fractions containing the product were collected and evaporated to obtain white solid compound of tert-butyl (1-(8-hydroxypyrido[2,3-e][1,2,4]triazolo[4,3-a]pyrazin-4-yl)azetidin-3-yl)(methyl)carbamate (40.0 mg, 34%).

LC/MS ESI (+): 372 (M+1)

(c) Synthesis of 1-(8-(difluoromethoxy)pyrido[2,3-e][1,2,4]triazolo[4,3-a]pyrazin-4-yl)-N-methylazetidin-3-amine tert-Butyl (1-(8-hydroxypyrido[2,3-e][1,2,4]triazolo[4,3-a]pyrazin-4-yl)azetidin-3-yl)(methyl)carbamate (20.0 mg, 0.05 mmol) was dissolved in CH$_3$CN (0.7 mL), and KOH (60.0 mg, 1.08 mmol) dissolved in water (0.7 mL) was added thereto, and diethyl (bromodifluoromethyl)phosphonate (60.0 μL, 0.32 mmol) was then added thereto. The mixture was stirred at room temperature for 2 hours. The reaction mixture was concentrated under reduced pressure and dissolved in DCM (1.0 mL) without further purification, and then TFA (0.2 mL) was added thereto. The reaction mixture was stirred at room temperature for one hour and purified by column chromatography (MeOH:DCM=5:95) on amine silica. The fractions containing the product were collected and evaporated to obtain white solid compound of 1-(8-(difluoromethoxy)pyrido[2,3-e][1,2,4]triazolo[4,3-a]pyrazin-4-yl)-N-methylazetidin-3-amine (10.0 mg, 17%).

LC/MS ESI (+): 322 (M+1)

$^1$H-NMR (300 MHz, MeOH-d$_4$); δ: 9.79 (s, 1H), 8.41 (m, 2H), 7.24-6.75 (m, 1H), 5.03 (m, 1H), 4.57 (m, 2H), 4.15 (m, 1H), 3.82 (m, 1H), 2.43 (s, 3H)

Example 60

Synthesis of 8-chloro-7-methoxy-4-(4-methylpiperazin-1-yl)pyrido[2,3-e][1,2,4]triazolo[4,3-a]pyrazine 7,8-Dichloro-4-(4-methylpiperazin-1-yl)pyrido[2,3-e][1,2,4]triazolo[4,3-a]pyrazine (10.0 mg, 0.03 mmol) and NaH (4.0 mg: in 60% oil, 0.12 mmol) were dissolved in MeOH (1.0 mL). The mixture was allowed to react in microwave under conditions of 60 W, 90° C. for one hour. The reaction mixture was distilled under reduced pressure and then purified by column chromatography (DCM:MeOH=99:1) on amine silica. The fractions containing the product were collected and evaporated to obtain ivory solid compound of 8-chloro-7-methoxy-4-(4-methylpiperazin-1-yl)pyrido[2,3-e][1,2,4]triazolo[4,3-a]pyrazine (3.7 mg, 37%).

LC/MS ESI (+): 334 (M+1), 336 (M+3)

$^1$H-NMR (300 MHz, DMSO-$d_6$); δ: 9.91 (s, 1H), 8.85 (s, 1H), 4.41 (m, 4H), 4.01 (m, 3H), 2.50 (m, 4H), 2.26 (s, 3H)

Example 61

Synthesis of 8-chloro-7-methoxy-4-(piperazin-1-yl)pyrido[2,3-e][1,2,4]triazolo[4,3-a]pyrazine tert-Butyl 4-(7,8-dichloropyrido[2,3-e][1,2,4]triazolo[4,3-a]pyrazin-4-yl)piperazin-1-carboxylate (20.0 mg, 0.05 mmol) obtained from 2,3,6,7-tetrachloropyrido[2,3-b]pyrazine in the same way as (c) to (e) of Example 2 and NaH (9.0 mg: in 60% oil, 0.25 mmol) were dissolved in MeOH (1.0 mL). The mixture was stirred in microwave under conditions of 60 W, 90° C. for one hour and then distilled under reduced pressure. The reaction mixture was purified by column chromatography (DCM:MeOH=100:0) on amine silica. The fractions containing the product were collected and evaporated to obtain ivory solid compound of tert-butyl 4-(8-chloro-7-methoxypyrido[2,3-e][1,2,4]triazolo[4,3-a]pyrazin-4-yl)piperazin-1-carboxylate. tert-Butyl 4-(8-chloro-7-methoxypyrido[2,3-e][1,2,4]triazolo[4,3-a]pyrazin-4-yl)piperazin-1-carboxylate was dissolved in DCM (2.0 mL), and then TFA (0.5 mL) was slowly added thereto at 0° C. The reaction mixture was stirred at room temperature for 2 hours and then distilled under reduced pressure. The residue was neutralized with TEA (pH=7) and then purified by column chromatography (DCM:MeOH=99:1) on amine silica. The fractions containing the product were collected and evaporated to obtain ivory solid compound of 8-chloro-7-methoxy-4-(piperazin-1-yl)pyrido[2,3-e][1,2,4]triazolo[4,3-a]pyrazine (9.0 mg, 60% in 2 steps).

LC/MS ESI (+): 320 (M+1), 322 (M+3)

$^1$H-NMR (300 MHz, DMSO-$d_6$); δ: 9.98 (s, 1H), 8.92 (s, 1H), 4.40 (m, 4H), 4.08 (s, 3H), 2.94 (m, 4H)

Example 62

Synthesis of 7,8-dichloro-4-(piperazin-1-yl)pyrido[2,3-e][1,2,4]triazolo[4,3-a]pyrazine tert-Butyl 4-(7,8-dichloropyrido[2,3-e][1,2,4]triazolo[4,3-a]pyrazin-4-yl)piperazin-1-carboxylate (20.0 mg, 0.05 mmol) was dissolved in DCM (2.0 mL), and TFA (0.5 mL) was slowly added thereto at 0° C. The reaction mixture was stirred at room temperature for 2 hours and distilled under reduced pressure. The residue was neutralized with TEA (pH=7) and purified by column chromatography (DCM:MeOH=99:1) on amine silica. The fractions containing the product were collected and evaporated to obtain ivory solid compound of 7,8-dichloro-4-(piperazin-1-yl)pyrido[2,3-e][1,2,4]triazolo[4,3-a]pyrazine (14.0 mg, 92%).

LC/MS ESI (+): 324 (M+1), 326 (M+3)

$^1$H-NMR (300 MHz, DMSO-$d_6$); δ: 10.01 (s, 1H), 9.08 (s, 1H), 5.00-4.00 (m, 4H), 2.95 (m, 4H)

Example 63

Synthesis of 8-chloro-7-ethoxy-4-(piperazin-1-yl)pyrido[2,3-e][1,2,4]triazolo[4,3-a]pyrazine tert-Butyl 4-(7,8-dichloropyrido[2,3-e][1,2,4]triazolo[4,3-a]pyrazin-4-yl)piperazin-1-carboxylate (20.0 mg, 0.05 mmol) and NaOEt (16.0 mg, 0.25 mmol) were dissolved in EtOH (1.0 mL). The mixture was allowed to react in microwave under conditions of 60 W, 90° C. for one hour, cooled to room temperature, distilled under reduced pressure and then purified by column chromatography (DCM:MeOH=99:1) on amine silica. The fractions containing the product were collected and evaporated to obtain ivory solid compound of tert-butyl 4-(8-chloro-7-ethoxypyrido[2,3-e][1,2,4]triazolo[4,3-a]pyrazin-4-yl)piperazin-1-carboxylate. tert-Butyl 4-(8-chloro-7-ethoxypyrido[2,3-e][1,2,4]triazolo[4,3-a]pyrazin-4-yl)piperazin-1-carboxylate was dissolved in DCM (2.0 mL), and TFA (0.5 mL) was slowly added thereto at 0° C. The reaction mixture was stirred at room temperature for 2 hours and distilled under reduced pressure. The residue was neutralized with TEA (pH=7) and then purified by column chromatography (DCM:MeOH=99:1) on amine silica. The fractions containing the product were collected and evaporated to obtain ivory solid compound of 8-chloro-7-ethoxy-4-(piperazin-1-yl)pyrido[2,3-e][1,2,4]triazolo[4,3-a]pyrazine (4.0 mg, 25% in 2 steps).

LC/MS ESI (+): 334 (M+1), 336 (M+3)

$^1$H-NMR (300 MHz, DMSO-$d_6$); δ: 9.98 (m, 1H), 8.91 (m, 1H), 4.53 (q, 2H, J=7.1 Hz), 4.40 (m, 4H), 2.95 (m, 4H), 1.46 (t, 3H, J=7.1 Hz)

Example 64

Synthesis of 8-chloro-4-(4-methylpiperazin-1-yl)-7-(2,2,2-trifluoroethoxy)pyrido[2,3-e][1,2,4]triazolo[4,3-a]pyrazine 7,8-Dichloro-4-(4-methylpiperazin-1-yl)pyrido[2,3-e][1,2,4]triazolo[4,3-a]pyrazin (10.0 mg, 0.03 mmol) and NaH (12.0 mg: in 60% oil, 0.30 mmol) were dissolved in $CF_3CH_2OH$ (1.0 mL). The mixture was then stirred in microwave under conditions of 60 W, 120° C. for one hour, distilled under reduced pressure and then purified by column chromatography (DCM:MeOH=99:1) on amine silica. The fractions containing the product were collected and evaporated to obtain ivory solid compound of 8-chloro-4-(4-methylpiperazin-1-yl)-7-(2,2,2-trifluoroethoxy)pyrido[2,3-e][1,2,4]triazolo[4,3-a]pyrazine (3.51 mg, 29%).

LC/MS ESI (+): 402 (M+1), 404 (M+3)

$^1$H-NMR (300 MHz, DMSO-$d_6$); δ: 9.93 (m, 1H), 8.93 (m, 1H), 5.14 (q, 2H, J=8.9 Hz), 4.43 (m, 4H), 2.50 (m, 4H), 2.25 (s, 3H)

Example 65

Synthesis of 1-(8-bromo-9-methylpyrido[2,3-e][1,2,4]triazolo[4,3-a]pyrazin-4-yl)-N-methylazetidin-3-amine (a) Synthesis of 5-bromo-4-methylpyridin-2,3-diamine 5-Bromo-4-methyl-3-nitropyridin-2-amine (700.0 mg, 3.02 mmol), Fe (1680.0 mg, 30.20 mmol) and conc. HCl (50.0 μL) were added to EtOH (2.8 mL) and water (0.7 mL). The suspension was stirred at 100° C. for 30 minutes. The reaction mixture was cooled to room temperature, filtered through celite and then distilled under reduced pressure. The residue was purified by column chromatography (MeOH:DCM=1:40) on silica. The fractions containing the product were collected and evaporated to obtain brown solid compound of 5-bromo-4-methylpyridin-2,3-diamine (550.0 mg, 90%).

LC/MS ESI(+): 202 (M+1), 204 (M+3)
$^1$H-NMR (300 MHz, DMSO-$d_6$); δ: 7.37 (s, 1H), 5.49 (s, 2H), 4.74 (s, 2H), 2.12 (s, 3H)

(b) Synthesis of 7-bromo-8-methylpyrido[2,3-b]pyrazin-2,3-diol

The mixture of 5-bromo-4-methylpyridin-2,3-diamine (550.0 mg, 2.72 mmol) and diethyloxalate (10.0 mL) was stirred at 100° C. for 12 hours and then cooled to room temperature. Et$_2$O was added to the reaction mixture to form a solid, and the formed solid was filtered and dried under reduced pressure to obtain brown solid compound of 7-bromo-8-methylpyrido[2,3-b]pyrazin-2,3-diol (595.0 mg, 85%).
LC/MS ESI(+): 256 (M+1), 258 (M+3)
$^1$H-NMR (300 MHz, DMSO-$d_6$); δ: 12.40 (s, 1H), 11.57 (s, 1H), 8.19 (s, 1H), 2.45 (s, 3H)

(c) Synthesis of 7-bromo-2,3-dichloro-8-methylpyrido[2,3-b]pyrazine

The mixture of 7-bromo-8-methylpyrido[2,3-b]pyrazin-2,3-diol (560.0 mg, 2.19 mmol) and POCl$_3$ (5.0 mL) was stirred at 100° C. for 12 hours and then cooled to room temperature. The reaction mixture was poured into ice water to form a solid. The formed solid was filtered and dried under reduced pressure. The resulting solid was dissolved in DCM and purified by column chromatography (EtOAc:n-Hex=1:9) on silica. The fractions containing the product were collected and evaporated to obtain red solid compound of 7-bromo-2,3-dichloro-8-methylpyrido[2,3-b]pyrazine (365.0 mg, 54%).
LC/MS ESI(+): 292 (M+1), 294 (M+3), 296 (M+5)
$^1$H-NMR (300 MHz, DMSO-$d_6$); δ: 9.25 (s, 1H), 2.78 (s, 3H)

(d) Synthesis of tert-butyl (1-(7-bromo-2-chloro-8-methylpyrido[2,3-b]pyrazin-3-yl)azetidin-3-yl)(methyl)carbamate TEA (72.0 μL, 0.51 mmol) was added to the mixture of 7-bromo-2,3-dichloro-8-methylpyrido[2,3-b]pyrazine (50.0 mg, 0.17 mmol), tert-butyl azetidin-3-yl(methyl)carbamate hydrochloride (40.0 mg, 0.18 mmol) and DCM (1.7 mL) at 0° C. and stirred for one hour. The reaction mixture was purified by column chromatography (EtOAc:n-Hex=1:5) on silica. The fractions containing the product were collected and evaporated to obtain yellow solid compound of tert-butyl (1-(7-bromo-2-chloro-8-methylpyrido[2,3-b]pyrazin-3-yl)azetidin-3-yl)(methyl)carbamate (58.0 mg, 76%).
LC/MS ESI(+): 442 (M+1), 444 (M+3)
$^1$H-NMR (300 MHz, DMSO-$d_6$); δ: 8.85 (s, 1H), 4.86 (m, 1H), 4.65-4.55 (m, 2H), 4.49-4.40 (m, 2H), 2.90 (s, 3H), 2.66 (s, 3H), 1.41 (s, 9H)

(e) Synthesis of tert-butyl (1-(8-bromo-9-methyl-pyrido[2,3-e][1,2,4]triazolo[4,3-a]pyrazin-4-yl)azetidin-3-yl)(methyl)carbamate Hydrazine monohydrate (20.0 μL, 0.63 mmol) was added to a suspension of tert-butyl (1-(7-bromo-2-chloro-8-methylpyrido[2,3-b]pyrazin-3-yl)azetidin-3-yl)(methyl)carbamate (56.0 mg, 0.13 mmol) and EtOH (1.0 mL). The reaction mixture was stirred at room temperature for one hour and then distilled under reduced pressure. Et$_2$O was added to the residue to form a solid. The formed solid was filtered and dried under reduced pressure to obtain brown solid compound of tert-butyl (1-(7-bromo-2-hydrazinyl-8-methylpyrido[2,3-b]pyrazin-3-yl)azetidin-3-yl)(methyl)carbamate. Unpurified tert-butyl (1-(7-bromo-2-hydrazinyl-8-methylpyrido[2,3-b]pyrazin-3-yl)azetidin-3-yl)(methyl)carbamate was dissolved in trimethyl orthoformate (2.0 mL), and it was stirred at 85° C. for 3 hours. The reaction mixture was cooled to room temperature and then distilled under reduced pressure. The residue was purified by column chromatography (MeOH:DCM=1:40) on silica. The fractions containing the product were collected and evaporated to obtain pale brown solid compound of tert-butyl (1-(8-bromo-9-methyl-pyrido[2,3-e][1,2,4]triazolo[4,3-a]pyrazin-4-yl)azetidin-3-yl)(methyl)carbamate (25.0 mg, 45%).
LC/MS ESI(+): 448 (M+1), 450 (M+3)

(f) Synthesis of 1-(8-bromo-9-methylpyrido[2,3-e][1,2,4]triazolo[4,3-a]pyrazin-4-yl)-N-methylazetidin-3-amine TFA (0.4 mL) was added to mixture of tert-butyl (1-(8-bromo-9-methylpyrido[2,3-e][1,2,4]triazolo[4,3-a]pyrazin-4-yl)azetidin-3-yl)(methyl)carbamate (25.0 mg, 0.06 mmol) and DCM (0.6 mL), and it was stirred at room temperature for one hour. The reaction mixture was purified by column chromatography (MeOH:DCM=1:40) on amine silica. The fractions containing the product were collected and evaporated. Et$_2$O was added to the residue and form a solid, and the formed solid was filtered and dried under reduced pressure to obtain ivory solid compound of 1-(8-bromo-9-methylpyrido[2,3-e][1,2,4]triazolo[4,3-a]pyrazin-4-yl)-N-methylazetidin-3-amine (13.0 mg, 68%).
LC/MS ESI(+): 348 (M+1), 350 (M+3)
$^1$H-NMR (300 MHz, DMSO-$d_6$); δ: 9.82 (s, 1H), 8.63 (s, 1H), 4.90 (m, 1H), 4.45-4.35 (m, 2H), 3.99 (m, 1H), 3.71 (m, 1H), 2.90 (s, 3H), 2.30 (s, 3H)

Example 66

Synthesis of 8-bromo-9-methyl-4-(4-methylpiperazin-1-yl)pyrido[2,3-e][1,2,4]triazolo[4,3-a]pyrazine (a) Synthesis of 7-bromo-2-chloro-8-methyl-3-(4-methylpiperazin-1-yl)pyrido[2,3-b]pyrazine TEA (72.0 μL, 0.51 mmol) was added to mixture of 7-bromo-2,3-dichloro-8-methylpyrido[2,3-b]pyrazine (50.0 mg, 0.17 mmol), N-methylpiperazine (20.0 μL, 0.18 mmol) and DCM (1.7 mL) at 0° C., and it was stirred for one hour. The reaction mixture was purified by column chromatography (EtOAc:n-Hex=1:5) on amine silica. The fractions containing the product were collected and evaporated to obtain yellow solid compound of 7-bromo-2-chloro-8-methyl-3-(4-methylpiperazin-1-yl)pyrido[2,3-b]pyrazine (50.0 mg, 82%).
LC/MS ESI(+): 356 (M+1), 358 (M+3), 360 (M+5)
$^1$H-NMR (300 MHz, DMSO-$d_6$); δ=8.96 (s, 1H), 3.64-3.58 (m, 4H), 2.69 (s, 3H), 2.55-2.50 (m, 4H), 2.25 (s, 3H)

(b) Synthesis of 8-bromo-9-methyl-4-(4-methylpiperazin-1-yl)pyrido[2,3-e][1,2,4]triazolo[4,3-a]pyrazine Hydrazine monohydrate (22.0 μL, 0.70 mmol) was added to suspension of 7-bromo-2-chloro-8-methyl-3-(4-methylpiperazin-1-yl)pyrido[2,3-b]pyrazine (50.0 mg, 0.14 mmol) and EtOH (1.0 mL). The reaction mixture was stirred at room temperature for one hour and then distilled under reduced pressure. Et$_2$O was added to the residue to form a solid, and the formed solid was filtered and then dried under reduced pressure to obtain yellow solid compound of 7-bromo-2-hydrazinyl-8-methyl-3-(4-methylpiperazin-1-yl) pyrido[2,3-b]pyrazine. Unpurified 7-bromo-2-hydrazinyl-8-methyl-3-(4-methylpiperazin-1-yl)pyrido[2,3-b]pyrazine was dissolved in trimethyl orthoformate (2.0 mL) and then stirred at 85° C. for 3 hours. The reaction mixture was then cooled to room temperature and distilled under reduced pressure. The residue was purified by column chromatography (MeOH:DCM=1:40) on amine silica. The fractions containing the product were collected and evaporated to obtain yellow solid compound of 8-bromo-9-methyl-4-(4-methylpiperazin-1-yl)pyrido[2,3-e][1,2,4]triazolo[4,3-a] pyrazine (24.0 mg, 47%).

LC/MS ESI(+): 362 (M+1), 364 (M+3)
$^1$H-NMR (300 MHz, DMSO-d$_6$); δ: 9.85 (s, 1H), 8.66 (s, 1H), 4.60-4.30 (m, 4H), 2.92 (s, 3H), 2.54-2.50 (m, 4H), 2.25 (s, 3H)

Example 67

Synthesis of 1-(8,9-dichloropyrido[2,3-e][1,2,4] triazolo[4,3-a]pyrazin-4-yl)-N-methylazetidin-3-amine (a) Synthesis of N-(4-chloropyridin-2-yl)pivalamide 4-Chloropyridin-2-amine (1500.0 mg, 11.70 mmol) was dissolved in pyridine (6.0 mL), and pivaloyl chloride (2.2 mL, 17.50 mmol) was slowly added thereto at 0° C. The reaction mixture was stirred at room temperature for 12 hours, poured into water and extracted with EtOAc (100.0 mL). The organic layer was washed with brine, dried over anhydrous Na$_2$SO$_4$, filtered and then distilled under reduced pressure. The residue was purified by column chromatography (n-Hex:EtOAc=90:10 to 80:20) on silica. The fractions containing the product were collected and evaporated to obtain white solid compound of N-(4-chloropyridin-2-yl) pivalamide (2460.0 mg, 99%).

LC/MS ESI (+): 213 (M+1), 215 (M+3)
$^1$H-NMR (300 MHz, DMSO-d$_6$); δ: 10.12 (s, 1H), 8.32 (d, 1H, J=5.3 Hz), 8.16 (s, 1H), 7.25 (d, 1H, J=5.3 Hz), 1.23 (s, 9H)

(b) Synthesis of N-(4,5-dichloropyridin-2-yl)pivalamide

N-(4-Chloropyridin-2-yl)pivalamide (2160.0 mg, 10.16 mmol) and N-chlorosuccinimide (6781.0 mg, 50.78 mmol) were dissolved in anhydrous CH$_3$CN (100.0 mL). The mixture was stirred at 70° C. for 2 hours and then cooled to room temperature. The reaction mixture was poured into water and extracted with EtOAc (100.0 mL). The organic layer was washed with 1N NaOH and brine, dried over anhydrous Na$_2$SO$_4$, filtered and then distilled under reduced pressure. The residue was purified by column chromatography (n-Hex:EtOAc=90:10) on silica. The fractions containing the product were collected and evaporated to obtain ivory solid compound of N-(4,5-dichloropyridin-2-yl)pivalamide (1990.0 mg, 79%).

LC/MS ESI (+): 247 (M+1), 249 (M+3), 251 (M+5)
$^1$H-NMR (300 MHz, DMSO-d$_6$); δ: 10.29 (s, 1H), 8.54 (s, 1H), 8.34 (s, 1H), 1.23 (s, 9H)

(c) Synthesis of 4,5-dichloro-3-nitropyridin-2-amine

N-(4,5-Dichloropyridin-2-yl)pivalamide (1990.0 mg, 8.05 mmol) was slowly added to and dissolved in conc. H$_2$SO$_4$ (11.0 mL) at 10° C., and then conc. HNO$_3$/conc. H$_2$SO$_4$ (332.0 μL/415.0 μL) was slowly added thereto. The reaction mixture was stirred at room temperature for 2.5 hours, poured into ice water, alkalized with 1N NaOH aqueous solution (pH=9) and then extracted with EtOAc (200.0 mL). The organic layer was washed with brine, dried over anhydrous Na$_2$SO$_4$, filtered and then distilled under reduced pressure. The residue was purified by column chromatography (n-Hex:EtOAc=90:10 to 80:20) on silica. The fractions containing the product were collected and evaporated to obtain yellow solid compound of 4,5-dichloro-3-nitropyridin-2-amine (548.0 mg, 32%).

LC/MS ESI (+): 208 (M+1), 210 (M+3), 212 (M+5)

(d) Synthesis of 4,5-dichloropyridin-2,3-diamine 4,5-Dichloro-3-nitropyridin-2-amine (548.0 mg, 2.63 mmol), Zn powder (1274.0 mg, 19.50 mmol) and anhydrous CaCl$_2$ (1578.0 mg, 14.20 mmol) were added to 95% of EtOH (20.0 mL), and the mixture was stirred at 100° C. for one hour. The reaction mixture was filtered through celite, and evaporated under reduced pressure to obtain brown solid compound of 4,5-dichloropyridin-2,3-diamine.

LC/MS ESI (+): 178 (M+1), 180 (M+3), 182 (M+5)

(e) Synthesis of 2,3,7,8-tetrachloropyrido[2,3-b]pyrazine

Unpurified 4,5-dichloropyridin-2,3-diamine was added to diethyl oxalate (10.0 mL). The mixture was stirred at 120° C. for 12 hours and then cooled to room temperature. Et$_2$O was filtered thereto to form a solid, and the formed solid was filtered and dried under reduced pressure to obtain light brown solid compound of 7,8-dichloropyrido[2,3-b]pyrazin-2,3(1H,4H)-dione. The mixture of unpurified 7,8-dichloropyrido[2,3-b]pyrazin-2,3(1H,4H)-dione and POCl$_3$ (10.0 mL) was stirred at 130° C. for 48 hours and then cooled to room temperature. The reaction mixture was poured into ice water to form a solid, and the formed solid was filtered and then dried under reduced pressure to obtain brown solid compound of 2,3,7,8-tetrachloropyrido[2,3-b]pyrazine (290.0 mg, 41% in 3 steps).

$^1$H-NMR (300 MHz, DMSO-d$_6$); δ: 9.35 (s, 1H)

(f) Synthesis of tert-butyl methyl(1-(2,7,8-trichloropyrido[2,3-b]pyrazin-3-yl)azetidin-3-yl)carbamate 2,3,7,8-Tetrachloropyrido[2,3-b]pyrazine (100.0 mg, 0.37 mmol) and TEA (0.3 mL, 1.85 mmol) were dissolved in DCM (8.0 mL), and tert-butyl azetidin-3-yl(methyl)carbamate hydrochloride (83.0 mg, 0.37 mmol) diluted in DCM (2.0 mL) and TEA (0.3 mL, 1.85 mmol) were slowly added thereto at 0° C. The reaction mixture was stirred at room temperature for one hour and poured into saturated NH$_4$Cl aqueous solution, and it was then extracted with DCM (30.0 mL). The organic layer was washed with brine, dried over anhydrous Na$_2$SO$_4$, filtered and distilled under reduced pressure. The residue was purified by column chromatography (DCM:MeOH=100:0) on amine silica. The fractions containing the product were collected and evaporated to obtain brown solid compound of tert-butyl methyl(1-(2,7,8-trichloropyrido[2,3-b]pyrazin-3-yl)azetidin-3-yl)carbamate.

LC/MS ESI (+): 418 (M+1), 420 (M+3)

(g) Synthesis of tert-butyl (1-(7,8-dichloro-2-hydrazinylpyrido[2,3-b]pyrazin-3-yl)azetidin-3-yl) (methyl)carbamate Unpurified tert-butyl methyl(1-(2,7,8-trichloropyrido[2, 3-b]pyrazin-3-yl)azetidin-3-yl)carbamate and hydrazine monohydrate (46.0 mg, 0.93 mmol) were dissolved in EtOH (3.0 mL). The mixture was stirred at room temperature for 20 minutes and distilled under reduced pressure to obtain tert-butyl (1-(7,8-dichloro-2-hydrazinylpyrido[2,3-b]pyrazin-3-yl)azetidin-3-yl)(methyl)carbamate.

LC/MS ESI (+): 414 (M+1), 416 (M+3)

(h) Synthesis of tert-butyl (1-(8,9-dichloropyrido[2,3-e][1,2,4]triazolo[4,3-a]pyrazin-4-yl)azetidin-3-yl)(methyl)carbamate The mixture of unpurified tert-butyl (1-(7,8-dichloro-2-hydrazinylpyrido[2,3-b]pyrazin-3-yl)azetidin-3-yl)(methyl)carbamate and trimethyl orthoformate (2.0 mL) was stirred at 80° C. for one hour and then cooled to room temperature. Et$_2$O was added thereto to form a solid, and the formed solid was filtered and then dried under reduced pressure to obtain tert-butyl (1-(8,9-dichloropyrido[2,3-e][1,2,4]triazolo[4,3-a]pyrazin-4-yl)azetidin-3-yl)(methyl)carbamate.

LC/MS ESI (+): 424 (M+1), 426 (M+3)

(i) Synthesis of 1-(8,9-dichloropyrido[2,3-e][1,2,4]triazolo[4,3-a]pyrazin-4-yl)-N-methylazetidin-3-amine Unpurified tert-butyl (1-(8,9-dichloropyrido[2,3-e][1,2,4]triazolo[4,3-a]pyrazin-4-yl)azetidin-3-yl)(methyl)carbamate was dissolved in DCM (2.0 mL), and TFA (0.5 mL) was slowly added thereto at 0° C. The reaction mixture was stirred at room temperature for one hour and distilled under reduced pressure. The residue was neutralized with TEA and purified by column chromatography (DCM:MeOH=98:2) on amine silica. The fractions containing the product were collected and evaporated to obtain ivory solid compound of 1-(8,9-dichloropyrido[2,3-e][1,2,4]triazolo[4,3-a]pyrazin-4-yl)-N-methylazetidin-3-amine (3.5 mg, 3% in 4 steps).

LC/MS ESI (+): 324 (M+1), 326 (M+3)
$^1$H-NMR (300 MHz, DMSO-d$_6$); δ: 10.30 (s, 1H), 8.68 (s, 1H), 4.94 (m, 1H), 4.46 (m, 2H), 4.03 (m, 1H), 3.73 (m, 1H), 2.30 (s, 3H)

Example 68

Synthesis of 1-(8-bromopyrido[2,3-e][1,2,4]triazolo[4,3-a]pyrazin-4-yl)-N-methylazetidin-3-amine hydrochloride The mixture of 1-(8-bromopyrido[2,3-e][1,2,4]triazolo[4,3-a]pyrazin-4-yl)-N-methylazetidin-3-amine (200.0 mg, 0.60 mmol) and 4N HCl dioxane solution (10.0 mL) was stirred at room temperature for 12 hours. The formed solid was filtered and then dried to obtain white solid compound of 1-(8-bromopyrido[2,3-e][1,2,4]triazolo[4,3-a]pyrazin-4-yl)-N-methylazetidin-3-amine hydrochloride (200.0 mg, 90%).

LC/MS ESI (+): 334 (M+1), 336 (M+3)
$^1$H-NMR (300 MHz, DMSO-d$_6$); δ: 10.0 (s, 1H), 9.69 (bs, 2H), 9.00 (d, 1H, J=2.2 Hz), 8.66 (d, 1H, J=2.2 Hz), 5.20-4.80 (m, 2H), 4.70-4.40 (m, 2H), 4.20 (m, 1H), 2.64 (m, 3H)

Example 69

Synthesis of 1-(8-bromopyrido[2,3-e]tetrazolo[1,5-a]pyrazin-4-yl)-N-methylazetidin-3-amine hydrochloride Suspension of 1-(8-bromopyrido[2,3-e]tetrazolo[1,5-a]pyrazin-4-yl)-N-methylazetidin-3-amine (190.0 mg, 0.57 mmol) and 4N HCl dioxane solution (5.0 mL) was stirred at room temperature for 8 hours. Et$_2$O was added thereto to form a solid, and the formed solid was filtered and dried under reduced pressure to obtain yellow solid compound of 1-(8-bromopyrido[2,3-e]tetrazolo[1,5-a]pyrazin-4-yl)-N-methylazetidin-3-amine hydrochloride (210.0 mg, 99%).

LC/MS ESI(+): 335 (M+1), 337 (M+3)
$^1$H-NMR (300 MHz, DMSO-d$_6$); δ: 9.77 (bs, 2H), 9.00 (d, 1H, J=2.4 Hz), 8.88 (d, 1H, J=2.4 Hz), 5.10-4.90 (m, 2H), 4.75-4.45 (m, 2H), 4.31 (m, 1H), 2.66 (s, 3H)

Example 70

Synthesis of 8-chloro-4-(5-methylhexahydropyrrolo[3,4-c]pyrrole-2(1H)-yl)pyrido[2,3-e][1,2,4]triazolo[4,3-a]pyrazine (a) Synthesis of 2,7-dichloro-3-(5-methylhexahydropyrrolo[3,4-c]pyrrole-2(1H)-yl)pyrido[2,3-b]pyrazine 2,3,7-Trichloropyrido[2,3-b]pyrazine (100.0 mg, 0.43 mmol) and TEA (0.6 mL, 4.26 mmol) were dissolved in DCM (3.0 mL), and 2-methyloctahydropyrrolo[3,4-c]pyrrole (59.1 mg, 0.47 mmol) diluted in DCM (1.0 mL) was slowly added thereto at 0° C. The reaction mixture was stirred at room temperature for 12 hours, then concentrated and purified by column chromatography (MeOH:DCM=5:95) on silica. The fractions containing the product were collected and evaporated to obtain yellow solid compound of 2,7-dichloro-3-(5-methylhexahydropyrrolo[3,4-c]pyrrole-2(1H)-yl)pyrido[2,3-b]pyrazine (72.0 mg, 52%).

LC/MS ESI (+): 324 (M+1), 326 (M+3)

(b) Synthesis of 7-chloro-2-hydrazinyl-3-(5-methylhexahydropyrrolo[3,4-c]pyrrole-2(1H)-yl)pyrido[2,3-b]pyrazine 2,7-Dichloro-3-(5-methylhexahydropyrrolo[3,4-c]pyrrole-2(1H)-yl)pyrido[2,3-b]pyrazine (72.0 mg, 0.22 mmol) and hydrazine monohydrate (32.0 µL, 0.67 mmol) were dissolved in EtOH (3.0 mL). The mixture was stirred at room temperature for 12 hours and a solid was formed. The formed solid was filtered to obtain yellow solid compound of 7-chloro-2-hydrazinyl-3-(5-methylhexahydropyrrolo[3,4-c]pyrrole-2(1H)-yl)pyrido[2,3-b]pyrazine (71.0 mg, 100%).

LC/MS ESI(+): 320 (M+1), 322 (M+3)

(c) Synthesis of 8-chloro-4-(5-methylhexahydropyrrolo[3,4-c]pyrrole-2(1H)-yl)pyrido[2,3-e][1,2,4]triazolo[4,3-a]pyrazine The mixture of 7-chloro-2-hydrazinyl-3-(5-methylhexahydropyrrolo[3,4-c]pyrrole-2(1H)-yl)pyrido[2,3-b]pyrazine (71.0 mg, 0.22 mmol) and trimethyl orthoformate (3.0 mL) was stirred at 80° C. for 3 hours and then cooled to room temperature. Et$_2$O was added thereto to form a solid, and the formed solid was filtered and dried under reduced pressure. The residue was purified by column chromatography (MeOH:DCM=5:95) on amine silica. The fractions containing the product were collected and evaporated to obtain yellow solid compound of 8-chloro-4-(5-methylhexahydropyrrolo[3,4-c]pyrrole-2(1H)-yl)pyrido[2,3-e][1,2,4]triazolo[4,3-a]pyrazine (20.0 mg, 27%).

LC/MS ESI(+): 330 (M+1), 332 (M+3)

¹H-NMR (300 MHz, CDCl₃); δ: 9.14 (s, 1H), 8.58 (d, 1H, J=2.4 Hz), 8.01 (d, 1H, J=2.4 Hz), 4.70-4.58 (m, 2H), 4.23-4.02 (m, 2H), 3.14-3.03 (m, 2H), 2.71-2.65 (m, 4H), 2.34 (s, 3H)

Example 71

Synthesis of 8-bromo-4-(5-methylhexahydropyrrolo[3,4-c]pyrrole-2(1H)-yl)pyrido[2,3-e][1,2,4]triazolo[4,3-a]pyrazine (a) Synthesis of 7-bromo-2-chloro-3-(5-methylhexahydropyrrolo[3,4-c]pyrrole-2(1H)-yl)pyrido[2,3-b]pyrazine 7-Bromo-2,3-dichloropyrido[2,3-b]pyrazine (100.0 mg, 0.36 mmol) and TEA (0.5 mL, 3.58 mmol) were dissolved in DCM (3.0 mL), and 2-methyloctahydropyrrolo[3,4-c]pyrrole (49.6 mg, 0.39 mmol) diluted in DCM (1.0 mL) was slowly added thereto at 0° C. The reaction mixture was stirred at room temperature for 12 hours, then concentrated and purified by column chromatography (MeOH:DCM=5:95) on silica. The fractions containing the product were collected and evaporated to obtain yellow solid compound of 7-bromo-2-chloro-3-(5-methylhexahydropyrrolo[3,4-c]pyrrole-2(1H)-yl)pyrido[2,3-b]pyrazine (63.0 mg, 48%).

LC/MS ESI (+): 368 (M+1), 370 (M+3)

(b) Synthesis of 7-bromo-2-hydrazinyl-3-(5-methylhexahydropyrrolo[3,4-c]pyrrole-2 (1H)-yl)pyrido[2,3-b]pyrazine 7-Bromo-2-chloro-3-(5-methylhexahydropyrrolo[3,4-c]pyrrole-2(1H)-yl)pyrido[2,3-b]pyrazine (63.0 mg, 0.17 mmol) and hydrazine monohydrate (25.0 µL, 0.51 mmol) were dissolved in EtOH (3.0 mL). The mixture was stirred at room temperature for 12 hours to form a solid. The formed solid was filtered to obtain yellow solid compound of 7-bromo-2-hydrazinyl-3-(5-methylhexahydropyrrolo[3,4-c]pyrrole-2(1H)-yl)pyrido[2,3-b]pyrazine (62.0 mg, 100%).

LC/MS ESI(+): 364 (M+1), 366 (M+3)

(c) Synthesis of 8-bromo-4-(5-methylhexahydropyrrolo[3,4-c]pyrrole-2(1H)-yl)pyrido[2,3-e][1,2,4]triazolo[4,3-a]pyrazine The mixture of 7-bromo-2-hydrazinyl-3-(5-methylhexahydropyrrolo[3,4-c]pyrrole-2(1H)-yl)pyrido[2,3-b]pyrazine (62.0 mg, 0.17 mmol) and trimethyl orthoformate (3.0 mL) was stirred at 90° C. for 6 hours and then cooled to room temperature. Et₂O was added thereto to form a solid, and the formed solid was filtered and dried under reduced pressure. The residue was purified by column chromatography (EtOAc:n-Hex:MeOH=4:4:1) on amine silica. The fractions containing the product were collected and evaporated to obtain yellow solid compound of 8-bromo-4-(5-methylhexahydropyrrolo[3,4-c]pyrrole-2(1H)-yl)pyrido[2,3-e][1,2,4]triazolo[4,3-a]pyrazine (11.0 mg, 16%).

LC/MS ESI(+): 374 (M+1), 376 (M+3)

¹H-NMR (300 MHz, CDCl₃); δ: 9.17 (s, 1H), 8.64 (d, 1H, J=2.1 Hz), 8.14 (d, 1H, J=2.1 Hz), 4.73-4.55 (m, 2H), 4.22-3.98 (m, 2H), 3.12-3.02 (m, 2H), 2.63 (m, 4H), 2.32 (s, 3H)

Example 72

Synthesis of 1-(8-bromopyrido[2,3-e][1,2,4]triazolo[4,3-a]pyrazin-4-yl)-3-methylazetidin-3-amine (a) Synthesis of tert-butyl (1-(7-bromo-2-chloropyrido[2,3-b]pyrazin-3-yl)-3-methylazetidin-3-yl)carbamate tert-Butyl (3-methylazetidin-3-yl)carbamate hydrochloride (43.0 mg, 0.23 mmol) and TEA (0.8 mL, 0.54 mmol) were added to the mixture of 7-bromo-2,3-dichloropyrido[2,3-b]pyrazine (50.0 mg, 0.18 mmol) and DCM (1.8 mL) at 0° C. and then stirred for one hour. The reaction mixture was concentrated under reduced pressure to obtain yellow solid compound of tert-butyl (1-(7-bromo-2-chloropyrido[2,3-b]pyrazin-3-yl)-3-methylazetidin-3-yl)carbamate.

LC/MS ESI(+): 428 (M+1), 430 (M+3)

(b) Synthesis of tert-butyl (1-(7-bromo-2-hydrazinylpyrido[2,3-b]pyrazin-3-yl)-3-methylazetidin-3-yl)carbamate Hydrazine monohydrate (28.0 µL, 0.90 mmol) was added to the suspension of unpurified tert-butyl (1-(7-bromo-2-chloropyrido[2,3-b]pyrazin-3-yl)-3-methylazetidin-3-yl)carbamate and EtOH (1.0 mL). The reaction mixture was stirred at room temperature for one hour and concentrated under reduced pressure to obtain yellow solid compound of tert-butyl (1-(7-bromo-2-hydrazinylpyrido[2,3-b]pyrazin-3-yl)-3-methylazetidin-3-yl)carbamate.

LC/MS ESI(+): 424 (M+1), 426 (M+3)

(c) Synthesis of tert-butyl (1-(8-bromopyrido[2,3-e][1,2,4]triazolo[4,3-a]pyrazin-4-yl)-3-methylazetidin-3-yl)carbamate Suspension of unpurified tert-butyl (1-(7-bromo-2-hydrazinylpyrido[2,3-b]pyrazin-3-yl)-3-methylazetidin-3-yl)carbamate and trimethyl orthoformate (3.0 mL) was stirred at 90° C. for 3 hours and then cooled to room temperature. Et₂O was added thereto to form a solid, and the formed solid was filtered, and pressure was reduced to obtain pale brown solid compound of tert-butyl (1-(8-bromopyrido[2,3-e][1,2,4]triazolo[4,3-a]pyrazin-4-yl)-3-methylazetidin-3-yl)carbamate (25.0 mg, 32% in 3 steps).

LC/MS ESI(+): 434 (M+1), 436 (M+3)

(d) Synthesis of 1-(8-bromopyrido[2,3-e][1,2,4]triazolo[4,3-a]pyrazin-4-yl)-3-methylazetidin-3-amine tert-Butyl (1-(8-bromopyrido[2,3-e][1,2,4]triazolo[4,3-a]pyrazin-4-yl)-3-methylazetidin-3-yl)carbamate (25.0 mg, 0.06 mmol) was dissolved in DCM (0.6 mL), and TFA (0.4 mL) was added thereto. The reaction mixture was stirred at room temperature for one hour and then purified by column chromatography (MeOH:DCM=1:40) on amine silica. The fractions containing the product were collected and evaporated to obtain brown solid compound of 1-(8-bromopyrido[2,3-e][1,2,4]triazolo[4,3-a]pyrazin-4-yl)-3-methylazetidin-3-amine (9.0 mg, 47%).

LC/MS ESI(+): 334 (M+1), 336 (M+3)

¹H-NMR (300 MHz, DMSO-d₆); δ: 9.95 (s, 1H), 8.90 (d, 1H, J=2.4 Hz), 8.59 (d, 1H, J=2.4 Hz), 4.58 (m, 1H), 4.47 (m, 1H), 4.15-3.95 (m, 2H), 2.40 (bs, 2H), 1.43 (s, 3H)

Example 73

Synthesis of 1-(8-bromopyrido[2,3-e][1,2,4]triazolo[4,3-a]pyrazin-4-yl)-N,3-dimethylazetidin-3-amine (a) Synthesis of benzyl 3-((tert-butoxy-carbonyl)amino)-3-methylazetidin-1-carboxylate tert-Butyl (3-methylazetidin-3-yl)carbamate hydrochloride (400.0 mg, 1.80 mmol) was dissolved in DCM (9.0 mL), and benzyl chloroformate (0.8 mL, 5.39 mmol) and TEA (1.3 mL, 9.00 mmol) were added thereto at 0° C. The reaction mixture was allowed to react at room temperature for 12 hours and then purified by column chromatography (EtOAc:n-Hex=1:4) on silica. The fractions containing the product were collected and evaporated to obtain white solid compound of benzyl 3-((tert-butoxycarbonyl)amino)-3-methylazetidin-1-carboxylate (680.0 mg, 99%).

LC/MS ESI(+): 321 (M+1)

$^1$H-NMR (300 MHz, CDCl$_3$); δ: 7.38-7.30 (m, 5H), 5.10 (s, 2H), 4.76 (bs, 1H), 4.20-4.10 (m, 2H), 3.90-3.75 (m, 2H), 1.53 (s, 3H), 1.44 (m, 9H)

(b) Synthesis of benzyl 3-((tert-butoxy-carbonyl)(methyl)amino)-3-methylazetidin-1-carboxylate Benzyl 3-((tert-butoxycarbonyl)amino)-3-methylazetidin-1-carboxylate (676.0 mg, 2.11 mmol) was dissolved in THF (21.0 mL), and NaH (110.0 mg, 2.74 mmol) was added thereto. The reaction mixture was stirred for 10 minutes, and MeI (0.2 mL, 3.17 mmol) was then added thereto, and stirred at room temperature for 12 hours and then allowed to react at 50° C. for 12 hours. The reaction mixture was cooled to room temperature and purified by column chromatography (EtOAc:n-Hex=1:7) on silica. The fractions containing the product were collected and evaporated to obtain sticky colorless liquid compound of benzyl 3-((tert-butoxy-carbonyl)(methyl)amino)-3-methylazetidin-1-carboxylate (180.0 mg, 26%).

LC/MS ESI(+): 335 (M+1)

$^1$H-NMR (300 MHz, CDCl$_3$); δ: 7.40-7.30 (m, 5H), 5.11 (s, 2H), 4.12-4.05 (m, 2H), 3.75-3.60 (m, 2H), 2.69 (s, 3H), 1.48 (s, 3H), 1.45 (m, 9H)

(c) Synthesis of tert-butyl methyl(3-methylazetidin-3-yl)carbamate

Benzyl 3-((tert-butoxycarbonyl)(methyl)amino)-3-methylazetidin-1-carboxylate (180.0 mg, 0.54 mmol) was dissolved in MeOH (2.0 mL), and 10% of Pd/C (18.0 mg) was added thereto. The flask was substituted with hydrogen and stirred for 12 hours. The reaction mixture was filtered through celite and distilled under reduced pressure to obtain sticky colorless liquid compound of tert-butyl methyl(3-methylazetidin-3-yl)carbamate (50.0 mg, 46%).

$^1$H-NMR (300 MHz, DMSO-d$_6$); δ: 3.85-3.75 (m, 2H), 3.23-3.15 (m, 2H), 2.64 (s, 3H), 1.52 (s, 3H), 1.44 (m, 9H)

(d) Synthesis of tert-butyl (1-(7-bromo-2-chloropyrido[2,3-b]pyrazin-3-yl)-3-methylazetidin-3-yl)(methyl)carbamate TEA (90.0 µL, 0.65 mmol) was added at 0° C. to a mixture of tert-butyl methyl(3-methylazetidin-3-yl)carbamate (47.0 mg, 0.24 mmol), 7-bromo-2,3-dichloropyrido[2,3-b]pyrazine (60.0 mg, 0.22 mmol) and DCM (2.2 mL), and it was stirred for one hour. The reaction mixture was purified by column chromatography (EtOAc:n-Hex=1:5) on silica. The fractions containing the product were collected and evaporated to obtain yellow solid compound of tert-butyl (1-(7-bromo-2-chloropyrido[2,3-b]pyrazin-3-yl)-3-methylazetidin-3-yl)(methyl)carbamate (10.0 mg, 11%).

LC/MS ESI(+): 442 (M+1), 444 (M+3)

(e) Synthesis of tert-butyl (1-(7-bromo-2-hydrazinylpyrido[2,3-b]pyrazin-3-yl)-3-methylazetidin-3-yl)(methyl)carbamate tert-Butyl (1-(7-bromo-2-chloropyrido[2,3-b]pyrazin-3-yl)-3-methylazetidin-3-yl)(methyl)carbamate (10.0 mg, 0.02 mmol) was dissolved in EtOH (1.0 mL), and hydrazine monohydrate (3.5 µL, 0.11 mmol) was added thereto. The reaction mixture was stirred at room temperature for one hour and concentrated under reduced pressure to obtain yellow solid compound of tert-butyl (1-(7-bromo-2-hydrazinylpyrido[2,3-b]pyrazin-3-yl)-3-methylazetidin-3-yl)(methyl)carbamate.

LC/MS ESI(+): 438 (M+1), 440 (M+3)

(f) Synthesis of tert-butyl (1-(8-bromopyrido[2,3-e][1,2,4]triazolo[4,3-a]pyrazin-4-yl)-3-methylazetidin-3-yl)(methyl)carbamate Unpurified tert-butyl (1-(7-bromo-2-hydrazinylpyrido[2,3-b]pyrazin-3-yl)-3-methylazetidin-3-yl)(methyl)carbamate was dissolved in trimethyl orthoformate (1.0 mL), and it was stirred at 80° C. for one hour. The reaction mixture was then cooled to room temperature and distilled under reduced pressure to obtain atypical yellow compound of tert-butyl (1-(8-bromopyrido[2,3-e][1,2,4]triazolo[4,3-a]pyrazin-4-yl)-3-methylazetidin-3-yl)(methyl)carbamate.

LC/MS ESI(+): 448 (M+1), 450 (M+3)

(g) Synthesis of 1-(8-bromopyrido[2,3-e][1,2,4]triazolo[4,3-a]pyrazin-4-yl)-N,3-dimethylazetidin-3-amine Unpurified tert-butyl (1-(8-bromopyrido[2,3-e][1,2,4]triazolo[4,3-a]pyrazin-4-yl)-3-methylazetidin-3-yl)(methyl)carbamate was dissolved in 4N HCl dioxane solution, and the reaction mixture was stirred at room temperature for one hour and distilled under reduced pressure. The residue was purified by column chromatography (MeOH:DCM=1:60) on amine silica. The fractions containing the product were collected and evaporated to obtain ivory solid compound of 1-(8-bromopyrido[2,3-e][1,2,4]triazolo[4,3-a]pyrazin-4-yl)-N,3-dimethylazetidin-3-amine (3.0 mg, 38% in 3 steps).

LC/MS ESI(+): 348 (M+1), 350 (M+3)

$^1$H-NMR (300 MHz, DMSO-d$_6$); δ: 9.95 (s, 1H), 8.90 (d, 1H, J=2.4 Hz), 8.59 (d, 1H, J=2.4 Hz), 4.60-4.40 (m, 2H), 4.18-3.96 (m, 2H), 2.27 (s, 3H), 1.41 (s, 3H)

Example 74

Synthesis of 8-bromo-4-(hexahydropyrrolo[1,2-a]pyrazin-2(1H)-yl)pyrido[2,3-e][1,2,4]triazolo[4,3-a]pyrazine (a) Synthesis of 7-bromo-2-chloro-3-(hexahydropyrrolo[1,2-a]pyrazin-2(1H)-yl)pyrido[2,3-b]pyrazine 7-Bromo-2,3-dichloropyrido[2,3-b]pyrazine (206.0 mg, 0.74 mmol) and octahydropyrrolo[1,2-a]pyrazine (102.0 mg, 0.81 mmol) were allowed to react in the same way as Example 24 (a) to obtain yellow solid compound of 7-bromo-2-chloro-3-(hexahydropyrrolo[1,2-a]pyrazin-2(1H)-yl)pyrido[2,3-b]pyrazine (180.0 mg, 66%).

LC/MS ESI(+): 370 (M+1), 372 (M+3)

¹H-NMR (300 MHz, CDCl₃); δ: 8.93 (d, 1H, J=2.4 Hz), 8.32 (d, 1H, J=2.4 Hz), 4.46 (m, 2H), 3.15 (m, 3H), 2.92 (m, 1H), 2.48 (m, 1H), 2.22 (m, 2H), 1.89 (m, 3H), 1.57 (m, 1H)

(b) Synthesis of 8-bromo-4-(hexahydropyrrolo[1,2-a]pyrazin-2(1H)-yl)pyrido[2,3-e][1,2,4]triazolo[4,3-a]pyrazine 7-Bromo-2-chloro-3-(hexahydropyrrolo[1,2-a]pyrazin-2(1H)-yl)pyrido[2,3-b]pyrazine (100.0 mg, 0.36 mmol) and hydrazine monohydrate (0.028 mL, 0.90 mmol) were dissolved in EtOH (8.0 mL), and the mixture was stirred at 40° C. for 12 hours. Et₂O/EtOH was added thereto to form a solid, and the formed solid was filtered and dried under reduced pressure to obtain yellow compound of 7-bromo-3-(hexahydropyrrolo[1,2-a]pyrazin-2(1H)-yl)-2-hydrazinylpyrido[2,3-b]pyrazine. The mixture of unpurified 7-bromo-3-(hexahydropyrrolo[1,2-a]pyrazin-2(1H)-yl)-2-hydrazinylpyrido[2,3-b]pyrazine (60.0 mg, 0.17 mmol) and trimethyl orthoformate (1.0 mL) was stirred at 80° C. for 1.5 hours and then cooled to room temperature. Et₂O was added thereto to form a solid, and the formed solid was filtered and dried under reduced pressure to obtain brown solid compound of 8-bromo-4-(hexahydropyrrolo[1,2-a]pyrazin-2(1H)-yl)pyrido[2,3-e][1,2,4]triazolo[4,3-a]pyrazine (35.0 mg, 26% in 2 steps).

LC/MS ESI(+): 374 (M+1), 376 (M+3)

¹H-NMR (300 MHz, CDCl₃); δ: 9.16 (s, 1H), 8.70 (d, 1H, J=2.1 Hz), 8.17 (d, 1H, J=2.1 Hz), 6.40 (m, 1H), 5.52 (m, 1H), 3.57 (m, 1H), 3.20 (m, 2H), 2.92 (m, 1H), 2.44 (m, 1H), 2.20 (m, 2H), 1.79 (m, 3H), 1.55 (m, 1H)

Example 75

Synthesis of 4-(hexahydropyrrolo[1,2-a]pyrazin-2(1H)-yl)-8-iodopyrido[2,3-e][1,2,4]triazolo[4,3-a]pyrazine (a) Synthesis of 2-chloro-3-(hexahydropyrrolo[1,2-a]pyrazin-2(1H)-yl)-7-iodopyrido[2,3-b]pyrazine 2,3-Dichloro-7-iodopyrido[2,3-b]pyrazine (50.0 mg, 0.15 mmol) and TEA (213.0 μL, 1.53 mmol) were dissolved in DCM (2.0 mL), and octahydropyrrolo[1,2-a]pyrazine (19.0 mg, 0.15 mmol) was added thereto at 0° C. The reaction mixture was stirred at 0° C. for one hour, then concentrated and purified by column chromatography (MeOH:DCM=3:97) on silica. The fractions containing the product were collected and evaporated to obtain yellow solid compound of 2-chloro-3-(hexahydropyrrolo[1,2-a]pyrazin-2(1H)-yl)-7-iodopyrido[2,3-b]pyrazine (38.0 mg, 58%).

LC/MS ESI (+): 416 (M+1), 418 (M+3)

(b) Synthesis of 3-(hexahydropyrrolo[1,2-a]pyrazin-2(1H)-yl)-2-hydrazinyl-7-iodopyrido[2,3-b]pyrazine 2-Chloro-3-(hexahydropyrrolo[1,2-a]pyrazin-2(1H)-yl)-7-iodopyrido[2,3-b]pyrazine (38.0 mg, 0.09 mmol) and hydrazine monohydrate (6.7 μL, 0.14 mmol) were dissolved in EtOH (1.0 mL). The mixture was stirred at room temperature for 3 hours to form a solid, and the formed solid was filtered to obtain yellow solid compound of 3-(hexahydropyrrolo[1,2-a]pyrazin-2(1H)-yl)-2-hydrazinyl-7-iodopyrido[2,3-b]pyrazin e (37.5 mg, 100%).

LC/MS ESI(+): 412 (M+1)

(c) Synthesis of 4-(hexahydropyrrolo[1,2-a]pyrazin-2(1H)-yl)-8-iodopyrido[2,3-e][1,2,4]triazolo[4,3-a]pyrazine The mixture of 3-(hexahydropyrrolo[1,2-a]pyrazin-2(1H)-yl)-2-hydrazinyl-7-iodopyrido[2,3-b]pyrazine (39.4 mg, 0.10 mmol) and trimethyl orthoformate (2.0 mL) was stirred at 80° C. for 3 hours and then cooled to room temperature. Et₂O was added thereto to form a solid, and the formed solid was filtered and dried under reduced pressure. The residue was purified by column chromatography (MeOH:DCM=5:95) on silica. The fractions containing the product were collected and evaporated to obtain yellow solid compound of 4-(hexahydropyrrolo[1,2-a]pyrazin-2(1H)-yl)-8-iodopyrido[2,3-e][1,2,4]triazolo[4,3-a]pyrazine (9.0 mg, 26%).

LC/MS ESI(+): 422 (M+1)

¹H-NMR (300 MHz, DMSO-d₆); δ: 10.01 (s, 1H), 9.01 (d, 1H, J=2.1 Hz), 8.71 (d, 1H, J=2.1 Hz), 6.18-5.25 (m, 1H), 3.42-3.35 (m, 1H), 3.28-3.24 (m, 1H), 3.20-3.15 (m, 1H), 3.08-2.87 (m, 2H), 2.25 (m, 1H), 2.15-2.03 (m, 2H), 1.88 (m, 1H), 1.81-1.68 (m, 2H), 1.45 (m. 1H)

Example 76

Synthesis of 8-chloro-4-(4-cyclopropylpiperazin-1-yl)pyrido[2,3-e][1,2,4]triazolo[4,3-a]pyrazine (a) Synthesis of 2,7-dichloro-3-(4-cyclopropylpiperazin-1-yl)pyrido[2,3-b]pyrazine 2,3,7-Trichloropyrido[2,3-b]pyrazine (70.0 mg, 0.30 mmol) and 1-cyclopropylpiperazine (59.7 mg, 0.30 mmol) were allowed to react in the same way as Example 2 (c) to obtain yellow solid compound of 2,7-dichloro-3-(4-cyclopropylpiperazin-1-yl)pyrido[2,3-b]pyrazine (59.5 mg, 61%).

LC/MS ESI(+): 324 (M+1), 326 (M+3)

¹H-NMR (300 MHz, CDCl₃); δ: 8.93 (d, 1H, J=2.7 Hz), 8.50 (d, 1H, J=2.7 Hz), 3.59 (m, 4H), 2.74 (m, 4H), 1.71 (m, 1H), 0.45 (m, 2H), 0.39 (m, 2H)

(b) Synthesis of 7-chloro-3-(4-cyclopropylpiperazin-1-yl)-2-hydrazinylpyrido[2,3-b]pyrazine 2,7-Dichloro-3-(4-cyclopropylpiperazin-1-yl)pyrido[2,3-b]pyrazine (56.7 mg, 0.17 mmol) and hydrazine monohydrate (14.0 μL, 0.43 mmol) were allowed to react in the same way as Example 2 (d) to obtain orange solid compound of 7-chloro-3-(4-cyclopropylpiperazin-1-yl)-2-hydrazinylpyrido[2,3-b]pyrazine (50.0 mg, 100%).

LC/MS ESI(+): 320 (M+1), 322 (M+3)

(c) Synthesis of 8-chloro-4-(4-cyclopropylpiperazin-1-yl)pyrido[2,3-e][1,2,4]triazolo[4,3-a]pyrazine 7-Chloro-3-(4-cyclopropylpiperazin-1-yl)-2-hydrazinylpyrido[2,3-b]pyrazine (64.0 mg, 0.14 mmol) and trimethyl orthoformate (2.0 mL) were allowed to react at 85° C. for 2 hours in the same way as Example 2 (e) to obtain ivory solid compound of 8-chloro-4-(4-cyclopropylpiperazin-1-yl)pyrido[2,3-e][1,2,4]triazolo[4,3-a]pyrazine (40.6 mg, 62%).

LC/MS ESI(+): 330 (M+1), 332 (M+3)
¹H-NMR (300 MHz, CDCl₃); δ: 10.01 (s, 1H), 8.85 (d, 1H, J=2.7 Hz), 8.57 (d, 1H, J=2.7 Hz), 4.80-3.93 (m, 4H), 2.73 (m, 4H), 1.68 (m, 1H), 0.46 (m, 2H), 0.40 (m, 2H)

Example 77

Synthesis of 4-((1S,4S)-2,5-diazabicyclo[2.2.1]heptan-2-yl)-8-chloropyrido[2,3-e][1,2,4]triazolo[4,3-a]pyrazine (a) Synthesis of (1S,4S)-tert-butyl 5-(2,7-dichloropyrido[2,3-b]pyrazin-3-yl)-2,5-diazabicyclo[2.2.1]heptan-2-carboxylate At 0° C., TEA (0.2 mL, 1.28 mmol) was added to a mixture of 2,3,7-trichloropyrido[2,3-b]pyrazine (100.0 mg, 0.43 mmol), (1S,4S)-tert-butyl 2,5-diazabicyclo[2.2.1]heptan-2-carboxylate (89.0 mg, 0.45 mmol) in DCM (4.3 mL), and then stirred for 3 hours. The reaction mixture was purified by column chromatography (EtOAc:n-Hex=1:5) on silica. The fractions containing the product were collected and evaporated to obtain yellow solid compound of (1S,4S)-tert-butyl 5-(2,7-dichloropyrido[2,3-b]pyrazin-3-yl)-2,5-diazabicyclo[2.2.1]heptan-2-carboxylate (120.0 mg, 71%).

LC/MS ESI(+): 396 (M+1), 398 (M+3)
¹H-NMR (300 MHz, CDCl₃); δ: 8.79 (d, 1H, J=2.7 Hz), 8.11 (d, 1H, J=2.7 Hz), 5.30 (m, 1H), 4.78-4.55 (m, 1H), 4.20 (m, 1H), 3.95-3.63 (m, 2H), 3.53 (m, 1H), 1.99 (m, 2H), 1.56 (m, 9H)

(b) Synthesis of (1S,4S)-tert-butyl 5-(8-chloropyrido[2,3-e][1,2,4]triazolo[4,3-a]pyrazin-4-yl)-2,5-diazabicyclo[2.2.1]heptan-2-carboxylate Hydrazine monohydrate (48.0 μL, 1.51 mmol) was added to suspension of (1S,4S)-tert-butyl 5-(2,7-dichloropyrido[2,3-b]pyrazin-3-yl)-2,5-diazabicyclo[2.2.1]heptan-2-carboxylate (120.0 mg, 0.30 mmol) and EtOH (1.5 mL). The reaction mixture was stirred at room temperature for one hour. Et₂O was then added thereto to form a solid, and the formed solid was filtered and dried under reduced pressure. Trimethyl orthoformate (3.0 mL) was added to the formed solid. The mixture was stirred at 85° C. for one hour and then cooled to room temperature. Et₂O was added thereto to form a solid, and the formed solid was filtered and then dried under reduced pressure to obtain yellow solid compound of (1S,4S)-tert-butyl 5-(8-chloropyrido[2,3-e][1,2,4]triazolo[4,3-a]pyrazin-4-yl)-2,5-diazabicyclo[2.2.1]heptan-2-carboxylate (91.0 mg, 83%).

LC/MS ESI(+): 402 (M+1), 404 (M+3)
¹H-NMR (300 MHz, DMSO-d₆); δ: 9.98 (m, 1H), 8.83 (m, 1H), 8.56 (m, 1H), 6.27 (s, 0.7H), 5.27 (s, 0.3H), 4.57 (m, 1H), 4.24 (m, 0.7H), 3.80 (m, 1H), 3.50 (m, 1H), 3.40 (m, 1.3H), 2.20-1.98 (m, 2H), 1.38-1.49 (m, 9H)

(c) Synthesis of 4-((1S,4S)-2,5-diazabicyclo[2.2.1]heptan-2-yl)-8-chloropyrido[2,3-e][1,2,4]triazolo[4,3-a]pyrazine TFA (0.8 mL) was added to the mixture of (1S,4S)-tert-butyl 5-(8-chloropyrido[2,3-e][1,2,4]triazolo[4,3-a]pyrazin-4-yl)-2,5-diazabicyclo[2.2.1]heptan-2-carboxylate (90.0 mg, 0.22 mmol) and DCM (1.2 mL), and it was then stirred at room temperature for one hour. The reaction mixture was purified by column chromatography (MeOH:DCM=1:60) on amine silica. The fractions containing the product were collected and evaporated. Et₂O was added to the residue to form a solid, and the formed solid was filtered and dried under reduced pressure to obtain ivory solid compound of 4-((1S,4S)-2,5-diazabicyclo[2.2.1]heptan-2-yl)-8-chloropyrido[2,3-e][1,2,4]triazolo[4,3-a]pyrazine (58.0 mg, 85%).

LC/MS ESI(+): 302 (M+1), 304 (M+3)
¹H-NMR (300 MHz, DMSO-d₆); δ: 9.96 (m, 1H), 8.79 (m, 1H), 8.52 (s, 1H), 6.19 (s, 0.7H), 5.17 (s, 0.3H), 4.16 (s, 0.7H), 3.78 (s, 1H), 3.70 (m, 1.3H), 3.12-2.80 (m, 2H), 1.95-1.70 (m, 2H)

Example 78

Synthesis of 8-chloro-4-((1S,4S)-5-methyl-2,5-diazabicyclo[2.2.1]heptan-2-yl)pyrido[2,3-e][1,2,4]triazolo[4,3-a]pyrazine 37% of formaldehyde (28.0 μL, 0.38 mmol) and NaBH₄ (14.0 mg, 0.38 mmol) were added to suspension of 4-((1S,4S)-2,5-diazabicyclo[2.2.1]heptan-2-yl)-8-chloropyrido[2,3-e][1,2,4]triazolo[4,3-a]pyrazine (38.0 mg, 0.13 mmol) and MeOH (1.3 mL). The reaction mixture was stirred at room temperature for one hour and then distilled under reduced pressure. EtOAc and water were added to the residue, and it was extracted with EtOAc. The organic layer was dried over anhydrous Na₂SO₄, filtered and then distilled under reduced pressure. The residue was purified by column chromatography (MeOH:DCM=1:60) on amine silica. The fractions containing the product were collected and evaporated, and then DCMEt₂O was added thereto to form a solid. The formed solid was filtered and then dried under reduced pressure to obtain ivory solid compound of 8-chloro-4-((1S,4S)-5-methyl-2,5-diazabicyclo[2.2.1]heptan-2-yl)pyrido[2,3-e][1,2,4]triazolo[4,3-a]pyrazine (20.0 mg, 50%).

LC/MS ESI(+): 316 (M+1), 318 (M+3)
¹H-NMR (300 MHz, DMSO-d₆); δ: 9.96 (m, 1H), 8.79 (m, 1H), 8.53 (m, 1H), 6.13 (s, 0.7H), 5.13 (s, 0.3H), 4.40 (m, 0.3H), 4.04 (m, 0.3H), 3.88 (m, 0.7H), 3.60 (m, 1.7H), 2.97 (m, 1H), 2.64 (m, 1H), 2.36 (s, 3H), 2.08-1.80 (m, 2H)

Example 79

Synthesis of 8-chloro-4-(1,4-diazepan-1-yl)pyrido[2,3-e][1,2,4]triazolo[4,3-a]pyrazine (a) Synthesis of tert-butyl 4-(2,7-dichloropyrido[2,3-b]pyrazin-3-yl)-1,4-diazepan-1-carboxylate 2,3,7-Trichloropyrido[2,3-b]pyrazine (70.0 mg, 0.30 mmol) was dissolved in DCM (3.0 mL), and then tert-butyl 1,4-diazepan-1-carboxylate (60.0 μL, 0.30 mmol) and TEA (135.0 μL, 0.90 mmol) were added thereto at 0° C. The reaction mixture was stirred at room temperature for 2 hours and then diluted with DCM. The organic layer was washed with water and brine, dried over anhydrous MgSO₄, filtered and then concentrated under reduced pressure. The residue was purified by column chromatography (n-Hex:EtOAc=3:1) on amine silica. The fractions containing the product were collected and concentrated to obtain yellow liquid compound of tert-butyl 4-(2,7-dichloropyrido[2,3-b]pyrazin-3-yl)-1,4-diazepan-1-carboxylate (85.0 mg, 71%).

LC/MS ESI(+): 398 (M+1), 400 (M+3)
¹H-NMR (300 MHz, CDCl₃); δ: 8.82 (d, 1H, J=2.67 Hz), 8.12 (d, 1H, J=2.67 Hz), 4.15-3.92 (m, 4H), 3.78-3.70 (m, 2H), 3.57-3.38 (m, 2H), 2.18-2.06 (m, 2H), 1.41 (s, 9H)

(b) Synthesis of tert-butyl 4-(7-chloro-2-hydrazinylpyrido[2,3-b]pyrazin-3-yl)-1,4-diazepan-1-carboxylate Hydrazine monohydrate (6.5 µL, 0.60 mmol) was added to the mixture of tert-butyl 4-(2,7-dichloropyrido[2,3-b]pyrazin-3-yl)-1,4-diazepan-1-carboxylate (82.0 mg, 0.20 mmol) and EtOH (2.0 mL), and then stirred at room temperature for 3 hours. The reaction mixture was diluted in Et$_2$O, and it was then stirred at room temperature for one hour. The formed solid was filtered and dried under reduced pressure to obtain yellow solid compound of tert-butyl 4-(7-chloro-2-hydrazinylpyrido[2,3-b]pyrazin-3-yl)-1,4-diazepan-1-carboxylate.
LC/MS ESI(+): 394 (M+1), 396 (M+3)

(c) Synthesis of 8-chloro-4-(1,4-diazepan-1-yl)pyrido[2,3-e][1,2,4]triazolo[4,3-a]pyrazine The mixture of unpurified tert-butyl 4-(7-chloro-2-hydrazinylpyrido[2,3-b]pyrazin-3-yl)-1,4-diazepan-1-carboxylate and trimethyl orthoformate (1.1 mL) was stirred at 80° C. for 2 hours and then cooled to room temperature. The reaction mixture was concentrated under reduced pressure. Unpurified tert-butyl 4-(8-chloropyrido[2,3-e][1,2,4]triazolo[4,3-a]pyrazin-4-yl)-1,4-diazepan-1-carboxylate was dissolved in DCM (1.0 mL), and TFA (0.5 mL) was slowly added thereto at room temperature, and it was then stirred at room temperature for 2 hours. The reaction mixture was concentrated under reduced pressure. The residue was purified by column chromatography (DCM:MeOH=10:1) on amine silica. The fractions containing the product were collected and evaporated to obtain yellow solid compound of 8-chloro-4-(1,4-diazepan-1-yl)pyrido[2,3-e][1,2,4]triazolo[4,3-a]pyrazine (28.0 mg, 35% in 3 steps).
LC/MS ESI(+): 304 (M+1), 306 (M+3)
$^1$H-NMR (300 MHz, CDCl$_3$); δ: 9.14 (s, 1H), 8.60 (d, 1H, J=2.3 Hz), 8.01 (d, 1H, J=2.3 Hz), 4.84-4.72 (m, 2H), 4.28-4.17 (m, 2H), 3.21 (t, 2H, J=5.7 Hz), 2.94 (t, 2H, J=5.7 Hz), 2.12-2.02 (m, 2H)

Example 80

Synthesis of 8-chloro-4-(4-methyl-1,4-diazepan-1-yl)pyrido[2,3-e][1,2,4]triazolo[4,3-a]pyrazine (a) Synthesis of 2,7-dichloro-3-(4-methyl-1,4-diazepan-1-yl)pyrido[2,3-b]pyrazine 2,3,7-Trichloropyrido[2,3-b]pyrazine (50.0 mg, 0.21 mmol) was dissolved in DCM (2.0 mL), and 1-methyl-1,4-diazepane (26.1 µL, 0.21 mmol) and TEA (94.7 µL, 0.63 mmol) were then added thereto at 0° C. The reaction mixture was stirred at room temperature for 2 hours and then diluted in DCM. The organic layer was washed with water and brine, dried anhydrous MgSO$_4$, filtered and then concentrated under reduced pressure. The residue was purified by column chromatography (DCM:MeOH=10:1) on amine silica. The fractions containing the product were collected and concentrated to obtain brown solid compound of 2,7-dichloro-3-(4-methyl-1,4-diazepan-1-yl)pyrido[2,3-b]pyrazine (42.0 mg, 64%).
LC/MS ESI(+): 312 (M+1), 314 (M+3)
$^1$H-NMR (300 MHz, CDCl$_3$); δ: 8.80 (d, 1H, J=2.6 Hz), 8.11 (d, 1H, J=2.6 Hz), 4.09-4.03 (m, 2H), 4.01-3.95 (m, 2H), 3.02-2.93 (m, 2H), 2.78-2.69 (m, 2H), 2.46 (s, 3H), 2.25-2.13 (m, 2H)

(b) Synthesis of 7-chloro-2-hydrazinyl-3-(4-methyl-1,4-diazepan-1-yl)pyrido[2,3-b]pyrazine Hydrazine monohydrate (3.9 µL, 0.36 mmol) was added to the mixture of 2,7-dichloro-3-(4-methyl-1,4-diazepan-1-yl)pyrido[2,3-b]pyrazine (38.5 mg, 0.12 mmol) and EtOH (1.2 mL), and it was then stirred at room temperature for 2 hours. The reaction mixture was diluted in Et$_2$O, and it was then stirred at room temperature for one hour. The formed solid was filtered and dried under reduced pressure to obtain unpurified yellow solid compound of 7-chloro-2-hydrazinyl-3-(4-methyl-1,4-diazepan-1-yl)pyrido[2,3-b]pyrazine.
LC/MS ESI(+): 308 (M+1), 310 (M+3)

(c) Synthesis of 8-chloro-4-(4-methyl-1,4-diazepan-1-yl)pyrido[2,3-e][1,2,4]triazolo[4,3-a]pyrazine The mixture of unpurified 7-chloro-2-hydrazinyl-3-(4-methyl-1,4-diazepan-1-yl)pyrido[2,3-b]pyrazine and trimethyl orthoformate (0.7 mL) was stirred at 80° C. for 2 hours and then cooled to room temperature. The reaction mixture was concentrated under reduced pressure and then purified by column chromatography (DCM:MeOH=20:1) on amine silica. The fractions containing the product were collected and concentrated to obtain yellow solid compound of 8-chloro-4-(4-methyl-1,4-diazepan-1-yl)pyrido[2,3-e][1,2,4]triazolo[4,3-a]pyrazine (16.0 mg, 42% in 2 steps).
LC/MS ESI(+): 318 (M+1), 320 (M+3)
$^1$H-NMR (300 MHz, CDCl$_3$); δ: 9.14 (s, 1H), 8.59 (d, 1H, J=2.3 Hz), 8.01 (d, 1H, J=2.3 Hz), 4.87-4.74 (m, 2H), 4.18-4.14 (m, 2H), 2.92-2.86 (m, 2H), 2.67-2.60 (m, 2H), 2.39 (s, 3H), 2.21-2.09 (m, 2H)

Example 81

Synthesis of (R)-1-(8-bromopyrido[2,3-e][1,2,4]triazolo[4,3-a]pyrazin-4-yl)-N-methylpyrrolidin-3-amine (a) Synthesis of (R)-tert-butyl (1-(7-bromo-2-chloropyrido[2,3-b]pyrazin-3-yl)pyrrolidin-3-yl)(methyl)carbamate 7-Bromo-2,3-dichloropyrido[2,3-b]pyrazine (70.0 mg, 0.25 mmol) and TEA (175.0 µL, 1.26 mmol) were dissolved in DCM (1.0 mL), and (R)-tert-butyl methyl(pyrrolidin-3-yl)carbamate (55.2 mg, 0.28 mmol) dissolved in DCM (0.5 mL) was added thereto at 0° C. The reaction mixture was stirred at 0° C. for 12 hours and then concentrated to obtain (R)-tert-butyl (1-(7-bromo-2-chloropyrido[2,3-b]pyrazin-3-yl)pyrrolidin-3-yl)(methyl)carbamate (111.1 mg, 100%).
LC/MS ESI (+): 442 (M+1), 444 (M+3)

(b) Synthesis of (R)-tert-butyl (1-(7-bromo-2-hydrazinylpyrido[2,3-b]pyrazin-3-yl)pyrrolidin-3-yl)(methyl)carbamate (R)-tert-Butyl (1-(7-bromo-2-chloropyrido[2,3-b]pyrazin-3-yl)pyrrolidin-3-yl)(methyl)carbamate (111.1 mg, 0.25 mmol) and hydrazine monohydrate (25.0 µL, 0.50 mmol) were dissolved in EtOH (1.5 mL). The mixture was stirred at room temperature for 3 hours to form a solid, and the formed solid was filtered to obtain yellow solid compound of (R)-tert-butyl (1-(7-bromo-2-hydrazinylpyrido[2,3-b]pyrazin-3-yl)pyrrolidin-3-yl)(methyl)carbamate (110.0 mg, 100%).
LC/MS ESI(+): 438 (M+1), 440 (M+3)

(c) Synthesis of (R)-tert-butyl (1-(8-bromopyrido[2,3-e][1,2,4]triazolo[4,3-a]pyrazin-4-yl)pyrrolidin-3-yl)(methyl)carbamate The mixture of (R)-tert-butyl (1-(7-bromo-2-hydrazinylpyrido[2,3-b]pyrazin-3-yl)pyrrolidin-3-yl)(methyl)carbamate (110.0 mg, 0.25 mmol) and trimethyl orthoformate (1.0 mL) was stirred at 80° C. for 2 hours and then cooled to room temperature. The reaction mixture was concentrated and then firstly purified by column chromatography (MeOH:DCM=5:95) on silica, and secondly purified by column chromatography (EtOAc:n-Hex=50:50) on amine silica.

The fractions containing the product were collected and evaporated to obtain yellow solid compound of (R)-tert-butyl (1-(8-bromopyrido[2,3-e][1,2,4]triazolo[4,3-a]pyrazin-4-yl)pyrrolidin-3-yl)(methyl)carbamate (40.0 mg, 36%).

LC/MS ESI(+): 448 (M+1), 450 (M+3)

(d) Synthesis of (R)-1-(8-bromopyrido[2,3-e][1,2,4]triazolo[4,3-a]pyrazin-4-yl)-N-methylpyrrolidin-3-amine (R)-tert-butyl (1-(8-bromopyrido[2,3-e][1,2,4]triazolo[4,3-a]pyrazin-4-yl)pyrrolidin-3-yl)(methyl)carbamate (40.0 mg, 0.09 mmol) was dissolved in DCM (1.0 mL), and TFA (0.4 mL) was added thereto. The reaction mixture was stirred at room temperature for one hour and then purified by column chromatography (MeOH:DCM=5:95) on amine silica. The fractions containing the product were collected and evaporated to obtain yellow solid compound of (R)-1-(8-bromopyrido[2,3-e][1,2,4]triazolo[4,3-a]pyrazin-4-yl)-N-methylpyrrolidin-3-amine (20.7 mg, 67%).

LC/MS ESI(+): 348 (M+1), 350 (M+3)
$^1$H-NMR (300 MHz, DMSO-$d_6$); δ: 9.98 (s, 1H), 8.89 (d, 1H, J=2.1 Hz), 8.57 (d, 1H, J=2.1 Hz), 4.36-4.20 (m, 2H), 3.81-3.61 (m, 2H), 3.30 (m, 1H), 2.32 (s, 3H), 2.11-1.86 (m, 3H)

Example 82

Synthesis of 8-chloro-4-(hexahydro-1H-pyrrolo[3,4-b]pyridin-6(2H)-yl)pyrido[2,3-e][1,2,4]triazolo[4,3-a]pyrazine (a) Synthesis of tert-butyl 6-(2,7-dichloropyrido[2,3-b]pyrazin-3-yl)octahydro-1H-pyrrolo[3,4-b]pyridin-1-carboxylate 2,3,7-Trichloropyrido[2,3-b]pyrazine (150.0 mg, 0.64 mmol) was dissolved in DCM (6.0 mL). tert-Butyl octahydro-1H-pyrrolo[3,4-b]pyridin-1-carboxylate (151.0 mg, 0.67 mmol) and TEA (288.0 μL, 1.92 mmol) were then added to the mixture at 0° C. The reaction mixture was stirred at room temperature for 2 hours and then diluted in DCM. The organic layer was washed water and brine, dried over anhydrous MgSO$_4$, filtered and then concentrated under reduced pressure. The residue was purified by column chromatography (n-Hex:EtOAc=3:1) on amine silica. The fractions containing the product were collected and concentrated to obtain ivory solid compound of tert-butyl 6-(2,7-dichloropyrido[2,3-b]pyrazin-3-yl)octahydro-1H-pyrrolo[3,4-b]pyridin-1-carboxylate (173.0 mg, 61%).

LC/MS ESI(+): 424 (M+1), 426 (M+3)
$^1$H-NMR (300 MHz, DMSO-$d_6$); δ: 8.81 (d, 1H, J=2.7 Hz), 8.38 (d, 1H, J=2.7 Hz), 4.69 (m, 1H), 4.00-3.80 (m, 4H), 3.70 (m, 1H), 2.85 (m, 1H), 2.26 (m, 1H), 1.77-1.61 (m, 2H), 1.42 (s, 9H), 1.38-1.26 (m, 2H)

(b) Synthesis of tert-butyl 6-(7-chloro-2-hydrazinylpyrido[2,3-b]pyrazin-3-yl)octahydro-1H-pyrrolo[3,4-b]pyridin-1-carboxylate Hydrazine monohydrate (37.7 μL, 1.20 mmol) was added to the mixture of tert-butyl 6-(2,7-dichloropyrido[2,3-b]pyrazin-3-yl)octahydro-1H-pyrrolo[3,4-b]pyridin-1-carboxylate (170.0 mg, 0.40 mmol) and EtOH (4.0 mL), and it was then stirred at room temperature for 3 hours. The reaction mixture was diluted in Et$_2$O and stirred at room temperature for one hour to form a solid. The formed solid was filtered and then dried under reduced pressure to obtain yellow solid compound of tert-butyl 6-(7-chloro-2-hydrazinylpyrido[2,3-b]pyrazin-3-yl)octahydro-1H-pyrrolo[3,4-b]pyridin-1-carboxylate.

LC/MS ESI(+): 420 (M+1), 422 (M+3)

(c) Synthesis of tert-butyl 6-(8-chloropyrido[2,3-e][1,2,4]triazolo[4,3-a]pyrazin-4-yl)octahydro-1H-pyrrolo[3,4-b]pyridin-1-carboxylate The mixture of unpurified tert-butyl 6-(7-chloro-2-hydrazinylpyrido[2,3-b]pyrazin-3-yl)octahydro-1H-pyrrolo[3,4-b]pyridin-1-carboxylate and trimethyl orthoformate (4.0 mL) was stirred at 80° C. for 2 hours and then cooled to room temperature. The reaction mixture was concentrated under reduced pressure and purified by column chromatography (n-Hex:EtOAc=3:1) on amine silica. The fractions containing the product were collected and concentrated to obtain yellow solid compound of tert-butyl 6-(8-chloropyrido[2,3-e][1,2,4]triazolo[4,3-a]pyrazin-4-yl)octahydro-1H-pyrrolo[3,4-b]pyridin-1-carboxylate (79.0 mg, 46% in 2 steps).

LC/MS ESI(+): 430 (M+1), 432 (M+3)
$^1$H-NMR (300 MHz, CDCl$_3$); δ: 9.16 (s, 1H), 8.59 (d, 1H, J=2.3 Hz), 8.03 (d, 1H, J=2.3 Hz), 4.91 (m, 1H), 4.75 (m, 1H), 4.35-4.00 (m, 3H), 3.94-3.71 (m, 1H), 2.81 (m, 1H), 2.37 (m, 1H), 1.91-1.68 (m, 2H), 1.62-1.31 (m, 11H)

(d) Synthesis of 8-chloro-4-(hexahydro-1H-pyrrolo[3,4-b]pyridin-6(2H)-yl)pyrido[2,3-e][1,2,4]triazolo[4,3-a]pyrazine tert-Butyl 6-(8-chloropyrido[2,3-e][1,2,4]triazolo[4,3-a]pyrazin-4-yl)octahydro-1H-pyrrolo[3,4-b]pyridin-1-carboxylate (76.0 mg, 0.17 mmol) was dissolved in DCM (2.0 mL), and TFA (126.0 μL, 1.70 mmol) was slowly added thereto at room temperature. The mixture was stirred at room temperature for 8 hours. The reaction mixture was concentrated under reduced pressure. The residue was purified by column chromatography (DCM:MeOH=10:1) on amine silica. The fractions containing the product were collected and evaporated to obtain ivory solid compound of 8-chloro-4-(hexahydro-1H-pyrrolo[3,4-b]pyridin-6(2H)-yl)pyrido[2,3-e][1,2,4]triazolo[4,3-a]pyrazine (51.0 mg, 91%).

LC/MS ESI(+): 330 (M+1), 332 (M+3)
$^1$H-NMR (300 MHz, DMSO-$d_6$); δ: 9.95 (s, 1H), 8.77 (d, 1H, J=2.7 Hz), 8.50 (d, 1H, J=2.7 Hz), 4.53-4.41 (m, 1H), 4.27-4.10 (m, 1H), 3.84-3.64 (m, 2H), 3.42-3.31 (m, 1H), 2.89-2.79 (m, 1H), 2.58-2.51 (m, 1H), 2.44-2.26 (m, 2H), 1.84-1.35 (m, 4H)

Example 83

Synthesis of 8-chloro-4-(1-methylhexahydro-1H-pyrrolo[3,4-b]pyridin-6(2H)-yl)pyrido[2,3-e][1,2,4]triazolo[4,3-a]pyrazine 8-Chloro-4-(hexahydro-1H-pyrrolo[3,4-b]pyridin-6(2H)-yl)pyrido[2,3-e][1,2,4]triazolo[4,3-a]pyrazine (35.0 mg, 0.10 mmol) was dissolved in MeOH (0.7 mL), and 37% of formaldehyde (40.5 mg, 0.50 mmol) dissolved in MeOH (0.3 mL) was added thereto at 0° C., and NaBH$_4$ (18.9 mg, 0.50 mmol) was then added thereto. The mixture was stirred at room temperature for 3 hours. The reaction mixture was diluted in EtOAc. The organic layer was then washed with water and brine, dried over anhydrous MgSO$_4$, filtered and then concentrated under reduced pressure. The residue was purified by column chromatography (DCM:MeOH=20:1) on amine silica. The fractions containing the product were collected and concentrated to obtain brown solid compound of 8-chloro-4-(1-methylhexahydro-1H-pyrrolo[3,4-b]pyridin-6(2H)-yl)pyrido[2,3-e][1,2,4]triazolo[4,3-a]pyrazine (7.4 mg, 22%).

LC/MS ESI(+): 344 (M+1), 346 (M+3)

$^1$H-NMR (300 MHz, CDCl$_3$); δ: 9.15 (s, 1H), 8.58 (d, 1H, J=2.3 Hz), 8.02 (d, 1H, J=2.3 Hz), 5.06 (m, 0.4H), 4.69-4.60 (m, 0.6H), 4.51-4.39 (m, 1H), 4.19 (m, 0.4H), 4.03 (m, 1H), 3.80 (m, 0.6H), 2.89-2.75 (m, 2H), 2.67-2.47 (m, 1H), 2.34 (s, 3H), 2.18 (m, 1H), 1.95-1.55 (m, 4H)

Example 84

Synthesis of 1-(8-chloropyrido[2,3-e][1,2,4]triazolo[4,3-a]pyrazin-4-yl)-N,N-dimethylazetidin-3-amine NaBH$_4$ (29.0 mg, 0.77 mmol) was added to suspension of 1-(8-chloropyrido[2,3-e][1,2,4]triazolo[4,3-a]pyrazin-4-yl)-N-methylazetidin-3-amine (74.0 mg, 0.26 mmol), 37% of formaldehyde (29.0 μL, 0.38 mmol) and MeOH (2.5 mL). The reaction mixture was stirred at room temperature for 5 hours, and EtOAc and water were added thereto, and it was extracted with EtOAc. The organic layer was washed with brine, dried over anhydrous Na$_2$SO$_4$, filtered and then distilled under reduced pressure. The residue was purified by column chromatography (MeOH:DCM=1:100) on amine silica. The fractions containing the product were collected and evaporated to obtain ivory solid compound of 1-(8-chloropyrido[2,3-e][1,2,4]triazolo[4,3-a]pyrazin-4-yl)-N,N-dimethylazetidin-3-amine (12.0 mg, 16%).

LC/MS ESI(+): 304 (M+1), 306 (M+3)

$^1$H-NMR (300 MHz, DMSO-d$_6$); δ: 9.95 (s, 1H), 8.81 (d, 1H, J=2.4 Hz), 8.54 (d, 1H, J=2.4 Hz), 4.81 (m, 1H), 4.53 (m, 1H), 4.34. (m, 1H), 4.11 (m, 1H), 3.35 (m, 1H), 2.18 (s, 6H)

Example 85

Synthesis of 1-(8-bromopyrido[2,3-e][1,2,4]triazolo[4,3-a]pyrazin-4-yl)-N,N-dimethylazetidin-3-amine NaBH$_4$ (11.0 mg, 0.29 mmol) was added to suspension of 1-(8-bromopyrido[2,3-e][1,2,4]triazolo[4,3-a]pyrazin-4-yl)-N-methylazetidin-3-amine (32.0 mg, 0.10 mmol), 37% of formaldehyde (11.0 μL, 0.14 mmol) and MeOH (1.0 mL). The reaction mixture was stirred at room temperature for 5 hours, and EtOAc and water were then added thereto, and it was extracted with EtOAc. The organic layer was washed with brine, dried over anhydrous Na$_2$SO$_4$, filtered and then distilled under reduced pressure. The residue was purified by column chromatography (MeOH:DCM=1:100) on amine silica. The fractions containing the product were collected and evaporated to obtain ivory solid compound of 1-(8-bromopyrido[2,3-e][1,2,4]triazolo[4,3-a]pyrazin-4-yl)-N,N-dimethylazetidin-3-amine (3.0 mg, 9%).

LC/MS ESI(+): 348 (M+1), 350 (M+3)

$^1$H-NMR (300 MHz, DMSO-d$_6$); δ: 9.95 (s, 1H), 8.90 (d, 1H, J=2.4 Hz), 8.60 (d, 1H, J=2.4 Hz), 4.81 (m, 1H), 4.51 (m, 1H), 4.31 (m, 1H), 4.10 (m, 1H), 3.40 (m, 1H), 2.18 (s, 6H)

Example 86

Synthesis of (1-(8-bromopyrido[2,3-e][1,2,4]triazolo[4,3-a]pyrazin-4-yl)azetidin-3-yl)(methyl)carbamic acid 1-(8-Bromopyrido[2,3-e][1,2,4]triazolo[4,3-a]pyrazin-4-yl)-N-methylazetidin-3-amine obtained from tert-butyl (1-(7-bromo-2-chloropyrido[2,3-b]pyrazin-3-yl)azetidin-3-yl)(methyl)carbamate (13000.0 mg, 30.3 mmol) in the same way as Example 3 (e) to (f) was purified by column chromatography (DCM:MeOH=90:10) on amine silica. The fractions containing the product were collected and evaporated to obtain ivory solid compound of (1-(8-bromopyrido[2,3-e][1,2,4]triazolo[4,3-a]pyrazin-4-yl)azetidin-3-yl)(methyl)carbamic acid (56.0 mg, 0.5%).

LC/MS ESI (+): 378 (M+1), 380 (M+3)

$^1$H-NMR (300 MHz, DMSO-d$_6$); δ: 9.97 (s, 1H), 9.03 (bs, 1H), 8.95 (d, 1H, J=2.2 Hz), 8.65 (d, 1H, J=2.2 Hz), 4.40-4.30 (m, 2H), 4.10-4.00 (m, 1H), 3.90-3.80 (m, 2H), 2.89 (m, 3H)

Example 87

Synthesis of 2-((8-chloropyrido[2,3-e][1,2,4]triazolo[4,3-a]pyrazin-4-yl)amino)ethanol

(a) Synthesis of 2-((2,7-dichloropyrido[2,3-b]pyrazin-3-yl)amino)ethanol 2,3,7-Trichloropyrido[2,3-b]pyrazine (500.0 mg, 2.14 mmol) was dissolved in DCM (20.0 mL), and ethanolamine (135.0 μL, 2.25 mmol) and TEA (965.0 μL, 6.42 mmol) were added thereto at 0° C. The reaction mixture was stirred at room temperature for 2 hours, diluted in DCM and then stirred at room temperature for one hour. The formed solid was filtered and dried under reduced pressure to obtain unpurified brown solid compound of 2-((2,7-dichloropyrido[2,3-b]pyrazin-3-yl)amino)ethanol.

LC/MS ESI(+): 259 (M+1), 261 (M+3)

(b) Synthesis of 2-((7-chloro-2-hydrazinylpyrido[2,3-b]pyrazin-3-yl)amino)ethanol Hydrazine monohydrate (276.0 μL, 8.79 mmol) was added to the mixture of unpurified 2-((2,7-dichloropyrido[2,3-b]pyrazin-3-yl)amino)ethanol and EtOH (30.0 mL), and it was then stirred at room temperature for 4 hours. The reaction mixture was diluted in Et$_2$O and then stirred at room temperature for one hour. The formed solid was filtered and then dried under reduced pressure to obtain unpurified brown solid compound of 2-((7-chloro-2-hydrazinylpyrido[2,3-b]pyrazin-3-yl)amino)ethanol.

LC/MS ESI(+): 255 (M+1), 257 (M+3)

(c) Synthesis of 2-((8-chloropyrido[2,3-e][1,2,4] triazolo[4,3-a]pyrazin-4-yl)amino)ethanol The mixture of unpurified 2-((7-chloro-2-hydrazinylpyrido[2,3-b]pyrazin-3-yl)amino)ethanol and trimethyl orthoformate (16.0 mL) was stirred at 80° C. for 4 hours and then cooled to room temperature. The reaction mixture was concentrated under reduced pressure and then dissolved in MeOH. EtOAc was added to the mixture and the mixture was diluted. The organic layer was washed with water and brine, dried over anhydrous MgSO$_4$, filtered and concentrated under reduced pressure. EtOAc (20.0 mL) was added to the residue, and it was stirred for one hour. The formed solid was filtered and dried under reduced pressure to obtain white solid compound of 2-((8-chloropyrido[2,3-e][1,2,4]triazolo[4,3-a]pyrazin-4-yl)amino)ethanol (82.0 mg, 14% in 3 steps).

LC/MS ESI(+): 265 (M+1), 267 (M+3)

$^1$H-NMR (300 MHz, DMSO-d$_6$); δ: 9.93 (s, 1H), 8.82 (d, 1H, J=2.7 Hz), 8.64-8.58 (brs, 1H), 8.55 (d, 1H, J=2.7 Hz), 4.84 (m, 1H), 3.70-3.64 (m, 4H)

Example 88

Synthesis of 1-(8-chloroimidazo[1,2-a]pyrido[2,3-e]pyrazin-4-yl)-N-methylazetidin-3-amine (a) Synthesis of tert-butyl (1-(7-chloro-2-((2,2-diethoxyethyl)amino)pyrido[2,3-b]pyrazin-3-yl)azetidin-3-yl)(methyl)carbamate tert-Butyl (1-(2,7-dichloropyrido[2,3-b]pyrazin-3-yl)azetidin-3-yl)(methyl)carbamate (180.0 mg, 0.47 mmol) was dissolved in 2,2-diethoxyethanamine (2.0 mL), stirred at room temperature for 12 hours, and EtOAc solvent was added thereto. The organic layer was washed with brine, dried over anhydrous Na$_2$SO$_4$, filtered and then distilled under reduced pressure to obtain yellow solid compound of tert-butyl (1-(7-chloro-2-((2,2-diethoxyethyl)amino)pyrido[2,3-b]pyrazin-3-yl)azetidin-3-yl)(methyl)carbamate.

(b) Synthesis of 1-(8-chloroimidazo[1,2-a]pyrido[2,3-e]pyrazin-4-yl)-N-methylazetidin-3-amine Unpurified tert-butyl (1-(7-chloro-2-((2,2-diethoxyethyl)amino)pyrido[2,3-b]pyrazin-3-yl)azetidin-3-yl)(methyl)carbamate (225.1 mg, 0.47 mmol) and 4-methylbenzene sulfonic acid (1160.0 mg, 6.08 mmol) were dissolved in IPA (3.0 mL), stirred at 100° C. for 2 hours and then cooled to room temperature. Water was added to the reaction mixture. The resulting solution was alkalized with saturated NaHCO$_3$ aqueous solution (pH=9) and then extracted with DCM. The organic layer was dried over anhydrous Na$_2$SO$_4$, filtered and then distilled under reduced pressure. The residue was purified by column chromatography (MeOH:DCM=5:95) on silica. The fractions containing the product were collected and evaporated to obtain ivory solid compound of 1-(8-chloroimidazo[1,2-a]pyrido[2,3-e]pyrazin-4-yl)-N-methylazetidin-3-amine (70.0 mg, 52%).

LC/MS ESI (+): 289 (M+1), 291 (M+3)

$^1$H-NMR (300 MHz, CDCl$_3$); δ: 8.53 (m, 1H), 7.94-7.89 (m, 2H), 7.66 (m, 1H), 5.12-4.13 (m, 4H), 3.83 (m, 1H), 2.49 (s, 3H)

Example 89

Synthesis of 1-(8-bromoimidazo[1,2-a]pyrido[2,3-e]pyrazin-4-yl)-N-methylazetidin-3-amine (a) Synthesis of tert-butyl (1-(7-bromo-2-((2,2-diethoxyethyl)amino)pyrido[2,3-b]pyrazin-3-yl)azetidin-3-yl)(methyl)carbamate tert-Butyl (1-(7-bromo-2-chloropyrido[2,3-b]pyrazin-3-yl)azetidin-3-yl)(methyl)carbamate (177.0 mg, 0.41 mmol) was dissolved in 2,2-diethoxyethanamine (2.0 mL), and the mixture was stirred at room temperature for 12 hours. EtOAc solvent was then added to the reaction mixture, and it was washed with brine, dried over anhydrous Na$_2$SO$_4$, filtered and then distilled under reduced pressure to obtain yellow solid compound of tert-butyl (1-(7-bromo-2-((2,2-diethoxyethyl)amino)pyrido[2,3-b]pyrazin-3-yl)azetidin-3-yl)(methyl)carbamate.

(b) Synthesis of 1-(8-bromoimidazo[1,2-a]pyrido[2,3-e]pyrazin-4-yl)-N-methylazetidin-3-amine Unpurified tert-butyl (1-(7-bromo-2-((2,2-diethoxyethyl)amino)pyrido[2,3-b]pyrazin-3-yl)azetidin-3-yl)(methyl)carbamate (215.0 mg, 0.41 mmol) and 4-methylbenzene sulfonic acid (1020.0 mg, 5.36 mmol) were dissolved in IPA (3.0 mL), and the mixture was stirred at 100° C. for 2 hours and then cooled to room temperature. Water was added to the reaction mixture, and it was alkalized with saturated NaHCO$_3$ aqueous solution (pH=9) and then extracted with DCM. The organic layer was dried over anhydrous Na$_2$SO$_4$, filtered and distilled under reduced pressure, and then purified by column chromatography (MeOH:DCM=5:95) on silica. The fractions containing the product were collected and evaporated to obtain ivory solid compound of 1-(8-bromoimidazo[1,2-a]pyrido[2,3-e]pyrazin-4-yl)-N-methylazetidin-3-amine (65.0 mg, 47%).

LC/MS ESI (+): 333 (M+1), 335 (M+3)

$^1$H-NMR (300 MHz, CDCl$_3$); δ: 8.60 (d, 1H, J=2.1 Hz), 8.06 (d, 1H, J=2.1 Hz), 7.89 (d, 1H, J=1.5 Hz), 7.65 (d, 1H, J=1.5 Hz), 5.08-4.20 (m, 4H), 3.82 (m, 1H), 2.48 (s, 3H)

Example 90

Synthesis of tert-butyl (1-(8-chloro-2-methyloxazolo[4,5-c][1,8]naphthylidine-4-yl)azetidin-3-yl)(methyl)carbamate (a) Synthesis of methyl 2,5-dichloronicotinate 2,5-Dichloronicotine acid (2150.0 mg, 11.20 mmol) was dissolved in mixture solution of DCM (10.0 mL) and MeOH (5.0 mL), and trimethylsilyldiazomethane (2.0M in hexane) (11.2 mL, 22.40 mmol) was slowly added thereto at 0° C. The reaction mixture was stirred at room temperature for one hour and then distilled under reduced pressure. The residue was purified by column chromatography (EtOAc:n-Hex=1:9) on silica. The fractions containing the product were collected and evaporated to obtain white solid compound of methyl 2,5-dichloronicotinate (2020.0 mg, 87%).

LC/MS ESI (+): 206 (M+1)

$^1$H-NMR (300 MHz, CDCl$_3$); δ: 8.48 (d, 1H, J=2.6 Hz), 8.16 (d, 1H, J=2.6 Hz), 3.98 (s, 3H)

(b) Synthesis of methyl 5-chloro-2-((4-methoxybenzyl)amino)nicotinate

EtOH (30.0 mL) was added to methyl 2,5-dichloronicotinate (2020.0 mg, 9.79 mmol), and then 4-methoxybenzylamine (2.6 mL, 19.60 mmol) was added thereto. The mixture was stirred at 65° C. for 12 hours and then cooled to room temperature. The reaction mixture was distilled under reduced pressure and the residue was purified by column chromatography (EtOAc:n-Hex=1:9) on silica. The fractions containing the product were collected and evaporated to obtain colorless liquid compound of methyl 5-chloro-2-((4-methoxybenzyl)amino)nicotinate (840.0 mg, 28%).

LC/MS ESI (+): 307 (M+1)

(c) Synthesis of 6-chloro-1-(4-methoxybenzyl)-1H-pyrido[2,3-d][1,3]oxazine-2,4-dione Methyl 5-chloro-2-((4-methoxybenzyl)amino)nicotinate (205.0 mg, 0.67 mmol) was dissolved in 1,4-dioxane (3.0 mL), and diphosgen (120.0 μL, 1.01 mmol) was slowly added thereto at room temperature. The reaction mixture was stirred at 110° C. for 12 hours. The reaction mixture was then distilled under reduced pressure. The residue was dissolved in toluene (5.0 mL), distilled again under reduced pressure and then dried to obtain pale yellow solid compound of 6-chloro-1-(4-methoxybenzyl)-1H-pyrido[2,3-d][1,3]oxazine-2,4-dione.

LC/MS ESI (+): 319 (M+1)

(d) Synthesis of 6-chloro-4-hydroxy-1-(4-methoxybenzyl)-3-nitro-1,8-naphthylidine-2(1H)-one DMA (3.0 mL) was added to NaH (40.4 mg: in 60% oil, 1.01 mmol), and ethylnitroacetate (110.0 μL, 1.01 mmol) was then added thereto. The mixture was stirred at room temperature for 30 minutes. Solution of 6-chloro-1-(4-methoxybenzyl)-1H-pyrido[2,3-d][1,3]oxazine-2,4-dione dissolved in DMA (1.0 mL) was slowly added to the reaction mixture at room temperature. The reaction mixture was stirred at 110° C. for 12 hours, cooled to room temperature and then filtered through celite. The filtrate was distilled under reduced pressure. The residue was dissolved in toluene (5.0 mL) and it was distilled under reduced pressure. The formed solid was stirred in the mixture of DCM and Et$_2$O and then filtered to obtain dark yellow solid compound of 6-chloro-4-hydroxy-1-(4-methoxybenzyl)-3-nitro-1,8-naphthylidine-2(1H)-one (232.0 mg, 95% in 2 steps).

LC/MS ESI (+): 362 (M+1)

(e) Synthesis of 8-chloro-5-(4-methoxybenzyl)-2-methyloxazolo[4,5-c][1,8]naphthylidine-4(5H)-one The mixture of 6-chloro-4-hydroxy-1-(4-methoxybenzyl)-3-nitro-1,8-naphthylidine-2(1H)-one (200.0 mg, 0.55 mmol), Zn (220.0 mg, 3.36 mmol), acetic acid anhydride (2.7 mL, 28.30 mmol) and acetic acid (4.0 mL) was stirred at 120° C. for 12 hours. The reaction mixture was cooled to room temperature and then filtered through celite. The filtrate was concentrated under reduced pressure, and TEA (0.5 mL) was added thereto, and it was purified by column chromatography (EtOAc:n-Hex=1:1) on silica. The fractions containing the product were collected and evaporated to obtain white solid compound of 8-chloro-5-(4-methoxybenzyl)-2-methyloxazolo[4,5-c][1,8]naphthylidine-4(5H)-one (108.0 mg, 52%).

LC/MS ESI (+): 356 (M+1)

(f) Synthesis of 4,8-dichloro-2-methyloxazolo[4,5-c][1,8]naphthylidine

8-Chloro-5-(4-methoxybenzyl)-2-methyloxazolo[4,5-c][1,8]naphthylidine-4(5H)-one (108.0 mg, 0.30 mmol) was dissolved in POCl$_3$ (2.0 mL) and the mixture was stirred at 140° C. for 12 hours. The reaction mixture was cooled to 0° C., poured into saturated Na$_2$CO$_3$ aqueous solution with pieces of ice and then extracted with DCM. The organic layer was dried over anhydrous Na$_2$SO$_4$, filtered and then distilled under reduced pressure. The residue was purified by column chromatography (EtOAc:n-Hex=1:3) on silica. The fractions containing the product were collected and evaporated to pale yellow solid compound of 4,8-dichloro-2-methyloxazolo[4,5-c][1,8]naphthylidine (42.0 mg, 54%).

LC/MS ESI (+): 254 (M+1)

$^1$H-NMR (300 MHz, CDCl$_3$); δ: 9.04 (d, 1H, J=2.7 Hz), 8.49 (d, 1H, J=2.7 Hz), 2.85 (s, 3H)

g) Synthesis of tert-butyl (1-(8-chloro-2-methyloxazolo[4,5-c][1,8]naphthylidine-4-yl)azetidin-3-yl)(methyl)carbamate DMF (2.0 mL) was added to 4,8-Dichloro-2-methyloxazolo[4,5-c][1,8]naphthylidine (19.4 mg, 0.08 mmol), and tert-butyl azetidin-3-yl(methyl)carbamate hydrochloride (26.0 mg, 0.12 mmol) and TEA (30.0 μL, 0.23 mmol) were then added thereto. The reaction mixture was stirred for 6 hours and distilled under reduced pressure. The residue was purified by column chromatography (EtOAc:n-Hex=1:2) on silica. The fractions containing the product were collected and evaporated to obtain pale yellow solid compound of tert-butyl (1-(8-chloro-2-methyloxazolo[4,5-c][1,8]naphthylidine-4-yl)azetidin-3-yl)(methyl)carbamate (30.0 mg, 97%).

LC/MS ESI (+): 404 (M+1)

$^1$H-NMR (300 MHz, CDCl$_3$); δ: 8.73 (d, 1H, J=2.7 Hz), 8.19 (d, 1H, J=2.7 Hz), 5.41-4.91 (m, 1H), 4.82-4.68 (m, 2H), 4.59-4.47 (m, 2H), 2.99 (s, 3H), 2.71 (s, 3H), 1.48 (s, 9H)

Example 91

Synthesis of 1-(8-chloro-2-methyloxazolo[4,5-c][1,8]naphthylidine-4-yl)-N-methylazetidin-3-amine tert-Butyl (1-(8-chloro-2-methyloxazolo[4,5-c][1,8]naphthylidine-4-yl)azetidin-3-yl)(methyl)carbamate (30.0 mg, 0.07 mmol) was dissolved in DCM (2.0 mL), and TFA (1.0 mL, 13.50 mmol) was added thereto. The mixture was stirred for 6 hours. The reaction mixture was distilled under reduced pressure. The residue was purified by column chromatography (MeOH:DCM=1:50) on amine silica. The fractions containing the product were collected and evaporated to obtain pale yellow solid compound of 1-(8-chloro-2-methyloxazolo[4,5-c][1,8]naphthylidine-4-yl)-N-methylazetidin-3-amine (20.3 mg, 87%).

LC/MS ESI (+): 304 (M+1)

$^1$H-NMR (300 MHz, CDCl$_3$); δ: 8.71 (d, 1H, J=2.7 Hz), 8.16 (d, 1H, J=2.7 Hz), 4.78-4.68 (m, 2H), 4.29-4.19 (m, 2H), 3.87-3.76 (m, 1H), 2.71 (s, 3H), 2.48 (s, 3H)

Example 92

Synthesis of 8-chloro-2-methyl-4-(4-methylpiperazin-1-yl)oxazolo[4,5-c][1,8]naphthylidine 4,8-Dichloro-2-methyloxazolo[4,5-c][1,8]naphthylidine (10.0 mg, 0.04 mmol) was added to DMF (1.0 mL), and N-methylpiperazine (26.0 mg, 0.12 mmol) and TEA (30.0 µL, 0.23 mmol) were added thereto. The reaction mixture was stirred for 12 hours and then distilled under reduced pressure. The residue was purified by column chromatography (MeOH:DCM=1:10) on silica. The fractions containing the product were collected and evaporated to obtain pale yellow solid compound of 8-chloro-2-methyl-4-(4-methylpiperazin-1-yl)oxazolo[4,5-c][1,8]naphthylidine (7.9 mg, 83%).

LC/MS ESI (+): 318 (M+1)

$^1$H-NMR (300 MHz, CDCl$_3$); δ: 8.72 (d, 1H, J=2.7 Hz), 8.17 (d, 1H, J=2.7 Hz), 4.51-4.28 (m, 4H), 2.72 (s, 3H), 2.62-2.53 (m, 4H), 2.36 (s, 3H)

Example 93

Synthesis of 1-(8-chloropyrido[2,3-e]tetrazolo[1,5-a]pyrazin-4-yl)-N-methylazetidin-3-amine (a) Synthesis of tert-butyl (1-(8-chloropyrido[2,3-e]tetrazolo[1,5-a]pyrazin-4-yl)azetidin-3-yl)(methyl)carbamate NaN$_3$ (122.0 mg, 1.87 mmol) was added to suspension of tert-butyl (1-(2,7-dichloropyrido[2,3-b]pyrazin-3-yl)azetidin-3-yl)(methyl)carbamate (80.0 mg, 0.21 mmol) and EtOH (2.1 mL). The reaction mixture was stirred at 70° C. for 12 hours, cooled to room temperature and then concentrated under reduced pressure. Water was added thereto to form a solid, and the formed solid was dried under reduced pressure to obtain white solid compound of tert-butyl (1-(8-chloropyrido[2,3-e]tetrazolo[1,5-a]pyrazin-4-yl)azetidin-3-yl)(methyl)carbamate (75.0 mg, 93%).

LC/MS ESI(+): 391 (M+1), 393 (M+3)

$^1$H-NMR (300 MHz, DMSO-d$_6$); δ: 8.88 (d, 1H, J=2.4 Hz), 8.78 (d, 1H, J=2.4 Hz), 5.21-4.85 (m, 2H), 4.82 (m, 1H), 4.46 (m, 1H), 4.45 (m, 1H), 2.93 (s, 3H), 1.42 (s, 9H)

(b) Synthesis of 1-(8-chloropyrido[2,3-e]tetrazolo[1,5-a]pyrazin-4-yl)-N-methylazetidin-3-amine TFA (0.4 mL) was added to a mixture of tert-Butyl (1-(8-chloropyrido[2,3-e]tetrazolo[1,5-a]pyrazin-4-yl)azetidin-3-yl)(methyl)carbamate (75.0 mg, 0.19 mmol) and DCM (0.6 mL), and it was stirred at room temperature for one hour. The reaction mixture was purified by column chromatography (MeOH:DCM=1:60) on amine silica. The fractions containing the product were collected and evaporated. Et$_2$O was added to the residue to form a solid, and the formed solid was filtered and then dried under reduced pressure to obtain white solid compound of 1-(8-chloropyrido[2,3-e]tetrazolo[1,5-a]pyrazin-4-yl)-N-methylazetidin-3-amine (42.0 mg, 75%).

LC/MS ESI(+): 291 (M+1), 293 (M+3)

$^1$H-NMR (300 MHz, DMSO-d$_6$); δ: 8.83 (d, 1H, J=2.4 Hz), 8.76 (d, 1H, J=2.4 Hz), 4.90 (m, 1H), 4.60-4.39 (m, 2H), 4.05 (m, 1H), 3.75 (m, 1H), 2.46 (m, 1H), 2.31 (s, 3H)

Example 94

Synthesis of 8-chloro-4-(4-methylpiperazin-1-yl)pyrido[2,3-e]tetrazolo[1,5-a]pyrazine NaN$_3$ (55.0 mg, 0.85 mmol) was added to suspension of 2,7-dichloro-3-(4-methylpiperazin-1-yl)pyrido[2,3-b]pyrazine (28.0 mg, 0.09 mmol) and EtOH (1.0 mL). The mixture was stirred at 70° C. for 12 hours. The reaction mixture was cooled to room temperature and distilled under reduced pressure. Water was then added thereto to form a solid, and the formed solid was filtered and dried under reduced pressure to obtain orange solid compound of 8-chloro-4-(4-methylpiperazin-1-yl)pyrido[2,3-e]tetrazolo[1,5-a]pyrazine (21.0 mg, 75%).

LC/MS ESI(+): 305 (M+1), 307 (M+3)

$^1$H-NMR (300 MHz, DMSO-d$_6$); δ: 8.87 (d, 1H, J=2.1 Hz), 8.79 (d, 1H, J=2.4 Hz), 4.80-3.90 (m, 4H), 2.58-2.50 (m, 4H), 2.26 (s, 3H)

Example 95

Synthesis of 1-(8-bromopyrido[2,3-e]tetrazolo[1,5-a]pyrazin-4-yl)-N-methylazetidin-3-amine (a) Synthesis of tert-butyl (1-(8-bromopyrido[2,3-e]tetrazolo[1,5-a]pyrazin-4-yl)azetidin-3-yl)(methyl)carbamate NaN$_3$ (71.0 mg 1.09 mmol) was added to a suspension of tert-butyl (1-(7-bromo-2-chloropyrido[2,3-b]pyrazin-3-yl)azetidin-3-yl)(methyl)carbamate (52.0 mg, 0.12 mmol) and EtOH (1.2 mL). The mixture was stirred at 70° C. for 12 hours. The reaction mixture was cooled to room temperature and then distilled under reduced pressure. Water was added thereto to form a solid, and the formed solid was filtered and dried under reduced pressure to obtain white solid compound of tert-butyl (1-(8-bromopyrido[2,3-e]tetrazolo[1,5-a]pyrazin-4-yl)azetidin-3-yl)(methyl)carbamate (45.0 mg, 85%).

LC/MS ESI(+): 435 (M+1), 437 (M+3)

$^1$H-NMR (300 MHz, DMSO-d$_6$); δ: 8.94 (d, 1H, J=2.4 Hz), 8.84 (d, 1H, J=2.4 Hz), 5.25-4.90 (m, 2H), 4.82 (m, 1H), 4.65-4.30 (m, 2H), 2.94 (s, 3H), 1.43 (s, 9H)

(b) Synthesis of 1-(8-bromopyrido[2,3-e]tetrazolo[1,5-a]pyrazin-4-yl)-N-methylazetidin-3-amine TFA (0.4 mL) was added to the mixture of tert-butyl (1-(8-bromopyrido[2,3-e]tetrazolo[1,5-a]pyrazin-4-yl)azetidin-3-yl)(methyl)carbamate (45.0 mg, 0.10 mmol) and DCM (0.6 mL). The reaction mixture was stirred at room temperature for one hour and purified by column chromatography (MeOH:DCM=1:60) on amine silica. The fractions containing the product were collected and evaporated. Et$_2$O was added to the residue to form a solid. The formed solid was filtered and then dried under reduced pressure to obtain white solid compound of 1-(8-bromopyrido[2,3-e]tetrazolo[1,5-a]pyrazin-4-yl)-N-methylazetidin-3-amine (28.0 mg, 80%).

LC/MS ESI(+): 335 (M+1), 337 (M+3)

$^1$H-NMR (300 MHz, DMSO-d$_6$); δ: 8.92 (bs, 1H), 8.81 (bs, 1H), 4.90 (m, 1H), 4.55-4.38 (m, 2H), 4.04 (m, 1H), 3.76 (m, 1H), 2.31 (s, 3H)

Example 96

Synthesis of 8-bromo-4-(4-methylpiperazin-1-yl) pyrido[2,3-e]tetrazolo[1,5-a]pyrazine NaN₃ (50.0 mg, 0.76 mmol) was added to suspension of 7-bromo-2-chloro-3-(4-methylpiperazin-1-yl)pyrido[2,3-b]pyrazine (29.0 mg, 0.08 mmol) and EtOH (1.0 mL). The reaction mixture was stirred at 70° C. for 12 hours, then cooled to room temperature and distilled under reduced pressure. Water was added thereto to form a solid, and the formed solid was filtered and dried under reduced pressure to obtain orange solid compound of 8-bromo-4-(4-methylpiperazin-1-yl)pyrido[2,3-e]tetrazolo[1,5-a]pyrazine (24.0 mg, 80%).

LC/MS ESI(+): 349 (M+1), 351 (M+3)
$^1$H-NMR (300 MHz, DMSO-d$_6$); δ: 8.95 (d, 1H, J=2.4 Hz), 8.85 (d, 1H, J=2.4 Hz), 4.65-4.05 (m, 4H), 2.60-2.50 (m, 4H), 2.26 (s, 3H)

Example 97

Synthesis of 1-(8-chloro-2-methylpyrido[2,3-e][1,2,4]triazolo[1,5-a]pyrazin-4-yl)-N-methylazetidin-3-amine (a) Synthesis of 5-chloro-3-fluoro-2-nitropyridine 5-Chloro-3-fluoropyridin-2-amine (500.0 mg, 3.41 mmol) was dissolved in H₂SO₄ (1.5 mL), and Na₂S₂O₈ (406.1 mg, 1.71 mmol) was added thereto. The mixture was stirred at room temperature for 12 hours and water was then poured into the reaction mixture. The resulting solution was alkalized with saturated NaHCO₃ aqueous solution (pH=9) and then extracted with EtOAc. The organic layer was dried over anhydrous Na₂SO₄, filtered and then distilled under reduced pressure. The residue was purified by column chromatography (EtOAc:n-Hex=10:90) on silica. The fractions containing the product were collected and evaporated to obtain white solid compound of 5-chloro-3-fluoro-2-nitropyridine (200.0 mg, 33%).

$^1$H-NMR (300 MHz, DMSO-d$_6$); δ: 8.21 (d, 1H, J=1.8 Hz), 8.17 (m, 1H)

(b) Synthesis of 5-chloro-3-hydrazinyl-2-nitropyridine

5-Chloro-3-fluoro-2-nitropyridin (190.0 mg, 1.08 mmol) and hydrazine monohydrate (80.0 μL, 1.61 mmol) were dissolved in EtOH (3.0 mL) and the mixture was stirred at room temperature for 2 hours. Et₂O was added thereto to form a solid, and the formed solid was filtered to obtain orange solid compound of 5-chloro-3-hydrazinyl-2-nitropyridine (170.0 mg, 84%).

$^1$H-NMR (300 MHz, DMSO-d$_6$); δ: 9.06 (brs, 1H), 8.10 (m, 1H), 7.76 (d, 1H, J=2.4 Hz)

(c) Synthesis of (Z)—N'-(5-chloro-2-nitropyridin-3-yl)acetohydrazone amide

5-Chloro-3-hydrazinyl-2-nitropyridine (100.0 mg, 0.53 mmol) and ethyl acetimidate hydrochloride (102.2 mg, 0.80 mmol) were added to pyridine (1.8 mL), and it was stirred at room temperature for 3 hours. Saturated Na₂CO₃ aqueous solution was added to the reaction mixture and it was then extracted with EtOAc. The organic layer was dried over anhydrous Na₂SO₄, filtered and then distilled under reduced pressure. The residue was purified by column chromatography (EtOAc:n-Hex=50:50) on silica. The fractions containing the product were collected and evaporated to obtain red solid compound of (Z)—N'-(5-chloro-2-nitropyridin-3-yl)acetohydrazone amide (77.0 mg, 63%).

$^1$H-NMR (300 MHz, DMSO-d$_6$); δ: 9.53 (brs, 1H), 7.88 (d, 1H, J=2.4 Hz), 7.78 (d, 1H, J=2.4 Hz), 6.62 (brs, 2H), 1.92 (s, 3H)

(d) Synthesis of ethyl 1-(5-chloro-2-nitropyridin-3-yl)-3-methyl-1H-1,2,4-triazole-5-carboxylate (Z)—N'-(5-chloro-2-nitropyridin-3-yl)acetohydrazone amid (60.0 mg, 0.26 mmol) and ethyl 2-chloro-2-oxoacetate (54.0 μL, 0.52 mmol) were dissolved in Et₂O (0.6 mL), stirred at room temperature for one hour, and toluene (6.0 mL) was then added thereto. The mixture was stirred at 80° C. for one hour, stirred at 180° C. for 2 hours and then cooled to room temperature, and water and EtOAc were added thereto, and it was then alkalized with KOH aqueous solution (pH=12) and extracted with EtOAc. The organic layer was dried over anhydrous Na₂SO₄, filtered and distilled under reduced pressure. The residue was purified by column chromatography (EtOAc:n-Hex=50:50) on silica. The fractions containing the product were collected and evaporated to obtain red solid compound of ethyl 1-(5-chloro-2-nitropyridin-3-yl)-3-methyl-1H-1,2,4-triazole-5-carboxylate (78.0 mg, 56%).

LC/MS ESI(+): 312 (M+1), 314 (M+3)
$^1$H-NMR (300 MHz, DMSO-d$_6$); δ: 8.95 (d, 1H, J=2.4 Hz), 8.83 (d, 1H, J=2.4 Hz), 4.28-4.21 (m, 2H), 2.40 (s, 3H), 1.20-1.15 (m, 3H)

(e) Synthesis of 8-chloro-2-methylpyrido[2,3-e][1,2,4]triazolo[1,5-a]pyrazin-4(5H)-one Ethyl 1-(5-chloro-2-nitropyridin-3-yl)-3-methyl-1H-1,2,4-triazole-5-carboxylate (62.0 mg, 0.20 mmol) and Fe (166.6 mg, 2.98 mmol) were added to acetic acid (13.0 mL), stirred at 90° C. for 2 hours and then cooled to room temperature. 1N of HCl aqueous solution was added to the reaction mixture to dissolve completely and then extracted with EtOAc. The organic layer was dried over anhydrous Na₂SO₄, filtered and then distilled under reduced pressure. The residue was purified by column chromatography (MeOH:DCM=5:95) on silica. The fractions containing the product were collected and evaporated white solid compound of 8-chloro-2-methylpyrido[2,3-e][1,2,4]triazolo[1,5-a]pyrazin-4(5H)-one (40.0 mg, 86%).

LC/MS ESI(+): 236 (M+1), 238 (M+3)
$^1$H-NMR (300 MHz, DMSO-d$_6$); δ: 12.89 (brs, 1H), 8.52 (d, 1H, J=2.4 Hz), 8.44 (d, 1H, J=2.4 Hz), 2.53 (s, 3H)

(f) Synthesis of 4,8-dichloro-2-methylpyrido[2,3-e][1,2,4]triazolo[1,5-a]pyrazine 8-Chloro-2-methylpyrido[2,3-e][1,2,4]triazolo[1,5-a]pyrazin-4(5H)-one (40.0 mg, 0.17 mmol) was dissolved in POCl₃ (1.0 mL), and DIPEA (60.0 μL, 0.34 mmol) was added thereto. The reaction mixture was refluxed for 5 hours and then cooled to room temperature. The reaction mixture was poured into ice water, neutralized with saturated NaHCO₃ aqueous solution, and it was then extracted with EtOAc. The organic layer was washed with brine, dried over anhydrous Na₂SO₄, filtered and then distilled under reduced pressure to obtain ivory solid compound of 4,8-dichloro-2-methylpyrido[2,3-e][1,2,4]triazolo[1,5-a]pyrazine (43.0 mg, 100%).

LC/MS ESI(+): 254 (M+1), 256 (M+3)
$^1$H-NMR (300 MHz, DMSO-$d_6$); δ: 9.03 (m, 1H), 8.94 (m, 1H), 2.67 (s, 3H)

(g) Synthesis of 1-(8-chloro-2-methylpyrido[2,3-e][1,2,4]triazolo[1,5-a]pyrazin-4-yl)-N-methylazetidin-3-amine 4,8-Dichloro-2-methylpyrido[2,3-e][1,2,4]triazolo[1,5-a]pyrazine (10.0 mg, 0.04 mmol) and TFA (16.5 μL, 0.12 mmol) were dissolve in DMF (0.2 mL), and tert-butyl azetidin-3-yl(methyl)carbamate hydrochloride (13.0 mg, 0.06 mmol) was added thereto. The reaction mixture was stirred at room temperature for 2 hours, then concentrated and purified by column chromatography (MeOH:DCM=5:95) on silica. The fractions containing the product were collected and evaporated to obtain white solid compound of tert-butyl (1-(8-chloro-2-methylpyrido[2,3-e][1,2,4]triazolo[1,5-a]pyrazin-4-yl)azetidin-3-yl)(methyl)carbamate. Unpurified tert-butyl (1-(8-chloro-2-methylpyrido[2,3-e][1,2,4]triazolo[1,5-a]pyrazin-4-yl)azetidin-3-yl)(methyl)carbamate was dissolved in DCM (1.0 mL), and TFA (0.4 mL) was added thereto. The reaction mixture was stirred at room temperature for one hour and then purified by column chromatography (MeOH:DCM=5:95) on amine silica. The fractions containing the product were collected and evaporated to obtain white solid compound of 1-(8-chloro-2-methylpyrido[2,3-e][1,2,4]triazolo[1,5-a]pyrazin-4-yl)-N-methylazetidin-3-amine (7.0 mg, 45%).

LC/MS ESI(+): 304 (M+1), 306 (M+3)
$^1$H-NMR (300 MHz, DMSO-$d_6$); δ: 8.60 (d, 1H, J=2.4 Hz), 8.45 (d, 1H, J=2.4 Hz), 4.83 (m, 1H), 4.50-4.30 (m, 2H), 4.00 (m, 1H), 3.69 (m, 1H), 2.57 (s, 3H), 2.30 (brs, 3H)

Example 98

Synthesis of 8-chloro-2-methyl-4-(4-methylpiperazin-1-yl)pyrido[2,3-e][1,2,4]triazolo[1,5-a]pyrazine 4,8-Dichloro-2-methylpyrido[2,3-e][1,2,4]triazolo[1,5-a]pyrazine (10.0 mg, 0.04 mmol) and TFA (16.5 μL, 0.12 mmol) were dissolved in DMF (0.2 mL), and N-methylpiperazine (6.5 μL, 0.06 mmol) was added thereto. The reaction mixture was stirred at room temperature for 2 hours, then concentrated and purified by column chromatography (MeOH:DCM=5:95) on silica. The fractions containing the product were collected and evaporated to obtain white solid compound of 8-chloro-2-methyl-4-(4-methylpiperazin-1-yl)pyrido[2,3-e][1,2,4]triazolo[1,5-a]pyrazine (8.0 mg, 66%).

LC/MS ESI(+): 318 (M+1), 320 (M+3)
$^1$H-NMR (300 MHz, DMSO-$d_6$); δ: 8.65 (d, 1H, J=2.4 Hz), 8.49 (d, 1H, J=2.4 Hz), 4.45-4.18 (m, 4H), 2.59 (s, 3H), 2.52 (m, 4H), 2.25 (s, 3H)

Example 99

Synthesis of 1-(8-bromo-7-methylpyrido[2,3-e][1,2,4]triazolo[4,3-a]pyrazin-4-yl)-N-methylazetidin-3-amine

(a) Synthesis of 7-bromo-6-methylpyrido[2,3-b]pyrazine-2,3-diol

The mixture of 5-bromo-6-methylpyridine-2,3-diamine (500.0 mg, 2.47 mmol) and diethyloxalate (3.0 mL) was stirred at 100° C. for 12 hours and then cooled to room temperature. Et$_2$O was added to the reaction mixture to form a solid. The formed solid was then filtered and dried under reduced pressure to obtain light brown solid compound of 7-bromo-6-methylpyrido[2,3-b]pyrazine-2,3-diol (611.0 mg, 97%).

LC/MS ESI (+): 256 (M+1), 258 (M+3)
$^1$H-NMR (400 MHz, DMSO-$d_6$); δ: 12.40 (s, 1H), 11.94 (s, 1H), 7.53 (s, 1H), 2.48 (s, 3H)

(b) Synthesis of 7-bromo-2,3-dichloro-6-methylpyrido[2,3-b]pyrazine

The mixture of 7-bromo-6-methylpyrido[2,3-b]pyrazine-2,3-diol (300.0 mg, 1.17 mmol) and POCl$_3$ (6.0 mL) was stirred at 95° C. for 12 hours and then cooled to room temperature. The reaction mixture was poured into ice water to form a solid. The formed solid was filtered and dried under reduced pressure to obtain black solid compound of 7-bromo-2,3-dichloro-6-methylpyrido[2,3-b]pyrazine (340.0 mg, 99%).

LC/MS ESI (+): 292 (M+1), 294 (M+3), 296 (M+5)
$^1$H-NMR (400 MHz, CDCl$_3$); δ: 8.53 (s, 1H), 2.95 (s, 3H)

(c) Synthesis of tert-butyl (1-(7-bromo-2-chloro-6-methylpyrido[2,3-b]pyrazin-3-yl)azetidin-3-yl)(methyl)carbamate TEA (140.0 μL, 1.02 mmol) was added to a mixture of 7-bromo-2,3-dichloro-6-methylpyrido[2,3-b]pyrazine (100.0 mg, 0.34 mmol), tert-butyl azetidin-3-yl(methyl)carbamate hydrochloride salt (76.0 mg, 0.34 mmol) and DCM (3.4 mL) at 0° C., and it was then stirred for 1 hour. The reaction mixture was purified by column chromatography (EtOAc:n-Hex=1:4) on silica. The fractions containing the product were collected and evaporated to obtain red solid compound of tert-butyl (1-(7-bromo-2-chloro-6-methylpyrido[2,3-b]pyrazin-3-yl)azetidin-3-yl)(methyl)carbamate (43.0 mg, 28%).

LC/MS ESI (+): 442 (M+1), 444 (M+3)
$^1$H-NMR (400 MHz, CDCl$_3$); δ: 8.23 (s, 1H), 5.02-4.90 (m, 1H), 4.78-4.68 (m, 2H), 4.50-4.49 (m, 2H), 2.96 (s, 3H), 2.836 (s, 3H), 1.48 (s, 9H)

(d) Synthesis of tert-butyl (1-(8-bromo-7-methylpyrido[2,3-e][1,2,4]triazolo[4,3-a]pyrazin-4-yl)azetidin-3-yl)(methyl)carbamate Hydrazine monohydrate (15.0 μL, 0.49 mmol) was added to suspension of tert-butyl (1-(7-bromo-2-chloro-6-methylpyrido[2,3-b]pyrazin-3-yl)azetidin-3-yl)(methyl)carbamate (43.0 mg, 0.10 mmol) and EtOH (1.0 mL). The reaction mixture was stirred at room temperature for 1 hour and then concentrated under reduced pressure. The residue was dissolved in trimethyl orthoformate (1.0 mL), and it was stirred at 85° C. for 1 hour. The reaction mixture was cooled to room temperature and then concentrated under reduced pressure. The residue was purified by column chromatography (MeOH:DCM=1:40) on silica. The fractions containing the product were collected and evaporated to obtain light brown solid compound of tert-butyl (1-(8-bromo-7-methylpyrido[2,3-e][1,2,4]triazolo[4,3-a]pyrazin-4-yl)azetidin-3-yl)(methyl)carbamate (35.0 mg, 80%).

LC/MS ESI (+): 448 (M+1), 450 (M+3)

(e) Synthesis of 1-(8-bromo-7-methylpyrido[2,3-e][1,2,4]triazolo[4,3-a]pyrazin-4-yl)-N-methylazetidin-3-amine TFA (0.4 mL) was added to a mixture of tert-butyl (1-(8-bromo-7-methylpyrido[2,3-e][1,2,4]triazolo[4,3-a]pyrazin-4-yl)azetidin-3-yl)(methyl)carbamate (35.0 mg, 0.08 mmol) and DCM (0.6 mL), and then stirred at room temperature for 1 hour. The reaction mixture was purified by column chromatography (MeOH:DCM=1:40) on amine silica. The fractions containing the product were collected and evaporated. Et$_2$O was added to the residue to form a solid. The formed solid was filtered and then dried under reduced pressure to obtain yellow solid compound of 1-(8-bromo-7-methylpyrido[2,3-e][1,2,4]triazolo[4,3-a]pyrazin-4-yl)-N-methylazetidin-3-amine (12.0 mg, 43%).

LC/MS ESI (+): 348 (M+1), 350 (M+3)

$^1$H-NMR (400 MHz, DMSO-d$_6$); δ: 9.93 (s, 1H), 8.63 (s, 1H), 4.90 (m, 1H), 4.45-4.35 (m, 2H), 3.97 (m, 1H), 3.71 (m, 1H), 2.60 (s, 3H), 2.30 (s, 3H)

Example 100

Synthesis of 8-bromo-7-methyl-4-(4-methylpiperazin-1-yl)pyrido[2,3-e][1,2,4]triazolo[4,3-a]pyrazine (a) Synthesis of 7-bromo-2-chloro-6-methyl-3-(4-methylpiperazin-1-yl)pyrido[2,3-b]pyrazine TEA (140.0 μL, 1.02 mmol) was added to a mixture of 7-bromo-2,3-dichloro-6-methylpyrido[2,3-b]pyrazine (100.0 mg, 0.34 mmol) obtained from the step (b) of Example 99, N-methylpiperazine (38.0 μL, 0.34 mmol) and DCM (3.4 mL) at 0° C., and then stirred for 1 hour. The reaction mixture was purified by column chromatography (EtOAc:n-Hex=1:4) on amine silica. The fractions containing the product were collected and evaporated to obtain red solid compound of 7-bromo-2-chloro-6-methyl-3-(4-methylpiperazin-1-yl)pyrido[2,3-b]pyrazine (23.0 mg, 19%).

LC/MS ESI (+): 356 (M+1), 358 (M+3), 360 (M+5)

$^1$H-NMR (400 MHz, DMSO-d$_6$); δ: 8.32 (s, 1H), 3.79-3.70 (m, 4H), 2.87 (s, 3H), 2.65-2.62 (m, 4H), 2.38 (s, 3H)

(b) Synthesis of 8-bromo-7-methyl-4-(4-methylpiperazin-1-yl)pyrido[2,3-e][1,2,4]triazolo[4,3-a]pyrazine Hydrazine monohydrate (10.0 μL, 0.32 mmol) was added to suspension of 7-bromo-2-chloro-6-methyl-3-(4-methylpiperazin-1-yl)pyrido[2,3-b]pyrazine (23.0 mg, 0.06 mmol) and EtOH (1.0 mL). The reaction mixture was stirred at room temperature for 1 hour and then concentrated under reduced pressure. The residue was dissolved in trimethyl orthoformate (1.0 mL), and it was stirred at 85° C. for 1 hour. The reaction mixture was cooled to room temperature and then concentrated under reduced pressure. The residue was purified by column chromatography (MeOH:DCM=1:40) on silica. The fractions containing the product were collected and evaporated to obtain yellow solid compound of compound of 8-bromo-7-methyl-4-(4-methylpiperazin-1-yl)pyrido[2,3-e][1,2,4]triazolo[4,3-a]pyrazine (1.1 mg, 4%).

LC/MS ESI (+): 362 (M+1), 364 (M+3)

$^1$H-NMR (400 MHz, DMSO-d$_6$); δ: 9.99 (s, 1H), 8.93 (s, 1H), 4.46-4.30 (m, 4H), 3.32 (s, 3H), 2.63 (s, 3H) 2.54-2.50 (m, 4H)

Example 101

Synthesis of 8-chloro-4-(3-(methylamino)azetidin-1-yl)pyrido[2,3-e][1,2,4]triazolo[4,3-a]pyrazin-7-ol HCl salt (a) Synthesis of tert-butyl (1-(8-chloro-7-hydroxypyrido[2,3-e][1,2,4]triazolo[4,3-a]pyrazin-4-yl)azetidin-3-yl)(methyl)carbamate CsF (32.2 mg, 0.21 mmol) was added to a mixture of tert-butyl (1-(7,8-dichloropyrido[2,3-e][1,2,4]triazolo[4,3-a]pyrazin-4-yl)azetidin-3-yl)(methyl)carbamate (30.0 mg, 0.07 mmol) obtained from the step (b) of Example 27 and NMP (1.0 mL). The reaction mixture was stirred at 135° C. for 12 hours and then cooled to room temperature. CsF (161.0 mg, 1.06 mmol) was further added thereto and stirred at 145° C. for 12 hours. The reaction mixture was cooled to room temperature and purified by column chromatography (MeOH:DCM=1:40) on silica. The fractions containing the product were collected and evaporated to obtain ivory solid compound of tert-butyl (1-(8-chloro-7-hydroxypyrido[2,3-e][1,2,4]triazolo[4,3-a]pyrazin-4-yl)azetidin-3-yl)(methyl)carbamate (10.0 mg, 35%).

LC/MS ESI (+): 406 (M+1), 408 (M+3)

(b) Synthesis of 8-chloro-4-(3-(methylamino)azetidin-1-yl)pyrido[2,3-e][1,2,4]triazolo[4,3-a]pyrazin-7-ol HCl salt Suspension of tert-butyl (1-(8-chloro-7-hydroxypyrido[2,3-e][1,2,4]triazolo[4,3-a]pyrazin-4-yl)azetidin-3-yl)(methyl)carbamate (9.0 mg, 0.02 mmol) and 4N HCl in 1,4-dioxane (0.5 mL) was stirred at room temperature for 1 hour. Et$_2$O was added to the reaction mixture to form a solid. The formed solid was filtered and dried under reduced pressure to obtain yellow solid compound of 8-chloro-4-(3-(methylamino)azetidin-1-yl)pyrido[2,3-e][1,2,4]triazolo[4,3-a]pyrazin-7-ol HCl salt (3.2 mg, 43%).

LC/MS ESI (+): 306 (M+1), 308 (M+3)

$^1$H-NMR (400 MHz, DMSO-d$_6$); δ: 13.00-12.30 (m, 1H), 9.80 (s, 1H), 9.75-9.65 (m, 2H), 8.76 (s, 1H), 5.02 (m, 1H), 4.89 (m, 1H), 4.53 (m, 2H), 4.23 (m, 1H), 2.63 (s, 3H)

Example 102

Synthesis of N-(1-(8-bromopyrido[2,3-e][1,2,4]triazolo[4,3-a]pyrazin-4-yl)azetidin-3-yl)-N-methylhydroxylamine (a) Synthesis of O-benzoyl-N-(1-(8-bromopyrido[2,3-e][1,2,4]triazolo[4,3-a]pyrazin-4-yl)azetidin-3-yl)-N-methylhydroxylamine CHCl$_3$ (5.0 mL) was added to a mixture of 1-(8-bromopyrido[2,3-e][1,2,4]triazolo[4,3-a]pyrazin-4-yl)-N-methylazetidin-3-amine (120.0 mg, 0.36 mmol), Benzoyl peroxide (116.0 mg, 0.36 mmol) and K$_2$CO$_3$ (174.0 mg, 1.26 mmol), and stirred at 65° C. for 12 hours. The reaction mixture was cooled to room temperature, filtered through celite and then concentrated under reduced pressure. The residue was purified by column chromatography (DCM:MeOH=98:2 to 93:7) on silica. The fractions containing the product were collected and evaporated to obtain gray solid compound of O-benzoyl-N-(1-(8-bromopyrido[2,3-e][1,2,4]triazolo[4,3-a]pyrazin-4-yl)azetidin-3-yl)-N-methylhydroxylamine (150.0 mg, 92%).

LC/MS ESI (+): 454 (M+1), 456 (M+3)

(b) Synthesis of N-(1-(8-bromopyrido[2,3-e][1,2,4]triazolo[4,3-a]pyrazin-4-yl)azetidin-3-yl)-N-methylhydroxylamine NaOH (24.0 mg, 0.60 mmol) was dissolved in MeOH (8.0 mL), and O-benzoyl-N-(1-(8-bromopyrido[2,3-e][1,2,4]triazolo[4,3-a]pyrazin-4-yl)azetidin-3-yl)-N-methylhydroxylamine (120.0 mg, 0.26 mmol) was added thereto. The mixture was stirred for 12 hours and purified by column chromatography (DCM:MeOH=91:9) on silica. The fractions containing the product were collected and evaporated. The residue was dissolved in DMSO, and it was then purified by reverse phase high performance chromatography (ACN:H$_2$O=65:35). The fractions containing the product were collected and evaporated to obtain beige solid. The obtained solid was stirred in Et$_2$O for 30 minutes and then filtered to obtain beige solid compound of N-(1-(8-bromopyrido[2,3-e][1,2,4]triazolo[4,3-a]pyrazin-4-yl)azetidin-3-yl)-N-methylhydroxylamine (71.0 mg, 77%).

LC/MS ESI (+): 350 (M+1), 352 (M+3)
$^1$H-NMR (400 MHz, DMSO-d$_6$); δ: 9.95 (s, 1H), 8.90 (d, 1H, J=2.2 Hz), 8.59 (d, 1H, J=2.2 Hz), 4.76 (m, 2H), 4.30 (m, 2H), 3.77 (m, 1H), 2.51 (s, 3H)

Example 103

Synthesis of 1-(2-bromopyrido[3,2-e]pyrrolo[1,2-c]pyrimidin-6-yl)-N-methylazetidin-3-amine (a) Synthesis of 2-bromopyrido[3,2-e]pyrrolo[1,2-c]pyrimidin-6-ol Pd(PPh$_3$)$_4$ (193.0 mg, 0.17 mmol) was added to suspension of 5-bromo-3-iodopyridin-2-amine (500.0 mg, 1.67 mmol), (1-(tert-butoxycarbonyl)-1H-pyrrol-2-yl)boronic acid (423.0 mg, 2.00 mmol), Cs$_2$CO$_3$ (1600.0 mg, 5.01 mmol), H$_2$O (4.0 mL) and DME (16.0 mL). The mixture was allowed to react in microwave under conditions of 100 W, 110° C. for 2 hours and then cooled to room temperature. Et$_2$O was added to the reaction mixture to form a solid. The formed solid was filtered and then dried under reduced pressure to form white solid compound of 2-bromopyrido[3,2-e]pyrrolo[1,2-c]pyrimidin-6-ol (180.0 mg, 41%).

LC/MS ESI (+): 264 (M+1), 266 (M+3)
$^1$H-NMR (400 MHz, DMSO-d$_6$); δ: 12.11 (s, 1H), 8.66 (d, 1H, J=1.5 Hz), 8.39 (d, 1H, J=1.5 Hz), 7.66 (m, 1H), 7.23 (m, 1H), 6.72 (m, 1H)

(b) Synthesis of tert-butyl (1-(2-bromopyrido[3,2-e]pyrrolo[1,2-c]pyrimidin-6-yl)azetidin-3-yl)(methyl)carbamate DIPEA (24.0 μL, 0.14 mmol) was added to suspension of 2-bromopyrido[3,2-e]pyrrolo[1,2-c]pyrimidin-6-ol (30.0 mg, 0.11 mmol) and POCl$_3$ (1.1 mL), and it was then stirred at 120° C. for 20 hours. The reaction mixture was cooled to room temperature and then concentrated under reduced pressure. The residue was dissolved in DCM (1.1 mL), and tert-butyl azetidin-3-yl(methyl)carbamate HCl salt (50.0 mg, 0.23 mmol) and DIPEA (200.0 μL, 1.13 mmol) were added thereto. The mixture was stirred at room temperature for 12 hours. The reaction mixture was purified by column chromatography (MeOH:DCM=1:50) on amine silica. The fractions containing the product were collected and evaporated to obtain yellow solid compound of tert-butyl (1-(2-bromopyrido[3,2-e]pyrrolo[1,2-c]pyrimidin-6-yl)azetidin-3-yl)(methyl)carbamate (28.0 mg, 57%).

LC/MS ESI (+): 433 (M+1), 435 (M+3)
$^1$H-NMR (400 MHz, DMSO-d$_6$); δ: 8.65 (d, 1H, J=1.8 Hz), 8.46 (d, 1H, J=1.8 Hz), 7.60 (m, 1H), 7.25 (m, 1H), 6.84 (m, 1H), 5.01-4.90 (m, 1H), 4.68 (m, 2H), 4.54 (m, 2H), 2.93 (s, 3H), 1.41 (s, 9H)

(c) Synthesis of 1-(2-bromopyrido[3,2-e]pyrrolo[1,2-c]pyrimidin-6-yl)-N-methylazetidin-3-amine TFA (0.4 mL) was added to a mixture of tert-butyl (1-(2-bromopyrido[3,2-e]pyrrolo[1,2-c]pyrimidin-6-yl)azetidin-3-yl)(methyl)carbamate (28.0 mg, 0.06 mmol) and DCM (0.6 mL), and it was stirred at room temperature for 1 hour. The reaction mixture was purified by column chromatography (MeOH:DCM=1:40) on amine silica and the fractions containing the product were collected and evaporated. Et$_2$O was added to the residue to form a solid. The formed solid was filtered and then dried under reduced pressure to obtain yellow solid compound of 1-(2-bromopyrido[3,2-e]pyrrolo[1,2-c]pyrimidin-6-yl)-N-methylazetidin-3-amine (14.0 mg, 64%).

LC/MS ESI (+): 332 (M+1), 334 (M+3)
$^1$H-NMR (400 MHz, DMSO-d$_6$); δ: 8.62 (d, 1H, J=1.8 Hz), 8.44 (d, 1H, J=1.8 Hz), 7.60 (m, 1H), 7.25 (m, 1H), 6.82 (m, 1H), 4.61 (m, 2H), 4.17 (m, 2H), 3.60 (m, 1H), 2.38 (m, 1H), 2.37 (s, 3H)

Example 104

Synthesis of 1-(8-bromopyrido[2,3-e][1,2,4]triazolo[4,3-a]pyrazin-4-yl)-N-methylazetidin-3-amine 2,2,2-trifluoroacetate Synthesis of 1-(8-bromopyrido[2,3-e][1,2,4]triazolo[4,3-a]pyrazin-4-yl)-N-methylazetidin-3-amine 2,2,2-trifluoroacetate tert-Butyl (1-(8-bromopyrido[2,3-e][1,2,4]triazolo[4,3-a]pyrazin-4-yl)azetidin-3-yl)(methyl)carbamate (300.0 mg, 0.69 mmol) was dissolved in DCM (1.8 mL), and TFA (0.9 mL) was slowly added thereto at room temperature. The reaction mixture was stirred at room temperature for 30 minutes and then concentrated under reduced pressure. MeOH (1.84 mL) was added thereto to form a solid. The formed solid was filtered and dried to obtain white solid compound of 1-(8-bromopyrido[2,3-e][1,2,4]triazolo[4,3-a]pyrazin-4-yl)-N-methylazetidin-3-amine 2,2,2-trifluoroacetate (270.0 mg, 90%).

LC/MS ESI (+): 334 (M+1)
$^1$H-NMR (400 MHz, DMSO-d$_6$); δ: 10.03 (s, 1H), 9.31 (s, 1H), 8.99 (d, 1H, J=1.5 Hz), 8.67 (d, 1H, J=1.5 Hz), 5.04 (m, 1H), 4.85 (m, 1H), 4.59 (m, 1H), 4.42 (m, 1H), 4.27 (m, 1H), 2.69 (s, 3H)

Example 105

Synthesis of (S)-1-(8-bromo-2-methyl-1,2-dihydroimidazo[1,2-a]pyrido[2,3-e]pyrazin-4-yl)-N-methylazetidin-3-amine (a) Synthesis of (S)-tert-butyl (1-(7-bromo-2-((1-hydroxypropan-2-yl)amino)pyrido[2,3-b]pyrazin-3-yl)azetidin-3-yl)(methyl)carbamate The mixture of tert-butyl (1-(7-bromo-2-chloropyrido[2,3-b]pyrazin-3-yl)azetidin-3-yl)(methyl)carbamate (500.0 mg, 1.17 mmol) and (S)-2-aminopropan-1-ol (193.0 mg, 2.57 mmol) in EtOH (20.0 mL) was stirred at 80° C. for 8 hours. The reaction mixture was then concentrated under reduced pressure. The residue was purified by column chromatography (DCM:MeOH=98:2 to 95:5) on silica. The fractions containing the product were collected and evaporated to obtain yellow solid compound of (S)-tert-butyl (1-(7-bromo-2-((1-hydroxypropan-2-yl)amino)pyrido[2,3-b]pyrazin-3-yl)azetidin-3-yl)(methyl)carbamate (349.0 mg, 64%).

LC/MS ESI (+): 467 (M+1), 469 (M+3)

$^1$H-NMR (400 MHz, DMSO-$d_6$); δ: 8.40 (d, 1H, J=2.4 Hz), 7.97 (d, 1H, J=2.4 Hz), 6.18 (d, 1H, J=7.8 Hz), 4.85 (brs, 1H), 4.80 (t, 1H, J=5.6 Hz), 4.48 (q, 2H, J=8.4 Hz), 4.20-4.35 (m, 3H), 3.50 (m, 2H), 2.88 (s, 3H), 1.40 (s, 9H), 1.19 (d, 3H, J=6.6 Hz)

(b) Synthesis of (S)-tert-butyl (1-(8-bromo-2-methyl-1,2-dihydroimidazo[1,2-a]pyrido[2,3-e]pyrazin-4-yl)azetidin-3-yl)(methyl)carbamate The mixture of (S)-tert-butyl (1-(7-bromo-2-((1-hydroxypropan-2-yl)amino)pyrido[2,3-b]pyrazin-3-yl)azetidin-3-yl)(methyl)carbamate (199.0 mg, 0.43 mmol), MsCl (63.0 mg, 0.56 mmol) and TEA (129.0 mg, 1.29 mmol) in DCM (10.0 mL) was stirred at room temperature for 2 hours and then concentrated under reduced pressure. The residue was purified by column chromatography (DCM:MeOH=98:2 to 95:5) on silica. The fractions containing the product were collected and evaporated to obtain yellow solid compound of (S)-tert-butyl (1-(8-bromo-2-methyl-1,2-dihydroimidazo[1,2-a]pyrido[2,3-e]pyrazin-4-yl)azetidin-3-yl)(methyl)carbamate (211.0 mg, quant.).

LC/MS ESI (+): 449 (M+1), 451 (M+3)

(c) Synthesis of (S)-1-(8-bromo-2-methyl-1,2-dihydroimidazo[1,2-a]pyrido[2,3-e]pyrazin-4-yl)-N-methylazetidin-3-amine (S)-tert-Butyl (1-(8-bromo-2-methyl-1,2-dihydroimidazo[1,2-a]pyrido[2,3-e]pyrazin-4-yl)azetidin-3-yl)(methyl)carbamate (100.0 mg, 0.22 mmol) was dissolved in DCM (1.0 mL), and TFA (1.0 mL) was slowly added thereto at 0° C. The reaction mixture was stirred at room temperature for 3 hours. The reaction mixture was concentrated under reduced pressure. The residue was neutralized with TEA and was purified by column chromatography (DCM:MeOH=90:10) on amine silica and silica. The fractions containing the product were collected and evaporated to obtain yellow solid compound of (S)-1-(8-bromo-2-methyl-1,2-dihydroimidazo[1,2-a]pyrido[2,3-e]pyrazin-4-yl)-N-methylazetidin-3-amine (42.0 mg, 54%).

LC/MS ESI (+): 349 (M+1), 351 (M+3)

$^1$H-NMR (400 MHz, DMSO-$d_6$); δ: 7.95 (d, 1H, J=2.2 Hz), 7.27 (d, 1H, J=2.2 Hz), 4.68 (m, 1H), 4.35 (m, 1H), 4.23 (m, 1H), 4.04 (t, 2H, J=10.6 Hz), 3.80 (m, 1H), 3.45-3.57 (m, 2H), 2.23 (s, 3H), 1.25 (d, 3H, J=6.7 Hz)

Example 106

Synthesis of (R)-1-(8-bromo-2-methyl-1,2-dihydroimidazo[1,2-a]pyrido[2,3-e]pyrazin-4-yl)-N-methylazetidin-3-amine (a) Synthesis of (R)-tert-butyl (1-(7-bromo-2-((1-hydroxypropan-2-yl)amino)pyrido[2,3-b]pyrazin-3-yl)azetidin-3-yl)(methyl)carbamate The mixture of tert-Butyl (1-(7-bromo-2-chloropyrido[2,3-b]pyrazin-3-yl)azetidin-3-yl)(methyl)carbamate (500.0 mg, 1.17 mmol) and (R)-2-aminopropan-1-ol (193.0 mg, 2.57 mmol) in EtOH (20.0 mL) was stirred at 80° C. for 8 hours. The reaction mixture was concentrated under reduced pressure. The residue was purified by column chromatography (DCM:MeOH=98:2 to 95:5) on silica. The fractions containing the product were collected and evaporated to obtain yellow solid compound of (R)-tert-butyl (1-(7-bromo-2-((1-hydroxypropan-2-yl)amino)pyrido[2,3-b]pyrazin-3-yl)azetidin-3-yl)(methyl)carbamate (378.0 mg, 69%).

LC/MS ESI (+): 467 (M+1), 469 (M+3)

(b) Synthesis of (R)-tert-butyl (1-(8-bromo-2-methyl-1,2-dihydroimidazo[1,2-a]pyrido[2,3-e]pyrazin-4-yl)azetidin-3-yl)(methyl)carbamate The mixture of (R)-tert-butyl (1-(7-bromo-2-((1-hydroxypropan-2-yl)amino)pyrido[2,3-b]pyrazin-3-yl)azetidin-3-yl)(methyl)carbamate (378.0 mg, 0.81 mmol), MsCl (120.0 mg, 1.05 mmol) and TEA (246.0 mg, 2.43 mmol) in DCM (10.0 mL) was stirred at room temperature for 12 hours and concentrated under reduced pressure. The residue was purified by column chromatography (DCM:MeOH=98:2 to 95:5) on silica. The fractions containing the product were collected and evaporated to obtain yellow solid compound of (R)-tert-butyl (1-(8-bromo-2-methyl-1,2-dihydroimidazo[1,2-a]pyrido[2,3-e]pyrazin-4-yl)azetidin-3-yl)(methyl)carbamate (320.0 mg, 88%).

LC/MS ESI (+): 449 (M+1), 451 (M+3)

(c) Synthesis of (R)-1-(8-bromo-2-methyl-1,2-dihydroimidazo[1,2-a]pyrido[2,3-e]pyrazin-4-yl)-N-methylazetidin-3-amine (R)-tert-Butyl (1-(8-bromo-2-methyl-1,2-dihydroimidazo[1,2-a]pyrido[2,3-e]pyrazin-4-yl)azetidin-3-yl)(methyl)carbamate (150.0 mg, 0.33 mmol) was dissolved in DCM (1.5 mL), and TFA (1.5 mL) was slowly added thereto at 0° C. The reaction mixture was stirred at room temperature for 3 hours and then concentrated under reduced pressure. The residue was neutralized with TEA and it was purified by column chromatography (DCM:MeOH=90:10) on amine silica and silica. The fractions containing the product were collected and evaporated to obtain yellow solid compound of (R)-1-(8-bromo-2-methyl-1,2-dihydroimidazo[1,2-a]pyrido[2,3-e]pyrazin-4-yl)-N-methylazetidin-3-amine (75.0 mg, 64%).

LC/MS ESI (+): 349 (M+1), 351 (M+3)

$^1$H-NMR (400 MHz, DMSO-$d_6$); δ: 7.95 (d, 1H, J=2.2 Hz), 7.27 (d, 1H, J=2.2 Hz), 4.68 (m, 1H), 4.35 (m, 1H), 4.22 (m, 1H), 4.03 (t, 2H, J=10.6 Hz), 3.80 (m, 1H), 3.44-3.58 (m, 2H), 2.24 (s, 3H), 1.25 (d, 3H, J=6.7 Hz)

Example 107

Synthesis of 1-(8-bromo-1,2-dihydroimidazo[1,2-a]pyrido[2,3-e]pyrazin-4-yl)-N-methylazetidin-3-amine (a) Synthesis of tert-butyl (1-(7-bromo-2-((2-hydroxyethyl)amino)pyrido[2,3-b]pyrazin-3-yl)azetidin-3-yl)(methyl)carbamate The mixture of tert-butyl (1-(7-bromo-2-chloropyrido[2,3-b]pyrazin-3-yl)azetidin-3-yl)(methyl)carbamate (500.0 mg, 1.17 mmol) and 2-aminoethanol (157.0 mg, 2.57 mmol) in EtOH (20.0 mL) was stirred at 90° C. for 12 hours. The reaction mixture was then concentrated under reduced pressure. The residue was purified by column chromatography (DCM:MeOH=98:2 to 95:5) on silica. The fractions containing the product were collected and evaporated to obtain yellow solid compound of tert-butyl (1-(7-bromo-2-((2-hydroxyethyl)amino)pyrido[2,3-b]pyrazin-3-yl)azetidin-3-yl)(methyl)carbamate (481.0 mg, 91%).

LC/MS ESI (+): 453 (M+1), 455 (M+3)

(b) Synthesis of tert-butyl (1-(8-bromo-1,2-dihydroimidazo[1,2-a]pyrido[2,3-e]pyrazin-4-yl)azetidin-3-yl)(methyl)carbamate The mixture of tert-butyl (1-(7-bromo-2-((2-hydroxyethyl)amino)pyrido[2,3-b]pyrazin-3-yl)azetidin-3-yl) (methyl)carbamate (481.0 mg, 1.06 mmol), MsCl (158.0 mg, 1.38 mmol) and TEA (322.0 mg, 3.18 mmol) in DCM (10.0 mL) was stirred at room temperature for 6 hours and then concentrated under reduced pressure. The residue was purified by column chromatography (DCM:MeOH=98:2) on amine silica. The fractions containing the product were collected and evaporated to obtain yellow solid compound of tert-butyl (1-(8-bromo-1,2-dihydroimidazo[1,2-a]pyrido[2,3-e]pyrazin-4-yl)azetidin-3-yl)(methyl)carbamate (435.0 mg, 94%).

LC/MS ESI (+): 435 (M+1), 437 (M+3)

$^1$H-NMR (400 MHz, DMSO-$d_6$); δ: 7.96 (d, 1H, J=2.2 Hz), 7.31 (d, 1H, J=2.2 Hz), 4.83 (brs, 1H), 4.74 (m, 1H), 4.57 (m, 1H), 4.31 (m, 1H), 4.20 (m, 1H), 4.04 (m, 2H), 3.92 (m, 2H), 2.87 (s, 3H), 1.41 (s, 9H)

(c) Synthesis of 1-(8-bromo-1,2-dihydroimidazo[1,2-a]pyrido[2,3-e]pyrazin-4-yl)-N-methylazetidin-3-amine tert-Butyl (1-(8-bromo-1,2-dihydroimidazo[1,2-a]pyrido[2,3-e]pyrazin-4-yl)azetidin-3-yl)(methyl)carbamate (435.0 mg, 1.00 mmol) was dissolved in DCM (1.0 mL), and TFA (2.0 mL) was slowly added thereto at 0° C. The reaction mixture was stirred at room temperature for 3 hours and then concentrated under reduced pressure. The residue was neutralized with TEA and then purified by column chromatography (DCM:MeOH=90:10) on amine silica. The fractions containing the product were collected and evaporated to obtain yellow solid compound of 1-(8-bromo-1,2-dihydroimidazo[1,2-a]pyrido[2,3-e]pyrazin-4-yl)-N-methylazetidin-3-amine (186.0 mg, 56%).

LC/MS ESI (+): 335 (M+1), 337 (M+3)

$^1$H-NMR (400 MHz, DMSO-$d_6$); δ: 7.95 (d, 1H, J=2.2 Hz), 7.28 (d, 1H, J=2.2 Hz), 4.67 (m, 1H), 4.23 (m, 2H), 4.03 (m, 2H), 3.91 (m, 2H), 3.81 (m, 1H), 3.53 (m, 1H), 2.32 (brs, 1H), 2.23 (s, 3H)

Example 108

Synthesis of 1-(8-bromo-2-methylimidazo[1,2-a]pyrido[2,3-e]pyrazin-4-yl)-N-methylazetidin-3-amine (a) Synthesis of tert-butyl (1-(8-bromo-2-methylimidazo[1,2-a]pyrido[2,3-e]pyrazin-4-yl)azetidin-3-yl)(methyl)carbamate The mixture of (S)-tert-butyl (1-(8-bromo-2-methyl-1,2-dihydroimidazo[1,2-a]pyrido[2,3-e]pyrazin-4-yl)azetidin-3-yl)(methyl)carbamate (139.0 mg, 0.31 mmol) and DDQ (140.0 mg, 0.62 mmol) in xylene (5.0 mL) is stirred at 90° C. for 8 hours and the reaction mixture was concentrated under reduced pressure. The residue was purified by column chromatography (DCM:MeOH=98:2) on silica. The fractions containing the product were collected and evaporated to obtain yellow solid compound which is the mixture of (S)-tert-butyl (1-(8-bromo-2-methyl-1,2-dihydroimidazo[1,2-a]pyrido[2,3-e]pyrazin-4-yl)azetidin-3-yl)(methyl)carbamate and tert-butyl (1-(8-bromo-2-methylimidazo[1,2-a]pyrido[2,3-e]pyrazin-4-yl)azetidin-3-yl)(methyl)carbamate.

LC/MS ESI (+): 447 (M+1), 449 (M+3)

(b) Synthesis of 1-(8-bromo-2-methylimidazo[1,2-a]pyrido[2,3-e]pyrazin-4-yl)-N-methylazetidin-3-amine The mixture of (S)-tert-butyl (1-(8-bromo-2-methyl-1,2-dihydroimidazo[1,2-a]pyrido[2,3-e]pyrazin-4-yl)azetidin-3-yl)(methyl)carbamate and tert-butyl (1-(8-bromo-2-methylimidazo[1,2-a]pyrido[2,3-e]pyrazin-4-yl)azetidin-3-yl) (methyl)carbamate was dissolved in DCM (1.0 mL), and TFA (2.0 mL) was slowly added thereto at 0° C. The reaction mixture was stirred at room temperature for 2 hours and concentrated under reduced pressure. The residue was neutralized with TEA (pH=7) and purified by column chromatography (DCM:MeOH=98:2 to 90:10) on silica. The fractions containing the product were collected and evaporated to obtain yellow solid compound of 1-(8-bromo-2-methylimidazo[1,2-a]pyrido[2,3-e]pyrazin-4-yl)-N-methylazetidin-3-amine (14.0 mg, 13% in two steps).

LC/MS ESI (+): 347 (M+1), 349 (M+3)

$^1$H-NMR (400 MHz, DMSO-$d_6$); δ: 8.75 (d, 1H, J=2.1 Hz), 8.53 (d, 1H, J=2.1 Hz), 8.43 (s, 1H), 4.85 (m, 1H), 4.38 (m, 2H), 3.96 (m, 1H), 3.63 (m, 1H), 2.38 (s, 3H), 2.30 (s, 3H)

Example 109

Synthesis of 1-(9-bromo-2-methylpyrazolo[1,5-c]pyrido[3,2-e]pyrimidin-5-yl)-N-methylazetidin-3-amine (a) Synthesis of 5-bromo-3-(3-methyl-1H-pyrazol-5-yl)pyridin-2-amine Pd(PPh$_3$)$_4$ (190.0 mg, 0.17 mmol) was added to suspension of 5-bromo-3-iodopyridin-2-amine (500.0 mg, 1.67 mmol), (1-(tert-butoxycarbonyl)-3-methyl-1H-pyrazol-5-yl) boronic acid (755.0 mg, 3.34 mmol), Cs$_2$CO$_3$ (1600.0 mg, 5.01 mmol), H$_2$O (3.0 mL) and DME (12.0 mL). The reaction mixture was allowed to react in microwave under conditions of 100 W and 130° C. for 2 hours and 30 minutes, followed by 100 W and 150° C. for 2 hours and then cooled to room temperature. Water was added to the reaction mixture, and it was extracted 2 times with EtOAc. The organic layer was dried over anhydrous Na$_2$SO$_4$, filtered and then concentrated under reduced pressure. The residue was purified by column chromatography (MeOH:DCM=1:40) on silica. The fractions containing the product were collected and evaporated to obtain brown solid compound which is the mixture of 5-bromo-3-(3-methyl-1H-pyrazol-5-yl)pyridin-2-amine and 9-bromo-2-methylpyrazolo[1,5-c]pyrido[3,2-e]pyrimidin-5-ol (78.0 mg).

(b) Synthesis of 9-bromo-2-methylpyrazolo[1,5-c]pyrido[3,2-e]pyrimidin-5-ol

Diphosgene (0.05 mL) was added to a suspension of mixture (78.0 mg) of 5-bromo-3-(3-methyl-1H-pyrazol-5- yl)pyridin-2-amine and 9-bromo-2-methylpyrazolo[1,5-c]pyrido[3,2-e]pyrimidin-5-ol and 1,4-dioxane (1.0 mL). The reaction mixture was stirred at 110° C. for 1 hour and then cooled to room temperature. Et$_2$O was added thereto to form a solid. The formed solid was filtered and dried under reduced pressure to obtain ivory compound of 9-bromo-2-methylpyrazolo[1,5-c]pyrido[3,2-e]pyrimidin-5-ol (57.0 mg, 12% in 2 steps).

LC/MS ESI (+): 279 (M+1), 281 (M+3)
$^1$H-NMR (400 MHz, DMSO-d$_6$); δ: 12.34 (s, 1H), 8.76 (m, 1H), 8.57 (m, 1H), 7.17 (s, 1H), 2.38 (s, 3H)

(c) Synthesis of tert-butyl (1-(9-bromo-2-methyl-pyrazolo[1,5-c]pyrido[3,2-e]pyrimidin-5-yl)azetidin-3-yl)(methyl)carbamate DIPEA (22.0 μL, 0.13 mmol) was added to suspension of 9-bromo-2-methylpyrazolo[1,5-c]pyrido[3,2-e]pyrimidin-5-ol (30.0 mg, 0.11 mmol) and POCl$_3$ (2.0 mL), and it was stirred at 120° C. for 20 hours. The reaction mixture was cooled to room temperature and then concentrated under reduced pressure. The residue was dissolved in DCM (1.0 mL). tert-Butyl azetidin-3-yl(methyl)carbamate HCl salt (119.0 mg, 0.54 mmol) and DIPEA (400.0 μL, 2.14 mmol) were added thereto. The mixture was then stirred at room temperature for 12 hours. The reaction mixture was purified by column chromatography (MeOH:DCM=1:50) on amine silica. The fractions containing the product were collected and evaporated to obtain yellow solid compound of tert-butyl (1-(9-bromo-2-methylpyrazolo[1,5-c]pyrido[3,2-e]pyrimidin-5-yl)azetidin-3-yl)(methyl)carbamate (32.0 mg, 67%).

LC/MS ESI (+): 448 (M+1), 450 (M+3)
$^1$H-NMR (400 MHz, CDCl$_3$); δ: 8.65 (m, 1H), 8.17 (m, 1H), 6.67 (s, 1H), 5.20-5.10 (m, 1H), 4.86 (m, 2H), 4.65 (m, 2H), 2.99 (s, 3H), 2.46 (m, 3H), 1.48 (s, 9H)

(d) Synthesis of 1-(9-bromo-2-methylpyrazolo[1,5-c]pyrido[3,2-e]pyrimidin-5-yl)-N-methylazetidin-3-amine TFA (0.4 mL) was added to the mixture of tert-butyl (1-(9-bromo-2-methylpyrazolo[1,5-c]pyrido[3,2-e]pyrimidin-5-yl)azetidin-3-yl)(methyl)carbamate (32.0 mg, 0.07 mmol) and DCM (0.6 mL), and it was stirred at room temperature for 30 minutes. The reaction mixture was purified by column chromatography (MeOH:DCM=1:40) on amine silica. The fractions containing the product were collected and evaporated. Et$_2$O was added to the residue and form a solid. The formed solid was filtered and dried under reduced pressure to obtain ivory compound of 1-(9-bromo-2-methylpyrazolo[1,5-c]pyrido[3,2-e]pyrimidin-5-yl)-N-methylazetidin-3-amine (15.0 mg, 60%).

LC/MS ESI (+): 347 (M+1), 349 (M+3)
$^1$H-NMR (400 MHz, CDCl$_3$); δ: 8.64 (d, 1H, J=1.8 Hz), 8.15 (d, 1H, J=1.8 Hz), 6.65 (s, 1H), 4.82 (m, 2H), 4.37 (m, 2H), 3.75 (m, 1H), 2.48 (s, 3H), 2.47 (s, 3H)

Example 110

Synthesis of 1-(9-bromopyrazolo[1,5-c]pyrido[3,2-e]pyrimidin-5-yl)-N-methylazetidin-3-amine (a) Synthesis of 5-bromo-3-(1H-pyrazol-5-yl)pyridin-2-amine Pd(PPh$_3$)$_4$ (39.0 mg, 0.03 mmol) was added to suspension of 5-bromo-3-iodopyridin-2-amine (100.0 mg, 0.34 mmol), (1-(tert-butoxycarbonyl)-1H-pyrazol-5-yl)boronic acid (99.0 mg, 0.47 mmol), Cs$_2$CO$_3$ (327.0 mg, 1.01 mmol), H2O (0.5 mL) and DME (2.0 mL). The reaction mixture was allowed to react in microwave under conditions of 100 W and 120° C. for 1 hour and 30 minutes, then cooled to room temperature and Pd(PPh$_3$)$_4$ (20.0 mg, 0.02 mmol) and (1-(tert-butoxycarbonyl)-1H-pyrazol-5-yl)boronic acid (50.0 mg, 0.24 mmol) were further added thereto. The reaction mixture was allowed to react in microwave under conditions of 100 W and 130° C. for 2 hours and then cooled to room temperature. Water was added to the reaction mixture, and it was extracted 2 times with DCM. The organic layer was dried over anhydrous Na$_2$SO$_4$, filtered and then concentrated under reduced pressure. The residue was purified by column chromatography (MeOH:DCM=1:50) on amine silica. The fractions containing the product were collected and evaporated to obtain brown solid compound which is the mixture of 5-bromo-3-(1H-pyrazol-5-yl)pyridin-2-amine and 9-bromopyrazolo[1,5-c]pyrido[3,2-e]pyrimidin-5-ol (39.0 mg).

(b) Synthesis of 9-bromopyrazolo[1,5-c]pyrido[3,2-e]pyrimidin-5-ol

Diphosgene (0.05 mL) was added to a suspension of mixture of 5-bromo-3-(1H-pyrazol-5-yl)pyridin-2-amine and 9-bromopyrazolo[1,5-c]pyrido[3,2-e]pyrimidin-5-ol and 1,4-dioxane (1.0 mL). The reaction mixture was stirred at 110° C. for 1 hour and then cooled to room temperature. Et$_2$O was added thereto to form a solid. The formed solid was filtered and dried under reduced pressure to obtain yellow solid compound of 9-bromopyrazolo[1,5-c]pyrido[3,2-e]pyrimidin-5-ol (32.0 mg, 36% in 2 steps).

LC/MS ESI (+): 265 (M+1), 267 (M+3)
$^1$H-NMR (400 MHz, CDCl$_3$+DMSO-d$_6$); δ: 8.51 (d, 1H, J=1.5 Hz), 8.43 (d, 1H, J=1.5 Hz), 8.04 (m, 1H), 7.11 (m, 1H)

(c) Synthesis of tert-butyl (1-(9-bromopyrazolo[1,5-c]pyrido[3,2-e]pyrimidin-5-yl)azetidin-3-yl)(methyl) carbamate DIPEA (25.0 μL, 0.15 mmol) was added to suspension of 9-bromopyrazolo[1,5-c]pyrido[3,2-e]pyrimidin-5-ol (32.0 mg, 0.12 mmol) and POCl$_3$ (2.0 mL), and it was stirred at 120° C. for 24 hours. The reaction mixture was cooled to room temperature and then concentrated under reduced pressure. The residue was dissolved in DCM (1.2 mL), and tert-butyl azetidin-3-yl(methyl)carbamate HCl salt (135.0 mg, 0.61 mmol) and DIPEA (420.0 μL, 2.42 mmol) were added thereto. The reaction mixture was stirred at room temperature for 12 hours and then purified by column chromatography (EtOAc:n-Hex=1:5) on amine silica. The fractions containing the product were collected and evaporated to obtain yellow solid compound of tert-butyl (1-(9-bromopyrazolo[1,5-c]pyrido[3,2-e]pyrimidin-5-yl)azetidin-3-yl)(methyl)carbamate (32.0 mg, 62%).

LC/MS ESI (+): 433 (M+1), 435 (M+3)
$^1$H-NMR (400 MHz, CDCl$_3$); δ: 8.68 (m, 1H), 8.24 (m, 1H), 7.97 (m, 1H), 6.89 (m, 1H), 5.20-5.10 (m, 1H), 4.89 (m, 2H), 4.68 (m, 2H), 2.99 (s, 3H), 1.48 (s, 9H)

(d) Synthesis of 1-(9-bromopyrazolo[1,5-c]pyrido[3,2-e]pyrimidin-5-yl)-N-methylazetidin-3-amine TFA (0.4 mL) was added to the mixture of tert-butyl (1-(9-bromopyrazolo[1,5-c]pyrido[3,2-e]pyrimidin-5-yl) azetidin-3-yl)(methyl)carbamate (32.0 mg, 0.07 mmol) and DCM (0.6 mL), and it was stirred at room temperature for 30 minutes. The reaction mixture was purified by column chromatography (MeOH:DCM=1:40) on amine silica. The fractions containing the product were collected and evaporated. Et$_2$O was added to the residue and form a solid. The formed solid was filtered and dried under reduced pressure to obtain ivory solid compound of 1-(9-bromopyrazolo[1,5-c]pyrido[3,2-e]pyrimidin-5-yl)-N-methylazetidin-3-amine (16.0 mg, 64%).

LC/MS ESI (+): 333 (M+1), 335 (M+3)

$^1$H-NMR (400 MHz, CDCl$_3$); δ: 8.67 (d, 1H, J=1.8 Hz), 8.22 (d, 1H, J=1.8 Hz), 7.97 (d, 1H, J=1.5 Hz), 6.88 (d, 1H, J=1.5 Hz), 4.86 (m, 2H), 4.40 (m, 2H), 3.76 (m, 1H), 2.48 (s, 3H)

Example 111

Synthesis of N-methyl-1-(8-nitropyrido[2,3-e][1,2,4]triazolo[4,3-a]pyrazin-4-yl)azetidin-3-amine (a) Synthesis of 5-nitropyridine-2,3-diamine 3,5-Dinitropyridin-2-amine (300.0 mg, 1.63 mmol) and ammonium sulfide solution (2.4 mL, 8.15 mmol) was dissolved in MeOH (11.3 mL), and it was stirred at 75° C. for 30 minutes and then cooled to room temperature. The formed solid was filtered and then dried under reduced pressure to obtain red solid compound of 5-nitropyridine-2,3-diamine (250.0 mg, 99%).

LC/MS ESI (+): 155 (M+1)

$^1$H-NMR (400 MHz, DMSO-d$_6$); δ: 8.29 (d, 1H, J=1.8 Hz), 7.36 (d, 1H, J=1.8 Hz), 6.99 (s, 2H), 5.32 (s, 2H)

(b) Synthesis of 7-nitropyrido[2,3-b]pyrazine-2,3-diol

5-Nitropyridine-2,3-diamine (25.0 mg, 1.63 mmol) was added to diethyloxalate (5.0 mL) and the reaction mixture was stirred at 180° C. for 72 hours and then cooled to room temperature. Et$_2$O was added to the reaction mixture to form a solid. The formed solid was filtered and dried under reduced pressure to obtain light brown solid compound of 7-nitropyrido[2,3-b]pyrazine-2,3-diol (167.0 mg, 49%).

$^1$H-NMR (400 MHz, DMSO-d$_6$); δ: 12.95 (s, 1H), 12.23 (s, 1H), 8.93 (d, 1H, J=1.8 Hz), 8.11 (d, 1H, J=1.8 Hz)

(c) Synthesis of 2,3-dichloro-7-nitropyrido[2,3-b]pyrazine

The mixture of 7-nitropyrido[2,3-b]pyrazine-2,3-diol (167.0 mg, 0.80 mmol) and POCl$_3$ (2.6 mL) was stirred at 150° C. for 48 hours and then cooled to room temperature. The reaction mixture was concentrated under reduced pressure. The residue was purified by column chromatography (n-Hex:EtOAc=80:20) on silica. The fractions containing the product were collected and evaporated to obtain white solid compound of 2,3-dichloro-7-nitropyrido[2,3-b]pyrazine (68.0 mg, 35%).

LC/MS ESI (+): 245 (M+1), 247 (M+3)

(d) Synthesis of tert-butyl (1-(2-chloro-7-nitropyrido[2,3-b]pyrazin-3-yl)azetidin-3-yl)(methyl)carbamate 2,3-Dichloro-7-nitropyrido[2,3-b]pyrazine (68.0 mg, 0.28 mmol) and tert-butyl azetidin-3-yl(methyl)carbamate HCl salt (61.8 mg, 0.28 mmol) were added to DCM (6.0 mL), and TEA (0.12 mL, 0.84 mmol) was slowly added thereto at 0° C. The reaction mixture was stirred at room temperature for 1 hour and then concentrated under reduced pressure. The residue was purified by column chromatography (n-Hex:EtOAc=70:30) on silica. The fractions containing the product were collected and evaporated to obtain white solid compound of tert-butyl (1-(2-chloro-7-nitropyrido[2,3-b]pyrazin-3-yl)azetidin-3-yl)(methyl)carbamate (95.0 mg, 87%).

LC/MS ESI (+): 395 (M+1)

(e) Synthesis of tert-butyl (1-(2-hydrazinyl-7-nitropyrido[2,3-b]pyrazin-3-yl)azetidin-3-yl)(methyl)carbamate tert-Butyl (1-(2-chloro-7-nitropyrido[2,3-b]pyrazin-3-yl)azetidin-3-yl)(methyl)carbamate (90.0 mg, 0.23 mmol) and hydrazine hydrate (24.0 μL, 0.68 mmol) were dissolved in EtOH (2.3 mL), and it was stirred at room temperature for 1 hour and then concentrated under reduced pressure. Et$_2$O was added to the reaction mixture and form a solid. The formed solid was filtered and dried under reduced pressure to obtain yellow solid compound of tert-butyl (1-(2-hydrazinyl-7-nitropyrido[2,3-b]pyrazin-3-yl)azetidin-3-yl)(methyl)carbamate. The mixture of unpurified tert-butyl (1-(2-hydrazinyl-7-nitropyrido[2,3-b]pyrazin-3-yl)azetidin-3-yl)(methyl)carbamate and trimethyl orthoformate (2.5 mL) was stirred at 75° C. for 5 hours and then cooled to room temperature. Et$_2$O was added thereto to form a solid. The formed solid was filtered and purified by column chromatography (DCM:MeOH=95:5) on amine silica. The fractions containing the product were collected and evaporated to obtain ivory solid compound of tert-butyl methyl(1-(8-nitropyrido[2,3-e][1,2,4]triazolo[4,3-a]pyrazin-4-yl)azetidin-3-yl)carbamate (64.0 mg, 66%).

LC/MS ESI (+): 401 (M+1)

$^1$H-NMR (400 MHz, DMSO-d$_6$); δ: 10.23 (s, 1H), 9.47 (d, 1H, J=1.8 Hz), 9.32 (d, 1H, J=1.8 Hz), 5.00 (m, 3H), 4.52 (m, 1H), 2.95 (s, 3H), 1.44 (s, 9H)

(f) Synthesis of N-methyl-1-(8-nitropyrido[2,3-e][1,2,4]triazolo[4,3-a]pyrazin-4-yl)azetidin-3-amine tert-Butyl methyl(1-(8-nitropyrido[2,3-e][1,2,4]triazolo[4,3-a]pyrazin-4-yl)azetidin-3-yl)carbamate (30.0 mg, 0.08 mmol) was dissolved in DCM (1.0 mL), and TFA (0.5 mL) was slowly added thereto at 0° C. The reaction mixture was stirred at room temperature for 1 hour and then concentrated under reduced pressure. The residue was purified by column chromatography (DCM:MeOH=95:5) on amine silica. The fractions containing the product were collected and evaporated to obtain yellow solid compound of N-methyl-1-(8-nitropyrido[2,3-e][1,2,4]triazolo[4,3-a]pyrazin-4-yl)azetidin-3-amine (20.0 mg, 89%).

LC/MS ESI (+): 301 (M+1)

$^1$H-NMR (400 MHz, DMSO-d$_6$); δ: 10.22 (s, 1H), 9.44 (d, 1H, J=1.8 Hz), 9.30 (d, 1H, J=1.8 Hz), 4.97 (m, 1H), 4.53 (m, 2H), 4.09 (m, 1H), 3.77 (m, 1H), 2.32 (s, 3H)

Example 112

Synthesis of 4-(3-(methylamino)azetidin-1-yl)pyrido[2,3-e][1,2,4]triazolo[4,3-a]pyrazin-8-amine (a) Synthesis of tert-butyl (1-(8-aminopyrido[2,3-e][1,2,4]triazolo[4,3-a]pyrazin-4-yl)azetidin-3-yl)(methyl)carbamate tert-Butyl methyl(1-(8-nitropyrido[2,3-e][1,2,4]triazolo[4,3-a]pyrazin-4-yl)azetidin-3-yl)carbamate (35.0 mg, 0.09 mmol) and 10% Pd/C (9.0 mg) were dissolved in MeOH (3.0 mL). The flask was substituted with hydrogen and then stirred at room temperature for 40 minutes. The reaction mixture was filtered with celite and then concentrated under reduced pressure to obtain tert-butyl (1-(8-aminopyrido[2,3-e][1,2,4]triazolo[4,3-a]pyrazin-4-yl)azetidin-3-yl)(methyl)carbamate (32.4 mg).

LC/MS ESI (+): 371 (M+1)

(b) Synthesis of 4-(3-(methylamino)azetidin-1-yl)pyrido[2,3-e][1,2,4]triazolo[4,3-a]pyrazin-8-amine Unpurified tert-butyl (1-(8-aminopyrido[2,3-e][1,2,4]triazolo[4,3-a]pyrazin-4-yl)azetidin-3-yl)(methyl)carbamate (32.4 mg, 0.09 mmol) was dissolved in DCM (1.5 mL), and TFA (0.5 mL) was slowly added thereto at room temperature. The reaction mixture was stirred at room temperature for 1 hour and then concentrated under reduced pressure. The residue was purified by column chromatography (n-Hex:EtOA:MeOH=40:40:20) on amine silica. The fractions containing the product were collected and evaporated to obtain yellow solid compound of 4-(3-(methylamino)azetidin-1-yl)pyrido[2,3-e][1,2,4]triazolo[4,3-a]pyrazin-8-amine (5.0 mg, 21% in 2 steps).

LC/MS ESI (+): 271 (M+1)
$^1$H-NMR (400 MHz, DMSO-d$_6$); δ: 9.83 (s, 1H), 8.05 (d, 1H, J=1.8 Hz), 7.56 (d, 1H, J=1.8 Hz), 5.63 (s, 2H), 4.55 (m, 2H), 4.11 (m, 2H), 3.68 (m, 1H), 2.29 (s, 3H)

Example 113

Synthesis of N-methyl-1-(8-phenylpyrido[2,3-e][1,2,4]triazolo[4,3-a]pyrazin-4-yl)azetidin-3-amine Pd(PPh$_3$)$_4$ (17.0 mg, 0.02 mmol) was added to a suspension of 1-(8-bromopyrido[2,3-e][1,2,4]triazolo[4,3-a]pyrazin-4-yl)-N-methylazetidin-3-amine (50.0 mg, 0.15 mmol), phenylboronic acid (27.0 mg, 0.22 mmol), Cs$_2$CO$_3$ (122.0 mg, 0.38 mmol), H$_2$O (0.3 mL) and DME (1.2 mL). The reaction mixture was reacted with microwave under conditions of 50 W and 80° C. for 30 minutes and then cooled to room temperature. The reaction mixture was purified by column chromatography (MeOH:DCM=1:40) on amine silica. The fractions containing the product were collected and concentrated. Et$_2$O was added to the residue and a solid was formed. The formed solid was filtered and dried under reduced pressure to obtain yellow solid compound of N-methyl-1-(8-phenylpyrido[2,3-e][1,2,4]triazolo[4,3-a]pyrazin-4-yl)azetidin-3-amine (42.0 mg, 85%).

LC/MS ESI (+): 332 (M+1)
$^1$H-NMR (400 MHz, DMSO-d$_6$); δ: 10.08 (s, 1H), 8.91 (m, 2H), 7.87 (m, 2H), 7.55 (m, 2H), 7.44 (m, 1H), 4.91 (m, 1H), 4.45 (m, 2H), 4.02 (m, 1H), 3.72 (m, 1H), 2.45 (m, 1H), 2.31 (s, 1H)

Example 114

Synthesis of 1-(8-(furan-2-yl)pyrido[2,3-e][1,2,4]triazolo[4,3-a]pyrazin-4-yl)-N-methylazetidin-3-amine Pd(PPh$_3$)$_4$ (17.0 mg, 0.02 mmol) was added to a suspension of 1-(8-bromopyrido[2,3-e][1,2,4]triazolo[4,3-a]pyrazin-4-yl)-N-methylazetidin-3-amine (50.0 mg, 0.15 mmol), furan-2-ylboronic acid (34.0 mg, 0.30 mmol), Cs$_2$CO$_3$ (122.0 mg, 0.38 mmol), H$_2$O (0.3 mL) and DME (1.2 mL). The reaction mixture was reacted with microwave under conditions of 50 W and 80° C. for 30 minutes and then cooled to room temperature. The reaction mixture was purified by column chromatography (MeOH:DCM=1:40) on amine silica. The fractions containing the product were collected and concentrated. Et$_2$O was added to the residue and a solid was formed. The formed solid was filtered and dried under reduced pressure to obtain yellow solid compound of 1-(8-(furan-2-yl)pyrido[2,3-e][1,2,4]triazolo[4,3-a]pyrazin-4-yl)-N-methylazetidin-3-amine (31.0 mg, 65%).

LC/MS ESI (+): 322 (M+1)
$^1$H-NMR (400 MHz, DMSO-d$_6$); δ: 10.07 (s, 1H), 8.91 (s, 1H), 8.82 (s, 1H), 7.87 (s, 1H), 7.12 (m, 1H), 6.70 (m, 1H), 4.91 (m, 1H), 4.44 (m, 2H), 4.02 (m, 1H), 3.72 (m, 1H), 2.31 (s, 3H)

Example 115

Synthesis of 1-(2-bromopyrido[2,3-e]pyrrolo[1,2-a]pyrazin-6-yl)-N-methylazetidin-3-amine (a) Synthesis of 5-bromo-3-(1H-pyrrol-1-yl)pyridin-2-amine A mixture of 5-bromopyridine-2,3-diamine (2000.0 mg, 10.6 mmol) and 2,5-dimethoxytetrahydrofuran (1.5 mL, 11.7 mmol) in AcOH (10.0 mL) was stirred at 90° C. for 4 hours. The reaction mixture was poured into water, neutralized with 10% NaOH aqueous solution (pH=7) and then extracted with EtOAc (200.0 mL). The organic layer was washed with brine, dried over anhydrous Na$_2$SO$_4$, filtered and then concentrated. The residue was purified by column chromatography (EtOAc:n-Hex=1:4) on silica. The fractions containing the product were collected and concentrated to obtain yellow solid compound of 5-bromo-3-(1H-pyrrol-1-yl)pyridin-2-amine (614.0 mg, 24%).

LC/MS ESI (+): 238 (M+1), 240 (M+3)
$^1$H-NMR (400 MHz, DMSO-d$_6$); δ: 8.13 (d, 1H, J=2.1 Hz), 7.53 (d, 1H, J=2.1 Hz), 6.83 (m, 2H), 6.37 (m, 2H), 4.63 (brs, 2H)

(b) Synthesis of 2-bromopyrido[2,3-e]pyrrolo[1,2-a]pyrazin-6(5H)-one

The mixture of 5-bromo-3-(1H-pyrrol-1-yl)pyridin-2-amine (200.0 mg, 0.84 mmol) and triphosgene (374.0 mg, 1.26 mmol) in anhydrous toluene (8.0 mL) was stirred at 110° C. for 3 hours, cooled to room temperature and then concentrated under reduced pressure. The residue was purified by column chromatography (DCM:MeOH=30:1) on silica. The fractions containing the product were collected and concentrated to obtain dark green solid compound of 2-bromopyrido[2,3-e]pyrrolo[1,2-a]pyrazin-6(5H)-one (178.0 mg, 80%).

LC/MS ESI (+): 264 (M+1), 266 (M+3)
$^1$H-NMR (400 MHz, DMSO-d$_6$); δ: 11.86 (s, 1H), 8.81 (m, 1H), 8.37 (m, 1H), 8.28 (m, 1H), 7.08 (m, 1H), 6.74 (m, 1H)

(c) Synthesis of tert-butyl (1-(2-bromopyrido[2,3-e]pyrrolo[1,2-a]pyrazin-6-yl)azetidin-3-yl)(methyl)carbamate 2-Bromopyrido[2,3-e]pyrrolo[1,2-a]pyrazin-6(5H)-one (178.0 mg, 0.67 mmol) was dissolved in POCl$_3$ (3.0 mL), and then DIPEA (141.0 μL, 0.81 mmol) was added thereto. The reaction mixture was stirred at 120° C. for 12 hours, cooled to room temperature and then concentrated under reduced pressure. Unpurified 2-bromo-6-chloropyrido[2,3-e]pyrrolo[1,2-a]pyrazine and TEA (0.5 mL, 3.35 mmol) were dissolved in DMA (7.0 mL), and tert-butyl azetidin-3-yl(methyl)carbamate hydrochloride (164.0 mg, 0.74 mmol) was added thereto. The reaction mixture was stirred at 110° C. for 12 hours, cooled to room temperature and then concentrated under reduced pressure. The residue was purified by column chromatography (DCM:MeOH=97:3) on amine silica. The fractions containing the product were collected and concentrated to obtain brown solid compound of tert-butyl (1-(2-bromopyrido[2,3-e]pyrrolo[1,2-a]pyrazin-6-yl)azetidin-3-yl)(methyl)carbamate (179.0 mg, 62% in 2 steps).

LC/MS ESI (+): 432 (M+1), 434 (M+3)

(d) Synthesis of 1-(2-bromopyrido[2,3-e]pyrrolo[1,2-a]pyrazin-6-yl)-N-methylazetidin-3-amine tert-Butyl (1-(2-bromopyrido[2,3-e]pyrrolo[1,2-a]pyrazin-6-yl)azetidin-3-yl)(methyl)carbamate (179.0 mg, 0.41 mmol) was dissolved in DCM (2.0 mL), and TFA (2.0 mL) was slowly added thereto at 0° C. The reaction mixture was stirred at room temperature for 2 hours and then concentrated under reduced pressure. The residue was neutralized with $NEt_3$ and purified by column chromatography (DCM:MeOH=100:0 to 90:10) on amine silica. The fractions containing the product were collected and concentrated to obtain brown solid compound of 1-(2-bromopyrido[2,3-e]pyrrolo[1,2-a]pyrazin-6-yl)-N-methylazetidin-3-amine (91.0 mg, 66%).

LC/MS ESI (+): 332 (M+1), 334 (M+3)

$^1$H-NMR (400 MHz, DMSO-$d_6$); δ: 8.75 (m, 1H), 8.39 (m, 2H), 6.90 (m, 1H), 6.82 (m, 1H), 4.54 (m, 2H), 4.09 (m, 2H), 3.65 (m, 1H), 2.28 (s, 3H)

Example 116

Synthesis of 1-(2-chloropyrido[3,2-e][1,2,4]triazolo[4,3-a]pyrazin-6-yl)-N-methylazetidin-3-amine (a) Synthesis of 6-bromo-3-nitropyridin-2-amine 2,6-Dibromo-3-nitropyridine (700.0 mg, 2.48 mmol) was added to 2M ammonia solution in EtOH (25.0 mL, 49.66 mmol). The mixture stirred at room temperature for 12 hours and concentrated under reduced pressure to obtain yellow solid compound of 6-bromo-3-nitropyridin-2-amine (526.0 mg, 97%).

$^1$H-NMR (400 MHz, DMSO-$d_6$); δ: 8.26 (m, 3H), 6.91 (d, 1H, J=8.4 Hz)

(b) Synthesis of 6-bromopyridine-2,3-diamine

6-Bromo-3-nitropyridin-2-amine (520.0 mg, 2.39 mmol) and $SnCl_2 \cdot 2H_2O$ (2140.0 mg, 9.54 mmol) were added to DMF (8.6 mL), and the reaction mixture was stirred at 80° C. for 2 hours. The reaction mixture was cooled to room temperature, basified with 1N NaOH (pH=9) and then extracted with EtOAc. The organic layer was dried over anhydrous $Na_2SO_4$, filtered and concentrated under reduced pressure to obtain brown solid compound of 6-bromopyridine-2,3-diamine (238.0 mg, 44%).

$^1$H-NMR (400 MHz, DMSO-$d_6$); δ: 6.62 (d, 1H, J=8.4 Hz), 6.48 (d, 1H, J=8.4 Hz), 5.81 (brs, 2H), 4.79 (brs, 2H)

(c) Synthesis of 6-bromopyrido[2,3-b]pyrazine-2,3-diol

6-Bromopyridine-2,3-diamine (238.0 mg, 1.26 mmol) was added to diethyl oxalate (4.0 mL). The mixture was stirred at 150° C. for 4 hours and then cooled to room temperature. $Et_2O$ was added to form a solid. The formed solid was filtered and then dried under reduced pressure to obtain brown solid compound of 6-bromopyrido[2,3-b]pyrazine-2,3-diol (250.0 mg, 82%).

$^1$H-NMR (400 MHz, DMSO-$d_6$); δ: 12.50 (brs, 1H), 12.06 (brs, 1H), 7.36 (m, 2H)

(d) Synthesis of 2,3,6-trichloropyrido[2,3-b]pyrazine

A mixture of 6-bromopyrido[2,3-b]pyrazine-2,3-diol (250.0 mg, 1.03 mmol) and $POCl_3$ (4.0 mL) was stirred at 150° C. for 10 hours and then cooled to room temperature. The reaction mixture was concentrated under reduced pressure. The residue was purified by column chromatography (n-Hex:EtOAc=70:30) on silica. The fractions containing the product were collected and concentrated to obtain white solid compound of 2,3,6-trichloropyrido[2,3-b]pyrazine (180.0 mg, 63%).

LC/MS ESI (+): 234 (M+1), 236 (M+3)

$^1$H-NMR (400 MHz, DMSO-$d_6$); δ: 8.65 (d, 1H, J=8.8 Hz), 8.08 (d, 1H, J=8.8 Hz)

(e) Synthesis of 2,6-dichloropyrido[3,2-e][1,2,4]triazolo[4,3-a]pyrazine

Hydrazine monohydrate (18.0 μL, 0.51 mmol) was added to a suspension of 2,3,6-trichloropyrido[2,3-b]pyrazine (80.0 mg, 0.34 mmol) and EtOH (1.4 mL). The reaction mixture was stirred at room temperature for 90 minutes. $Et_2O$ was added thereto to form a solid. The formed solid was filtered and dried under reduced pressure to obtain yellow solid compound of 2,6-dichloro-3-hydrazinylpyrido[2,3-b]pyrazine. Unpurified 2,6-dichloro-3-hydrazinylpyrido[2,3-b]pyrazine (60.0 mg, 0.26 mmol) was dissolved in trimethyl orthoformate (3.0 mL) and then stirred at 85° C. for 12 hours. The reaction mixture was cooled to room temperature and then concentrated under reduced pressure. The residue was purified by column chromatography (n-Hex:EtOAc=70:30) on silica. The fractions containing the product were collected and concentrated to obtain beige solid compound of 2,6-dichloropyrido[3,2-e][1,2,4]triazolo[4,3-a]pyrazine (35.0 mg, 56% in 2 steps).

$^1$H-NMR (400 MHz, DMSO-$d_6$); δ: 10.14 (s, 1H), 8.60 (d, 1H, J=8.4 Hz), 7.96 (d, 1H, J=8.4 Hz)

(f) Synthesis of 1-(2-chloropyrido[3,2-e][1,2,4]triazolo[4,3-a]pyrazin-6-yl)-N-methylazetidin-3-amine 2,6-Dichloropyrido[3,2-e][1,2,4]triazolo[4,3-a]pyrazine (35.0 mg, 0.12 mmol) and tert-butyl azetidin-3-yl(methyl)carbamate hydrochloride (41.0 mg, 0.18 mmol) were added to DCM (1.0 mL), and TEA (51.0 μL, 0.37 mmol) was slowly added thereto at room temperature. The reaction mixture was stirred at room temperature for 30 minutes and then concentrated under reduced pressure. The residue was purified column chromatography (n-Hex:EtOAc=70:30) on silica. The fractions containing the product were collected and concentrated to obtain yellow solid compound of tert-butyl (1-(2-chloropyrido[3,2-e][1,2,4]triazolo[4,3-a]pyrazin-6-yl)azetidin-3-yl)(methyl)carbamate. TFA (0.4 mL) was added to a mixture of tert-butyl (1-(2-chloropyrido[3,2-e][1,2,4]triazolo[4,3-a]pyrazin-6-yl)azetidin-3-yl)(methyl)carbamate and DCM (1.0 mL), and the reaction mixture was stirred at room temperature for 30 minutes. The reaction mixture was concentrated under reduced pressure.

The residue was purified by column chromatography (MeOH:DCM=5:95) on amine silica. The fractions containing the product were collected and concentrated to obtain beige solid compound of 1-(2-chloropyrido[3,2-e][1,2,4]triazolo[4,3-a]pyrazin-6-yl)-N-methylazetidin-3-amine (30.0 mg, 86% in 2 steps).

LC/MS ESI (+): 290 (M+1)

$^1$H-NMR (400 MHz, DMSO-d$_6$); δ: 9.31 (s, 1H), 8.02 (d, 1H, J=8.4 Hz), 7.61 (d, 1H, J=8.4 Hz), 4.90 (m, 1H), 4.43 (m, 2H), 4.00 (m, 1H), 3.73 (m, 1H), 2.30 (s, 3H)

Example 117

Synthesis of 1-(8-chloropyrido[3,4-e][1,2,4]triazolo[4,3-a]pyrazin-4-yl)-N-methylazetidin-3-amine (a) Synthesis of 6-bromopyridine-3,4-diamine 2-Bromo-5-nitropyridin-4-amine (300.0 mg, 2.48 mmol) and Fe (300.0 mg, 5.37 mmol) were added to AcOH, and the reaction mixture was stirred at 75° C. for 4 hours and then cooled to room temperature. The reaction mixture was filtered through celite and then concentrated under reduced pressure. The residue was purified by column chromatography (n-Hex:EtOAc=50:50) on amine silica. The fractions containing the product were collected and concentrated to obtain brown solid compound of 6-bromopyridine-3,4-diamine (200.0 mg, 78%).

$^1$H-NMR (400 MHz, DMSO-d$_6$); δ: 7.39 (s, 1H), 6.42 (s, 1H), 5.74 (brs, 2H), 4.66 (brs, 2H)

(b) Synthesis of 7-bromopyrido[3,4-b]pyrazine-2,3-diol

6-Bromopyridine-3,4-diamine (200.0 mg, 1.06 mmol) was added to diethyl oxalate (3.0 mL). The mixture was stirred at 130° C. for 12 hours and then cooled to room temperature. Et$_2$O was added thereto to form a solid. The formed solid was filtered and dried under reduced pressure to obtain brown solid compound of 7-bromopyrido[3,4-b]pyrazine-2,3-diol (195.0 mg, 76%).

$^1$H-NMR (400 MHz, DMSO-d$_6$); δ: 12.23 (brs, 1H), 12.11 (brs, 1H), 8.09 (s, 1H), 7.05 (s, 1H)

(c) Synthesis of 2,3,7-trichloropyrido[3,4-b]pyrazine

A mixture of 7-bromopyrido[3,4-b]pyrazine-2,3-diol (190.0 mg, 0.79 mmol) and POCl$_3$ (3.0 mL) was stirred at 150° C. for 12 hours and then cooled to room temperature. Et$_2$O was added thereto to form a solid and the formed solid was filtered. The resulting solid was purified by column chromatography (n-Hex:EtOAc=50:50) on silica. The fractions containing the product were collected and concentrated to obtain white solid compound of 2,3,7-trichloropyrido[3,4-b]pyrazine (1.0 mg, 5%).

LC/MS ESI (+): 234 (M+1), 236 (M+3)

$^1$H-NMR (400 MHz, DMSO-d$_6$); δ: 9.39 (s, 1H), 8.31 (s, 1H)

(d) Synthesis of 4,8-dichloropyrido[3,4-e][1,2,4]triazolo[4,3-a]pyrazine

Hydrazine monohydrate (1.9 μL, 0.05 mmol) was added to a suspension of 2,3,7-trichloropyrido[3,4-b]pyrazine (10.0 mg, 0.03 mmol) and EtOH (0.5 mL) at 0° C. The reaction mixture was stirred at room temperature for 3 hours. Et$_2$O was added thereto to form a solid. The formed solid was filtered and dried under reduced pressure to obtain red solid compound of 3,7-dichloro-2-hydrazinylpyrido[3,4-b]pyrazine. Unpurified 3,7-dichloro-2-hydrazinylpyrido[3,4-b]pyrazine was dissolved in trimethyl orthoformate (0.3 mL), and the reaction mixture was stirred at 80° C. for 5 hours. The reaction mixture was cooled to room temperature. Et$_2$O was added thereto to form a solid. The formed solid was filtered and dried under reduced pressure to form orange solid compound of 4,8-dichloropyrido[3,4-e][1,2,4]triazolo[4,3-a]pyrazine (3.5 mg, 42% in 2 steps).

LC/MS ESI (+): 240 (M+1)

$^1$H-NMR (400 MHz, CDCl$_3$); δ: 9.35 (s, 1H), 9.19 (s, 1H), 7.90 (s, 1H)

(e) Synthesis of 1-(8-chloropyrido[3,4-e][1,2,4]triazolo[4,3-a]pyrazin-4-yl)-N-methylazetidin-3-amine 4,8-Dichloropyrido[3,4-e][1,2,4]triazolo[4,3-a]pyrazine (3.5 mg, 0.01 mmol) and tert-butyl azetidin-3-yl(methyl)carbamate hydrochloride (4.1 mg, 0.02 mmol) were added to DCM (0.2 mL), and TEA (5.0 μL, 0.04 mmol) was added thereto at room temperature. The reaction mixture was stirred at room temperature for 1 hour and concentrated under reduced pressure to obtain tert-butyl (1-(8-chloropyrido[3,4-e][1,2,4]triazolo[4,3-a]pyrazin-4-yl)azetidin-3-yl)(methyl)carbamate. TFA (0.2 mL) was added to a mixture of unpurified tert-butyl (1-(8-chloropyrido[3,4-e][1,2,4]triazolo[4,3-a]pyrazin-4-yl)azetidin-3-yl)(methyl)carbamate and DCM (1.0 mL), and the reaction mixture was stirred at room temperature for 1 hour. The reaction mixture was concentrated under reduced pressure and the residue was purified by column chromatography (MeOH:DCM=5:95) on amine silica. The fractions containing the product were collected and concentrated to obtain beige solid compound of 1-(8-chloropyrido[3,4-e][1,2,4]triazolo[4,3-a]pyrazin-4-yl)-N-methylazetidin-3-amine (2.0 mg, 57% in 2 steps).

LC/MS ESI (+): 290 (M+1)

$^1$H-NMR (400 MHz, CDCl$_3$); δ: 9.12 (s, 1H), 8.77 (s, 1H), 7.62 (s, 1H), 5.07 (m, 1H), 4.59 (m, 2H), 4.18 (m, 1H), 3.88 (m, 1H), 2.50 (s, 3H)

Example 118

Synthesis of 1-(8-bromopyrido[2,3-e][1,2,4]triazolo[4,3-a]pyrazin-4-yl)-N-methylazetidin-3-amine methanesulfonic acid salt Methanesulfonic acid (38.9 μL, 0.60 mmol) was slowly added to a suspension of 1-(8-bromopyrido[2,3-e][1,2,4]triazolo[4,3-a]pyrazin-4-yl)-N-methylazetidin-3-amine (200.0 mg, 0.60 mmol) and ethanol (3.0 mL). The reaction mixture was stirred at room temperature for 20 hours to form a solid. The formed solid was filtered under reduced pressure, washed with ethanol and then dried under reduced pressure to obtain ivory solid compound of 1-(8-bromopyrido[2,3-e][1,2,4]triazolo[4,3-a]pyrazin-4-yl)-N-methylazetidin-3-amine methanesulfonic acid salt (226.0 mg, 88%).

LC/MS ESI (+): 334 (M+1), 336 (M+3)

$^1$H-NMR (400 MHz, DMSO-d$_6$); δ: 10.02 (s, 1H), 9.14 (brs, 2H), 8.99 (d, 1H, J=2.3 Hz), 8.67 (d, 1H, J=2.3 Hz), 5.03 (m, 1H), 4.84 (m, 1H), 4.58 (m, 1H), 4.40 (m, 1H), 4.27 (m, 1H), 2.68 (s, 3H), 2.30 (s, 3H)

Example 119

Synthesis of 1-(8-bromopyrido[2,3-e][1,2,4]triazolo[4,3-a]pyrazin-4-yl)-N-methylazetidin-3-amine maleic acid salt Maleic acid (139.0 mg, 1.20 mmol) was slowly added to a suspension of 1-(8-bromopyrido[2,3-e][1,2,4]triazolo[4,3-a]pyrazin-4-yl)-N-methylazetidin-3-amine (200.0 mg, 0.60 mmol) and ethanol (3.0 mL). The reaction mixture was stirred at room temperature for 20 hours. The formed solid was filtered under reduced pressure, washed with ethanol and then dried under reduced pressure to obtain white solid compound of 1-(8-bromopyrido[2,3-e][1,2,4]triazolo[4,3-a]pyrazin-4-yl)-N-methylazetidin-3-amine maleic acid salt (242.0 mg, 90%).

LC/MS ESI (+): 334 (M+1), 336 (M+3)

$^1$H-NMR (400 MHz, DMSO-d$_6$); δ: 10.02 (s, 1H), 8.99 (brs, 2H), 8.98 (d, 1H, J=2.3 Hz), 8.66 (d, 1H, J=2.3 Hz), 6.02 (s, 2H), 5.03 (m, 1H), 4.82 (m, 1H), 4.58 (m, 1H), 4.38 (m, 1H), 4.23 (m, 1H), 2.66 (s, 3H)

Example 120

Synthesis of 1-(8-bromopyrido[2,3-e][1,2,4]triazolo[4,3-a]pyrazin-4-yl)-N-methylazetidin-3-amine 2-hydroxypropane-1,2,3-tricarboxylic acid salt 2-Hydroxypropane-1,2,3-tricarboxylic acid (230.0 mg, 1.20 mmol) was slowly added to a suspension of 1-(8-bromopyrido[2,3-e][1,2,4]triazolo[4,3-a]pyrazin-4-yl)-N-methylazetidin-3-amine (200.0 mg, 0.60 mmol) and THF (6.0 mL). The reaction mixture was stirred at room temperature for 20 hours. The formed solid was filtered under reduced pressure, washed with ethanol and then dried under reduced pressure to obtain white solid compound of 1-(8-bromopyrido[2,3-e][1,2,4]triazolo[4,3-a]pyrazin-4-yl)-N-methylazetidin-3-amine 2-hydroxypropane-1,2,3-tricarboxylic acid salt (246.0 mg, 78%).

LC/MS ESI (+): 334 (M+1), 336 (M+3)

$^1$H-NMR (400 MHz, DMSO-d$_6$); δ: 9.98 (s, 1H), 8.94 (d, 1H, J=2.3 Hz), 8.63 (d, 1H, J=2.3 Hz), 4.96 (m, 1H), 4.62 (m, 1H), 4.50 (m, 1H), 4.18 (m, 1H), 3.95 (m, 1H), 2.55 (m, 4H), 2.47 (s, 3H)

Example 121

Synthesis of 1-(8-bromopyrido[2,3-e][1,2,4]triazolo[4,3-a]pyrazin-4-yl)-N-methylazetidin-3-amine nitric acid salt 70% Nitric acid (13.0 μL, 0.30 mmol) was added to a suspension of 1-(8-Bromopyrido[2,3-e][1,2,4]triazolo[4,3-a]pyrazin-4-yl)-N-methylazetidin-3-amine (50.0 mg, 0.15 mmol) and ethanol (1.5 mL). The reaction mixture was stirred at room temperature for 12 hours. The formed solid was filtered under reduced pressure, washed with ethanol and then dried under reduced pressure to obtain white solid compound of 1-(8-bromopyrido[2,3-e][1,2,4]triazolo[4,3-a]pyrazin-4-yl)-N-methylazetidin-3-amine nitric acid salt (55.8 mg, 94%).

LC/MS ESI (+): 334 (M+1), 336 (M+3)

$^1$H-NMR (400 MHz, DMSO-d$_6$); δ: 10.02 (s, 1H), 9.15 (brs, 2H), 8.98 (d, 1H, J=2.4 Hz), 8.66 (d, 1H, J=2.4 Hz), 5.03 (m, 1H), 4.83 (m, 1H), 4.58 (m, 1H), 4.40 (m, 1H), 4.27 (m, 1H), 2.69 (s, 3H)

Example 122

Synthesis of 1-(8-bromopyrido[2,3-e][1,2,4]triazolo[4,3-a]pyrazin-4-yl)-N-methylazetidin-3-amine hydroiodic acid salt 55% HI (41.0 μL, 0.30 mmol) was added to a suspension of 1-(8-bromopyrido[2,3-e][1,2,4]triazolo[4,3-a]pyrazin-4-yl)-N-methylazetidin-3-amine (50.0 mg, 0.15 mmol) and ethanol (1.5 mL). The reaction mixture was stirred at room temperature for 12 hours. The formed solid was filtered under reduced pressure, washed with ethanol and then dried under reduced pressure to obtain yellow solid compound of 1-(8-bromopyrido[2,3-e][1,2,4]triazolo[4,3-a]pyrazin-4-yl)-N-methylazetidin-3-amine hydroiodic acid salt (60.0 mg, 87%).

LC/MS ESI (+): 334 (M+1), 336 (M+3)

$^1$H-NMR (400 MHz, DMSO-d$_6$); δ: 10.02 (s, 1H), 9.11 (brs, 2H), 8.99 (d, 1H, J=2.0 Hz), 8.67 (d, 1H, J=2.0 Hz), 5.03 (m, 1H), 4.83 (m, 1H), 4.58 (m, 1H), 4.40 (m, 1H), 4.26 (m, 1H), 2.69 (s, 3H)

Example 123

Synthesis of 1-(8-bromopyrido[2,3-e][1,2,4]triazolo[4,3-a]pyrazin-4-yl)-N-methylazetidin-3-amine phosphoric acid salt 85% phosphoric acid (25.9 μL, 0.22 mmol) was slowly added to a suspension of 1-(8-bromopyrido[2,3-e][1,2,4]triazolo[4,3-a]pyrazin-4-yl)-N-methylazetidin-3-amine (50.0 mg, 0.15 mmol) and ethanol (2.0 mL). The reaction mixture was stirred at room temperature for 20 hours. The formed solid was filtered under reduced pressure, washed with ethanol and then dried under reduced pressure to obtain white solid compound of 1-(8-bromopyrido[2,3-e][1,2,4]triazolo[4,3-a]pyrazin-4-yl)-N-methylazetidin-3-amine phosphoric acid salt (59.0 mg, 91%).

LC/MS ESI (+): 334 (M+1), 336 (M+3)

$^1$H-NMR (400 MHz, DMSO-d$_6$); δ: 9.97 (s, 1H), 8.93 (d, 1H, J=2.3 Hz), 8.61 (d, 1H, J=2.3 Hz), 4.94 (m, 1H), 4.59 (m, 1H), 4.48 (m, 1H), 4.15 (m, 1H), 3.90 (m, 1H), 2.42 (s, 3H)

Example 124

Synthesis of 1-(8-bromopyrido[2,3-e][1,2,4]triazolo[4,3-a]pyrazin-4-yl)-N-methylazetidin-3-amine 4,4'-methylenebis(3-hydroxy-2-naphthoic acid) salt Pamoic acid (87.2 mg, 0.22 mmol) was added to a suspension of 1-(8-bromopyrido[2,3-e][1,2,4]triazolo[4,3-a]pyrazin-4-yl)-N-methylazetidin-3-amine (50.0 mg, 0.15 mmol) and ethanol (2.0 mL). The reaction mixture was stirred at room temperature for 20 hours. The formed solid was filtered under reduced pressure, washed with ethanol and then dried under reduced pressure to obtain green solid compound of 1-(8-bromopyrido[2,3-e][1,2,4]triazolo[4,3-a]pyrazin-4-yl)-N-methylazetidin-3-amine 4,4'-methylenebis(3-hydroxy-2-naphthoic acid) salt (95.0 mg, 88%).

LC/MS ESI (+): 334 (M+1), 336 (M+3)

$^1$H-NMR (400 MHz, DMSO-d$_6$); δ: 9.98 (s, 1H), 8.91 (d, 1H, J=2.3 Hz), 8.63 (d, 1H, J=2.3 Hz), 8.35 (s, 2H), 8.14 (m, 2H), 7.79 (m, 2H), 7.30 (m, 2H), 7.15 (m, 2H), 5.04 (m, 1H), 4.91 (m, 1H), 4.74 (s, 2H), 4.59 (m, 1H), 4.47 (m, 1H), 4.29 (m, 1H), 2.72 (s, 3H)

Example 125

Synthesis of 1-(8-bromopyrido[2,3-e][1,2,4]triazolo[4,3-a]pyrazin-4-yl)-N-methylazetidin-3-amine hydrobromic acid salt 33% Hydrogen bromide in acetic acid (41.3 µL, 0.23 mmol) was slowly added to a suspension of 1-(8-bromopyrido[2,3-e][1,2,4]triazolo[4,3-a]pyrazin-4-yl)-N-methylazetidin-3-amine (50.0 mg, 0.15 mmol) and ethanol (1.5 mL). The reaction mixture was stirred at room temperature for 20 hours. The formed solid was filtered under reduced pressure, washed with ethanol and dried under reduced pressure to obtain white solid compound of 1-(8-bromopyrido[2,3-e][1,2,4]triazolo[4,3-a]pyrazin-4-yl)-N-methylazetidin-3-amine hydrobromic acid salt (54.3 mg, 87%).

LC/MS ESI (+): 334 (M+1), 336 (M+3)

$^1$H-NMR (400 MHz, DMSO-d$_6$); δ: 10.04 (s, 1H), 9.23 (brs, 2H), 9.00 (d, 1H, J=2.2 Hz), 8.67 (d, 1H, J=2.2 Hz), 5.05 (m, 1H), 4.87 (m, 1H), 4.59 (m, 1H), 4.43 (m, 1H), 4.29 (m, 1H), 2.69 (s, 3H)

Example 126

Synthesis of 1-(8-bromopyrido[2,3-e][1,2,4]triazolo[4,3-a]pyrazin-4-yl)-N-methylazetidin-3-amine sulfuric acid salt Sulfuric acid solution (22.5 mg, 0.23 mmol) in ethanol (0.5 mL) was slowly added to a suspension of 1-(8-bromopyrido[2,3-e][1,2,4]triazolo[4,3-a]pyrazin-4-yl)-N-methylazetidin-3-amine (50.0 mg, 0.15 mmol) and ethanol (1.0 mL). The reaction mixture was stirred at room temperature for 20 hours. The formed solid was filtered under reduced pressure, washed with ethanol and dried under reduced pressure to obtain white solid compound of 1-(8-bromopyrido[2,3-e][1,2,4]triazolo[4,3-a]pyrazin-4-yl)-N-methylazetidin-3-amine sulfuric acid salt (64.6 mg, 99%).

LC/MS ESI (+): 334 (M+1), 336 (M+3)

$^1$H-NMR (400 MHz, DMSO-d$_6$); δ: 10.03 (s, 1H), 9.20 (brs, 2H), 9.01 (d, 1H, J=2.2 Hz), 8.67 (d, 1H, J=2.2 Hz), 5.05 (m, 1H), 4.86 (m, 1H), 4.60 (m, 1H), 4.43 (m, 1H), 4.29 (m, 1H), 2.69 (t, 3H, J=5.0 Hz)

Example 127

Synthesis of 1-(8-bromopyrido[2,3-e][1,2,4]triazolo[4,3-a]pyrazin-4-yl)-N-methylazetidin-3-amine (2R,3R)-2,3-dihydroxysuccinic acid salt (2R,3R)-2,3-Dihydroxysuccinic acid solution (45 mg, 0.30 mmol) in ethanol (0.5 mL) was slowly added to a suspension of 1-(8-bromopyrido[2,3-e][1,2,4]triazolo[4,3-a]pyrazin-4-yl)-N-methylazetidin-3-amine (50.0 mg, 0.15 mmol) and ethanol (1.0 mL). The reaction mixture was stirred at room temperature for 48 hours. The formed solid was filtered under reduced pressure, washed with ethanol and dried under reduced pressure to obtain white solid compound of 1-(8-bromopyrido[2,3-e][1,2,4]triazolo[4,3-a]pyrazin-4-yl)-N-methylazetidin-3-amine (2R,3R)-2,3-dihydroxysuccinic acid salt (62.9 mg, 86%).

LC/MS ESI (+): 334 (M+1), 336 (M+3)

$^1$H-NMR (400 MHz, DMSO-d$_6$); δ: 9.97 (s, 1H), 8.92 (d, 1H, J=2.2 Hz), 8.60 (d, 1H, J=2.2 Hz), 4.94 (m, 1H), 4.57 (m, 1H), 4.47 (m, 1H), 4.14 (m, 1H), 4.13 (s, 2H), 3.90 (m, 1H), 2.42 (s, 3H)

Example 128

Synthesis of 1-(8-bromopyrido[2,3-e][1,2,4]triazolo[4,3-a]pyrazin-4-yl)-N-methylazetidin-3-amine (1S)-(+)-10-Camphorsulfonic acid salt (1S)-(+)-10-Camphorsulfonic acid (69.5 mg, 0.30 mmol) was added to a suspension of 1-(8-bromopyrido[2,3-e][1,2,4]triazolo[4,3-a]pyrazin-4-yl)-N-methylazetidin-3-amine (50.0 mg, 0.15 mmol) and ethanol (1.5 mL). The reaction mixture was stirred at room temperature for 12 hours. The formed solid was filtered under reduced pressure, washed with ethanol and dried under reduced pressure to obtain white solid compound of 1-(8-bromopyrido[2,3-e][1,2,4]triazolo[4,3-a]pyrazin-4-yl)-N-methylazetidin-3-amine (1S)-(+)-10-Camphorsulfonic acid salt (39.0 mg, 46%).

LC/MS ESI(+): 334 (M+1), 336 (M+3)

$^1$H-NMR (400 MHz, DMSO-d$_6$); δ: 10.03 (s, 1H), 9.03 (brs, 2H), 8.99 (d, 1H, J=2.0 Hz), 8.67 (d, 1H, J=2.0 Hz), 5.04 (m, 1H), 4.84 (m, 1H), 4.59 (m, 1H), 4.40 (m, 1H), 4.25 (m, 1H), 2.86 (d, 1H, J=14.8 Hz), 2.71 (m, 1H), 2.68 (S, 3H), 2.36 (d, 1H, J=14.8 Hz), 2.23 (m, 1H), 1.93 (m, 1H), 1.85 (1H, m), 1.80 (d, 1H, J=18.4 Hz), 1.27 (m, 2H), 1.05 (S, 3H), 0.75 (S, 3H)

Example 129

Synthesis of 8-bromo-N-(1-methylpyrrolidin-3-yl)pyrido[2,3-e][1,2,4]triazolo[4,3-a]pyrazin-4-amine (a) Synthesis of 7-bromo-2-chloro-N-(1-methylpyrrolidin-3-yl)pyrido[2,3-b]pyrazin-3-amine TEA (150.0 µL, 1.07 mmol) was added to a mixture of 7-bromo-2,3-dichloropyrido[2,3-b]pyrazine (100.0 mg, 0.36 mmol), 1-methylpyrrolidin-3-amine (43.0 mg, 0.43 mmol) and DCM (1.8 mL), and the reaction mixture was stirred at room temperature for 5 hours. The reaction mixture was purified by column chromatography (MeOH:DCM=1:40) on amine silica. The fractions containing the product were collected and concentrated to obtain yellow solid compound of 7-bromo-2-chloro-N-(1-methylpyrrolidin-3-yl)pyrido[2,3-b]pyrazin-3-amine (30.0 mg, 24%).

LC/MS ESI (+): 342 (M+1), 344 (M+3)

(b) Synthesis of 8-bromo-N-(1-methylpyrrolidin-3-yl)pyrido[2,3-e][1,2,4]triazolo[4,3-a]pyrazin-4-amine Hydrazine monohydrate (5.5 µL, 0.18 mmol) was added to a suspension of 7-bromo-2-chloro-N-(1-methylpyrrolidin-3-yl)pyrido[2,3-b]pyrazin-3-amine (26.0 mg, 0.06 mmol) and EtOH (1.0 mL). The reaction mixture was stirred at room temperature for 1 hour and then concentrated under reduced pressure. The residue was dissolved in trimethyl orthoformate (1.0 mL), and the reaction mixture was stirred at 100° C. for 5 hours. The reaction mixture was cooled to room temperature and then concentrated under reduced pressure. The residue was purified by column chromatography (MeOH:DCM=1:40) on amine silica. The fractions containing the product were collected and concentrated. Et$_2$O was added to the residue to form a solid. The formed solid was filtered and dried under reduced pressure to obtain yellow solid compound of 8-bromo-N-(1-methylpyrrolidin-3-yl)pyrido[2,3-e][1,2,4]triazolo[4,3-a]pyrazin-4-amine (6.0 mg, 30%).

LC/MS ESI (+): 348 (M+1), 350 (M+3)

¹H-NMR (400 MHz, DMSO-d₆); δ: 9.95 (s, 1H), 8.92 (d, 1H, J=2.0 Hz), 8.78 (m, 1H), 8.61 (d, 1H, J=2.0 Hz), 4.72 (m, 1H), 2.86 (m, 1H), 2.68-2.50 (m, 3H), 2.33-2.10 (m, 4H), 2.01 (m, 1H)

Example 130

Synthesis of 1-(8-bromopyrido[2,3-e][1,2,4]triazolo[4,3-a]pyrazin-4-yl)-N-methylazetidin-3-amine (S)-2-hydroxypropanoic acid salt (S)-2-Hydroxypropanoic acid solution (135.0 mg, 1.50 mmol) in water (0.8 mL) was added to a suspension of 1-(8-bromopyrido[2,3-e][1,2,4]triazolo[4,3-a]pyrazin-4-yl)-N-methylazetidin-3-amine (50.0 mg, 0.15 mmol) and ethanol (0.8 mL). The reaction mixture was stirred at room temperature for 3 hours and then concentrated under reduced pressure. EtOH and Et₂O were added to the residue to form a solid. The resulting solid was filtered, washed with Et₂O and dried under reduced pressure to obtain yellow solid compound of 1-(8-bromopyrido[2,3-e][1,2,4]triazolo[4,3-a]pyrazin-4-yl)-N-methylazetidin-3-amine (S)-2-hydroxypropanoic acid salt (34.0 mg, 53%).

LC/MS ESI (+): 334 (M+1), 336 (M+3)
¹H-NMR (400 MHz, DMSO-d₆); δ: 9.96 (s, 1H), 8.91 (d, 1H, J=2.0 Hz), 8.60 (d, 1H, J=2.0 Hz), 4.91 (m, 1H), 4.45 (m, 2H), 4.02 (m, 2H), 3.75 (m, 1H), 2.33 (s, 3H), 1.22 (m, 3H)

Example 131

Synthesis of N-(azetidin-3-ylmethyl)-8-bromopyrido[2,3-e][1,2,4]triazolo[4,3-a]pyrazin-4-amine trifluoroacetic acid salt (a) Synthesis of tert-butyl 3-(((7-bromo-2-chloropyrido[2,3-b]pyrazin-3-yl)amino)methyl)azetidine-1-carboxylate 7-Bromo-2,3-dichloropyrido[2,3-b]pyrazine (100.0 mg, 0.56 mmol) was dissolved in DCM (5.6 mL), and tert-butyl 3-(aminomethyl)azetidine-1-carboxylate (104.1 mg, 0.56 mmol) and TEA (0.23 mL, 1.68 mmol) were slowly added thereto at 0° C. The reaction mixture was stirred at room temperature for 48 hours and then concentrated under reduced pressure. The residue was purified by column chromatography (n-Hex:EtOAc=70:30) on silica. The fractions containing the product were collected and concentrated to obtain yellow solid compound of tert-butyl 3-(((7-bromo-2-chloropyrido[2,3-b]pyrazin-3-yl)amino)methyl)azetidine-1-carboxylate (72.0 mg, 30%).

LC/MS ESI (+): 428 (M+1)
¹H-NMR (400 MHz, DMSO-d₆); ?: 8.85 (d, 1H, J=2.4 Hz), 8.48 (d, 1H, J=2.4 Hz), 8.20 (t, 1H, J=5.6 Hz), 3.90 (m, 2H), 3.70 (m, 4H), 2.92 (m, 1H), 1.38 (s, 9H)

(b) Synthesis of tert-butyl 3-(((7-bromo-2-hydrazinylpyrido[2,3-b]pyrazin-3-yl)amino)methyl)azetidine-1-carboxylate tert-Butyl 3-(((7-bromo-2-chloropyrido[2,3-b]pyrazin-3-yl)amino)methyl)azetidine-1-carboxylate (50.0 mg, 0.12 mmol) and hydrazine monohydrate (12.0 μL, 0.35 mmol) were dissolved in EtOH (0.6 mL), and the reaction mixture was stirred at room temperature for 1 hour. Et₂O was added thereto to form a solid. The formed solid was filtered and dried under reduced pressure to obtain yellow solid compound of tert-butyl 3-(((7-bromo-2-hydrazinylpyrido[2,3-b]pyrazin-3-yl)amino)methyl)azetidine-1-carboxylate (48.0 mg, 98%).

LC/MS ESI (+): 424 (M+1)

(c) Synthesis of N-(azetidin-3-ylmethyl)-8-bromopyrido[2,3-e][1,2,4]triazolo[4,3-a]pyrazin-4-amine trifluoroacetic acid salt A reaction mixture of tert-butyl 3-(((7-bromo-2-hydrazinylpyrido[2,3-b]pyrazin-3-yl)amino)methyl)azetidine-1-carboxylate (50.0 mg, 0.12 mmol) and trimethyl orthoformate (1.5 mL) was stirred at 70° C. for 12 hours, cooled to room temperature and then dried under reduced pressure to obtain tert-butyl 3-(((8-bromopyrido[2,3-e][1,2,4]triazolo[4,3-a]pyrazin-4-yl)amino)methyl)azetidine-1-carboxylate.
TFA (0.3 mL) was added to mixture of unpurified tert-butyl 3-(((8-bromopyrido[2,3-e][1,2,4]triazolo[4,3-a]pyrazin-4-yl)amino)methyl)azetidine-1-carboxylate and DCM (1.0 mL), and the reaction mixture was then stirred at room temperature for 1 hour. The reaction mixture was concentrated under reduced pressure and the residue was purified by column chromatography (MeOH:DCM=5:95) on amine silica. The fractions containing the product were collected and concentrated to obtain beige solid compound of N-(azetidin-3-ylmethyl)-8-bromopyrido[2,3-e][1,2,4]triazolo[4,3-a]pyrazin-4-amine trifluoroacetic acid salt (1.5 mg, 3% in 2 steps).

LC/MS ESI (+): 334 (M+1)
¹H-NMR (400 MHz, MeOH-d₄); δ: 9.77 (s, 1H), 8.80 (d, 1H, J=2.0 Hz), 8.64 (m, 1H), 3.94 (m, 2H), 3.76 (m, 2H), 3.63 (m, 2H), 3.35 (s, 1H)

Example 132

Synthesis of 4-(azetidin-3-ylmethoxy)-8-bromopyrido[2,3-e][1,2,4]triazolo[4,3-a]pyrazine hydrochloric acid salt (a) Synthesis of tert-butyl 3-(((7-bromo-2-chloropyrido[2,3-b]pyrazin-3-yl)oxy)methyl)azetidine-1-carboxylate 60% NaH (10 mg, 0.25 mmol) was added to a solution of tert-butyl 3-(hydroxymethyl)azetidine-1-carboxylate (47.9 mg, 0.25 mmol) dissolved in THF (2.5 mL) under nitrogen at room temperature. The mixture was stirred at room temperature for 30 minutes, and 7-bromo-2,3-dichloropyrido[2,3-b]pyrazine (60.0 mg, 0.25 mmol) was then added thereto at room temperature. The reaction mixture was stirred at room temperature for 2 hours and diluted with EtOAc. The organic layer was washed with water and brine, dried over anhydrous MgSO₄, filtered and then concentrated under reduced pressure. The residue was purified by column chromatography (n-Hex:EtOAc=2:1) on silica. The fractions containing the product were collected and concentrated to obtain white solid compound of tert-butyl 3-(((7-bromo-2-chloropyrido[2,3-b]pyrazin-3-yl)oxy)methyl)azetidine-1-carboxylate (65.8 mg, 61%).

LC/MS ESI (+): 429 (M+1), 431 (M+3), 451 (M+23), 453 (M+25)
¹H-NMR (400 MHz, CDCl₃); δ: 9.00 (d, 1H, J=2.3 Hz), 8.45 (d, 1H, J=2.3 Hz), 4.79 (d, 2H, J=6.6 Hz), 4.13 (t, 2H, J=8.5 Hz), 3.85 (dd, 2H, J=5.2, 3.6 Hz), 3.13 (m, 1H), 1.45 (s, 9H)

(b) Synthesis of tert-butyl 3-(((8-bromopyrido[2,3-e][1,2,4]triazolo[4,3-a]pyrazin-4-yl)oxy)methyl)azetidine-1-carboxylate Hydrazine monohydrate (14.1 μL, 0.45 mmol) was added to a mixture of tert-butyl 3-(((7-bromo-2-chloropyrido[2,3-b]pyrazin-3-yl)oxy)methyl)azetidine-1-carboxylate (63.8 mg, 0.15 mmol) and EtOH (1.5 mL), and the reaction mixture was stirred at room temperature for 4 hours. The reaction mixture was concentrated under reduced pressure, and unpurified tert-butyl 3-(((7-bromo-2-hydrazinylpyrido[2,3-b]pyrazin-3-yl)oxy)methyl)azetidine-1-carboxylate was dissolved in trimethyl orthoformate (1.5 mL). The reaction mixture was stirred at 80° C. for 4 hours and concentrated under reduced pressure to obtain unpurified brown solid compound of tert-butyl 3-(((8-bromopyrido[2,3-e][1,2,4]triazolo[4,3-a]pyrazin-4-yl)oxy)methyl)azetidine-1-carboxylate.

LC/MS ESI (+): 435 (M+1), 437 (M+3), 457 (M+23), 459 (M+25)

(c) Synthesis of 4-(azetidin-3-ylmethoxy)-8-bromopyrido[2,3-e][1,2,4]triazolo[4,3-a]pyrazine hydrochloride Unpurified tert-butyl 3-(((8-bromopyrido[2,3-e][1,2,4]triazolo[4,3-a]pyrazin-4-yl)oxy)methyl)azetidine-1-carboxylate was dissolved in DCM (1.5 mL), and then 4N HCl of 1,4-dioxane solution (75.0 μL, 0.30 mmol) was slowly added thereto at room temperature. The mixture was stirred at room temperature for 2 hours and then concentrated under reduced pressure. The residue was dissolved in DMSO (0.5 mL) and then purified by prep. HPLC (YL9110S YoungLin, acetonitrile:water=8:92). The fractions containing the product were collected and freeze-dried to obtain white solid compound of 4-(azetidin-3-ylmethoxy)-8-bromopyrido[2,3-e][1,2,4]triazolo[4,3-a]pyrazine hydrochloric acid salt (6.4 mg, 11% in 3 steps).

LC/MS ESI (+): 335 (M+1), 337 (M+3)

$^1$H-NMR (400 MHz, DMSO-d$_6$); δ: 10.05 (s, 1H), 9.15 (d, 1H, J=2.0 Hz), 8.97 (brs, 2H), 8.78 (d, 1H, J=2.0 Hz), 4.79 (d, 2H, J=6.64 Hz), 4.04 (m, 2H), 3.90 (m, 2H), 3.33 (m, 1H)

| Structure | Compound No. |
|---|---|
| 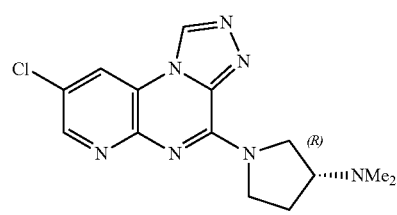 | 9 |
| 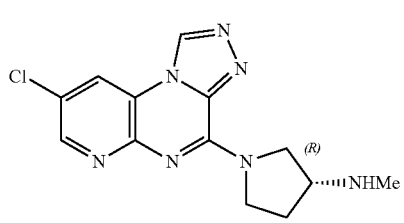 | 10 |
| 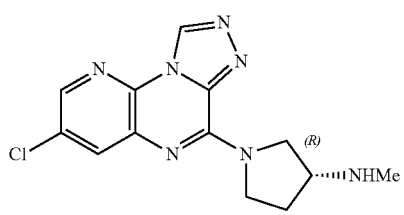 | 11 |
| 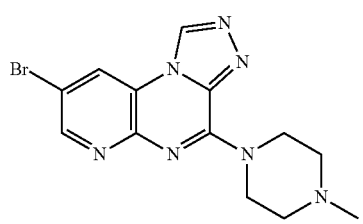 [SMILES: CN1CCN(c2nc3ncc(Br)cc3n3cnnc23)CC1] | 12 |
| 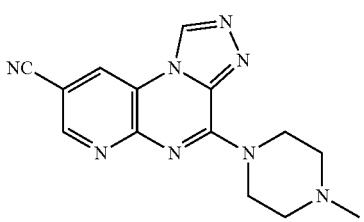 [SMILES: CN1CCN(c2nc3ncc(C#N)cc3n3cnnc23)CC1] | 13 |
| 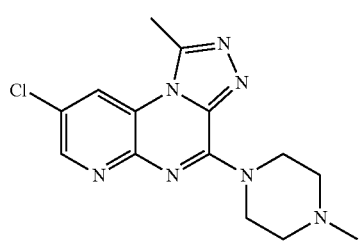 [SMILES: Cc1nnc2c(N3CCN(C)CC3)nc3ncc(Cl)cc3n12] | 14 |
| Structure | Compound No. |
|---|---|
| 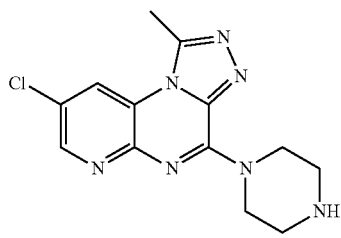 [SMILES: Cc1nnc2c(N3CCNCC3)nc3ncc(Cl)cc3n12] | 15 |
| 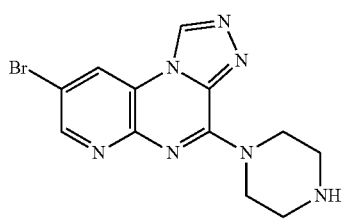 [SMILES: Brc1cnc2nc(N3CCNCC3)c3nncn3c2c1] | 16 |
| 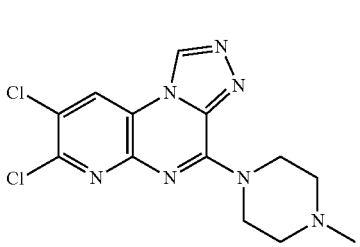 [SMILES: CN1CCN(c2nc3nc(Cl)c(Cl)cc3n3cnnc23)CC1] | 17 |
| 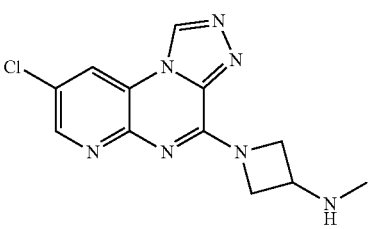 [SMILES: CNC1CN(c2nc3ncc(Cl)cc3n3cnnc23)C1] | 18 |
| 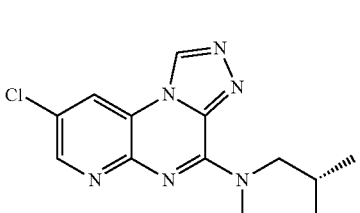 | 19 |
| 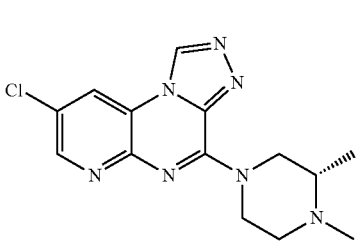 [SMILES: C[C@H]1CN(c2nc3ncc(Cl)cc3n3cnnc23)CCN1C] | 20 |

-continued

| Structure | Compound No. |
|---|---|
| (structure) | 21 |
| (structure) | 22 |
| (structure) | 23 |
| (structure) | 24 |
| (structure) | 25 |
| (structure) | 26 |
| (structure) | 27 |
| (structure) | 28 |
| (structure) | 29 |
| (structure) | 30 |
| (structure) | 31 |
| (structure) | 32 |

-continued
| Structure | Compound No. |
|---|---|
| 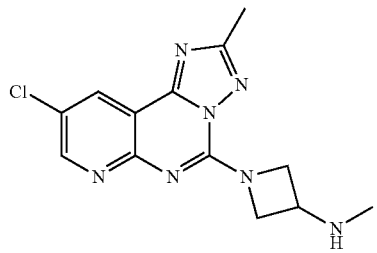 [SMILES: CNC1CN(c2nc3ncc(Cl)cc3c3nc(C)nn23)C1] | 33 |
| 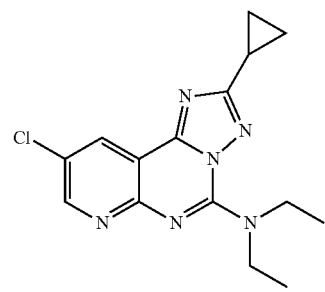 [SMILES: CCN(CC)c1nc2ncc(Cl)cc2c2nc(C3CC3)nn12] | 34 |
| 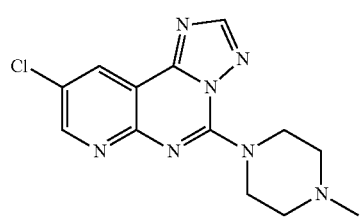 [SMILES: CN1CCN(c2nc3ncc(Cl)cc3c3ncnn23)CC1] | 35 |
| 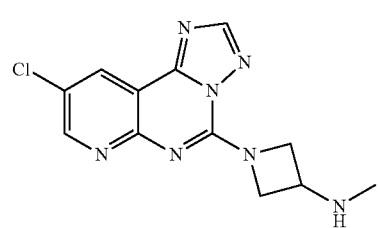 [SMILES: CNC1CN(c2nc3ncc(Cl)cc3c3ncnn23)C1] | 36 |
| 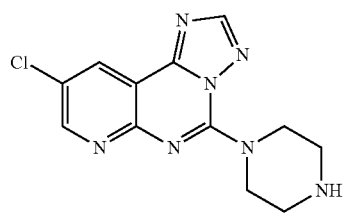 [SMILES: Clc1cnc2nc(N3CCNCC3)n3ncnc3c2c1] | 37 |
| 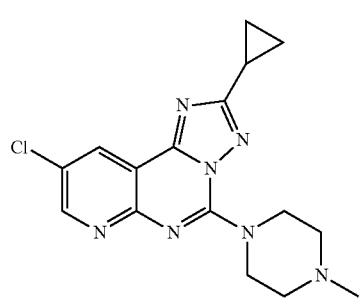 [SMILES: CN1CCN(c2nc3ncc(Cl)cc3c3nc(C4CC4)nn23)CC1] | 38 |
-continued
| Structure | Compound No. |
|---|---|
| 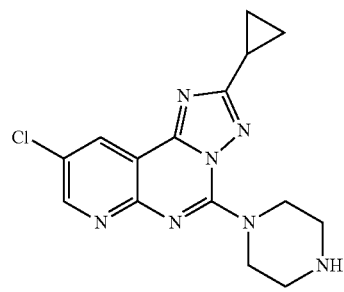 [SMILES: Clc1cnc2nc(N3CCNCC3)n3nc(C4CC4)nc3c2c1] | 39 |
| 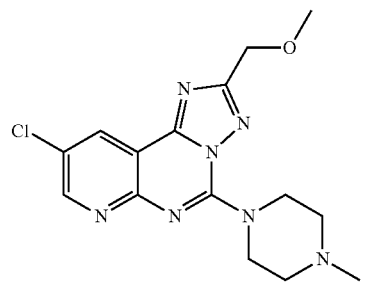 [SMILES: COCc1nc2c3cc(Cl)cnc3nc(N3CCN(C)CC3)n2n1] | 40 |
| 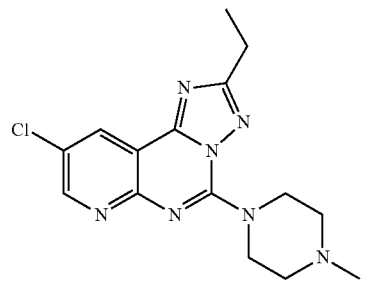 [SMILES: CCc1nc2c3cc(Cl)cnc3nc(N3CCN(C)CC3)n2n1] | 41 |
| 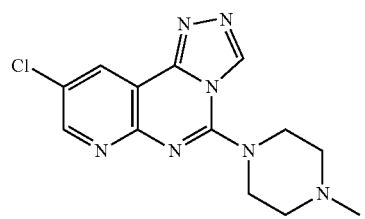 [SMILES: CN1CCN(c2nc3ncc(Cl)cc3c3nncn23)CC1] | 42 |
| 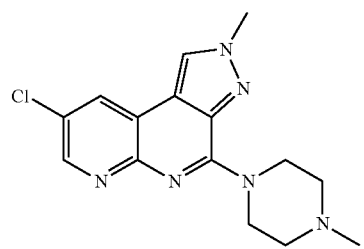 [SMILES: CN1CCN(c2nc3ncc(Cl)cc3c3cn(C)nc23)CC1] | 43 |

-continued

| Structure | Compound No. |
|---|---|
| (structure) | 44 |
| (structure) | 45 |
| (structure) | 46 |
| (structure) | 47 |
| (structure) | 48 |
| (structure) | 49 |

-continued

| Structure | Compound No. |
|---|---|
| (structure) | 50 |
| (structure) | 51 |
| (structure) | 52 |
| (structure) | 53 |
| (structure) | 54 |
| (structure) | 55 |

| Structure | Compound No. |
|---|---|
| 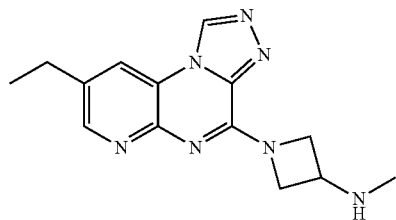 [SMILES: CCc1cnc2nc(N3CC(NC)C3)c3nncn3c2c1] | 56 |
| 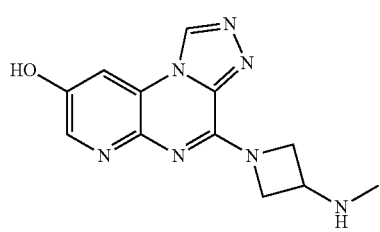 [SMILES: CNC1CN(c2nc3ncc(O)cc3n3cnnc23)C1] | 57 |
| 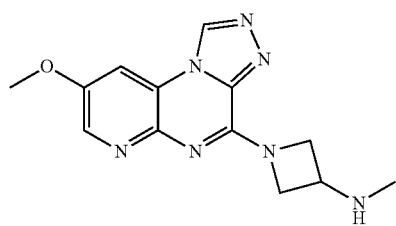 | 58 |
| 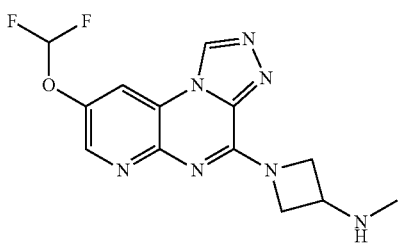 [SMILES: CNC1CN(c2nc3ncc(OC(F)F)cc3n3cnnc23)C1] | 59 |
| 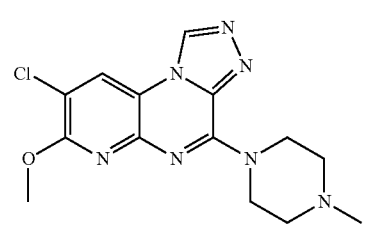 [SMILES: COc1nc2nc(N3CCN(C)CC3)c3nncn3c2cc1Cl] | 60 |
| 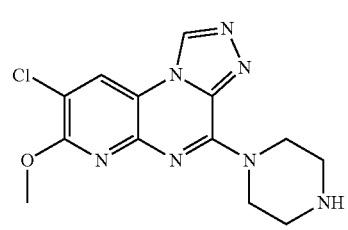 [SMILES: COc1nc2nc(N3CCNCC3)c3nncn3c2cc1Cl] | 61 |
| Structure | Compound No. |
|---|---|
| 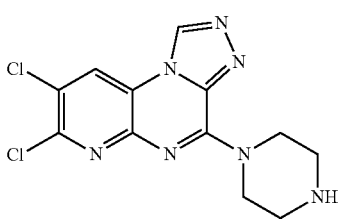 [SMILES: Clc1cc2c(nc1Cl)nc(N1CCNCC1)c1nncn12] | 62 |
| 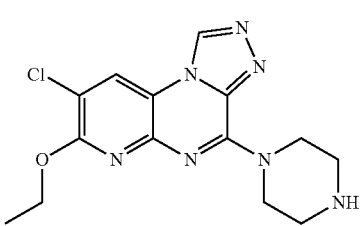 [SMILES: CCOc1nc2nc(N3CCNCC3)c3nncn3c2cc1Cl] | 63 |
| 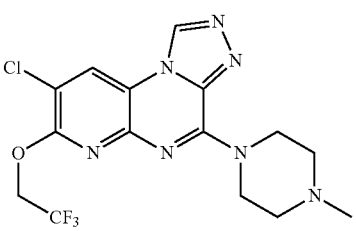 [SMILES: CN1CCN(c2nc3nc(OCC(F)(F)F)c(Cl)cc3n3cnnc23)CC1] | 64 |
| 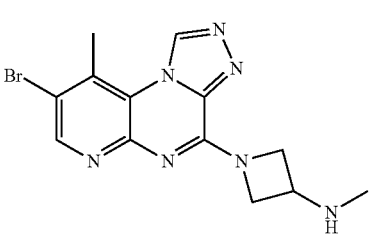 [SMILES: CNC1CN(c2nc3ncc(Br)c(C)c3n3cnnc23)C1] | 65 |
| 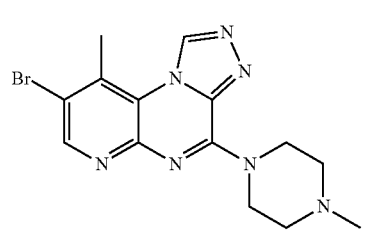 [SMILES: Cc1c(Br)cnc2nc(N3CCN(C)CC3)c3nncn3c12] | 66 |
| 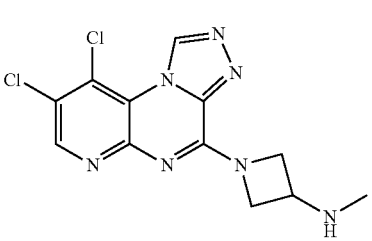 [SMILES: CNC1CN(c2nc3ncc(Cl)c(Cl)c3n3cnnc23)C1] | 67 |

| Structure | Compound No. |
|---|---|
| (structure) | 68 |
| (structure) | 69 |
| (structure) | 70 |
| (structure) | 71 |
| (structure) | 72 |
| (structure) | 73 |
| (structure) | 74 |
| (structure) | 75 |
| (structure) | 76 |
| (structure) | 77 |
| (structure) | 78 |
| (structure) | 79 |

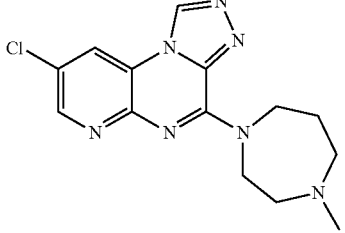
| Structure | Compound No. |
|---|---|
| 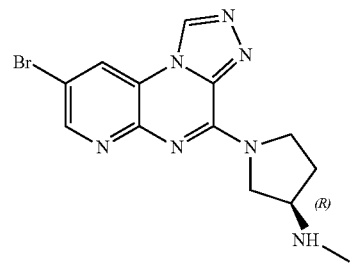 | 80 |
| 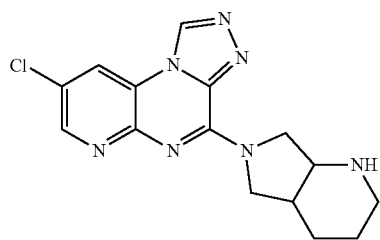 [SMILES: Clc1cnc2nc(N3CC4CCCNC4C3)c3nncn3c2c1] | 81 |
| 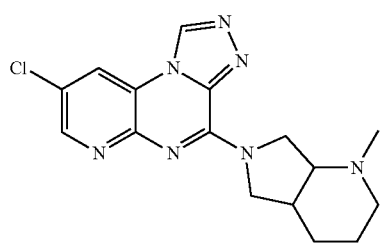 [SMILES: CN1CCCC2CN(c3nc4ncc(Cl)cc4n4cnnc34)CC21] | 82 |
| 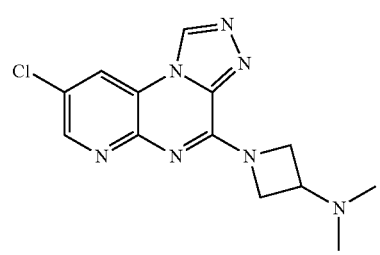 | 83 |
| 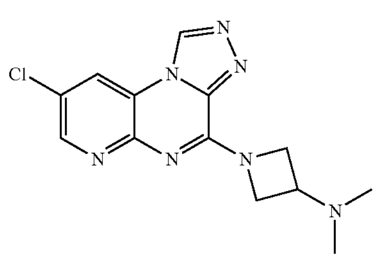 [SMILES: CN(C)C1CN(c2nc3ncc(Cl)cc3n3cnnc23)C1] | 84 |
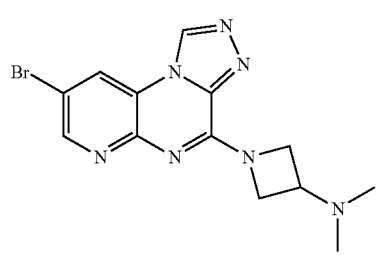
| Structure | Compound No. |
|---|---|
| 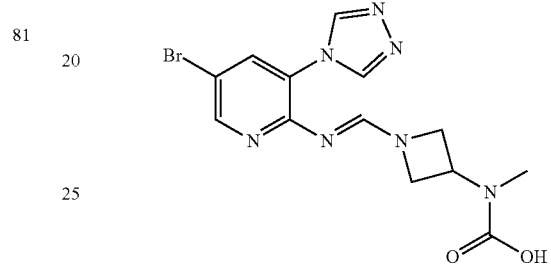 | 85 |
| 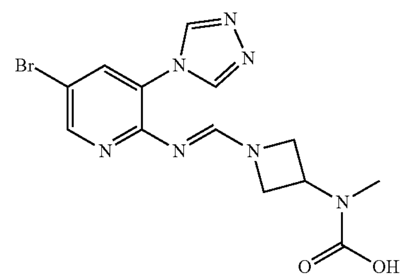 [SMILES: CN(C(=O)O)C1CN(/C=N/c2ncc(Br)cc2-n2cnnc2)C1] | 86 |
| 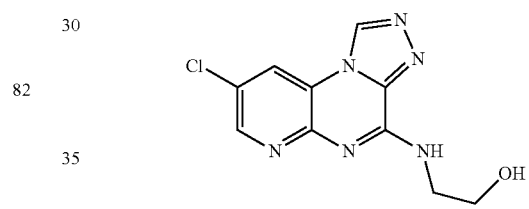 | 87 |
| 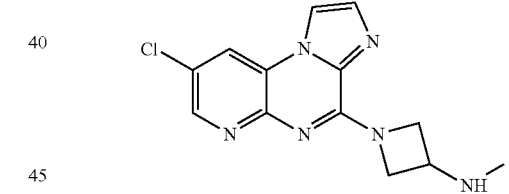 | 88 |
| 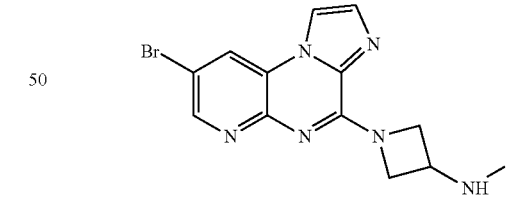 | 89 |
| 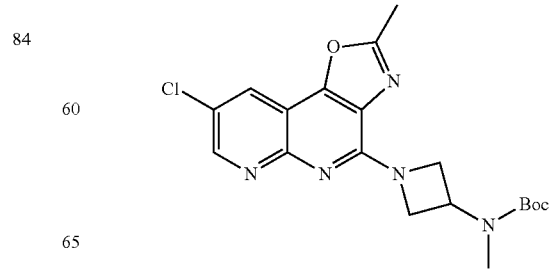 | 90 |

169
-continued
| Structure | Compound No. |
|---|---|
| 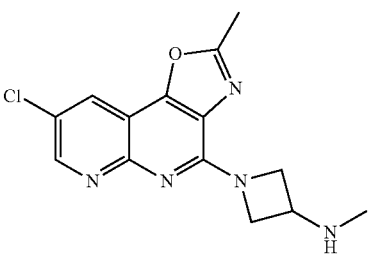 [SMILES: CNC1CN(c2nc3ncc(Cl)cc3c3oc(C)nc23)C1] | 91 |
| 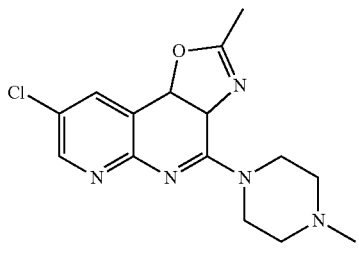 [SMILES: CC1=NC2C(N3CCN(C)CC3)=Nc3ncc(Cl)cc3C2O1] | 92 |
| 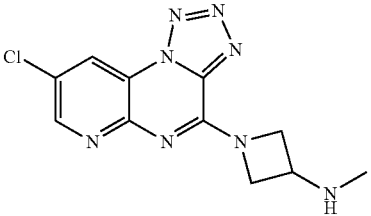 [SMILES: CNC1CN(c2nc3ncc(Cl)cc3n3nnnc23)C1] | 93 |
| 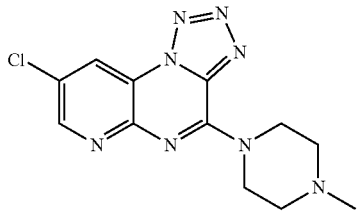 [SMILES: CN1CCN(c2nc3ncc(Cl)cc3n3nnnc23)CC1] | 94 |
| 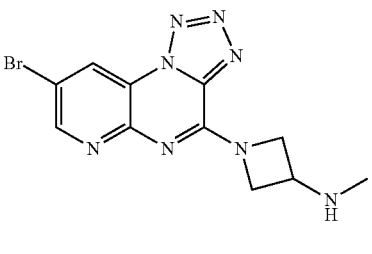 | 95 |
| 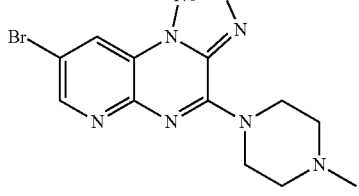 | 96 |
170
-continued
| Structure | Compound No. |
|---|---|
| 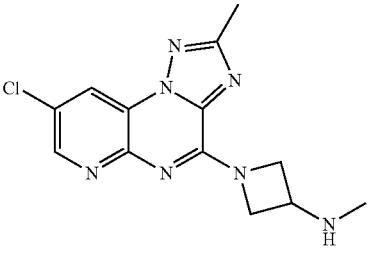 [SMILES: CNC1CN(c2nc3ncc(Cl)cc3n3nc(C)nc23)C1] | 97 |
| 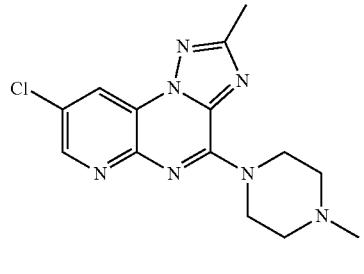 [SMILES: Cc1nc2c(N3CCN(C)CC3)nc3ncc(Cl)cc3n2n1] | 98 |
| 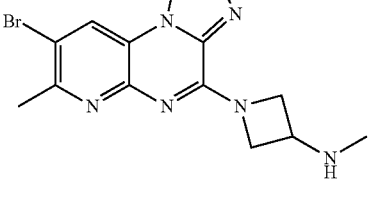 | 99 |
| 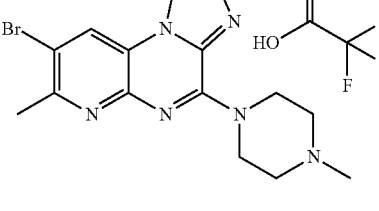 | 100 |
| 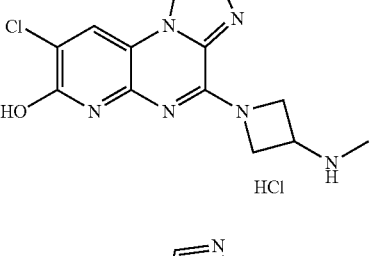 | 101 |
| 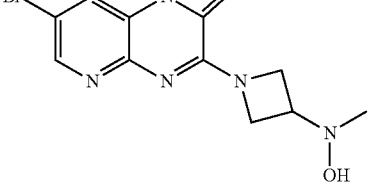 | 102 |

-continued

| Structure | Compound No. |
|---|---|
| (structure) | 103 |
| (structure with TFA) | 104 |
| (structure, (S)-methyl) | 105 |
| (structure, (R)-methyl) | 106 |
| (structure) | 107 |

-continued

| Structure | Compound No. |
|---|---|
| (structure) | 108 |
| (structure) | 109 |
| (structure) | 110 |
| (structure, O$_2$N-) | 111 |
| (structure, H$_2$N-) | 112 |
| (structure, phenyl-) | 113 |

| Structure | Compound No. |
|---|---|
| (structure) | 114 |
| (structure) | 115 |
| (structure) | 116 |
| (structure) | 117 |
| (structure) | 118 |
| (structure) | 119 |

| Structure | Compound No. |
|---|---|
| (structure) | 120 |
| (structure) | 121 |
| (structure) | 122 |
| (structure) | 123 |
| (structure) | 124 |
| (structure) | 125 |

| Structure | Compound No. |
|---|---|
| 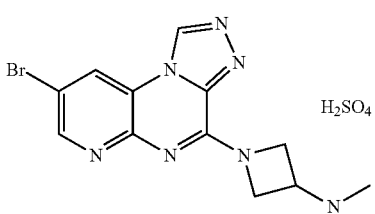 | 126 |
| 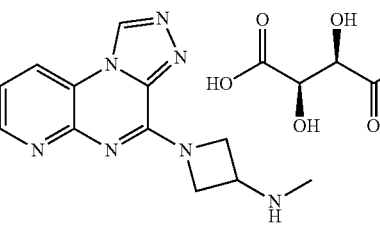 | 127 |
| 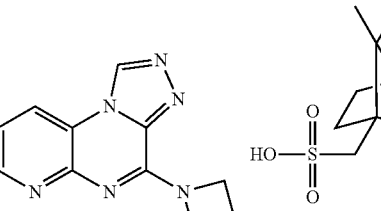 | 128 |
| 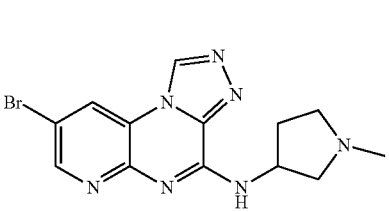 [SMILES: CN1CCC(Nc2nc3ncc(Br)cc3n3cnnc23)C1] | 129 |
| 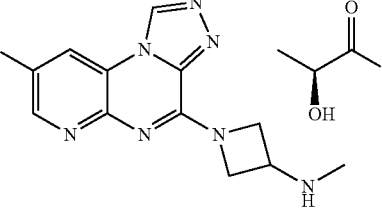 | 130 |
| 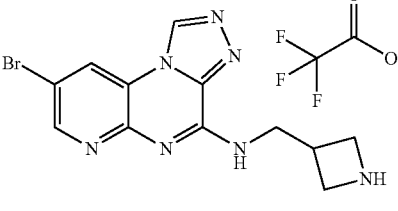 | 131 |
| 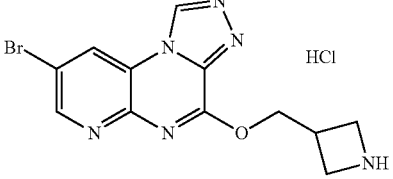 | 132 |

Experimental Example 1

Analysis for Binding Affinity of Human Histamine 4 Receptor (hH4R)

Each compound of the present invention prepared in the examples was diluted by 1000 fold (vw) with DMSO, and then 1 μL of the diluted compound solution was mixed with 99 μL of the analysis buffer solution (50 mM tris-HCl pH 7.4, 5 mM EDTA) to obtain concentrations of 0.1, 0.3, 1, 3, 10 and 100 μM. 20 μL of the prepared compound solution was transferred to each well of a 96-well plate, and then 20 μL of 100 μM histamine diluted with analysis buffer solution and 1% DMSO were transferred to each well to calculate non-specific binding and total binding degree. 25 μg of human histamine 4 receptor-overexpressed cell membrane (PerkinElmer) was diluted into 160 μL of analysis buffer solution and that was transferred to each well. [³H] labeled histamine (PerkinElmer) was diluted into 1 μM concentration, 20 μL was allocated in each well, and then it was kept in a 27° C. incubator for 30 minutes. After the reaction, 200 μL of the mixture was transferred to a glass fiber plate in which 0.5% polyethylene amine was presoaked, and then non-binding [³H] labeled histamine was removed in vacuum. After 4 times washing with 200 μL of washing buffer solution (50 mM tris-HCl, pH 7.4), the plate was dried in a 37° C. oven for 18 hours. 100 μL of betascint cocktail solution was added to each well, and after 1 hour CPM (count per minute) value of [³H] labeled histamine was measured by using Wallac beta-counter TriLux. The binding affinity (IC50) of the human histamine 4 receptor for the present invention was analyzed by an Excel program, and the results of analysis are shown in Table 1.

TABLE 1

| Compound | Binding affinity (IC50) of human histamine 4 receptor (hH4R) |
|---|---|
| Compound 2 | 506 nM |
| Compound 4 | 40 nM |
| Compound 7 | 133 nM |
| Compound 12 | 67 nM |
| Compound 13 | 238 nM |
| Compound 16 | 65 nM |
| Compound 17 | 177 nM |
| Compound 18 | 55 nM |
| Compound 19 | 760 nM |
| Compound 20 | 380 nM |
| Compound 21 | 270 nM |
| Compound 23 | 140 nM |
| Compound 24 | 36 nM |
| Compound 25 | 100 nM |
| Compound 26 | 220 nM |

TABLE 1-continued

| Compound | Binding affinity (IC50) of human histamine 4 receptor (hH4R) |
|---|---|
| Compound 28 | 490 nM |
| Compound 29 | 49 nM |
| Compound 31 | 16 nM |
| Compound 32 | 73 nM |
| Compound 35 | 170 nM |
| Compound 39 | 130 nM |
| Compound 43 | 70 nM |
| Compound 46 | 154 nM |
| Compound 47 | 618 nM |
| Compound 48 | 65 nM |
| Compound 49 | 34 nM |
| Compound 50 | 190 nM |
| Compound 51 | 710 nM |
| Compound 52 | 220 nM |
| Compound 53 | 280 nM |
| Compound 54 | 200 nM |
| Compound 55 | 260 nM |
| Compound 58 | 210 nM |
| Compound 59 | 890 nM |
| Compound 60 | 610 nM |
| Compound 62 | 510 nM |
| Compound 63 | 580 nM |
| Compound 64 | 240 nM |
| Compound 65 | 730 nM |
| Compound 66 | 300 nM |
| Compound 67 | 314 nM |
| Compound 68 | 130 nM |
| Compound 69 | 35 nM |
| Compound 74 | 60 nM |
| Compound 75 | 64 nM |
| Compound 77 | 490 nM |
| Compound 78 | 430 nM |
| Compound 88 | 260 nM |
| Compound 89 | 360 nM |
| Compound 92 | 42 nM |
| Compound 93 | 65 nM |
| Compound 94 | 62 nM |
| Compound 95 | 44 nM |
| Compound 96 | 28 nM |
| Compound 98 | 11 nM |
| Compound 100 | 231 nM |
| Compound 104 | 30 nM |
| Compound 107 | 620 nM |
| Compound 110 | 160 nM |
| Compound 111 | 240 nM |
| Compound 116 | 240 nM |
| Compound 117 | 210 nM |
| Compound disclosed in WO 2010030785, Example 55 | 22 nM |

Experimental Example 2

Analysis for Binding Affinity of Human Histamine 3 Receptor (hH3R)

Each compound of the present invention prepared in the examples was prepared in DMSO into concentrations of 0.02, 0.06, 0.3 and 2 mM. 10 μL of the prepared compound solution was allocated in each well of a 96-well plate, and then 10 μL of 200 μM (R)(−)-α-methylhistamine (RaMH) diluted with analysis buffer and 1% of DMSO were transferred to each well to calculate non-specific binding and total binding degree. 15 μg of human histamine 3 receptor-overexpressed cell membrane (PerkinElmer) was diluted with 180 μL of analysis buffer solution (50 mM tris-HCl pH 7.4, 5 mM MgCl$_2$), and that was transferred to each well. [$^3$H] labeled Na-methylhistamine (PerkinElmer) was diluted into 20 μM concentration, 10 μL of that was added to each well, and then it was kept in a 27° C. incubator for 30 minutes. After the reaction, 200 μL of the mixture was transferred to a glass fiber plate in which 0.5% polyethylene amine was presoaked, and then non-binding [$^3$H] labeled Na-methylhistamine was removed in vacuum. After 5 times washing with 200 μL of washing buffer solution (50 mM tris-HCl, pH 7.4), the plate was dried in a 37° C. oven for 18 hours. 100 μL of betascint cocktail solution was added to each well, and after 1 hour CPM of [$^3$H] labeled N-α-methylhistamine was measured by using Wallac beta-counter TriLux. The binding affinity (IC50) of the human histamine 3 receptor for the present invention was analyzed by an Excel program, and the results of analysis are shown in Table 2.

TABLE 2

| Compound | Binding affinity (IC50) of human histamine 3 receptor (hH3R) |
|---|---|
| Compound 1 | >100 μM |
| Compound 2 | >100 μM |
| Compound 3 | >100 μM |
| Compound 4 | 90 μM |
| Compound 5 | >100 μM |
| Compound 6 | >100 μM |
| Compound 7 | >100 μM |
| Compound 8 | >100 μM |
| Compound 9 | >100 μM |
| Compound 10 | >100 μM |
| Compound 11 | >100 μM |
| Compound 13 | >100 μM |
| Compound 14 | >100 μM |
| Compound 15 | >100 μM |
| Compound 16 | >100 μM |
| Compound 17 | >100 μM |
| Compound 18 | >100 μM |
| Compound 19 | >100 μM |
| Compound 20 | >100 μM |
| Compound 22 | >100 μM |
| Compound 23 | >100 μM |
| Compound 24 | >100 μM |
| Compound 25 | >100 μM |
| Compound 26 | >100 μM |
| Compound 27 | >100 μM |
| Compound 28 | >100 μM |
| Compound 30 | >100 μM |
| Compound 31 | >100 μM |
| Compound 32 | >100 μM |
| Compound 33 | >100 μM |
| Compound 36 | >100 μM |
| Compound 37 | >100 μM |
| Compound 38 | >100 μM |
| Compound 39 | >100 μM |
| Compound 40 | >100 μM |
| Compound 41 | >100 μM |
| Compound 43 | 97 μM |
| Compound 44 | >100 μM |
| Compound 45 | >100 μM |
| Compound 48 | >100 μM |
| Compound 49 | >100 μM |
| Compound 50 | >100 μM |
| Compound 51 | >100 μM |
| Compound 52 | >100 μM |
| Compound 54 | >100 μM |
| Compound 55 | >100 μM |
| Compound 56 | >100 μM |
| Compound 57 | >100 μM |
| Compound 58 | >100 μM |
| Compound 59 | >100 μM |
| Compound 60 | >100 μM |
| Compound 61 | >100 μM |
| Compound 62 | >100 μM |
| Compound 63 | >100 μM |
| Compound 64 | >100 μM |
| Compound 65 | >100 μM |
| Compound 67 | >100 μM |
| Compound 68 | >100 μM |
| Compound 69 | >100 μM |
| Compound 70 | >100 μM |
| Compound 71 | >100 μM |
| Compound 72 | >100 μM |

TABLE 2-continued

| Compound | Binding affinity (IC50) of human histamine 3 receptor (hH3R) |
|---|---|
| Compound 73 | >100 μM |
| Compound 76 | >100 μM |
| Compound 77 | >100 μM |
| Compound 78 | >100 μM |
| Compound 79 | >100 μM |
| Compound 81 | >100 μM |
| Compound 82 | >100 μM |
| Compound 83 | >100 μM |
| Compound 84 | >100 μM |
| Compound 85 | >100 μM |
| Compound 87 | >100 μM |
| Compound 88 | >100 μM |
| Compound 89 | >100 μM |
| Compound 90 | >100 μM |
| Compound 91 | >100 μM |
| Compound 92 | >100 μM |
| Compound 93 | >100 μM |
| Compound 95 | >100 μM |
| Compound 97 | 87 μM |
| Compound 99 | >100 μM |
| Compound 100 | >100 μM |
| Compound 101 | >100 μM |
| Compound 102 | >100 μM |
| Compound 104 | >100 μM |
| Compound 105 | >100 μM |
| Compound 106 | >100 μM |
| Compound 107 | >100 μM |
| Compound 108 | >100 μM |
| Compound 109 | >100 μM |
| Compound 110 | >100 μM |
| Compound 111 | >100 μM |
| Compound 112 | >100 μM |
| Compound 113 | >100 μM |
| Compound 114 | >100 μM |
| Compound 115 | >100 μM |
| Compound 116 | >100 μM |
| Compound 117 | >100 μM |
| Compound disclosed in WO 2010030785, Example 55 | 9.0 μM |

Experimental Example 3

Analysis for Binding Affinity of Human Serotonin 3 Receptor (Human 5-HT3 Receptor)

The binding assays of the human serotonin 3 receptor for present invention were performed at Cerep (Poitiers, France), and the results of analysis are shown in Table 3.

TABLE 3

| Compound | Binding affinity (IC50) of human serotonin 3 receptor (h5-HT3R) |
|---|---|
| Compound 18 | 2.9 μM |
| Compound 24 | 9.1 μM |
| Compound 25 | >10 μM (0%*) |
| Compound 48 | >10 μM (28%*) |
| Compound 93 | >10 μM (18%*) |
| Compound 95 | >10 μM (25%*) |

*indicates % inhibition degree at 10 μM

Experimental Example 4

Test for Solubility in Artificial Gastrointestinal Tract Solution

[First Solution]

2.0 g of sodium chloride was added in 7.0 mL of 37% of hydrochloric acid and water to make the total volume of 1 L. The pH was adjusted to exactly 1.2 with 1N sodium hydroxide or 1N hydrochloric acid. A small amount (20 mL) of this solution was taken and added in 25 μL of triton X-100 to make the total volume of 25 mL.

[Second Solution]

0.348 g sodium hydroxide, 3.438 g $NaH_2PO_4$, 6.186 g sodium chloride and water were added to make the total volume of 1 L. The pH was adjusted to exactly 6.5 with 1N sodium hydroxide or 1N hydrochloric acid. A small amount (20 mL) of this solution was taken and 41.25 mg of sodium taurocholate hydrate and 25 μL of 750 mM lecithin dissolved in ethanol was added to make the total volume of 25 mL.

[Experiment]

For the compound of the present invention prepared in the examples, the test samples were prepared in each of the first and second solutions with 2 mg/mL concentration, and then they were agitated for 1 minute, sonicated for 1 minute and heated at 37° C. for 1 hour for the first solution and 2 hours for the second solution. The heated test sample solutions were filtered to remove undissolved compounds therein. Finally, 100 μL of the completely compound-dissolved solution was sampled and 100 μL of $CH_3CN$ was added thereto to make the test sample solution. For each analysis of the test sample solution, the solubility was measured by using liquid chromatography. The results of the solubility test in the first and second solutions are shown in Table 4.

TABLE 4

| | Solubility (μg/mL) | |
|---|---|---|
| Compound | First solution (pH = 1.2) | Second solution (pH = 6.5) |
| Compound 4 | 2008.9 | 1243.6 |
| Compound 7 | 1373.7 | 1151.2 |
| Compound 12 | 1928.6 | 679.2 |
| Compound 16 | 1932.6 | 758.0 |
| Compound 18 | 1593.9 | 791.2 |
| Compound 19 | 1975.0 | 1695.5 |
| Compound 20 | 2067.6 | 1645.0 |
| Compound 24 | 1690.2 | 939.0 |
| Compound 25 | 1926.5 | 1385.0 |
| Compound 29 | 1558.4 | 1993.3 |
| Compound 31 | 2010.3 | 1978.8 |
| Compound 32 | 1346.4 | 1151.5 |
| Compound 46 | 1912.7 | 1102.8 |
| Compound 48 | 1608.2 | 676.6 |
| Compound 50 | 1986.8 | 1872.6 |
| Compound 52 | 1674.4 | 1464.6 |
| Compound 68 | 1820.3 | 1755.5 |
| Compound 69 | 1813.0 | 1924.9 |
| Compound 74 | 1527.2 | 646.5 |
| Compound 75 | 2003.2 | 722.8 |
| Compound 88 | 1821.3 | 1576.7 |
| Compound 91 | 1836.1 | 1944.6 |
| Compound 93 | 1971.8 | 1305.9 |
| Compound 95 | 1790.7 | 1126.0 |
| Compound 98 | 1702.7 | 1092.0 |
| Compound 104 | 1506.8 | 1559.8 |
| Compound 107 | 1415.2 | 1569.6 |
| Compound 110 | 1871.9 | 708.1 |
| Compound 111 | 1900.7 | 1065.4 |
| Compound 116 | 1939.9 | 960.4 |
| Compound disclosed in WO 2010030785, Example 55 | 1708.3 | 320.1 |

Experimental Example 5

Test for Metabolic Stability

[Preparation of Microsome Solution]

The microsome of 20 mg/mL protein concentration (human, mouse, rat) was diluted with 0.1 M phosphate buffer (pH: 7.4) and prepared into a concentration of 1.316 mg/mL. The compound of the present invention prepared in the examples was dissolved in DMSO to make a 2.5 mM solution, and diluted with distilled water to make a 125 µM solution. The microsome-diluted solution prepared above and the compound-diluted solution was mixed to make the microsome solution in 1.25 mg/mL protein concentration and 6.25 µM compound concentration.

[Preparation of NADPH Solution]

NADPH was dissolved in 0.1 M phosphate buffer to make a 5 mM solution.

[Experiment]

The microsome solution in 6.25 µM concentration of the compound of the present invention prepared in the examples was allocated for each 80 µL, placed in a 37° C. bath and kept for 5 minutes, and then reaction was initiated by adding 20 µL of 5 mM NADPH to make final concentrations of 1 mg/mL microsome protein, 5 µM compound and 1 mM NADPH. The reaction was terminated by adding 100 µL of acetonitrile at 0, 10, 20 and 30 minutes, centrifuged, and then supernatant was analyzed by using liquid chromatography. The half-life was determined using the peak area of the remaining compound at 0, 10, 20 and 30 minutes, and $CL_{h,int}$ parameter representing metabolism stability was then calculated therefrom. The results of the metabolic stability test are shown in Table 5.

TABLE 5

| Compound | Metabolic stability $(CL_{h.int})$(mL/min/mg) | |
| --- | --- | --- |
| | Mouse | Human |
| Compound 4 | 10.22 | 2.20 |
| Compound 7 | 6.90 | $NC^y$ |
| Compound 12 | 14.42 | 3.73 |
| Compound 13 | 3.07 | 2.71 |
| Compound 16 | 10.42 | 4.08 |
| Compound 17 | 17.13 | 5.88 |
| Compound 18 | 1.76 | 4.20 |
| Compound 19 | 26.16 | 0.96 |
| Compound 20 | 7.57 | 1.62 |
| Compound 21 | 7.13 | 4.87 |
| Compound 24 | 3.05 | 1.33 |
| Compound 25 | 4.59 | 4.16 |
| Compound 26 | 6.74 | 2.45 |
| Compound 27 | 7.27 | 1.24 |
| Compound 29 | 12.07 | 3.95 |
| Compound 31 | 28.63 | 5.19 |
| Compound 32 | 8.39 | 1.03 |
| Compound 38 | 14.90 | 7.18 |
| Compound 39 | 5.09 | 2.84 |
| Compound 45 | 12.99 | 3.26 |
| Compound 48 | 5.31 | 0.40 |
| Compound 50 | 9.08 | 1.90 |
| Compound 52 | 2.05 | 1.32 |
| Compound 53 | 3.38 | 2.34 |
| Compound 54 | 0.68 | 1.16 |
| Compound 58 | 12.74 | 2.80 |
| Compound 59 | 1.23 | 1.32 |
| Compound 62 | 7.98 | 4.17 |
| Compound 65 | 6.49 | 3.21 |
| Compound 68 | 3.93 | 0.30 |
| Compound 69 | 14.04 | 5.69 |
| Compound 77 | 0.32 | 1.33 |
| Compound 78 | 1.46 | 2.36 |
| Compound 88 | 11.77 | 2.87 |
| Compound 89 | 10.71 | 3.19 |
| Compound 93 | 9.47 | 4.48 |
| Compound 95 | 18.10 | 5.50 |
| Compound 102 | 6.78 | 1.99 |
| Compound 107 | 8.15 | 5.16 |
| Compound 110 | 1.78 | 3.88 |
| Compound 111 | 5.23 | 4.20 |

TABLE 5-continued

| Compound | Metabolic stability $(CL_{h.int})$(mL/min/mg) | |
| --- | --- | --- |
| | Mouse | Human |
| Compound disclosed in WO 2010030785, Example 55 | 111.63 | 10.99 |

$NC^y$: Not calculable (99.8% remaining in 30 minutes)

Experimental Example 6

Test for Pharmacokinetics

[Preparation of Drug]

The compound of the present invention prepared in the examples was dissolved in 20% hydroxypropyl-β-cyclodextrine solution to make 5 mg/mL administration solution for mice, and DMSO (5%), 5% dextrose solution (94.75%) and 2N hydrochloric acid (0.25%) were added sequentially to make 2 mg/mL administration solution for rats.

[Experiment]

The weight of each ICR mouse and SD rat was properly 20~30 g and 200~300 g, and dosage of the compound of the present invention was 10 mL/kg for mice and 5 mL/kg for rats, and administered orally using Zonde. Blood collection was performed at 0.25, 0.5, 1, 2, 4, 6, 8 and 24 hours by orbital venous blood collection using a capillary tube coated with an anticoagulant, and then plasma was isolated using a centrifuge and kept in a freezer.

[Analysis]

Plasma collected from animals and standard concentration material were pretreated using solid-phase extraction, and concentration of the compound of the invention was determined using a liquid chromatography mass spectrometer (Agilent HPLC, API-3000).

According to the resulting concentration value, the pharmacokinetics parameter was found using WinNonlin (Version 6.2) and half-life ($t_{1/2}$), maximum blood concentration ($C_{max}$) and infinite area under the curve ($AUC_{inf}$) are shown in Tables 6 and 7 below.

TABLE 6

| Compound | Mouse pharmacokinetics | | |
| --- | --- | --- | --- |
| | $t_{1/2}$ (h) | $C_{max}$ (µg/mL) | $AUC_{inf}$ (µg · hr/mL) |
| Compound 4 | 2.21 | 14.87 | 35.58 |
| Compound 7 | 1.28 | 6.57 | 16.49 |
| Compound 16 | 1.18 | 8.27 | 15.90 |
| Compound 18 | 1.32 | 12.29 | 23.71 |
| Compound 24 | 0.96 | 18.87 | 32.17 |
| Compound 25 | 1.17 | 9.76 | 13.98 |
| Compound 31 | 1.79 | 11.66 | 22.36 |
| Compound 32 | 5.39 | 10.07 | 74.90 |
| Compound 48 | 1.46 | 10.21 | 21.62 |
| Compound 93 | 15.56 | 10.85 | 121.23 |
| Compound 95 | 4.03 | 15.43 | 98.33 |
| Compound disclosed in WO 2010030785, Example 55 | 3.49 | 3.84 | 6.65 |

TABLE 7

Rat pharmacokinetics

| Compound | $t_{1/2}$ (h) | $C_{max}$ (µg/mL) | $AUC_{inf}$ (µg · hr/mL) |
|---|---|---|---|
| Compound 4 | 1.88 | 1.95 | 7.74 |
| Compound 7 | 1.62 | 1.33 | 3.11 |
| Compound 18 | 1.04 | 2.59 | 4.56 |
| Compound 24 | 1.30 | 2.42 | 4.51 |
| Compound 25 | 2.21 | 0.97 | 2.92 |
| Compound disclosed in WO 2010030785, Example 55 | 1.09 | 0.49 | 1.06 |

Experimental Example 7

Histamine-Induced Mast Cell Migration

[Animal]

Female, Balb/c mice (7 weeks old, 20±3 g) were purchased from OrientBio Co., Ltd.

The animals were housed under conditions of controlled temperature (23±3° C.), humidity (50±5%) and lighting with food and water available ad libitum.

[Experiment]

Mice were dosed with either vehicle (20% cyclodextrin in second distilled water) or the compound by orally administration. The Compound (20 mg/kg) dissolved in a vehicle and administered orally at a volume of 10 mL/kg. After 15 minutes, mice were challenged by a 20 min aerosol inhalation of PBS (phosphate buffered saline) or 0.1 M histamine (dissolving in PBS). This process was repeated for 2 days. After a final challenge, the tracheae were cleared of blood via perfusion of PBS and tracheae were extracted, the tracheae were fixed in 10% (w/v) formaldehyde for subsequent paraffin cross-sectioning and toluidine blue staining. Total mast cells were calculated, and a mean was reported. (The Journal of Pharmacology and Experimental Therapeutics, 2004, 309, 404-413). The inhibitory effects of the compound are shown in Table 8. Statistical analysis was analyzed using one-way ANOVA with Dunnett test. Values of p<0.05 were considered statistically significant.

Inhibitory effect of the compound (%) =

$$\frac{\left(\text{mast cell } No. \text{ of control group} - \text{mast cell } No. \text{ of normal group}\right) - \left(\text{mast cell } No. \text{ of experimental group} - \text{mast cell } No. \text{ of normal group}\right)}{\left(\text{mast cell } No. \text{ of control group} - \text{mast cell } No. \text{ of normal group}\right)} \times 100$$

TABLE 8

| Compound | Mast cell migration (% change from control group) |
|---|---|
| Compound 4 | 70.3[1] |
| Compound 7 | 43.1[1] |
| Compound 24 | 60.0[1] |
| Compound 25 | 48.4[1] |
| Compound disclosed in WO 2010030785, Example 55 | 23.1[1] |

[1] means statistical significance.

Experimental Example 8

Histamine-Induced Itching Model in ICR Mice

[Animal]

Female, ICR mice (8 weeks old) were purchased from OrientBio Co., Ltd. The animals were housed under conditions of controlled temperature (23±3° C.), humidity (50±5%) and lighting with food and water available ad libitum.

[Experiment: Itch-Inducement and its Measurement]

The hair was clipped using clippers (8000AD, THRIVE) over the rostral part of the back 24 hours before the experiment under anesthesia with isoflurane. Histamine (300 nmol) was dissolved in saline and a volume of 40 µL injected intradermally into the rostral part of the back. Mice were dosed with either vehicle (20% cyclodextrin in second distilled water) or the compound by orally administration. The Compound (50 mg/kg) dissolved in a vehicle (20% cyclodextrin in second distilled water) and administered orally at a volume of 10 mL/kg.

Mice (n=10 per group) were divided into 3 groups (normal group, control group and experimental group). The animals were randomized for similar body weight distribution. A vehicle or the compound was administered 20 minutes before injection of histamine or saline. Immediately after intradermal injection, the animals were returned to an acrylic cage (approximately 30×30×30 cm, access production) composed of four cells, to which they had been acclimated for at least 1 hour before the experiment, for observation of itch responses. A camera (Samsung, VLU-UNV30) was positioned above the mice to record their response. Itch was measured by blinded counting of the number of scratching in the 20 min period immediately after the intradermal injection. A number of scratching was defined as 3 or more individual rapid scratch movements with the hind paws around the injection site (J. Allergy Clin. Immunol. 2007, 19(1), 176-183). All data were analyzed by using Excel and Prism, and all values are expressed as the mean±S.E.M. The inhibitory effect of compounds is shown as a percentage of the maximal response to histamine (100% control group).

Statistical analysis was analyzed using one-way ANOVA with Dunnett test. Values of p<0.05 were considered statistically significant. The inhibitory effects of the compound are shown in Table 9.

Inhibitory effect of the compound (%) =

$$\frac{\text{Number of scratching of control group} - \text{Number of scratching of experimental group}}{\text{Number of scratching of control group}} \times 100$$

TABLE 9

| Compound | Number of scratching (% changes from control group) |
|---|---|
| Compound 4 | 94.3[1] |
| Compound 7 | 61.2[1] |
| Compound 18 | 84.3[1] |
| Compound 24 | 93.6[1] |
| Compound 31 | 89.3[1] |
| Compound 48 | 67.3[1] |
| Compound 95 | 98.2[1] |

[1] means statistical significance.

Experimental Example 9

Substance P-Induced Itching Model in ICR Mice

[Animal]

Female, ICR mice (8 weeks old) were purchased from OrientBio Co., Ltd. The animals were housed under conditions of controlled temperature (23±3° C.), humidity (50±5%) and lighting with food and water available ad libitum.

[Experiment: Itch-Inducement and its Measurement]

The hair was clipped using clippers (8000AD, THRIVE) over the rostral part of the back 24 hours before the experiment under anesthesia with isoflurane. Substance P (100 nmol) was dissolved in saline and a volume of 40 μL injected intradermally into the rostral part of the back. Mice were dosed with either vehicle (20% cyclodextrin in second distilled water) or the compound by orally administration. The Compound (50 mg/kg) dissolved in a vehicle (20% cyclodextrin in second distilled water) and administered orally at a volume of 10 mL/kg.

Mice (n=10 per group) were divided into 3 groups (normal group, control group and experimental group). The animals were randomized for similar body weight distribution. A Vehicle or the compound was administered 20 minutes before injection of substance P or saline. Immediately after intradermal injection, the animals were returned to an acrylic cage (approximately 30×30×30 cm, access production) composed of four cells, to which they had been acclimated for at least 1 hour before the experiment, for observation of itch responses. A camera (Samsung, VLU-UNV30) was positioned above the mice to record their response. Itch was measured by blinded counting of the number of scratching in the 20 min period immediately after the intradermal injection. A number of scratching was defined as 3 or more individual rapid scratch movements with the hind paws around the injection site (J. Toxicol. Sci. 2009, 34(4), 427-431; J. Pharmacol. Sci. 2006, 100, 285-288). All data were analyzed by using Excel and Prism, and all values are expressed as the mean±S.E.M. The inhibitory effect of compounds is shown as a percentage of the maximal response to histamine (100% control group). Statistical analysis was analyzed using one-way ANOVA with Dunnett test. Values of p<0.05 were considered statistically significant. The inhibitory effects of the compound are shown in Table 10.

$$\text{Inhibitory effect of the compound (\%)} = \frac{\text{Number of scratching of control group} - \text{Number of scratching of experimental group}}{\text{Number of scratching of control group}} \times 100$$

TABLE 10

| Compound | Number of scratching (% change from control group) |
|---|---|
| Compound 4 | 50.8 |
| Compound 7 | 60.5[1] |
| Compound 18 | 42.6 |
| Compound 24 | 74.5[1] |
| Compound 48 | 33.5 |
| Compound 95 | 80.7[1] |

[1]means statistical significance.

Experimental Example 10

Compound 48/80-Induced Itching Model in ICR Mice

[Animal]

Female, ICR mice (8 weeks old) were purchased from OrientBio Co., Ltd. The animals were housed under conditions of controlled temperature (23±3° C.), humidity (50±5%) and lighting with food and water available ad libitum.

[Experiment: Itch-Inducement and its Measurement]

The hair was clipped using clippers (8000AD, THRIVE) over the rostral part of the back 24 hours before the experiment under anesthesia with isoflurane. Compound 48/80 (100 μg) were dissolved in saline and a volume of 40 μL injected intradermally into the rostral part of the back. Mice were dosed by orally with either vehicle (20% cyclodextrin in second distilled water) or the compound by orally administration. The Compound (50 mg/kg) dissolved in a vehicle (20% cyclodextrin in second distilled water) and administered orally at a volume of 10 mL/kg.

Mice (n=8-10 per group) were divided into 3 groups (normal group, control group and experimental group). The animals were randomized for similar body weight distribution. A vehicle or the compound was administered 20 minutes before injection of compound 48/80 or saline. Immediately after intradermal injection, the animals were returned to an acrylic cage (approximately 30×30×30 cm, access production) composed of four cells, to which they had been acclimated for at least 1 hour before the experiment, for observation of itch responses. A camera (Samsung, VLUUNV30) was positioned above the mice to record their response. Itch was measured by blinded counting of the number of bouts in the 20 min period immediately after the intradermal injection. A number of scratching was defined as 3 or more individual rapid scratch movements with the hind paws around the injection site (J. Pharmacol. Sci. 2006, 100, 285-288; European J. of Pharmacol. 2002, 448, 175-183). All data were analyzed by using Excel and Prism, and all values are expressed as the mean±S.E.M. The inhibitory effect of compounds is shown as a percentage of the maximal response to histamine (100% control group). Statistical analysis was analyzed using one-way ANOVA with Dunnett test. Values of p<0.05 were considered statistically significant. The inhibitory effects of the compound are shown in Table 11.

$$\text{Inhibitory effect of the compound (\%)} = \frac{\text{Number of scratching of control group} - \text{Number of scratching of experimental group}}{\text{Number of scratching of control group}} \times 100$$

TABLE 11

| Compound | Number of scratching (% change from control group) |
|---|---|
| Compound 4 | 49.6[1] |
| Compound 18 | 50.9[1] |
| Compound 24 | 47.9[1] |
| Compound 48 | 30.3 |
| Compound 95 | 93.6[1] |

[1]means statistical significance.

Experimental Example 11

Oxazolone-Induced Atopic Dermatitis Model in Balb/c Mice

[Animal]

Female, Balb/c mice (6 weeks old, 20±3 g) were purchased from OrientBio Co., Ltd. The animals were housed under conditions of controlled temperature (23±3° C.), humidity (50±5%) and lighting with food and water available ad libitum.

[Experiment]

On the beginning day (day 1), mice were sensitized by the topical application of 50 μL of 1% oxazolone in acetone and olive oil (4:1 ratio) on the abdominal skin. On day 8, 10, 12, 15, 17, 19, 22, 24 and 26, 25 μL of 0.2% oxazolone was applied topically on the inner side of right ear of each mouse. Between days 8 and 28, the compound of the invention was administered orally (10 mL/kg) twice a day in the morning and afternoon, and on days 12, 19 and 27, the thickness of the right ear of the mouse was measured. On day 28, the ear tissue of the mouse was extracted, fixed in 10% formalin solution, and then a tissue slide was prepared, stained with H&E (hematoxylin & eosin), and then the thickness of the ear was observed (Journal of Investigative Dermatology, 2008, 128, 79-86). Statistical analysis was analyzed using one-way ANOVA with Dunnett test. Values of p<0.05 were considered statistically significant. The inhibitory effects of the compounds of are shown in Table 12.

Inhibitory effect of the compound (%) =

$$\frac{\left(\begin{array}{c}\text{Ear thickness of control group} -\\ \text{Ear thickness of normal group}\end{array}\right) - \left(\begin{array}{c}\text{Ear thickness of experimental group} -\\ \text{Ear thickness of normal group}\end{array}\right)}{\left(\begin{array}{c}\text{Ear thickness of control group} -\\ \text{Ear thickness of normal group}\end{array}\right)} \times 100$$

TABLE 12

| Compound | Ear epidermis thickness (% change from control group) |
|---|---|
| Compound 4 (100 mg/kg, BID) | 47.2 |
| Compound 24 (100 mg/kg, BID) | 51.2[1] |
| Compound 95 (50 mg/kg, BID) | 34.9 |
| Compound disclosed in WO 2010030785, Example 55 (100 mg/kg, BID) | 8.0 |

[1]means statistical significance.

Experimental Example 12

Determination of Pharmacological Effect in Dermatophagoides Farina External Application-Induced Atopic Dermatis NC/Nga Mouse

[Animal]

Female, NC/Nga mice (3 weeks old, 15-17 g) were purchased from Central Lab. Animal Inc. The animals were housed in conditions of controlled temperature (23±3° C.), humidity (50±5%) and lighting with food and water available ad libitum.

[Experiment]

The hair of back of the mice was shaved with clipper, and the remaining hair was removed completely using shaving cream. For barrier disruption, 150 μL of 4% sodium dodecyl sulfate (SDS) was applied to the shaved back skin The Df ointment (100 mg/mouse) was applied twice a week for 3 weeks. The compound were administered orally twice a day in the morning and afternoon for 3 weeks, and then the severity of dermatitis was evaluated on days 2, 7, 10, 14 and 21. The development of (1) erythema/haemorrhage, (2) scarring/dryness, (3) oedema, (4) excoriation/erosion was scored as 0 (none), 1 (mild), 2 (moderate) and 3 (severe). The total skin score was defined as the sum of the individual scores. (Scandinavian Journal of Immunol. 2011, 73, 536-545). Statistical analysis was analyzed using one-way ANOVA with Dunnett test. Values of p<0.05 were considered statistically. Skin lesions improvement effects are shown in Table 13.

TABLE 13

| Compound | Scoring of Skin lesions (day 21) |
|---|---|
| Normal group (non-Df) | 0.0 |
| Control group (Df) | 9.0 |
| Compound 24 (25 mg/kg, BID) | 7.2 |
| Compound 24 (50 mg/kg, BID) | 4.4[1] |

[1]means statistical significance.

As indicated above, the compound of the present invention was substantially improved in solubility and metabolic stability as compared with conventional drugs. As results of comparative analysis of pharmacokinetics using ICR mouse and SD rat animal models as compared with the compound disclosed in WO 2010/030785, the compound of the present invention showed superior effects in pharmacokinetic profile such as AUC and maximum blood concentration, 7-8 times as much as the comparison compound. It was found that the histamine-induced migration of inflammatory cells such as mast cells and eosinophils is mediated by the histamine 4 receptor (The Journal of Pharmacology and Experimental Therapeutics, 2003, 305, 1212-1221), and histamine 4 receptor antagonists could have an anti-inflammatory effect by a suppression of the increase of inflammatory cells. According to the improvement of the pharmacokinetic profile, the compound of the present invention showed superior pharmacological effects, 3 times as much as the compound disclosed in WO 2010/030785 as the result of an experiment for suppression of migration into the trachea of mast cells by histamine. The compound of the present invention showed strong anti-pruritic effects in the histamine-induced itch model and the like, and strong anti-inflammatory effects in oxazolone-induced atopic model which is one of the human mimics (J. Invest. Dermatol. 2008, 128, 79-86) compared with the compound disclosed in WO 2010/030785.

In addition, the compound of the present invention showed the same or stronger effects on skin appearance improvement in NC/Nga mice atopic model which is the human mimics (J. Clin. Invest. 1999, 104, 1097-1105), as compared with Tacrolimus which is currently used as an atopy drug. Accordingly, it is expected to be very effective for treating atopy patients.

The invention claimed is:
1. A compound of formula 1:

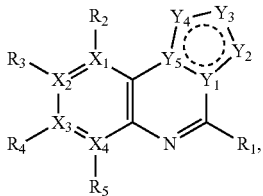

or a pharmaceutically acceptable salt or stereoisomer thereof,
wherein formula 1 is selected from the group consisting of:

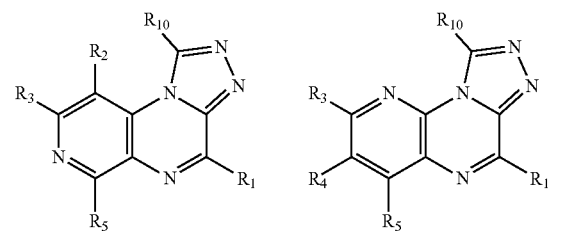

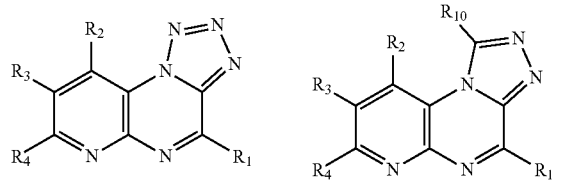

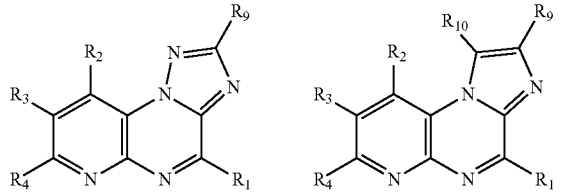

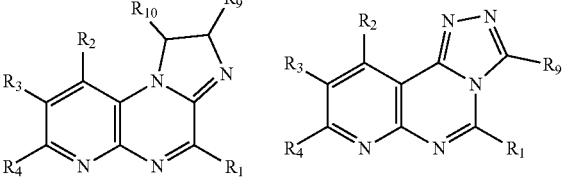

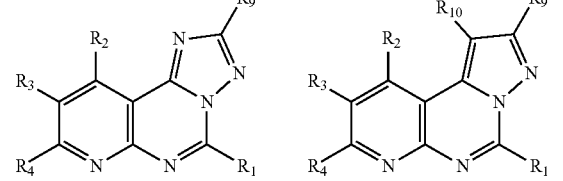

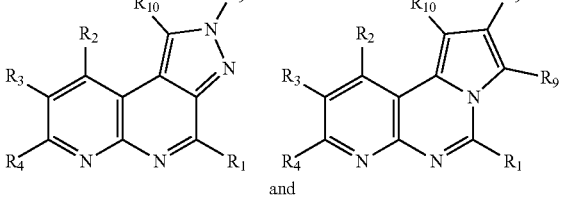

and

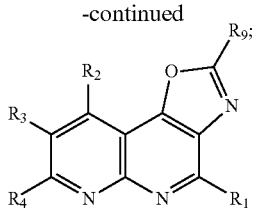

wherein:
$R_1$ is a saturated or unsaturated 3-12 membered monocyclic or polycyclic heterocyclyl containing 1-3 heteroatoms, where $R_1$ is optionally substituted with 1-3 substituents selected from the group consisting of —$NR_6R_7$, —$C_1$-$C_6$alkyl-$NR_6R_7$, —$C_1$-$C_6$alkyl, -amino and $R_8$; or $R_1$ is —$NR_6R_7$ or $R_8$;

$R_2$ is —H, —$C_1$-$C_6$alkyl, $C_1$-$C_6$haloalkyl, —$C_1$-$C_6$perhaloalkyl, -amino-$C_1$-$C_6$alkyl, —$C_3$-$C_8$cycloalkyl, -halogen, —CN, —$C_1$-$C_6$alkoxy, —$C_1$-$C_6$haloalkoxy, —$C_1$-$C_6$perhaloalkoxy, —$C_2$-$C_7$alkenyl, —$C_2$-$C_8$alkynyl, -amino, -amido, —$C_1$-$C_6$alkylcarboxy, -carboxy, —$C_1$-$C_6$acyl, —OH, -nitro, —$C_6$-$C_{10}$aryl, -heterocyclyl or —O—$C_1$-$C_6$alkyl-heterocyclyl, where the heterocyclyl is a saturated or unsaturated 3-6 membered heterocyclyl containing 1-3 heteroatoms;

$R_3$ is —H, —$C_1$-$C_6$alkyl, $C_1$-$C_6$haloalkyl, —$C_1$-$C_6$perhaloalkyl, -amino-$C_1$-$C_6$alkyl, —$C_3$-$C_8$cycloalkyl, -halogen, —CN, —$C_1$-$C_6$alkoxy, —$C_1$-$C_6$haloalkoxy, —$C_1$-$C_6$perhaloalkoxy, —$C_2$-$C_7$alkenyl, —$C_2$-$C_8$alkynyl, -amino, -amido, —$C_1$-$C_6$alkylcarboxy, -carboxy, —$C_1$-$C_6$acyl, —OH, -nitro, —$C_6$-$C_{10}$aryl, -heterocyclyl or —O—$C_1$-$C_6$alkyl-heterocyclyl, where the heterocyclyl is a saturated or unsaturated 3-6 membered heterocyclyl containing 1-3 heteroatoms;

$R_4$ is —H, —$C_1$-$C_6$alkyl, $C_1$-$C_6$haloalkyl, —$C_1$-$C_6$perhaloalkyl, -amino-$C_1$-$C_6$alkyl, —$C_3$-$C_8$cycloalkyl, -halogen, —CN, —$C_1$-$C_6$alkoxy, —$C_1$-$C_6$haloalkoxy, —$C_1$-$C_6$perhaloalkoxy, —$C_2$-$C_7$alkenyl, —$C_2$-$C_8$alkynyl, -amino, -amido, —$C_1$-$C_6$alkylcarboxy, -carboxy, —$C_1$-$C_6$acyl, —OH, -nitro, —$C_6$-$C_{10}$aryl, -heterocyclyl or —O—$C_1$-$C_6$alkyl-heterocyclyl, where the heterocyclyl is a saturated or unsaturated 3-6 membered heterocyclyl containing 1-3 heteroatoms;

$R_5$ is —H, —$C_1$-$C_6$alkyl, $C_1$-$C_6$haloalkyl, —$C_1$-$C_6$perhaloalkyl, -amino-$C_1$-$C_6$alkyl, —$C_3$-$C_8$cycloalkyl, -halogen, —CN, —$C_1$-$C_6$alkoxy, —$C_1$-$C_6$haloalkoxy, —$C_1$-$C_6$perhaloalkoxy, —$C_2$-$C_7$alkenyl, —$C_2$-$C_8$alkynyl, -amino, -amido, —$C_1$-$C_6$alkylcarboxy, -carboxy, —$C_1$-$C_6$acyl, —OH, -nitro, —$C_6$-$C_{10}$aryl, -heterocyclyl or —O—$C_1$-$C_6$alkyl-heterocyclyl, where the heterocyclyl is a saturated or unsaturated 3-6 membered heterocyclyl containing 1-3 heteroatoms;

$R_6$ is —H, —$C_1$-$C_6$alkyl, —$C_3$-$C_8$cycloalkyl, -heterocyclyl, —$NHC_1$-$C_6$alkyl, —$N(C_1$-$C_6$alkyl$)_2$, —$C_1$-$C_6$alkyl-$NHC_1$-$C_6$alkyl, —$C_1$-$C_6$alkyl-$N(C_1$-$C_6$alkyl$)_2$, —$C_1$-$C_6$alkylheterocyclyl, —$C_1$-$C_6$alkylcarboxy or -carboxy, where the heterocyclyl is a saturated or unsaturated 3-6 membered heterocyclyl containing 1-3 heteroatoms;

$R_7$ is —$C_1$-$C_6$alkyl, —$C_3$-$C_8$cycloalkyl, -heterocyclyl, —$NHC_1$-$C_6$alkyl, —$N(C_1$-$C_6$alkyl$)_2$, —$C_1$-$C_6$alkyl- NHC$_1$-C$_6$alkyl, —C$_1$-C$_6$alkyl-N(C$_1$-C$_6$alkyl)$_2$, —C$_1$-C$_6$alkylheterocyclyl, —C$_1$-C$_6$alkylcarboxy or carboxy, where the heterocyclyl is a saturated or unsaturated 3-6 membered heterocyclyl containing 1-3 heteroatoms;

R$_8$ is —C$_1$-C$_6$alkyl-amino, —C$_3$-C$_8$cycloalkyl, —S—C$_1$-C$_6$alkyl-NHC$_1$-C$_6$alkyl, —S—C$_1$-C$_6$alkyl-N(C$_1$-C$_6$alkyl)$_2$, —S—C$_1$-C$_6$alkyl-heterocyclyl or —O—C$_1$-C$_6$alkyl-heterocyclyl, where the heterocyclyl is a saturated or unsaturated 3-6 membered heterocyclyl containing 1-3 heteroatoms;

R$_9$ is —H, —OH, —C$_1$-C$_6$alkyl, C$_1$-C$_6$haloalkyl, —C$_1$-C$_6$perhaloalkyl, —NHC$_1$-C$_6$alkyl, N(C$_1$-C$_6$alkyl)$_2$, —C$_3$-C$_7$cycloalkyl, -heterocyclyl, —C$_6$-C$_{10}$aryl, -5-12 membered heteroaryl, —C$_1$-C$_6$alkoxy, —C$_1$-C$_6$haloalkoxy, -halogen, -amino, -amido, —C$_1$-C$_6$acyl, —CN, -carboxy, —C$_1$-C$_6$alkylcarboxy or -nitro; and R$_{10}$ is —H or —C$_1$-C$_6$alkyl;

wherein each alkyl, cycloalkyl, heterocyclyl, alkoxy, alkenyl, alkynyl, acyl and aryl is independently and optionally substituted with one or more substituents selected from the group consisting of —C$_1$-C$_4$alkyl, -halogen, —CN, —C$_1$-C$_4$alkoxy, -amino, -amido, -carboxy, —C$_1$-C$_6$acyl, —OH, -nitro, -heterocyclyl and -phenyl, where the heterocyclyl is a saturated or unsaturated 3-6 membered heterocyclyl containing 1-3 heteroatoms.

2. The compound according to claim 1, or a pharmaceutically acceptable salt or stereoisomer thereof, wherein:
R$_1$ is a saturated or unsaturated 3-8 membered monocyclic or polycyclic heterocyclyl containing 1-3 heteroatoms, where R$_1$ is optionally substituted with 1-3 substituents selected from the group consisting of —NR$_6$R$_7$, —C$_1$-C$_6$alkyl-NR$_6$R$_7$, —C$_1$-C$_6$alkyl, -amino and R$_8$.

3. The compound according to claim 1, or a pharmaceutically acceptable salt or stereoisomer thereof, wherein:
R$_3$ is —H, —C$_1$-C$_6$alkyl, C$_1$-C$_6$haloalkyl, —C$_1$-C$_6$perhaloalkyl, -halogen, —CN, —C$_1$-C$_6$alkoxy, —C$_1$-C$_6$haloalkoxy, —C$_1$-C$_6$perhaloalkoxy, —C$_2$-C$_7$alkenyl, —C$_2$-C$_8$alkynyl or —OH.

4. The compound according to claim 1, or a pharmaceutically acceptable salt or stereoisomer thereof, wherein:
X$_1$ is C;
X$_3$ is C or N;
X$_4$ is C or N;
with the proviso that at least one of X$_3$ and X$_4$ is N;
R$_1$ is a saturated or unsaturated 3-12 membered monocyclic or polycyclic heterocyclyl containing 1-3 heteroatoms, where R$_1$ is optionally substituted with 1-3 substituents selected from the group consisting of —NR$_6$R$_7$, —C$_1$-C$_6$alkyl-NR$_6$R$_7$ and R$_8$; or
R$_1$ is —NR$_6$R$_7$ or R$_8$;
R$_2$ is —H, —C$_1$-C$_6$alkyl, C$_1$-C$_6$haloalkyl, —C$_1$-C$_6$perhaloalkyl, -halogen, —CN, —C$_1$-C$_6$alkoxy, —C$_1$-C$_6$haloalkoxy, —C$_1$-C$_6$perhaloalkoxy, —C$_2$-C$_7$alkenyl, —C$_2$-C$_8$alkynyl or —OH;
R$_3$ is —H, —C$_1$-C$_6$alkyl, C$_1$-C$_6$haloalkyl, —C$_1$-C$_6$perhaloalkyl, -halogen, —CN, —C$_1$-C$_6$alkoxy, —C$_1$-C$_6$haloalkoxy, —C$_1$-C$_6$perhaloalkoxy, —C$_2$-C$_7$alkenyl, —C$_2$-C$_8$alkynyl or —OH;
R$_4$ is —H, —C$_1$-C$_6$alkyl, C$_1$-C$_6$haloalkyl, —C$_1$-C$_6$perhaloalkyl, -halogen, —CN, —C$_1$-C$_6$alkoxy, —C$_1$-C$_6$haloalkoxy, —C$_1$-C$_6$perhaloalkoxy, —C$_2$-C$_7$alkenyl, —C$_2$-C$_8$alkynyl or —OH;
R$_5$ is —H, —C$_1$-C$_6$alkyl, C$_1$-C$_6$haloalkyl, —C$_1$-C$_6$perhaloalkyl, -halogen, —CN, —C$_1$-C$_6$alkoxy, —C$_1$-C$_6$haloalkoxy, —C$_1$-C$_6$perhaloalkoxy, —C$_2$-C$_7$alkenyl, —C$_2$-C$_8$alkynyl or —OH;
R$_6$ is —H, —C$_1$-C$_6$alkyl or -carboxy;
R$_7$ is —C$_1$-C$_6$alkyl or carboxy;
R$_8$ is —C$_3$-C$_8$cycloalkyl; and
R$_9$ is —H, —C$_1$-C$_6$alkyl or —C$_3$-C$_7$cycloalkyl;
wherein each alkyl, cycloalkyl, alkoxy, alkenyl and alkynyl is independently and optionally substituted with one or more substituents selected from the group consisting of —C$_1$-C$_4$alkyl, —C$_1$-C$_4$alkoxy and —OH.

5. The compound according to claim 1, or a pharmaceutically acceptable salt or stereoisomer thereof, wherein:
X$_1$ is C;
X$_2$ is C;
X$_3$ is C;
X$_4$ is N;
R$_1$ is a saturated or unsaturated 3-12 membered monocyclic or polycyclic heterocyclyl containing 1-3 heteroatoms, where R$_1$ is optionally substituted with 1-3 substituents selected from the group consisting of —NR$_6$R$_7$, —C$_1$-C$_6$alkyl, -amino and R$_8$;
R$_2$ is —H, —C$_1$-C$_6$alkyl, C$_1$-C$_6$haloalkyl, -halogen, —CN, —C$_1$-C$_6$alkoxy, —C$_1$-C$_6$haloalkoxy, —C$_2$-C$_7$alkenyl or —C$_2$-C$_8$alkynyl;
R$_3$ is —H, —C$_1$-C$_6$alkyl, C$_1$-C$_6$haloalkyl, -halogen, —CN, —C$_1$-C$_6$alkoxy, —C$_1$-C$_6$haloalkoxy, —C$_2$-C$_7$alkenyl or —C$_2$-C$_8$alkynyl;
R$_4$ is —H, —C$_1$-C$_6$alkyl, C$_1$-C$_6$haloalkyl, -halogen, —CN, —C$_1$-C$_6$alkoxy, —C$_1$-C$_6$haloalkoxy, —C$_2$-C$_7$alkenyl or —C$_2$-C$_8$alkynyl;
R$_6$ is —H, —C$_1$-C$_6$alkyl or -carboxy;
R$_7$ is —C$_1$-C$_6$alkyl or carboxy; and
R$_9$ is —H, —C$_1$-C$_6$alkyl or —C$_3$-C$_7$cycloalkyl;
wherein each alkyl, cycloalkyl, alkoxy, alkenyl and alkynyl is independently and optionally substituted with one or more substituents selected from the group consisting of —C$_1$-C$_4$alkyl, —C$_1$-C$_4$alkoxy and —OH.

6. The compound according to claim 1, or a pharmaceutically acceptable salt or stereoisomer thereof, wherein:
X$_1$ is C;
X$_2$ is C;
X$_3$ is C;
X$_4$ is N;
R$_1$ is a saturated or unsaturated 3-6 membered monocyclic heterocyclyl containing 1-3 heteroatoms, where R$_1$ is optionally substituted with —NR$_6$R$_7$;
R$_2$ is —H, —C$_1$-C$_6$alkyl, C$_1$-C$_6$haloalkyl, -halogen, —CN, —C$_1$-C$_6$alkoxy, —C$_1$-C$_6$haloalkoxy, —C$_2$-C$_7$alkenyl or —C$_2$-C$_8$alkynyl;
R$_3$ is —H, —C$_1$-C$_6$alkyl, C$_1$-C$_6$haloalkyl, -halogen, —CN, —C$_1$-C$_6$alkoxy, —C$_1$-C$_6$haloalkoxy, —C$_2$-C$_7$alkenyl or —C$_2$-C$_8$alkynyl;
R$_4$ is —H, —C$_1$-C$_6$alkyl, C$_1$-C$_6$haloalkyl, -halogen, —CN, —C$_1$-C$_6$alkoxy, —C$_1$-C$_6$haloalkoxy, —C$_2$-C$_7$alkenyl or —C$_2$-C$_8$alkynyl;
R$_6$ is —H, —C$_1$-C$_6$alkyl or -carboxy;
R$_7$ is —C$_1$-C$_6$alkyl or carboxy; and
R$_9$ is —H, —C$_1$-C$_6$alkyl or —C$_3$-C$_7$cycloalkyl;
wherein each alkyl, cycloalkyl, alkoxy, alkenyl and alkynyl is independently and optionally substituted with one or more substituents selected from the group consisting of —C$_1$-C$_4$alkyl, —C$_1$-C$_4$alkoxy and —OH.

7. The compound according to claim 1, or a pharmaceutically acceptable salt or stereoisomer thereof, wherein:
  $X_1$ is C;
  $X_2$ is C;
  $X_3$ is C;
  $X_4$ is N;
  $R_1$ is a saturated or unsaturated 3-6 membered monocyclic heterocyclyl containing 1-3 heteroatoms, where $R_1$ is optionally substituted with —$NR_6R_7$;
  $R_2$ is —H, —$C_1$-$C_6$alkyl, $C_1$-$C_6$haloalkyl, -halogen or —$C_2$-$C_8$alkynyl;
  $R_3$ is —H, —$C_1$-$C_6$alkyl, $C_1$-$C_6$haloalkyl, -halogen or —$C_2$-$C_8$alkynyl;
  $R_4$ is —H, —$C_1$-$C_6$alkyl, $C_1$-$C_6$haloalkyl, -halogen or —$C_2$-$C_8$alkynyl;
  $R_6$ is —H, —$C_1$-$C_6$alkyl or -carboxy;
  $R_7$ is —$C_1$-$C_6$alkyl or carboxy; and
  $R_9$ is —H or —$C_1$-$C_6$alkyl;
  wherein each alkyl is independently and optionally substituted with one or more substituents selected from the group consisting of —$C_1$-$C_4$alkyl, —$C_1$-$C_4$alkoxy and —OH.

8. A pharmaceutical composition comprising an effective amount of a compound according to claim 1, or a pharmaceutically acceptable salt or stereoisomer thereof, and a pharmaceutically acceptable carrier.

9. A method for inhibiting a human histamine 4 receptor, comprising administering to a human in need thereof the pharmaceutical composition according to claim 8.

10. The method according to claim 9, wherein the human suffers from a disease selected from the group consisting of an inflammatory disease, an autoimmune disease, an allergic disease, an ocular disease, a skin disease, a respiratory disease, a pain disease and a cardiac disease.

11. The method according to claim 9, wherein the human suffers from a disease selected from the group consisting of nasal polyps, allergic rhinitis, non-allergic rhinitis, viral rhinitis, nasal itch, sinusitis, nasal congestion, asthma, chronic obstructive pulmonary disease, rheumatoid arthritis, atopic dermatitis, psoriasis, eczema, pruritus, itchy skin, urticaria, idiopathic chronic urticaria, scleroderma, conjunctivitis, keratoconjunctivitis, ocular inflammation, dry eye, cardiac dysfunction, arrhythmia, atherosclerosis, multiple sclerosis, inflammatory bowel disease, inflammatory pain, neuropathic pain, osteoarthritic pain, autoimmune thyroid disease, immune-mediated diabetes, lupus, cancer, a post-operative adhesion and a vestibular disorder.

12. A method for preparing a compound of formula 1 according to claim 1:

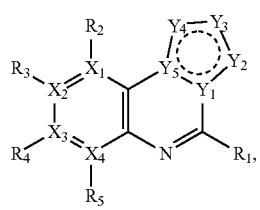

wherein $Y_1$ is C and $X_1$, $X_2$, $X_3$, $X_4$, $R_1$, $R_2$, $R_3$, $R_4$, $R_5$, $R_9$, $R_{10}$, $Y_2$, $Y_3$, $Y_4$ and $Y_5$ are as defined in claim 1;

comprising the steps of:
(a) reacting a compound of formula 4:

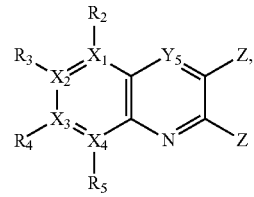

wherein each Z is independently —F, —Cl or —Br and $X_1$, $X_2$, $X_3$, $X_4$, $R_2$, $R_3$, $R_4$, $R_5$ and $Y_5$ are as defined in claim 1; with a compound of formula:

$R_1$—H, wherein $R_1$ is as defined in claim 1;
in the presence of solvent and base to provide a compound of formula 3:

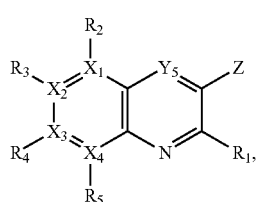

wherein Z is —F, —Cl or —Br and $X_1$, $X_2$, $X_3$, $X_4$, $R_1$, $R_2$, $R_3$, $R_4$, $R_5$ and $Y_5$ are as defined in claim 1;
(b) reacting a compound of formula 3:

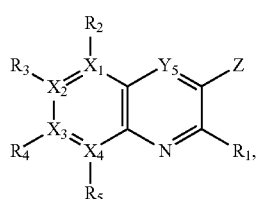

wherein Z is —F, —Cl or —Br and $X_1$, $X_2$, $X_3$, $X_4$, $R_1$, $R_2$, $R_3$, $R_4$, $R_5$ and $Y_5$ are as defined in claim 1;
with a compound of formula:

$R_9$—$NH_2$, wherein $R_9$ is as defined in claim 1;
in the presence of solvent to provide a compound of formula 2:

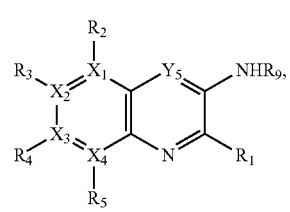

wherein $X_1$, $X_2$, $X_3$, $X_4$, $R_1$, $R_2$, $R_3$, $R_4$, $R_5$, $R_9$ and $Y_5$ are as defined in claim 1; and (c) cyclizing a compound of formula 2:

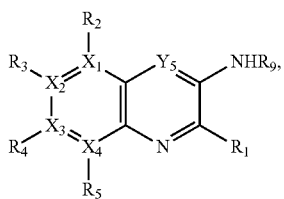

wherein $X_1$, $X_2$, $X_3$, $X_4$, $R_1$, $R_2$, $R_3$, $R_4$, $R_5$, $R_9$ and $Y_5$ are as defined in claim 1;
with a compound of formula:

CH(OR)$_3$, wherein R is —CH$_3$ or —CH$_2$CH$_3$;
in the presence of solvent to provide a compound of formula 1:

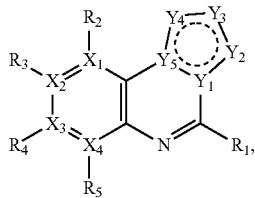

wherein $Y_1$ is C and $X_1$, $X_2$, $X_3$, $X_4$, $R_1$, $R_2$, $R_3$, $R_4$, $R_5$, $R_9$, $R_{10}$, $Y_2$, $Y_3$, $Y_4$ and $Y_5$ are as defined in claim 1.

13. A compound selected from the group consisting of:
3-Methyl-6-(4-methylpiperazin-1-yl)pyrido[3,2-e][1,2,4]triazolo[4,3-a]pyrazine;
8-Methyl-4-(4-methylpiperazin-1-yl)pyrido[2,3-e][1,2,4]triazolo[4,3-a]pyrazine;
4-(4-Methylpiperazin-1-yl)pyrido[2,3-e][1,2,4]triazolo[4,3-a]pyrazine;
8-Chloro-4-(4-methylpiperazin-1-yl)pyrido[2,3-e][1,2,4]triazolo[4,3-a]pyrazine;
3-Chloro-6-(4-methylpiperazin-1-yl)pyrido[3,2-e][1,2,4]triazolo[4,3-a]pyrazine;
6-(4-Methylpiperazin-1-yl)pyrido[3,2-e][1,2,4]triazolo[4,3-a]pyrazine;
8-Chloro-4-(piperazin-1-yl)pyrido[2,3-e][1,2,4]triazolo[4,3-a]pyrazine;
1-(8-Chloropyrido[2,3-e][1,2,4]triazolo[4,3-a]pyrazin-4-yl)azetidin-3-amine;
(R)-1-(8-chloropyrido[2,3-e][1,2,4]triazolo[4,3-a]pyrazin-4-yl)-N,N-dimethylpyrrolidin-3-amine;
(R)-1-(8-chloropyrido[2,3-e][1,2,4]triazolo[4,3-a]pyrazin-4-yl)-N-methylpyrrolidin-3-amine;
(R)-1-(3-chloropyrido[3,2-e][1,2,4]triazolo[4,3-a]pyrazin-6-yl)-N-methylpyrrolidin-3-amine;
8-Bromo-4-(4-methylpiperazin-1-yl)pyrido[2,3-e][1,2,4]triazolo[4,3-a]pyrazine;
4-(4-Methylpiperazin-1-yl)pyrido[2,3-e][1,2,4]triazolo[4,3-a]pyrazin-8-carbonitrile;
8-Chloro-1-methyl-4-(4-methylpiperazin-1-yl)pyrido[2,3-e][1,2,4]triazolo[4,3-a]pyrazine;
8-Chloro-1-methyl-4-(piperazin-1-yl)pyrido[2,3-e][1,2,4]triazolo[4,3-a]pyrazine;
8-Bromo-4-(piperazin-1-yl)pyrido[2,3-e][1,2,4]triazolo[4,3-a]pyrazine;
7,8-Dichloro-4-(4-methylpiperazin-1-yl)pyrido[2,3-e][1,2,4]triazolo[4,3-a]pyrazine;
1-(8-Chloropyrido[2,3-e][1,2,4]triazolo[4,3-a]pyrazin-4-yl)-N-methylazetidin-3-amine;
(S)-8-chloro-4-(3-methylpiperazin-1-yl)pyrido[2,3-e][1,2,4]triazolo[4,3-a]pyrazine;
(S)-8-chloro-4-(3,4-dimethylpiperazin-1-yl)pyrido[2,3-e][1,2,4]triazolo[4,3-a]pyrazine;
8-Chloro-4-(4-methylpiperazin-1-yl)pyrido[2,3-e][1,2,4]triazolo[4,3-a]pyrazin-7-carbonitrile;
8-Chloro-4-(3,4,5-trimethylpiperazin-1-yl)pyrido[2,3-e][1,2,4]triazolo[4,3-a]pyrazine;
8-Chloro-7-ethoxy-4-(4-methylpiperazin-1-yl)pyrido[2,3-e][1,2,4]triazolo[4,3-a]pyrazine;
1-(8-Bromopyrido[2,3-e][1,2,4]triazolo[4,3-a]pyrazin-4-yl)-N-methylazetidin-3-amine;
4-(3-(Methylamino)azetidin-1-yl)pyrido[2,3-e][1,2,4]triazolo[4,3-a]pyrazin-8-carbonitrile;
4-(Piperazin-1-yl)pyrido[2,3-e][1,2,4]triazolo[4,3-a]pyrazin-8-carbonitrile;
1-(7,8-Dichloropyrido[2,3-e][1,2,4]triazolo[4,3-a]pyrazin-4-yl)-N-methylazetidin-3-amine;
8-Chloro-4-(3-(methylamino)azetidin-1-yl)pyrido[2,3-e][1,2,4]triazolo[4,3-a]pyrazin-7-carbonitrile;
8-Chloro-4-(hexahydropyrrolo[1,2-a]pyrazin-2(1H)-yl)pyrido[2,3-e][1,2,4]triazolo[4,3-a]pyrazine;
(R)-1-(8-chloropyrido[2,3-e][1,2,4]triazolo[4,3-a]pyrazin-4-yl)pyrrolidin-3-amine;
9-Chloro-2-methyl-5-(4-methylpiperazin-1-yl)pyrido[3,2-e][1,2,4]triazolo[1,5-c]pyrimidine;
9-Chloro-2-methyl-5-(piperazin-1-yl)pyrido[3,2-e][1,2,4]triazolo[1,5-c]pyrimidine;
1-(9-Chloro-2-methylpyrido[3,2-e][1,2,4]triazolo[1,5-c]pyrimidin-5-yl)-N-methylazetidin-3-amine;
9-Chloro-2-cyclopropyl-N,N-diethylpyrido[3,2-e][1,2,4]triazolo[1,5-c]pyrimidin-5-amine;
9-Chloro-5-(4-methylpiperazin-1-yl)pyrido[3,2-e][1,2,4]triazolo[1,5-c]pyrimidine;
1-(9-Chloropyrido[3,2-e][1,2,4]triazolo[1,5-c]pyrimidin-5-yl)-N-methylazetidin-3-amine;
9-Chloro-5-(piperazin-1-yl)pyrido[3,2-e][1,2,4]triazolo[1,5-c]pyrimidine;
9-Chloro-2-cyclopropyl-5-(4-methylpiperazin-1-yl)pyrido[3,2-e][1,2,4]triazolo[1,5-c]pyrimidine;
9-Chloro-2-cyclopropyl-5-(piperazin-1-yl)pyrido[3,2-e][1,2,4]triazolo[1,5-c]pyrimidine;
9-Chloro-2-(methoxymethyl)-5-(4-methylpiperazin-1-yl)pyrido[3,2-e][1,2,4]triazolo[1,5-c]pyrimidine;
9-Chloro-2-ethyl-5-(4-methylpiperazin-1-yl)pyrido[3,2-e][1,2,4]triazolo[1,5-c]pyrimidine;
9-Chloro-5-(4-methylpiperazin-1-yl)pyrido[3,2-e][1,2,4]triazolo[4,3-c]pyrimidine;
8-Chloro-2-methyl-4-(4-methylpiperazin-1-yl)-2H-pyrazolo[3,4-c][1,8]naphthylidine;
1-(8-Chloro-2-methyl-2H-pyrazolo[3,4-c][1,8]naphthylidine-4-yl)-N-methylazetidin-3-amine;
8-Chloro-2-methyl-4-(piperazin-1-yl)-2H-pyrazolo[3,4-c][1,8]naphthylidine;
8-Chloro-4-(4-methylpiperazin-1-yl)imidazo[1,2-a]pyrido[2,3-e]pyrazine;
8-Chloro-4-(piperazin-1-yl)imidazo[1,2-a]pyrido[2,3-e]pyrazine;
1-(8-Iodopyrido[2,3-e][1,2,4]triazolo[4,3-a]pyrazin-4-yl)-N-methylazetidin-3-amine;
8-Iodo-4-(4-methylpiperazin-1-yl)pyrido[2,3-e][1,2,4]triazolo[4,3-a]pyrazine;

N-Methyl-1-(8-methylpyrido[2,3-e][1,2,4]triazolo[4,3-a]pyrazin-4-yl)azetidin-3-amine;
1-(8-(Difluoromethyl)pyrido[2,3-e][1,2,4]triazolo[4,3-a]pyrazin-4-yl)-N-methylazetidin-3-amine;
N-Methyl-1-(8-(trifluoromethyl)pyrido[2,3-e][1,2,4]triazolo[4,3-a]pyrazin-4-yl)azetidin-3-amine;
4-(4-Methylpiperazin-1-yl)-8-(trifluoromethyl)pyrido[2,3-e][1,2,4]triazolo[4,3-a]pyrazine;
1-(8-Ethynylpyrido[2,3-e][1,2,4]triazolo[4,3-a]pyrazin-4-yl)-N-methylazetidin-3-amine;
N-Methyl-1-(8-vinylpyrido[2,3-e][1,2,4]triazolo[4,3-a]pyrazin-4-yl)azetidin-3-amine;
1-(8-Ethylpyrido[2,3-e][1,2,4]triazolo[4,3-a]pyrazin-4-yl)-N-methylazetidin-3-amine;
4-(3-(Methylamino)azetidin-1-yl)pyrido[2,3-e][1,2,4]triazolo[4,3-a]pyrazin-8-ol;
1-(8-Methoxypyrido[2,3-e][1,2,4]triazolo[4,3-a]pyrazin-4-yl)-N-methylazetidin-3-amine;
1-(8-(Difluoromethoxy)pyrido[2,3-e][1,2,4]triazolo[4,3-a]pyrazin-4-yl)-N-methylazetidin-3-amine;
8-Chloro-7-methoxy-4-(4-methylpiperazin-1-yl)pyrido[2,3-e][1,2,4]triazolo[4,3-a]pyrazine;
8-Chloro-7-methoxy-4-(piperazin-1-yl)pyrido[2,3-e][1,2,4]triazolo[4,3-a]pyrazine;
7,8-Dichloro-4-(piperazin-1-yl)pyrido[2,3-e][1,2,4]triazolo[4,3-a]pyrazine;
8-Chloro-7-ethoxy-4-(piperazin-1-yl)pyrido[2,3-e][1,2,4]triazolo[4,3-a]pyrazine;
8-Chloro-4-(4-methylpiperazin-1-yl)-7-(2,2,2-trifluoroethoxy)pyrido[2,3-e][1,2,4]triazolo[4,3-a]pyrazine;
1-(8-Bromo-9-methylpyrido[2,3-e][1,2,4]triazolo[4,3-a]pyrazin-4-yl)-N-methylazetidin-3-amine;
8-Bromo-9-methyl-4-(4-methylpiperazin-1-yl)pyrido[2,3-e][1,2,4]triazolo[4,3-a]pyrazine;
1-(8,9-Dichloropyrido[2,3-e][1,2,4]triazolo[4,3-a]pyrazin-4-yl)-N-methylazetidin-3-amine;
1-(8-Bromopyrido[2,3-e][1,2,4]triazolo[4,3-a]pyrazin-4-yl)-N-methylazetidin-3-amine hydrochloride;
1-(8-Bromopyrido[2,3-e]tetrazolo[1,5-a]pyrazin-4-yl)-N-methylazetidin-3-amine hydrochloride;
8-Chloro-4-(5-methylhexahydropyrrolo[3,4-c]pyrrole-2(1H)-yl)pyrido[2,3-e][1,2,4]triazolo[4,3-a]pyrazine;
8-Bromo-4-(5-methylhexahydropyrrolo[3,4-c]pyrrole-2(1H)-yl)pyrido[2,3-e][1,2,4]triazolo[4,3-a]pyrazine;
1-(8-Bromopyrido[2,3-e][1,2,4]triazolo[4,3-a]pyrazin-4-yl)-3-methylazetidin-3-amine;
1-(8-Bromopyrido[2,3-e][1,2,4]triazolo[4,3-a]pyrazin-4-yl)-N,3-dimethylazetidin-3-amine;
8-Bromo-4-(hexahydropyrrolo[1,2-a]pyrazin-2(1H)-yl)pyrido[2,3-e][1,2,4]triazolo[4,3-a]pyrazine;
4-(Hexahydropyrrolo[1,2-a]pyrazin-2(1H)-yl)-8-iodopyrido[2,3-e][1,2,4]triazolo[4,3-a]pyrazine;
8-Chloro-4-(4-cyclopropylpiperazin-1-yl)pyrido[2,3-e][1,2,4]triazolo[4,3-a]pyrazine;
4-((1 S,4S)-2,5-diazabicyclo[2.2.1]heptan-2-yl)-8-chloropyrido[2,3-e][1,2,4]triazolo[4,3-a]pyrazine;
8-Chloro-4-((1 S,4S)-5-methyl-2,5-diazabicyclo[2.2.1]heptan-2-yl)pyrido[2,3-e][1,2,4]triazolo[4,3-a]pyrazine;
8-Chloro-4-(1,4-diazepan-1-yl)pyrido[2,3-e][1,2,4]triazolo[4,3-a]pyrazine;
8-Chloro-4-(4-methyl-1,4-diazepan-1-yl)pyrido[2,3-e][1,2,4]triazolo[4,3-a]pyrazine;
(R)-1-(8-bromopyrido[2,3-e][1,2,4]triazolo[4,3-a]pyrazin-4-yl)-N-methylpyrrolidin-3-amine;
8-Chloro-4-(hexahydro-1H-pyrrolo[3,4-b]pyridin-6(2H)-yl)pyrido[2,3-e][1,2,4]triazolo[4,3-a]pyrazine;
8-Chloro-4-(1-methylhexahydro-1H-pyrrolo[3,4-b]pyridin-6(2H)-yl)pyrido[2,3-e][1,2,4]triazolo[4,3-a]pyrazine;
1-(8-Chloropyrido[2,3-e][1,2,4]triazolo[4,3-a]pyrazin-4-yl)-N,N-dimethylazetidin-3-amine;
1-(8-Bromopyrido[2,3-e][1,2,4]triazolo[4,3-a]pyrazin-4-yl)-N,N-dimethylazetidin-3-amine;
(1-(8-Bromopyrido[2,3-e][1,2,4]triazolo[4,3-a]pyrazin-4-yl)azetidin-3-yl)(methyl)carbamic acid;
2-((8-Chloropyrido[2,3-e][1,2,4]triazolo[4,3-a]pyrazin-4-yl)amino)ethanol;
1-(8-Chloroimidazo[1,2-a]pyrido[2,3-e]pyrazin-4-yl)-N-methylazetidin-3-amine;
1-(8-Bromoimidazo[1,2-a]pyrido[2,3-e]pyrazin-4-yl)-N-methylazetidin-3-amine;
tert-Butyl (1-(8-chloro-2-methyloxazolo[4,5-c][1,8]naphthylidine-4-yl)azetidin-3-yl)(methyl)carbamate;
1-(8-Chloro-2-methyloxazolo[4,5-c][1,8]naphthylidine-4-yl)-N-methylazetidin-3-amine;
8-Chloro-2-methyl-4-(4-methylpiperazin-1-yl)oxazolo[4,5-c][1,8]naphthylidine;
1-(8-Chloropyrido[2,3-e]tetrazolo[1,5-a]pyrazin-4-yl)-N-methylazetidin-3-amine;
8-Chloro-4-(4-methylpiperazin-1-yl)pyrido[2,3-e]tetrazolo[1,5-a]pyrazine;
1-(8-Bromopyrido[2,3-e]tetrazolo[1,5-a]pyrazin-4-yl)-N-methylazetidin-3-amine;
8-Bromo-4-(4-methylpiperazin-1-yl)pyrido[2,3-e]tetrazolo[1,5-a]pyrazine;
1-(8-Chloro-2-methylpyrido[2,3-e][1,2,4]triazolo[1,5-a]pyrazin-4-yl)-N-methylazetidin-3-amine;
8-Chloro-2-methyl-4-(4-methylpiperazin-1-yl)pyrido[2,3-e][1,2,4]triazolo[1,5-a]pyrazine;
1-(8-bromo-7-methylpyrido[2,3-e][1,2,4]triazolo[4,3-a]pyrazin-4-yl)-N-methylazetidin-3-amine;
8-bromo-7-methyl-4-(4-methylpiperazin-1-yl)pyrido[2,3-e][1,2,4]triazolo[4,3-a]pyrazine;
8-chloro-4-(3-(methylamino)azetidin-1-yl)pyrido[2,3-e][1,2,4]triazolo[4,3-a]pyrazin-7-ol HCl salt;
N-(1-(8-bromopyrido[2,3-e][1,2,4]triazolo[4,3-a]pyrazin-4-yl)azetidin-3-yl)-N-methylhydroxylamine;
1-(2-bromopyrido[3,2-e]pyrrolo[1,2-c]pyrimidin-6-yl)-N-methylazetidin-3-amine;
1-(8-bromopyrido[2,3-e][1,2,4]triazolo[4,3-a]pyrazin-4-yl)-N-methylazetidin-3-amine 2,2,2-trifluoroacetate;
(S)-1-(8-bromo-2-methyl-1,2-dihydroimidazo[1,2-a]pyrido[2,3-e]pyrazin-4-yl)-N-methylazetidin-3-amine;
(R)-1-(8-bromo-2-methyl-1,2-dihydroimidazo[1,2-a]pyrido[2,3-e]pyrazin-4-yl)-N-methylazetidin-3-amine;
1-(8-bromo-1,2-dihydroimidazo[1,2-a]pyrido[2,3-e]pyrazin-4-yl)-N-methylazetidin-3-amine;
1-(8-bromo-2-methylimidazo[1,2-a]pyrido[2,3-e]pyrazin-4-yl)-N-methylazetidin-3-amine;
1-(9-bromo-2-methylpyrazolo[1,5-c]pyrido[3,2-e]pyrimidin-5-yl)-N-methylazetidin-3-amine;
1-(9-bromopyrazolo[1,5-c]pyrido[3,2-e]pyrimidin-5-yl)-N-methylazetidin-3-amine;
N-methyl-1-(8-nitropyrido[2,3-e][1,2,4]triazolo[4,3-a]pyrazin-4-yl)azetidin-3-amine;
4-(3-(methylamino)azetidin-1-yl)pyrido[2,3-e][1,2,4]triazolo[4,3-a]pyrazin-8-amine;
N-methyl-1-(8-phenylpyrido[2,3-e][1,2,4]triazolo[4,3-a]pyrazin-4-yl)azetidin-3-amine;
1-(8-(furan-2-yl)pyrido[2,3-e][1,2,4]triazolo[4,3-a]pyrazin-4-yl)-N-methylazetidin-3-amine;
1-(2-bromopyrido[2,3-e]pyrrolo[1,2-a]pyrazin-6-yl)-N-methylazetidin-3-amine;

1-(2-chloropyrido[3,2-e][1,2,4]triazolo[4,3-a]pyrazin-6-yl)-N-methylazetidin-3-amine;
1-(8-chloropyrido[3,4-e][1,2,4]triazolo[4,3-a]pyrazin-4-yl)-N-methylazetidin-3-amine;
1-(8-bromopyrido[2,3-e][1,2,4]triazolo[4,3-a]pyrazin-4-yl)-N-methylazetidin-3-amine methanesulfonic acid salt;
1-(8-bromopyrido[2,3-e][1,2,4]triazolo[4,3-a]pyrazin-4-yl)-N-methylazetidin-3-amine maleic acid salt;
1-(8-bromopyrido[2,3-e][1,2,4]triazolo[4,3-a]pyrazin-4-yl)-N-methylazetidin-3-amine 2-hydroxypropane-1,2,3-tricarboxylic acid salt;
1-(8-bromopyrido[2,3-e][1,2,4]triazolo[4,3-a]pyrazin-4-yl)-N-methylazetidin-3-amine nitric acid salt;
1-(8-bromopyrido[2,3-e][1,2,4]triazolo[4,3-a]pyrazin-4-yl)-N-methylazetidin-3-amine hydroiodic acid salt;
1-(8-bromopyrido[2,3-e][1,2,4]triazolo[4,3-a]pyrazin-4-yl)-N-methylazetidin-3-amine phosphoric acid salt;
1-(8-bromopyrido[2,3-e][1,2,4]triazolo[4,3-a]pyrazin-4-yl)-N-methylazetidin-3-amine 4,4'-methylenebis(3-hydroxy-2-naphthoic acid) salt;
1-(8-bromopyrido[2,3-e][1,2,4]triazolo[4,3-a]pyrazin-4-yl)-N-methylazetidin-3-amine hydrobromic acid salt;
1-(8-bromopyrido[2,3-e][1,2,4]triazolo[4,3-a]pyrazin-4-yl)-N-methylazetidin-3-amine sulfuric acid salt;
1-(8-bromopyrido[2,3-e][1,2,4]triazolo[4,3-a]pyrazin-4-yl)-N-methylazetidin-3-amine (2R,3R)-2,3-dihydroxysuccinic acid salt;
1-(8-bromopyrido[2,3-e][1,2,4]triazolo[4,3-a]pyrazin-4-yl)-N-methylazetidin-3-amine (1S)-(+)-10-Camphorsulfonic acid salt;
8-bromo-N-(1-methylpyrrolidin-3-yl)pyrido[2,3-e][1,2,4]triazolo[4,3-a]pyrazin-4-amine;
1-(8-bromopyrido[2,3-e][1,2,4]triazolo[4,3-a]pyrazin-4-yl)-N-methylazetidin-3-amine (S)-2-hydroxypropanoic acid salt;
N-(azetidin-3-ylmethyl)-8-bromopyrido[2,3-e][1,2,4]triazolo[4,3-a]pyrazin-4-amine trifluoroacetic acid salt; and
4-(azetidin-3-ylmethoxy)-8-bromopyrido[2,3-e][1,2,4]triazolo[4,3-a]pyrazine hydrochloric acid salt,
or a pharmaceutically acceptable salt or stereoisomer thereof.

* * * * *